(12) United States Patent
Jolly et al.

(10) Patent No.: US 6,818,439 B1
(45) Date of Patent: Nov. 16, 2004

(54) METHODS FOR ADMINISTRATION OF RECOMBINANT GENE DELIVERY VEHICLES FOR TREATMENT OF HEMOPHILIA AND OTHER DISORDERS

(75) Inventors: Douglas J. Jolly, Leucadia, CA (US); Stephen Chang, Poway, CA (US); James G. Respess, Pacific Beach, CA (US); Nicholas J. DePolo, Solano Beach, CA (US); David Chi-Tang Hsu, San Diego, CA (US); Carlos E. Ibanez, San Diego, CA (US); Judith Greengard, San Diego, CA (US); Lee Will, Carlsbad, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/001,039

(22) Filed: Dec. 30, 1997

Related U.S. Application Data

(63) Continuation-in-part of application No. 08/869,309, filed on Jun. 4, 1997, now abandoned, which is a continuation-in-part of application No. 08/696,381, filed on Aug. 13, 1996, now abandoned, which is a continuation-in-part of application No. 08/645,601, filed on Jul. 3, 1996, now abandoned, which is a continuation-in-part of application No. 08/367,071, filed on Dec. 30, 1994, now abandoned.

(51) Int. Cl.$^7$ ............................................. C12N 15/867
(52) U.S. Cl. ............................... 435/320.1; 435/235.1; 435/69.1; 435/69.6; 530/350; 530/384; 536/23.1; 536/23.5
(58) Field of Search ............................. 435/320.1, 235.1, 435/69.1, 69.6, 455, 456; 530/350, 384; 536/23.1, 23.5

(56) References Cited

U.S. PATENT DOCUMENTS

| | | | |
|---|---|---|---|
| 4,861,719 A | | 8/1989 | Miller |
| 5,328,470 A | | 7/1994 | Nabel et al. |
| 5,512,421 A | | 4/1996 | Burnes et al. |
| 5,643,770 A | * | 7/1997 | Mason et al. ............ 435/320.1 |
| 5,674,722 A | * | 10/1997 | Mulligan et al. ........ 435/172.3 |
| 5,691,177 A | | 11/1997 | Gruber et al. |
| 5,792,643 A | * | 8/1998 | Herrmann et al. |
| 6,329,199 B1 | * | 12/2001 | Pensiero et al. ......... 435/320.1 |

FOREIGN PATENT DOCUMENTS

| | | |
|---|---|---|
| EP | 260148 | 3/1988 |
| WO | WO 90/08771 | 8/1990 |
| WO | WO 91/09122 | 6/1991 |
| WO | WO 92/95266 | 4/1992 |
| WO | WO 92/07943 | 5/1992 |
| WO | WO 92/14829 | 9/1992 |
| WO | WO 93/25698 | 12/1993 |
| WO | WO 94/29440 | 12/1994 |
| WO | WO 94/29471 | 12/1994 |
| WO | WO 95/16582 | 6/1995 |
| WO | WO 95/27512 | 10/1995 |
| WO | WO 95/34669 | 12/1995 |
| WO | WO 96/21014 | 7/1996 |

OTHER PUBLICATIONS

Anderson (1998) Human gene therapy. Nature 392:25–30, Apr. 1998.*
Verma et al. (1997) Gene therapy–promises, problems and prospects. Nature 389:239–242, Sep. 1997.*
Kay et al. (1993) In vivo gene therapy of hemophilia B: sustained partial correction in factor IX–deficient dogs. Science 262:117–119, Oct. 1993.*
Takeuchi et al. (1994) Type C retrovirus inactivation by human complement is determined by both the viral genome and the producer cell. J. Virol. 68:8001–8007, Dec. 1994.*
Connelly et al., "In Vivo Gene Delivery and Expression of Physiological Levels of Functional Human Factor VIII in Mice" *Human Gene Therapy* 6:185–192, Feb., 1995.
Connelly et al., "High Level Tissue–Specific Expression of Functional Human Factor VIII in Mice" *Human Gene Therapy* 7:183–195, Jan., 1996.
Connelly et al., "Complete Short–Term Correction of Canine Hemophilia A by In Vivo Gene Therapy" *Blood* 88(10):3846–3853, 1996.
Connelly et al., "Sustained Expression of Therapeutic Levels of Human Factor VIII in Mice" *Blood* 87(11):4671–4677, 1996.
Dwarki et al., "Gene Therapy for Hemophilia A: Production of Therapeutic Levels of Human Factor VIII in vivo in Mice" *Proc. Natl. Acad. Sci.* 92:1023–1027, Feb., 1995.
Gorgas and Krisana, "Zonal Heterogeneity of Peroxisome Proliferation and Morphology in rat Liver After Gemfibrozil Treatment" *J. Lipid Research* 30:1859–1875, 1989.
Hoeben et al., "Toward Gene Therapy for Hemophilia A: Long–Term Persistence of Factor VIII–Secreting Fibroblasts after Transplantation into Immunodeficient Mice" *Human Gene Therapy* 4:179–186, 1993.
Hoeben et al., "Toward Gene Therapy in Haemophilia A: Retrovirus–Mediated Transfer of a Factor VIII Gene into Murine Haematopoietic Progenitor Cells" *Thrombosis and Kaemostasis* 67(3):341–345, 1992.

(List continued on next page.)

*Primary Examiner*—David Guzo
(74) *Attorney, Agent, or Firm*—Louis C. Cullman; Alisa A. Harbin; Robert P. Blackburn

(57) ABSTRACT

Methods are provided for obtaining measurable levels of a protein, nucleic acid molecule, or enzymatic product in a bodily fluid or cells of a human, comprising the step of administering to a human a recombinant retroviral preparation having a titer on HT1080 cells of greater than $10^5$ cfu/ml, wherein the recombinant retroviral preparation is capable of directing the expression of a protein, nucleic acid molecule, or enzyme which generates an enzymatic product, such that measurable levels of the protein, nucleic acid molecule, or enzymatic product may be obtained in the bodily fluid or cells of the human.

20 Claims, 41 Drawing Sheets

OTHER PUBLICATIONS

Issemann and Green, "Activation of a Member of the Steroid Hormone Receptor Superfamily by Peroxisome Proliferators" *Nature 347*:645–650, Oct., 1990.

Izumi et al., "Induction of Hepatic Ornithine Decarboxylase by Hypolipidemic Drugs with Hepatic Peroxisome Proliferative Activity" *Carcinogenesis 2*(7):623–627, 1981.

Joplin et al., "Human Intrahepatic Biliary Epithelial Cells Proliferate in Vitro in Response to Human Hepatocyte Growth Factor" *J. Clin. Invest. 90*:1284–1289, Oct., 1992.

Kakei et al., "Effects of Long–Term Omaprazole Treatment on Adult Rat Gastric Mucosa–Enhancement of the Epithelial Cell Proliferation and Suppression of its Differentiation" *Biochemical and Biophysical Research Communications 214*(3):861–868, Sep., 1995.

Liu et al., "Collagenase Pretreatment and the Mitogenic Effects of Hepatocyte Growth Factor and Transforming Growth Factor–α in Adult Rat Liver" *Hepatology 19*(6):1521–1527, 1994.

Lundgren et al., "Effects of Dietary Treatment with Clofibrate, Nafenopin or WY–14.643 on Mitochondria and DNA in Mouse Liver" *Biochimica et Biophysica Acta 1035*:132–138, 1990.

Mars et al., "Activation of Hepatocyte Growth Factor by the Plasminogen Activators uPA and tPA" *American Journal of Pathology 143*(3):949–958. Sep., 1993.

Mead et al., "Induction of Replicative Competence ("Priming") in Normal Liver" *Cancer Research 50*:7023–7030, Nov., 1990.

Miller et al., "Compact Organization of the Hepatitis B Virus Genome" *Hepatology 9*(2):322–327, 1989.

Mizuno et al., "Purification and Characterization of Hepatocyte Growth Factor (HGP)–Converting Enzyme: Activation of Pro–HGF" *Biochemical and Biophysical Research Communications 198*(3):1161–1169, Feb., 1994.

Moscioni et al., "In vivo Regional Delivery of Retrovirally Mediated Foreign Genes to rat Liver Cells: Need for Partial Hepatectomy for Successful Foreign Gene Expression" *Surgery 113*(3):304–311, Mar., 1993.

Motojima and Goto, "Rat Liver BiP/GRP78 is Down–Regulated by a Peroxisome–Proliferator, Clofibrate" *FEBS 308*(2):207–210, Aug., 1992.

Ohmura et al., "Hepatocyte Proliferation Induced by a Single Dose of a Peroxisome Proliferator" *American J. Pathology 148*(3):815–824, Mar., 1996.

Reddy et al., "Carcinogenesis by Hepatic Peroxisome Proliferators: Evaluation of the Risk of Hypolipidemic Drugs and Industrial Plasticizers to Humans" *CRC Critical Reviews in Toxicology 12*(1):1–58, 1983.

Rettinger et al., "Liver Directed Gene Therapy: Quantitative Evaluation of Promotor Elements by using in vivo Retroviral Transduction" *Proc. Natl. Acad. Sci. USA 91*:1460–1464, Feb., 1994.

Roberts et al., "Non–Genotoxic Hepatocarcinogens Stimulate DNA Synthesis and Their Withdrawal Induces Apoptosis, but in Different Hepatocyte Populations" *Carcinogenesis 16*(8):1693–1698, 1995.

Sausen et al., "Gemfibrozil–Induced Peroxisome Proliferation and Hepatomoegaly in Male F344 Rats" *Cancer Letters 97*:263–268, 1995.

Schechter et al., "The neu Oncogene: an erb–B–related Gene Encoding a 185,000–M, Tumour Antigen" *Nature 312*:513–516, Dec., 1984.

Shih et al., "Transforming Genes of Carcinomas and Neuroblastomas Introduted into Mouse Fibroblasts" *Nature 290*:261–264, Mar., 1981.

Shimomura et al., "Activation of Hepatocyte Growth Factor by Two Homologous Proteases, Blood–Coagulation Factor XIIa and hepatocyte Growth Factor Activator" *Eur. J. Biochem. 229*:257–261, 1995.

Shimomura et al., "A Novel Protease Obtained from FBS–Containing Culture Supernatant,that Processes Single Chain form Hepatocyte Growth Factor to Two Chain form in Serum–Free Culture" *Cytotechnology 8*:219–229, 1992.

Slamon et al., "Studies of the HER–2/neu Proto–Oncogene in Human Breast Cancer" *Cancer Cells 7*:371–384, 1989.

Uribe, "Indomethacin Accelerates Clearance of Labeled Cells and Increases DNA Synthesis in Gastrointestinal Mucosa of the Rat" *Digestive Diseases and Sciences 37*(3):403–408, Mar., 1992.

Zatloukal et al., "In vivo Production of Human Factor VIII in Mice After Intrasplenic Implantation of Primary Fibroblasts Transfected by Receptor–Mediated, Adenovirius–Augmented Gene Delivery" *Proc. Natl. Acad. Sci. USA 91*:5148–5152, May, 1994.

Archer et al., "Human Growth Hormone (hGH) Secretion in Milk of Goats After Direct Transfer of the hGH Gene into the Mammary Gland by Using Replication–Defective Retrovirus Vectors" *Proc. Natl. Acad. Sci. USA 91*:6840–6844, Jul., 1994.

Bralet et al., "Cell Lineage Study in the Liver Using Retroviral Mediated Gene Transfer" *American J. Pathology 144*(5):896–905, May, 1994.

Fassati et al., "Transplantation of Retroviral Producer Cells for In Vivo Gene Transfer into Mouse Skeletal Muscle" *Human Gene Therapy 7*:595–602, Mar., 1996.

Hafenrichter et al., "Quantitative Evaluation of Liver–Specific Promoters from Retroviral Vectors After In Vivo Transduction of Hepatocytes" *Blood 84*(10):3394–3404, Nov., 1994.

Hatzoglou et al., "Hepatic Gene Transfer in Animals Using Retroviruses Containing the Promoter from the Gene for Phosphoenolpyruvate Carboxykinase" *J. Biological Chemistry 265*(28):17285–17293, 1990.

Kolodka et al., "Hepatic Gene Therapy: Efficient Retroviral–Mediated Gene Transfer into Rat Hepatocytes In Vivo" *Somatic Cell and Molecular Genetics 19*(5):491–497, 1993.

Pitt et al., "Retrovirus–Mediated Gene Transfer in Lungs of Living Fetal Sheep" *Gene Therapy 2*:344–350, 1995.

Markowitz et al., "Retroviral Gene Transfer Using Safe and Efficient Packaging Cell Line" *Annals of the New York Academy of Sciences 612*:407–414, 1990.

Bodine et al., "Development of a High–Titer Retrovirus Producer Cell Line and Strategies for Retrovirus–Mediated Gene Transfer into Rhesus Monkey Hematopoietic Stem Cells" *Annals of the New York Academy of Sciences 612*:415–426, 1990.

Bodine et al., "Development of a High Titer Retrovirus Producer Cell Line Capable of Gene Transfer in Rhesus Monkey Hematopietic Stem Cells" *Proceedings of the National Academy of Sciences 87*:3738–3742, 1990.

Jolly et al., "Viral Vector Systems for Gene Therapy" *Cancer Gene Therapy 1*(1):51–64, 1994.

Yi Fan et al., "High Efficient Transfer and Expression of Human Clotting Factor IX cDNA in Cultured Human Primary Skin Fibroblasts from Hemophilia B Patient by Retroviral Vectors" *Science in China* 35(2):183–193, Feb., 1992.

Mulligan, "The Basic Science of Gene Therapy" *Science* 260:926–930.

Marshall, "Gene Therapy's Growing Pains" *Science* 69:1050–1055.

Hodgson, "Advances in Vector Systems for Gene Therapy" *Exp. Opin. Ther. Patents* 5(5):459–468.

Culver et al., "Gene Therapy for Cancer" *TIG* 10(5):174–178.

Orkin et al., "Report and Recommendations of the Panel to Assess the NIH Investment in Research on Gene Therapy" NIK ad hoc Committee findings.

Miller et al., "Targeted Vectors for Gene Therapy" *FASEB J.* 9:190–199.

Kaleko et al., "Presistent Gene Expression After Retroviral Gene Transfer into Liver Cells In Vivo" *Human Gene Therapy* 2:27–32, 1991.

Kimura et al., "Retroviral Delivery of DNA into the Livers of Transgenic Mice Bearing Premalignant and Malignant Hepatocellular Carcinomas" *Human Gene Therapy* 5:845–852, 1994.

Roth et al., "Retrovirus–Mediated Wild–Type p53 Gene Transfer to Tumors of Patients with Lung Cancer" *Nature Medicine* 2(9):985–991, Sep., 1996.

Lynch and Miller, "Production of High–Titer Helper Virus–Free Retroviral Vectors by Cultivation of Packaging Cells with Different Host Ranges" *J. Virology* 65(7):3887–3890, Jul. 1991.

Coser et al., "Use of Helper Cells with Two Host Ranges to Generate High–Titer Retroviral Venors" *Virology* 193:385–395, 1993.

Chuah et al., "Development and Analysis of Retroviral Vectors Expressing Human Factor VIII as a Potential Gene Theraphy for Hemophilia A" *Human Gene Therapy* 6:1363–1377, Nov., 1995.

Fallaux et al., "State and Prospects of Gene Therapy for the Hemophilias" *Thrombosis and Haemostasis* 74(1):263–273, Jul., 1995.

Brownlee, "Prospects for Gene Therapy of Hemophilia A and B" *British Medical Bulletin* 5:91–105, 1995.

Toolee et al., "Molecular Cloning of a cDNA Encoding Human Antihaemophilic Factor" *Nature* 31:342–347, Nov., 1994.

Kaufman et al., "Selection and Amplification of Heterologous Genes Encoding Adenosine Deaminase in Mammalian Cells" *Proc. Natl. Acad. Sci. USA* 83:3136–3140, May, 1986.

Onodera et al., "Successful Peripheral T–Lymphocyte–Directed Gene Transfer for a Patient with Severe Combined Immune Deficiency Caused by Adenosine Doaminase Deficiency" *Blood* 91(1):3–36, Jan. 1, 1998.

* cited by examiner

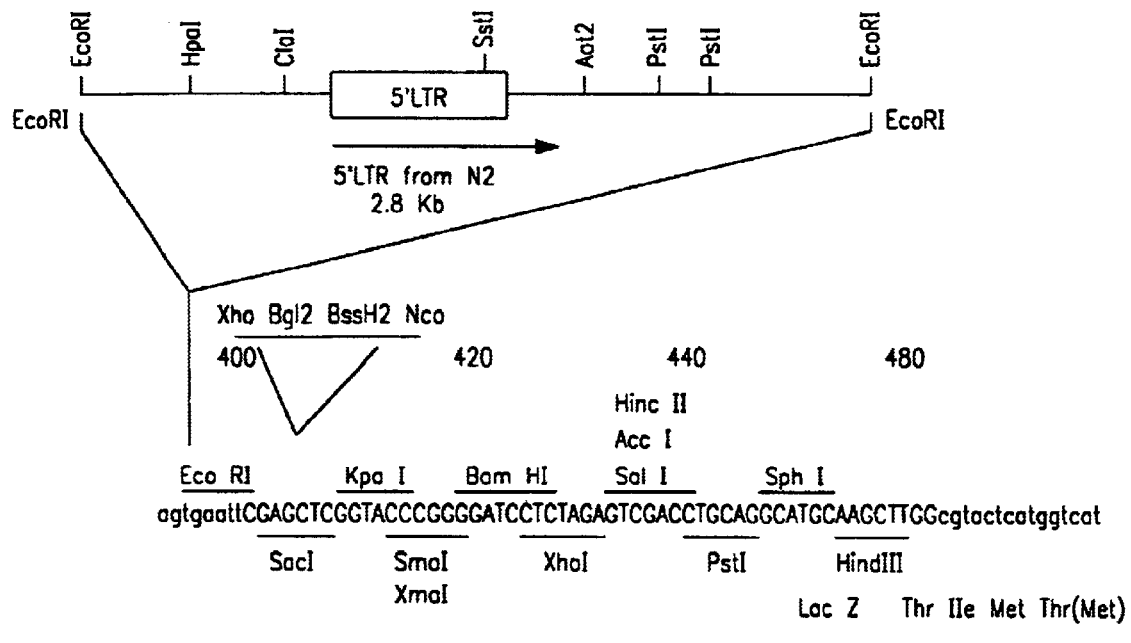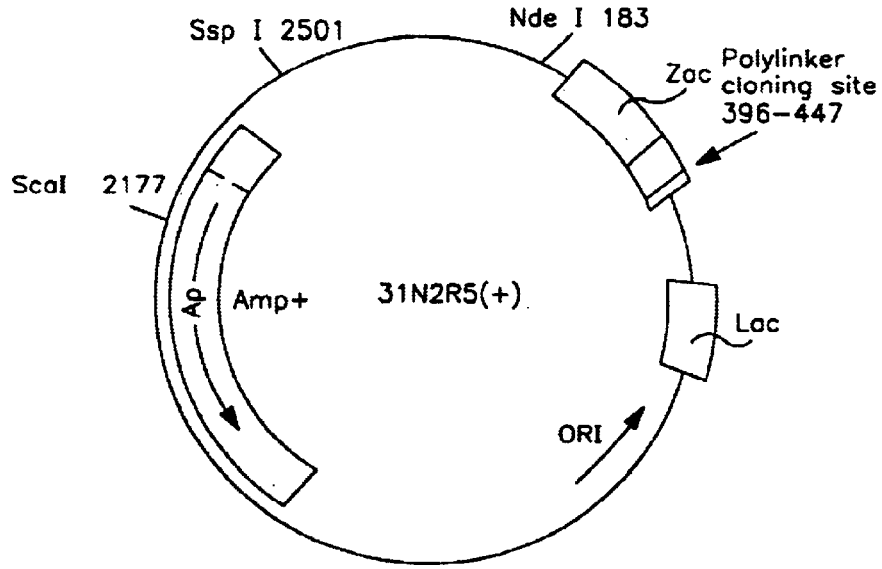
FIG. 1

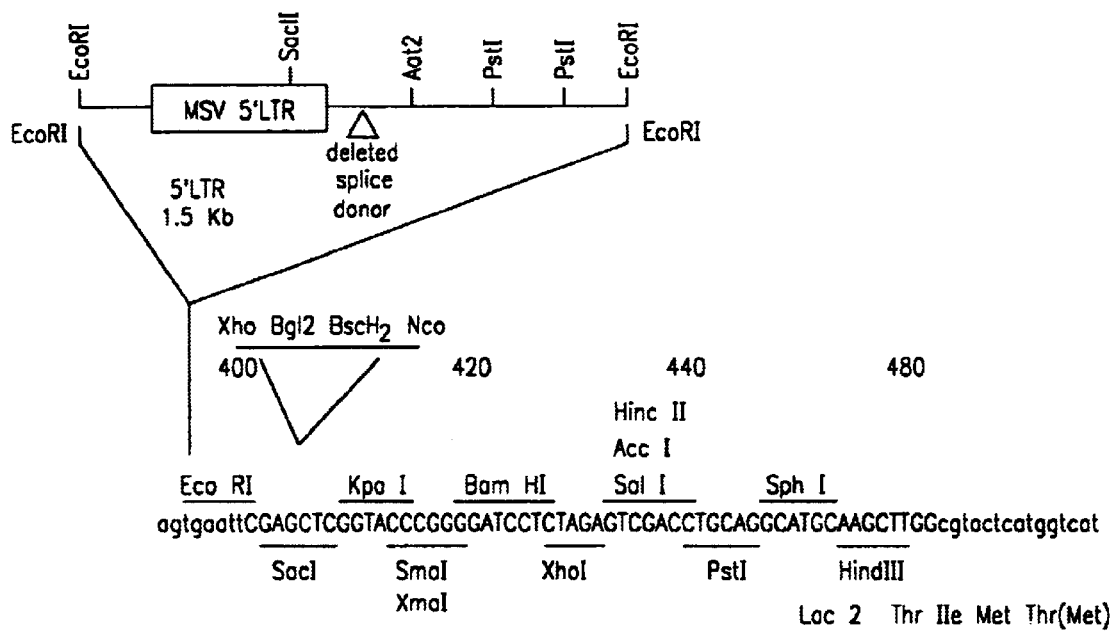
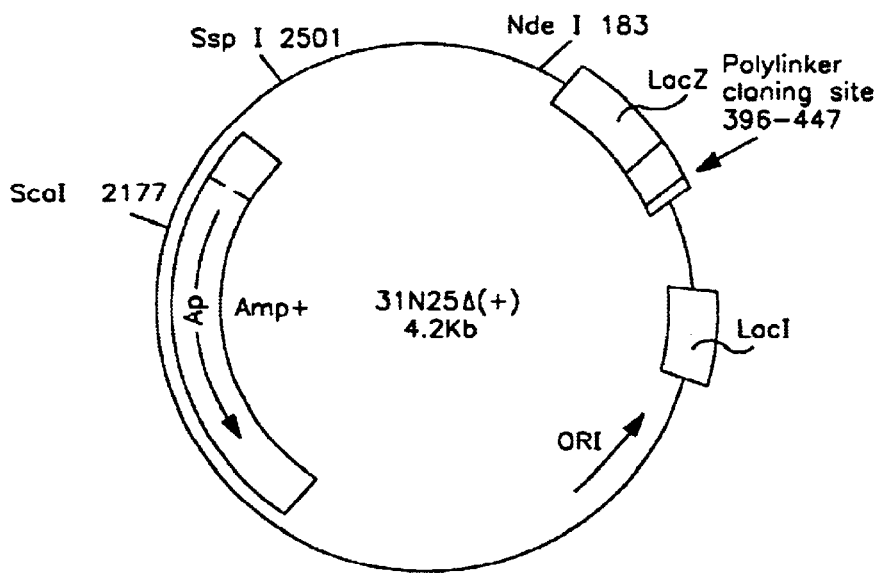
FIG. 3

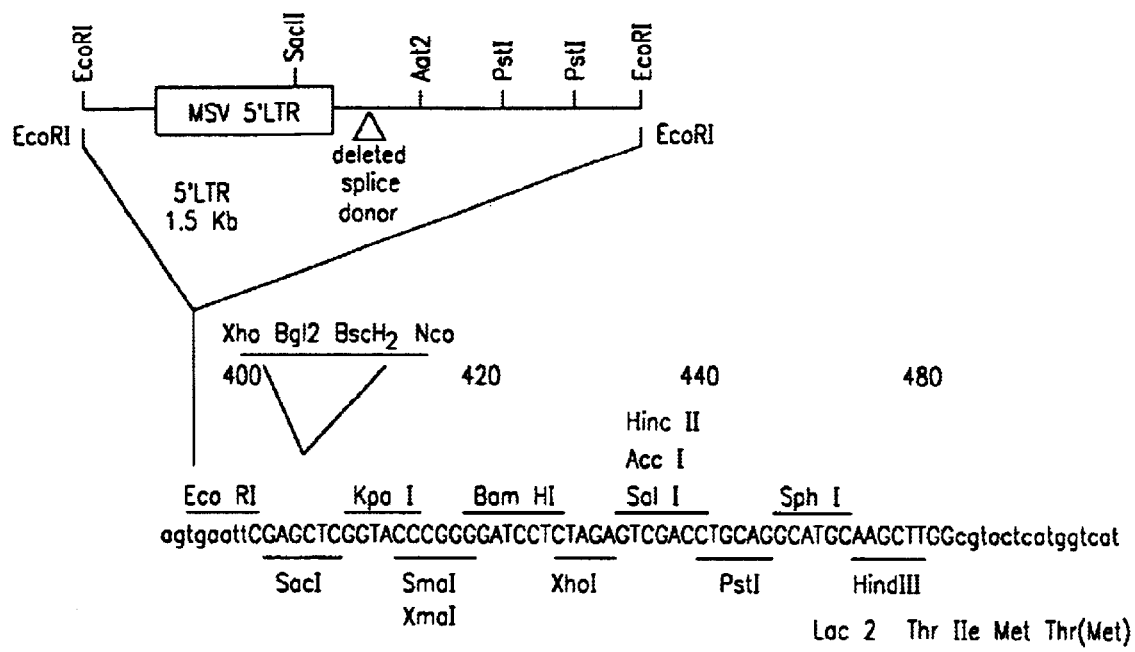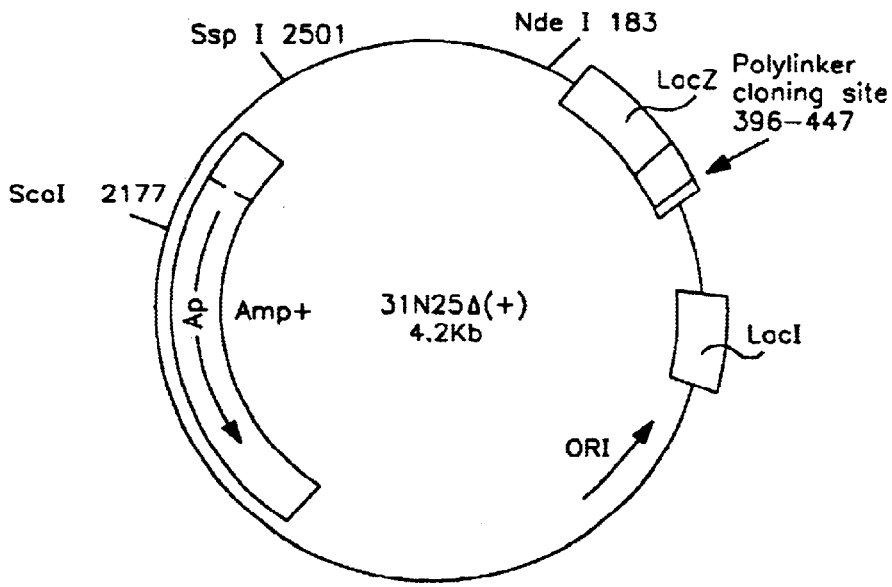
FIG. 6

```
                                                                Seq ID No. 48
                                                                Seq ID No. 49

ArgGlyMetThrAlaLeuLeuLysValSerSerCysAspLysAsnThrGlyAspTyrTyr
2341  AGAGGCATGACCGCCTTACTGTTCTGAAGGTTTCTGTGACAAGAACACTGGTGATTATTAC
      TCTCCGTACTGGCGGAATGACTTCCAAAGATCAACACTGTTCTTGTGACCACTAATAATG

GluAspSerTyrGluAspIleSerAlaTyrLeuLeuSerLysAsnAsnAlaIleGluPro
2401  GAGGACAGTTATGAAGATATTTCAGCATACTTGCTGAGTAAAAACAATGCCATTGAACCA
      CTCCTGTCAATACTTCTATAAAGTCGTATGAACGACTCATTTTTGTTACGGTAACTTGGT

<---------N-terminus of beta domain--------------------->

ArgSerPheSerGlnAsnSerArgHisProSerThrArgGlnLysGlnPheAsnAlaThr
2461  AGAAGCTTCTCCCAGAATTCTAGACACCTAGCACTAGGCAAAAGCAATTTAATGCCACC
      TCTTCGAAGAGGGTCTTAAGATCGTGATCCGTTCGTTAAATTACGGTGG
      ^                  ^
      2463 HIND3, 2475 ECORI, 2479 XBAI,

<-- IgA hinge ---><-- C-term. beta domain -->

ProProThrProProValLeuLysArgHisGlnArgGluIleThrArgThr
2521  CCTCCTACACCACCAACCCCACCAGTACTGAAACGCCATCAACGGGAAATAACTCGTACT
      GGAGGATGTGGTGGTTGGGGTGGTCATGACTTTGCGGTAGTTGCCCTTTATTGAGCATGA
                                                      ^
                                                      2544 SCAI,

ThrLeuGlnSerAspGlyGluGlyIleAspTyrAspAspThrIleSerValGluMetLys
2581  ACTCTTCAGTCTGATCAAGAGGAAATTGACTATGATGATACCATATCAGTGAAATGAAG
      TGAGAAGTCAGACTAGTTCTTCCTTTAACTGATACTACTATGGTATAGTCAACTTTACTTC
                       ^
                       2592 BCLI,
```

FIG. 38

```
                    ECORI                    MLUI    BCLI
                     NRUI                                          begin
              β region                                              80K
                   5   6   7   8   9  10    11 12 13 14 15 16 17 18 19 20 21
Seq ID No. 75    AsnSerArgHisProSer         GlnAsnProProValLeuLysArgHisGlnArgGluIleThr
                         F8-14E                        F8-16E          Seq ID No. 78
Seq ID No. 77 2  AATTCGACACACCCTAGC         CAAAACCCACCAGTCTTGAAACGCCATCAACGGGAAATAACG
                                                                        Seq ID No. 80
Seq ID No. 79       GCGCTGTGGGATCGGTTTTGGGTGGTCAGAAC  TTTGCGGGTAGTTGCCCTTTATTGC  ∧
                                F8-15E                       F8-17E

↑ ECOR1, 5 NRU1, 59 MLU1,

Seq ID No. 81       ArgThrLeuGlnSerAsp
                         F8-16E
Seq ID No. 8262     CGTACTCTTCAGTCT

Seq ID No. 83       GCATGAGAAGTCAGACTAG  ∧
                            F8-17E

76 BCL1,
```

FIG. 39

Linkers for pSVF8-500B end 92 19aa C terminal
to thrombin cleavage at 740    Seq ID No. 50
                                Seq ID No. 51

```
         SerArgHisProSerThrArgGlnLysGlnPheAsnAlaThrProProValLeuLysArg
mutant   TCGCGACACCCTAGCACTAGGCAAAAGCAATTTAATGCCACCCCACCAGTCCTGAAACGC
wild type AGCGCTGTGGGATCGTGATCCGTTTTCGTTAAATTACGGTGGGGTGGTCATGACTTTGCG
         (TT)                                                     (CT)
         NRU1
                Start 80K
         HisGlnArgGluIleThrArg
         CATCAACGGGAAATAACGCGT
         GTAGTTGCCCTTTATTGCGCA
         MLU1
         9aa N terminal to 80K
```

FIG. 41

SEQUENCE LISTING (1) GENERAL INFORMATION:

(iii) NUMBER OF SEQUENCES: 84

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GAGAGATGGG GGAGGCTAAC TGAG                                          24

(2) INFORMATION FOR SEQ ID NO:2:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

GATCCTCAGT TAGCCTCCCC CATCTCTC                                      28

(2) INFORMATION FOR SEQ ID NO:3:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

TATATCTCCA GATGAGGTAC ATGATTTTAG GCTTG                              35

(2) INFORMATION FOR SEQ ID NO:4:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

TATATATCGA TTCAAGGCAT TTTCTTTTCA TCAATAAAAC                         40

(2) INFORMATION FOR SEQ ID NO:5:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

TCGAGGATCC GCCCGGGCGG CCGCATCGAT GTCGACG    37

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCGTCGACA TCGATGCGGC CGCCCGGGCG GATCC    35

(2) INFORMATION FOR SEQ ID NO:7:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGTGAATTCG AGCTCGGTAC CCGGGGATCC TCTAGAGTCG ACCTGCAGGC ATGCAAGCTT    60

GGCGTACTCA TGGTCAT    77

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Arg Glu Met Gly Glu Ala Asn
1               5

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCCGAGAGAT GGGGGAGGCT AACTGAG    27

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGGCTCTCTA CCCCCTCCGA TTGACACCTA G												31

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Thr Ile Met Thr Met
1               5

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCCTGTGCCT TATTTGAACT AACC												24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CCCACCACAA CCACATATCC CTCC												24

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCAGTCCTCC GATTGACTG													19

(2) INFORMATION FOR SEQ ID NO:15:

(i) SEQUENCE CHARACTERISTICS:
        (A) LENGTH: 8332 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCGCCAGTCC TCCGATTGAC TGAGTCGCCC GGGTACCCGT GTATCCAATA AACCCTCTTG		60

CAGTTGCATC CGACTTGTGG TCTCGCTGTT CCTTGGGAGG GTCTCCTCTG AGTGATTGAC		120

```
TACCCGTCAG CGGGGGTCTT TCATTTGGGG GCTCGTCCGG GATCGGGAGA CCCCTGCCCA    180

GGGACCACCG ACCCACCACC GGGAGGTAAG CTGGCCAGCA ACTTATCTGT GTCTGTCCGA    240

TTGTCTAGTG TCTATGACTG ATTTTATGCG CCTGCGTCGG TACTAGTTAG CTAACTAGCT    300

CTGTATCTGG CGGACCCGTG GTGGAACTGA CGAGTTCGGA ACACCCGGCC GCAACCCTGG    360

GAGACGTCCC AGGGACTTCG GGGGCCGTTT TTGTGGCCCG ACCTGAGTCC AAAAATCCCG    420

ATCGTTTTGG ACTCTTTGGT GCACCCCCCT TAGAGGAGGG ATATGTGGTT CTGGTAGGAG    480

ACGAGAACCT AAAACAGTTC CCGCCTCCGT CTGAATTTTT GCTTTCGGTT TGGGACCGAA    540

GCCGCGCCGC GCGTCTTGTC TGCTGCAGCA TCGTTCTGTG TTGTCTCTGT CTGACTGTGT    600

TTCTGTATTT GTCTGAGAAT ATGGGCCAGA CTGTTACCAC TCCCTTAAGT TTGACCTTAG    660

GTCACTGGAA AGATGTCGAG CGGATCGCTC ACAACCAGTC GGTAGATGTC AAGAAGAGAC    720

GTTGGGTTAC CTTCTGCTCT GCAGAATGGC CAACCTTTAA CGTCGGATGG CCGCGAGACG    780

GCACCTTTAA CCGAGACCTC ATCACCCAGG TTAAGATCAA GGTCTTTTCA CCTGGCCCGC    840

ATGGACACCC AGACCAGGTC CCCTACATCG TGACCTGGGA AGCCTTGGCT TTTGACCCCC    900

CTCCCTGGGT CAAGCCCTTT GTACACCCTA AGCCTCCGCC TCCTCTTCCT CCATCCGCCC    960

CGTCTCTCCC CCTTGAACCT CCTCGTTCGA CCCCGCCTCG ATCCTCCCTT TATCCAGCCC   1020

TCACTCCTTC TCTAGGCGCC AAACCTAAAC CTCAAGTTCT TTCTGACAGT GGGGGCCGC   1080

TCATCGACCT ACTTACAGAA GACCCCCGC CTTATAGGGA CCCAAGACCA CCCCCTTCCG   1140

ACAGGGACGG AAATGGTGGA GAAGCGACCC CTGCGGGAGA GGCACCGGAC CCCTCCCCAA   1200

TGGCATCTCG CCTACGTGGG AGACGGGAGC CCCCTGTGGC CGACTCCACT ACCTCGCAGG   1260

CATTCCCCCT CCGCGCAGGA GGAAACGGAC AGCTTCAATA CTGGCCGTTC TCCTCTTCTG   1320

ACCTTTACAA CTGGAAAAAT AATAACCCTT CTTTTTCTGA AGATCCAGGT AAACTGACAG   1380

CTCTGATCGA GTCTGTTCTC ATCACCCATC AGCCCACCTG GACGACTGT CAGCAGCTGT   1440

TGGGGACTCT GCTGACCGGA AAGAAAAAC AACGGGTGCT CTTAGAGGCT AGAAAGGCGG   1500

TGCGGGGCGA TGATGGGCGC CCCACTCAAC TGCCCAATGA AGTCGATGCC GCTTTTCCCC   1560

TCGAGCGCCC AGACTGGGAT TACACCACCC AGGCAGGTAG GAACCACCTA GTCCACTATC   1620

GCCAGTTGCT CCTAGCGGGT CTCCAAAACG CGGGCAGAAG CCCCACCAAT TTGGCCAAGG   1680

TAAAAGGAAT AACACAAGGG CCCAATGAGT CTCCCTCGGC CTTCCTAGAG AGACTTAAGG   1740

AAGCCTATCG CAGGTACACT CCTTATGACC CTGAGGACCC AGGCAAGAA ACTAATGTGT   1800

CTATGTCTTT CATTTGGCAG TCTGCCCCAG ACATTGGGAG AAAGTTAGAG AGGTTAGAAG   1860

ATTTAAAAAA CAAGACGCTT GGAGATTTGG TTAGAGAGGC AGAAAAGATC TTTAATAAAC   1920

GAGAAACCCC GGAAGAAAGA GAGGAACGTA TCAGGAGAGA AACAGAGGAA AAAGAAGAAC   1980

GCCGTAGGAC AGAGGATGAG CAGAAAGAGA AGAAAGAGA TCGTAGGAGA CATAGAGAGA   2040

TGAGCAAGCT ATTGGCCACT GTCGTTAGTG GACAGAAACA GGATAGACAG GGAGGAGAAC   2100

GAAGGAGGTC CCAACTCGAT CGCGACCAGT GTGCCTACTG CAAAGAAAAG GGCACTGGG   2160

CTAAAGATTG TCCCAAGAAA CCACGAGGAC CTCGGGGACC AAGACCCCAG ACCTCCCTCC   2220

TGACCCTAGA TGACTAGGGA GGTCAGGGTC AGGAGCCCCC CCCTGAACCC AGGATAACCC   2280

TCAAAGTCGG GGGGCAACCC GTCACCTTCC TGGTAGATAC TGGGGCCCAA CACTCCGTGC   2340

TGACCCAAAA TCCTGGACCC CTAAGTGATA AGTCTGCCTG GTCCAAGGG GCTACTGGAG   2400

GAAAGCGGTA TCGCTGGACC ACGGATCGCA AAGTACATCT AGCTACCGGT AAGGTCACCC   2460
```

```
ACTCTTTCCT CCATGTACCA GACTGTCCCT ATCCTCTGTT AGGAAGAGAT TTGCTGACTA    2520

AACTAAAAGC CCAAATCCAC TTTGAGGGAT CAGGAGCTCA GGTTATGGGA CCAATGGGGC    2580

AGCCCCTGCA AGTGTTGACC CTAAATATAG AAGATGAGCA TCGGCTACAT GAGACCTCAA    2640

AAGAGCCAGA TGTTTCTCTA GGGTCCACAT GGCTGTCTGA TTTTCCTCAG GCCTGGGCGG    2700

AAACCGGGGG CATGGGACTG GCAGTTCGCC AAGCTCCTCT GATCATACCT CTGAAAGCAA    2760

CCTCTACCCC CGTGTCCATA AAACAATACC CCATGTCACA AGAAGCCAGA CTGGGGATCA    2820

AGCCCCACAT ACAGAGACTG TTGGACCAGG GAATACTGGT ACCCTGCCAG TCCCCCTGGA    2880

ACACGCCCCT GCTACCCGTT AAGAAACCAG GGACTAATGA TTATAGGCCT GTCCAGGATC    2940

TGAGAGAAGT CAACAAGCGG GTGGAAGACA TCCACCCCAC CGTGCCCAAC CCTTACAACC    3000

TCTTGAGCGG GCTCCCACCG TCCCACCAGT GGTACACTGT GCTTGATTTA AAGGATGCCT    3060

TTTTCTGCCT GAGACTCCAC CCCACCAGTC AGCCTCTCTT CGCCTTTGAG TGGAGAGATC    3120

CAGAGATGGG AATCTCAGGA CAATTGACCT GGACCAGACT CCCACAGGGT TTCAAAAACA    3180

GTCCCACCCT GTTTGATGAG GCACTGCACA GAGACCTAGC AGACTTCCGG ATCCAGCACC    3240

CAGACTTGAT CCTGCTACAG TACGTGGATG ACTTACTGCT GGCCGCCACT TCTGAGCTAG    3300

ACTGCCAACA AGGTACTCGG GCCCTGTTAC AAACCCTAGG GAACCTCGGG TATCGGGCCT    3360

CGGCCAAGAA AGCCCAAATT TGCCAGAAAC AGGTCAAGTA TCTGGGGTAT CTTCTAAAAG    3420

AGGGTCAGAG ATGGCTGACT GAGGCCAGAA AAGAGACTGT GATGGGGCAG CCTACTCCGA    3480

AGACCCCTCG ACAACTAAGG GAGTTCCTAG GGACGGCAGG CTTCTGTCGC CTCTGGATCC    3540

CTGGGTTTGC AGAAATGGCA GCCCCCTTGT ACCCTCTCAC CAAAACGGGG ACTCTGTTTA    3600

ATTGGGGCCC AGACCAACAA AAGGCCTATC AAGAAATCAA GCAAGCTCTT CTAACTGCCC    3660

CAGCCCTGGG GTTGCCAGAT TTGACTAAGC CCTTTGAACT CTTTGTCGAC GAGAAGCAGG    3720

GCTACGCCAA AGGTGTCCTA ACGCAAAAAC TGGGACCTTG GCGTCGGCCG GTGGCCTACC    3780

TGTCCAAAAA GCTAGACCCA GTAGCAGCTG GGTGGCCCCC TTGCCTACGG ATGGTAGCAG    3840

CCATTGCCGT ACTGACAAAG GATGCAGGCA AGCTAACCAT GGGACAGCCA CTAGTCATTC    3900

TGGCCCCCCA TGCAGTAGAG GCACTAGTCA AACAACCCCC CGACCGCTGG CTTTCCAACG    3960

CCCGGATGAC TCACTATCAG GCCTTGCTTT TGGACACGGA CCGGGTCCAG TTCGGACCGG    4020

TGGTAGCCCT GAACCCGGCT ACGCTGCTCC CACTGCCTGA GGAAGGGCTG CAACACAACT    4080

GCCTTGATAT CCTGGCCGAA GCCCACGGAA CCCGACCCGA CCTAACGGAC CAGCCGCTCC    4140

CAGACGCCGA CCACACCTGG TACACGGATG GAAGCAGTCT CTTACAAGAG GGACAGCGTA    4200

AGGCGGGAGC TGCGGTGACC ACCGAGACCG AGGTAATCTG GGCTAAAGCC CTGCCAGCCG    4260

GGACATCCGC TCAGCGGGCT GAACTGATAG CACTCACCCA GGCCCTAAAG ATGGCAGAAG    4320

GTAAGAAGCT AAATGTTTAT ACTGATAGCC GTTATGCTTT TGCTACTGCC CATATCCATG    4380

GAGAAATATA CAGAAGGCGT GGGTTGCTCA CATCAGAAGG CAAAGAGATC AAAAATAAAG    4440

ACGAGATCTT GGCCCTACTA AAAGCCCTCT TTCTGCCCAA AAGACTTAGC ATAATCCATT    4500

GTCCAGGACA TCAAAAGGGA CACAGCGCCG AGGCTAGAGG CAACCGGATG GCTGACCAAG    4560

CGGCCCGAAA GGCAGCCATC ACAGAGACTC CAGACACCTC TACCCTCCTC ATAGAAAATT    4620

CATCACCCTA CACCTCAGAA CATTTTCATT ACACAGTGAC TGATATAAAG GACCTAACCA    4680

AGTTGGGGGC CATTTATGAT AAAACAAAGA AGTATTGGGT CTACCAAGGA AAACCTGTGA    4740

TGCCTGACCA GTTTACTTTT GAATTATTAG ACTTTCTTCA TCAGCTGACT CACCTCAGCT    4800

TCTCAAAAAT GAAGGCTCTC CTAGAGAGAA GCCACAGTCC CTACTACATG CTGAACCGGG    4860
```

-continued

| | |
|---|---|
| ATCGAACACT CAAAAATATC ACTGAGACCT GCAAAGCTTG TGCACAAGTC AACGCCAGCA | 4920 |
| AGTCTGCCGT TAAACAGGGA ACTAGGGTCC GCGGGCATCG GCCCGGCACT CATTGGGAGA | 4980 |
| TCGATTTCAC CGAGATAAAG CCCGGATTGT ATGGCTATAA ATATCTTCTA GTTTTTATAG | 5040 |
| ATACCTTTTC TGGCTGGATA GAAGCCTTCC CAACCAAGAA AGAAACCGCC AAGGTCGTAA | 5100 |
| CCAAGAAGCT ACTAGAGGAG ATCTTCCCCA GGTTCGGCAT GCCTCAGGTA TTGGGAACTG | 5160 |
| ACAATGGGCC TGCCTTCGTC TCCAAGGTGA GTCAGACAGT GGCCGATCTG TTGGGGATTG | 5220 |
| ATTGGAAATT ACATTGTGCA TACAGACCCC AAAGCTCAGG CCAGGTAGAA GAATGAATA | 5280 |
| GAACCATCAA GGAGACTTTA ACTAAATTAA CGCTTGCAAC TGGCTCTAGA GACTGGGTGC | 5340 |
| TCCTACTCCC CTTAGCCCTG TACCGAGCCC GCAACACGCC GGGCCCCAT GGCCTCACCC | 5400 |
| CATATGAGAT CTTATATGGG GCACCCCGC CCCTTGTAAA CTTCCCTGAC CCTGACATGA | 5460 |
| CAAGAGTTAC TAACAGCCCC TCTCTCCAAG CTCACTTACA GGCTCTCTAC TTAGTCCAGC | 5520 |
| ACGAAGTCTG GAGACCTCTG GCGGCAGCCT ACCAAGAACA ACTGGACCGA CCGGTGGTAC | 5580 |
| CTCACCCTTA CCGAGTCGGC GACACAGTGT GGGTCCGCCG ACACCAGACT AAGAACCTAG | 5640 |
| AACCTCGCTG GAAAGGACCT TACACAGTCC TGCTGACCAC CCCCACCGCC CTCAAAGTAG | 5700 |
| ACGGCATCGC AGCTTGGATA CACGCCGCCC ACGTGAAGGC TGCCGACCCC GGGGGTGGAC | 5760 |
| CATCCTCTAG ACTGACATGG CGCGTTCAAC GCTCTCAAAA CCCCTTAAAA ATAAGGTTAA | 5820 |
| CCCGCGAGGC CCCCTAATCC CCTTAATTCT TCTGATGCTC AGAGGGGTCA GTACTGCTTC | 5880 |
| GCCCGGCTCC AGTCCTCATC AAGTCTATAA TATCACCTGG GAGGTAACCA ATGGAGATCG | 5940 |
| GGAGACGGTA TGGGCAACTT CTGGCAACCA CCCTCTGTGG ACCTGGTGGC CTGACCTTAC | 6000 |
| CCCAGATTTA TGTATGTTAG CCCACCATGG ACCATCTTAT TGGGGGCTAG AATATCAATC | 6060 |
| CCCTTTTTCT TCTCCCCCGG GGCCCCCTTG TTGCTCAGGG GGCAGCAGCC CAGGCTGTTC | 6120 |
| CAGAGACTGC GAAGAACCTT TAACCTCCCT CACCCCTCGG TGCAACACTG CCTGGAACAG | 6180 |
| ACTCAAGCTA GACCAGACAA CTCATAAATC AAATGAGGGA TTTTATGTTT GCCCCGGGCC | 6240 |
| CCACCGCCCC CGAGAATCCA AGTCATGTGG GGGTCCAGAC TCCTTCTACT GTGCCTATTG | 6300 |
| GGGCTGTGAG ACAACCGGTA GAGCTTACTG GAAGCCCTCC TCATCATGGG ATTTCATCAC | 6360 |
| AGTAAACAAC AATCTCACCT CTGACCAGGC TGTCCAGGTA TGCAAAGATA ATAAGTGGTG | 6420 |
| CAACCCCTTA GTTATTCGGT TTACAGACGC CGGGAGACGG GTTACTTCCT GGACCACAGG | 6480 |
| ACATTACTGG GGCTTACGTT TGTATGTCTC CGGACAAGAT CCAGGGCTTA CATTTGGGAT | 6540 |
| CCGACTCAGA TACCAAAATC TAGGACCCCG CGTCCCAATA GGGCCAAACC CCGTTCTGGC | 6600 |
| AGACCAACAG CCACTCTCCA AGCCCAAACC TGTTAAGTCG CCTTCAGTCA CCAAACCACC | 6660 |
| CAGTGGGACT CCTCTCTCCC CTACCCAACT TCCACCGGCG GGAACGGAAA ATAGGCTGCT | 6720 |
| AAACTTAGTA GACGGAGCCT ACCAAGCCCT CAACCTCACC AGTCCTGACA AAACCCAAGA | 6780 |
| GTGCTGGTTG TGTCTAGTAG CGGGACCCCC CTACTACGAA GGGGTTGCCG TCCTGGGTAC | 6840 |
| CTACTCCAAC CATACCTCTG CTCCAGCCAA CTGCTCCGTG GCCTCCCAAC ACAAGTTGAC | 6900 |
| CCTGTCCGAA GTGACCGGAC AGGGACTCTG CATAGGAGCA GTTCCCAAAA CACATCAGGC | 6960 |
| CCTATGTAAT ACCACCCAGA CAAGCAGTCG AGGGTCCTAT TATCTAGTTG CCCCTACAGG | 7020 |
| TACCATGTGG GCTTGTAGTA CCGGGCTTAC TCCATGCATC TCCACCACCA TACTGAACCT | 7080 |
| TACCACTGAT TATTGTGTTC TTGTCGAACT CTGGCCAAGA GTCACCTATC ATTCCCCCAG | 7140 |
| CTATGTTTAC GGCCTGTTTG AGAGATCCAA CCGACACAAA AGAGAACCGG TGTCGTTAAC | 7200 |

```
CCTGGCCCTA TTATTGGGTG GACTAACCAT GGGGGGAATT GCCGCTGGAA TAGGAACAGG    7260

GACTACTGCT CTAATGGCCA CTCAGCAATT CCAGCAGCTC CAAGCCGCAG TACAGGATGA    7320

TCTCAGGGAG GTTGAAAAAT CAATCTCTAA CCTAGAAAAG TCTCTCACTT CCCTGTCTGA    7380

AGTTGTCCTA CAGAATCGAA GGGGCCTAGA CTTGTTATTT CTAAAAGAAG GAGGGCTGTG    7440

TGCTGCTCTA AAAGAAGAAT GTTGCTTCTA TGCGGACCAC ACAGGACTAG TGAGAGACAG    7500

CATGGCCAAA TTGAGAGAGA GGCTTAATCA GAGACAGAAA CTGTTTGAGT CAACTCAAGG    7560

ATGGTTTGAG GGACTGTTTA ACAGATCCCC TTGGTTTACC ACCTTGATAT CTACCATTAT    7620

GGGACCCCTC ATTGTACTCC TAATGATTTT GCTCTTCGGA CCCTGCATTC TTAATCGATT    7680

AGTCCAATTT GTTAAAGACA GGATATCAGT GGTCCAGGCT CTAGTTTTGA CTCAACAATA    7740

TCACCAGCTG AAGCCTATAG AGTACGAGCC ATAGATAAAA TAAAAGATTT TATTTAGTCT    7800

CCAGAAAAAG GGGGGAATGA AAGACCCCAC CTGTAGGTTT GGCAAGCTAG CTTAAGTAAC    7860

GCCATTTTGC AAGGCATGGA AAATACATA ACTGAGAATA GAGAAGTTCA GATCAAGGTC     7920

AGGAACAGAT GGAACAGCTG AATATGGGCC AAACAGGATA TCTGTGGTAA GCAGTTCCTG    7980

CCCCGGCTCA GGGCCAAGAA CAGATGGAAC AGCTGAATAT GGGCCAAACA GGATATCTGT    8040

GGTAAGCAGT TCCTGCCCCG GCTCAGGGCC AAGAACAGAT GGTCCCCAGA TGCGGTCCAG    8100

CCCTCAGCAG TTTCTAGAGA ACCATCAGAT GTTTCCAGGG TGCCCAAGG ACCTGAAATG     8160

ACCCTGTGCC TTATTTGAAC TAACCAATCA GTTCGCTTCT CGCTTCTGTT CGCGCGCTTC    8220

TGCTCCCCGA GCTCAATAAA AGAGCCCACA ACCCCTCACT CGGGGCGCCA GTCCTCCGAT    8280

TGACTGAGTC GCCCGGGTAC CCGTGTATCC AATAAACCCT CTTGCAGTTG CA            8332

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGAGTGGTA ACAGTCTGGC CTTAATTCTC AG                                    32

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGGTCGACCT CGAGAATTAA TTC                                              23

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)
```

-continued (xi) SEQUENCE DESCRIPTION: SEQ ID NO:18:

CTGGGAGACG TCCCAGGGAC TTC                                      23

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGCCAGACTG TTACCACTCC CTGAAGTTTG AC                            32

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CATCGATAAA ATAAAAGATT TTATTTAGTC                               30

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CAAATGAAAG ACCCCCGCTG AC                                       22

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GAAGCTTCTC CCAGAACCCA CCAGTCTTGA AACGCCATC                     39

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GTACCAGCTT TTGGTCTCAT CAAAG                                    25

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTCCTCGAGC TAAAGATATT TTAGAGAAGA ATTAAC                    36

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TTCCTCTGGA CAGCTGTCTA CTTTG                              25

(2) INFORMATION FOR SEQ ID NO:26:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TCGAGGGGCC CAGATCTGCG GCCGCTCGCG AGTCGACAAG CTTGGATCCA T      51

(2) INFORMATION FOR SEQ ID NO:27:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CGATGGATCC AAGCTTGTCG ACTCGCGAGC GGCCGCAGAT CTGGGCCCC        49

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CACCGTCGTC GACTTATGCT                                    20

(2) INFORMATION FOR SEQ ID NO:29:

(i) SEQUENCE CHARACTERISTICS:

```
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GACCGTCGAC TCAATTCTGG GAGAAGCTTC TTGG                                   34

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CACCGTCGTC GACTTATGCT                                                   20

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CAACGCTCGA GAAGCAGAAT CGCAAAAGGC                                        30

(2) INFORMATION FOR SEQ ID NO:32:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

TCGGCTCGAG GCATCAACGG GAAATAACTC GT                                     32

(2) INFORMATION FOR SEQ ID NO:33:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CCGACTCGAG TCAGTAGAGG TCCTGTGCCT C                                      31

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

```
        (ii) MOLECULE TYPE: DNA (genomic)

(xi) SEQUENCE DESCRIPTION: SEQ ID NO:34:

GCGACTCGAG CATGGGGCCC TGGGGC                                        26

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

GCACTGGAAT TCGTCAGGGC G                                             21

(2) INFORMATION FOR SEQ ID NO:36:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

CGCGCCGCTC GAGTCTACAA TGGCCTTGAC CTTTGCTTTA CTGG                     44

(2) INFORMATION FOR SEQ ID NO:37:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

GCGCCCATCG ATTCATTCCT TACTTCTTAA ACTTTCTTGC AAG                      43

(2) INFORMATION FOR SEQ ID NO:38:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

CGCGCCGCTC GAGCATCCAA TGGCCCTGTC CTTTTCTTTA CTTATGG                  47

(2) INFORMATION FOR SEQ ID NO:39:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:
```

```
CCATCGATTC AATCCTTCCT CCTTAATCTT TTTTGCAAG                              39

(2) INFORMATION FOR SEQ ID NO:40:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:40:

CCGGATCCTC TACAATGGCC TTGACCTTTG CTTTACTGG                              39

(2) INFORMATION FOR SEQ ID NO:41:

(i) SEQUENCE CHARACTERISTICS:
         (A) LENGTH: 46 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:41:

CGCGCCGGCG GCCGCTCATT CCTTACTTCT TAAACTTTCT TGCAAG                      46

(2) INFORMATION FOR SEQ ID NO:42:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:42:

CCGGATCCCA TCCAATGGCC CTGTCCTTTT CTTTACTTAT GG                          42

(2) INFORMATION FOR SEQ ID NO:43:

(i) SEQUENCE CHARACTERISTICS:
         (A) LENGTH: 46 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:43:

CGCGCCGGCG GCCGCTCAAT CCTTCCTCCT TAATCTTTTT TGCAAG                      46

(2) INFORMATION FOR SEQ ID NO:44:

(i) SEQUENCE CHARACTERISTICS:
         (A) LENGTH: 9080 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:44:

GGGGGGGGGG GGGGGGGGGG GGGTGAGCAC ATCCAGTGGG TAAAGTTCCT TAAAATGCTC       60

TGCAAAGAAA TTGGGACTTT TCATTAAATC AGAAATTTTA CTTTTTTCCC CTCCTGGGAG      120
```

```
CTAAAGATAT TTTAGAGAAG AATTAACCTT TGCTTCTCC  AGTTGAACAT TTGTAGCAAT      180

AAGTCATGCA AATAGAGCTC TCCACCTGCT TCTTTCTGTG CCTTTTGCGA TTCTGCTTTA      240

GTGCCACCAG AAGATACTAC CTGGGTGCAG TGGAACTGTC ATGGGACTAT ATGCAAAGTG      300

ATCTCGGTGA GCTGCCTGTG GACGCAAGAT TTCCTCCTAG AGTGCCAAAA TCTTTTCCAT      360

TCAACACCTC AGTCGTGTAC AAAAAGACTC TGTTTGTAGA ATTCACGGAT CACCTTTTCA      420

ACATCGCTAA GCCAAGGCCA CCCTGGATGG GTCTGCTAGG TCCTACCATC CAGGCTGAGG      480

TTTATGATAC AGTGGTCATT ACACTTAAGA ACATGGCTTC CCATCCTGTC AGTCTTCATG      540

CTGTTGGTGT ATCCTACTGG AAAGCTTCTG AGGGAGCTGA ATATGATGAT CAGACCAGTC      600

AAAGGGAGAA AGAAGATGAT AAAGTCTTCC CTGGTGGAAG CCATACATAT GTCTGGCAGG      660

TCCTGAAAGA GAATGGTCCA ATGGCCTCTG ACCCACTGTG CCTTACCTAC TCATATCTTT      720

CTCATGTGGA CCTGGTAAAA GACTTGAATT CAGGCCTCAT TGGAGCCCTA CTAGTATGTA      780

GAGAAGGGAG TCTGGCCAAG GAAAAGACAC AGACCTTGCA CAAATTTATA CTACTTTTTG      840

CTGTATTTGA TGAAGGGAAA AGTTGGCACT CAGAAACAAA GAACTCCTTG ATGCAGGATA      900

GGGATGCTGC ATCTGCTCGG GCCTGGCCTA AAATGCACAC AGTCAATGGT TATGTAAACA      960

GGTCTCTGCC AGGTCTGATT GGATGCCACA GGAAATCAGT CTATTGGCAT GTGATTGGAA     1020

TGGGCACCAC TCCTGAAGTG CACTCAATAT TCCTCGAAGG TCACACATTT CTTGTGAGGA     1080

ACCATCGCCA GGCGTCCTTG GAAATCTCGC CAATAACTTT CCTTACTGCT CAAACACTCT     1140

TGATGGACCT TGGACAGTTT CTACTGTTTT GTCATATCTC TTCCCACCAA CATGATGGCA     1200

TGGAAGCTTA TGTCAAAGTA GACAGCTGTC CAGAGGAACC CCAACTACGA ATGAAAAATA     1260

ATGAAGAAGC GGAAGACTAT GATGATGATC TTACTGATTC TGAAATGGAT GTGGTCAGGT     1320

TTGATGATGA CAACTCTCCT TCCTTTATCC AAATTCGCTC AGTTGCCAAG AAGCATCCTA     1380

AAACTTGGGT ACATTACATT GCTGCTGAAG AGGAGGACTG GGACTATGCT CCCTTAGTCC     1440

TCGCCCCCGA TGACAGAAGT TATAAAAGTC AATATTTGAA CAATGGCCCT CAGCGGATTG     1500

GTAGGAAGTA CAAAAAAGTC CGATTTATGG CATACACAGA TGAAACCTTT AAGACTCGTG     1560

AAGCTATTCA GCATGAATCA GGAATCTTGG GACCTTTACT TTATGGGGAA GTTGGAGACA     1620

CACTGTTGAT TATATTTAAG AATCAAGCAA GCAGACCATA TAACATCTAC CCTCACGGAA     1680

TCACTGATGT CCGTCCTTTG TATTCAAGGA GATTACCAAA AGGTGTAAAA CATTTGAAGG     1740

ATTTTCCAAT TCTGCCAGGA GAAATATTCA AATATAAATG GACAGTGACT GTAGAAGATG     1800

GGCCAACTAA ATCAGATCCT CGGTGCCTGA CCCGCTATTA CTCTAGTTTC GTTAATATGG     1860

AGAGAGATCT AGCTTCAGGA CTCATTGGCC CTCTCCTCAT CTGCTACAAA GAATCTGTAG     1920

ATCAAAGAGG AAACCAGATA ATGTCAGACA AGAGGAATGT CATCCTGTTT TCTGTATTTG     1980

ATGAGAACCG AAGCTGGTAC CTCACAGAGA ATATACAACG CTTTCTCCCC AATCCAGCTG     2040

GAGTGCAGCT TGAGGATCCA GAGTTCCAAG CCTCCAACAT CATGCACAGC ATCAATGGCT     2100

ATGTTTTTGA TAGTTTGCAG TTGTCAGTTT GTTTGCATGA GGTGGCATAC TGGTACATTC     2160

TAAGCATTGG AGCACAGACT GACTTCCTTT CTGTCTTCTT CTCTGGATAT ACCTTCAAAC     2220

ACAAAATGGT CTATGAAGAC ACACTCACCC TATTCCCATT CTCAGGAGAA ACTGTCTTCA     2280

TGTCGATGGA AAACCCAGGT CTATGGATTC TGGGGTGCCA CAACTCAGAC TTTCGGAACA     2340

GAGGCATGAC CGCCTTACTG AAGGTTTCTA GTTGTGACAA GAACACTGGT GATTATTACG     2400

AGGACAGTTA TGAAGATATT TCAGCATACT TGCTGAGTAA AAACAATGCC ATTGAACCAA     2460
```

```
GAAGCTTCTC CCAGAATTCA AGACACCCTA GCACTAGGCA AAAGCAATTT AATGCCACCA    2520

CAATTCCAGA AAATGACATA GAGAAGACTG ACCCTTGGTT TGCACACAGA ACACCTATGC    2580

CTAAAATACA AAATGTCTCC TCTAGTGATT TGTTGATGCT CTTGCGACAG AGTCCTACTC    2640

CACATGGGCT ATCCTTATCT GATCTCCAAG AAGCCAAATA TGAGACTTTT TCTGATGATC    2700

CATCACCTGG AGCAATAGAC AGTAATAACA GCCTGTCTGA AATGACACAC TTCAGGCCAC    2760

AGCTCCATCA CAGTGGGGAC ATGGTATTTA CCCCTGAGTC AGGCCTCCAA TTAAGATTAA    2820

ATGAGAAACT GGGACAACT GCAGCAACAG AGTTGAAGAA ACTTGATTTC AAAGTTTCTA    2880

GTACATCAAA TAATCTGATT TCAACAATTC CATCAGACAA TTTGGCAGCA GGTACTGATA    2940

ATACAAGTTC CTTAGGACCC CCAAGTATGC CAGTTCATTA TGATAGTCAA TTAGATACCA    3000

CTCTATTTGG CAAAAAGTCA TCTCCCCTTA CTGAGTCTGG TGGACCTCTG AGCTTGAGTG    3060

AAGAAAATAA TGATTCAAAG TTGTTAGAAT CAGGTTTAAT GAATAGCCAA GAAAGTTCAT    3120

GGGGAAAAAA TGTATCGTCA ACAGAGAGTG GTAGGTTATT TAAAGGGAAA AGAGCTCATG    3180

GACCTGCTTT GTTGACTAAA GATAATGCCT TATTCAAAGT TAGCATCTCT TTGTTAAAGA    3240

CAAACAAAAC TTCCAATAAT TCAGCAACTA ATAGAAAGAC TCACATTGAT GGCCCATCAT    3300

TATTAATTGA GAATAGTCCA TCAGTCTGGC AAAATATATT AGAAAGTGAC ACTGAGTTTA    3360

AAAAAGTGAC ACCTTTGATT CATGACAGAA TGCTTATGGA CAAAAATGCT ACAGCTTTGA    3420

GGCTAAATCA TATGTCAAAT AAAACTACTT CATCAAAAAA CATGGAAATG GTCCAACAGA    3480

AAAAAGAGGG CCCCATTCCA CCAGATGCAC AAAATCCAGA TATGTCGTTC TTTAAGATGC    3540

TATTCTTGCC AGAATCAGCA AGGTGGATAC AAAGGACTCA TGGAAAGAAC TCTCTGAACT    3600

CTGGGCAAGG CCCCAGTCCA AAGCAATTAG TATCCTTAGG ACCAGAAAAA TCTGTGGAAG    3660

GTCAGAATTT CTTGTCTGAG AAAAACAAAG TGGTAGTAGG AAAGGGTGAA TTTACAAAGG    3720

ACGTAGGACT CAAAGAGATG GTTTTTCCAA GCAGCAGAAA CCTATTTCTT ACTAACTTGG    3780

ATAATTTACA TGAAAATAAT ACACACAATC AAGAAAAAAA AATTCAGGAA GAAATAGAAA    3840

AGAAGGAAAC ATTAATCCAA GAGAATGTAG TTTTGCCTCA GATACATACA GTGACTGGCA    3900

CTAAGAATTT CATGAAGAAC CTTTTCTTAC TGAGCACTAG GCAAAATGTA GAAGGTTCAT    3960

ATGACGGGGC ATATGCTCCA GTACTTCAAG ATTTTAGGTC ATTAAATGAT TCAACAAATA    4020

GAACAAAGAA ACACACAGCT CATTTCTCAA AAAAAGGGGA GGAAGAAAAC TTGGAAGGCT    4080

TGGGAAATCA AACCAAGCAA ATTGTAGAGA AATATGCATG CACCACAAGG ATATCTCCTA    4140

ATACAAGCCA GCAGAATTTT GTCACGCAAC GTAGTAAGAG AGCTTTGAAA CAATTCAGAC    4200

TCCCACTAGA AGAAACAGAA CTTGAAAAAA GGATAATTGT GGATGACACC TCAACCCAGT    4260

GGTCCAAAAA CATGAAACAT TTGACCCCGA GCACCCTCAC ACAGATAGAC TACAATGAGA    4320

AGGAGAAAGG GGCCATTACT CAGTCTCCCT TATCAGATTG CCTTACGAGG AGTCATAGCA    4380

TCCCTCAAGC AAATAGATCT CCATTACCCA TTGCAAAGGT ATCATCATTT CCATCTATTA    4440

GACCTATATA TCTGACCAGG GTCCTATTCC AAGACAACTC TTCTCATCTT CCAGCAGCAT    4500

CTTATAGAAA GAAAGATTCT GGGGTCCAAG AAAGCAGTCA TTTCTTACAA GGAGCCAAAA    4560

AAAATAACCT TTCTTTAGCC ATTCTAACCT TGGAGATGAC TGGTGATCAA AGAGAGGTTG    4620

GCTCCCTGGG GACAAGTGCC ACAAATTCAG TCACATACAA GAAAGTTGAG AACACTGTTC    4680

TCCCGAAACC AGACTTGCCC AAAACATCTG GCAAAGTTGA ATTGCTTCCA AAAGTTCACA    4740

TTTATCAGAA GGACCTATTC CCTACGGAAA CTAGCAATGG GTCTCCTGGC CATCTGGATC    4800

TCGTGGAAGG GAGCCTTCTT CAGGGAACAG AGGGAGCGAT TAAGTGGAAT GAAGCAAACA    4860
```

```
GACCTGGAAA AGTTCCCTTT CTGAGAGTAG CAACAGAAAG CTCTGCAAAG ACTCCCTCCA      4920

AGCTATTGGA TCCTCTTGCT TGGGATAACC ACTATGGTAC TCAGATACCA AAAGAAGAGT      4980

GGAAATCCCA AGAGAAGTCA CCAGAAAAAA CAGCTTTTAA GAAAAAGGAT ACCATTTTGT      5040

CCCTGAACGC TTGTGAAAGC AATCATGCAA TAGCAGCAAT AAATGAGGGA CAAAATAAGC      5100

CCGAAATAGA AGTCACCTGG GCAAAGCAAG GTAGGACTGA AAGGCTGTGC TCTCAAAACC      5160

CACCAGTCTT GAAACGCCAT CAACGGGAAA TAACTCGTAC TACTCTTCAG TCAGATCAAG      5220

AGGAAATTGA CTATGATGAT ACCATATCAG TTGAAATGAA GAAGGAAGAT TTTGACATTT      5280

ATGATGAGGA TGAAAATCAG AGCCCCCGCA GCTTTCAAAA GAAAACACGA CACTATTTTA      5340

TTGCTGCAGT GGAGAGGCTC TGGGATTATG GGATGAGTAG CTCCCCACAT GTTCTAAGAA      5400

ACAGGGCTCA GAGTGGCAGT GTCCCTCAGT TCAAGAAAGT TGTTTTCCAG GAATTTACTG      5460

ATGGCTCCTT TACTCAGCCC TTATACCGTG GAGAACTAAA TGAACATTTG GGACTCCTGG      5520

GGCCATATAT AAGAGCAGAA GTTGAAGATA ATATCATGGT AACTTTCAGA AATCAGGCCT      5580

CTCGTCCCTA TTCCTTCTAT TCTAGCCTTA TTTCTTATGA GGAAGATCAG AGGCAAGGAG      5640

CAGAACCTAG AAAAAACTTT GTCAAGCCTA ATGAAACCAA AACTTACTTT TGGAAAGTGC      5700

AACATCATAT GGCACCCACT AAAGATGAGT TTGACTGCAA AGCCTGGGCT TATTTCTCTG      5760

ATGTTGACCT GGAAAAAGAT GTGCACTCAG GCCTGATTGG ACCCCTTCTG GTCTGCCACA      5820

CTAACACACT GAACCCTGCT CATGGGAGAC AAGTGACAGT ACAGGAATTT GCTCTGTTTT      5880

TCACCATCTT TGATGAGACC AAAAGCTGGT ACTTCACTGA AAATATGGAA AGAAACTGCA      5940

GGGCTCCCTG CAATATCCAG ATGGAAGATC CCACTTTTAA AGAGAATTAT CGCTTCCATG      6000

CAATCAATGG CTACATAATG GATACACTAC CTGGCTTAGT AATGGCTCAG GATCAAAGGA      6060

TTCGATGGTA TCTGCTCAGC ATGGGCAGCA ATGAAAACAT CCATTCTATT CATTTCAGTG      6120

GACATGTGTT CACTGTACGA AAAAAAGAGG AGTATAAAAT GGCACTGTAC AATCTCTATC      6180

CAGGTGTTTT TGAGACAGTG GAAATGTTAC CATCCAAAGC TGGAATTTGG CGGGTGGAAT      6240

GCCTTATTGG CGAGCATCTA CATGCTGGGA TGAGCACACT TTTTCTGGTG TACAGCAATA      6300

AGTGTCAGAC TCCCCTGGGA ATGGCTTCTG GACACATTAG AGATTTTCAG ATTACAGCTT      6360

CAGGACAATA TGGACAGTGG GCCCCAAAGC TGGCCAGACT TCATTATTCC GGATCAATCA      6420

ATGCCTGGAG CACCAAGGAG CCCTTTTCTT GGATCAAGGT GGATCTGTTG GCACCAATGA      6480

TTATTCACGG CATCAAGACC CAGGGTGCCC GTCAGAAGTT CTCCAGCCTC TACATCTCTC      6540

AGTTTATCAT CATGTATAGT CTTGATGGGA AGAAGTGGCA GACTTATCGA GGAAATTCCA      6600

CTGGAACCTT AATGGTCTTC TTTGGCAATG TGGATTCATC TGGGATAAAA CACAATATTT      6660

TTAACCCTCC AATTATTGCT CGATACATCC GTTTGCACCC AACTCATTAT AGCATTCGCA      6720

GCACTCTTCG CATGGAGTTG ATGGGCTGTG ATTTAAATAG TTGCAGCATG CCATTGGGAA      6780

TGGAGAGTAA AGCAATATCA GATGCACAGA TTACTGCTTC ATCCTACTTT ACCAATATGT      6840

TTGCCACCTG GTCTCCTTCA AAAGCTCGAC TTCACCTCCA AGGGAGGAGT AATGCCTGGA      6900

GACCTCAGGT GAATAATCCA AAAGAGTGGC TGCAAGTGGA CTTCCAGAAG ACAATGAAAG      6960

TCACAGGAGT AACTACTCAG GGAGTAAAAT CTCTGCTTAC CAGCATGTAT GTGAAGGAGT      7020

TCCTCATCTC CAGCAGTCAA GATGGCCATC AGTGGACTCT CTTTTTTCAG AATGGCAAAG      7080

TAAAGGTTTT TCAGGGAAAT CAAGACTCCT TCACACCTGT GGTGAACTCT CTAGACCCAC      7140

CGTTACTGAC TCGCTACCTT CGAATTCACC CCCAGAGTTG GGTGCACCAG ATTGCCCTGA      7200
```

```
GGATGGAGGT TCTGGGCTGC GAGGCACAGG ACCTCTACTG AGGGTGGCCA CTGCAGCACC    7260

TGCCACTGCC GTCACCTCTC CCTCCTCAGC TCCAGGGCAG TGTCCCTCCC TGGCTTGCCT    7320

TCTACCTTTG TGCTAAATCC TAGCAGACAC TGCCTTGAAG CCTCCTGAAT TAACTATCAT    7380

CAGTCCTGCA TTTCTTTGGT GGGGGGCCAG GAGGGTGCAT CCAATTTAAC TTAACTCTTA    7440

CCTATTTTCT GCAGCTGCTC CCAGATTACT CCTTCCTTCC AATATAACTA GGCAAAAAGA    7500

AGTGAGGAGA AACCTGCATG AAAGCATTCT TCCCTGAAAA GTTAGGCCTC TCAGAGTCAC    7560

CACTTCCTCT GTTGTAGAAA AACTATGTGA TGAAACTTTG AAAAGATAT TTATGATGTT     7620

AACATTTCAG GTTAAGCCTC ATACGTTTAA AATAAAACTC TCAGTTGTTT ATTATCCTGA    7680

TCAAGCATGG AACAAAGCAT GTTTCAGGAT CAGATCAATA CAATCTTGGA GTCAAAAGGC    7740

AAATCATTTG GACAATCTGC AAAATGGAGA GAATACAATA ACTACTACAG TAAAGTCTGT    7800

TTCTGCTTCC TTACACATAG ATATAATTAT GTTATTTAGT CATTATGAGG GGCACATTCT    7860

TATCTCCAAA ACTAGCATTC TTAAACTGAG AATTATAGAT GGGGTTCAAG AATCCCTAAG    7920

TCCCCTGAAA TTATATAAGG CATTCTGTAT AAATGCAAAT GTGCATTTTT CTGACGAGTG    7980

TCCATAGATA TAAAGCCATT TGGTCTTAAT TCTGACCAAT AAAAAAATAA GTCAGGAGGA    8040

TGCAATTGTT GAAAGCTTTG AAATAAAATA ACAATGTCTT CTTGAAATTT GTGATGGCCA    8100

AGAAAGAAAA TGATGATGAC ATTAGGCTTC TAAAGGACAT ACATTTAATA TTTCTGTGGA    8160

AATATGAGGA AAATCCATGG TTATCTGAGA TAGGAGATAC AAACTTTGTA ATTCTAATAA    8220

TGCACTCAGT TTACTCTCTC CCTCTACTAA TTTCCTGCTG AAAATAACAC AACAAAAATG    8280

TAACAGGGGA AATTATATAC CGTGACTGAA AACTAGAGTC CTACTTACAT AGTTGAAATA    8340

TCAAGGAGGT CAGAAGAAAA TTGGACTGGT GAAAACAGAA AAAACACTCC AGTCTGCCAT    8400

ATCACCACAC AATAGGATCC CCCTTCTTGC CCTCCACCCC CATAAGATTG TGAAGGGTTT    8460

ACTGCTCCTT CCATCTGCCT GACCCCTTCA CTATGACTAC ACAGAATCTC CTGATAGTAA    8520

AGGGGGCTGG AGGCAAGGAT AAGTTATAGA GCAGTTGGAG GAAGCATCCA AAGATTGCAA    8580

CCCAGGGCAA ATGGAAAACA GGAGATCCTA ATATGAAAGA AAAATGGATC CCAATCTGAG    8640

AAAAGGCAAA AGAATGGCTA CTTTTTTCTA TGCTGGAGTA TTTTCTAATA ATCCTGCTTG    8700

ACCCTTATCT GACCTCTTTG GAAACTATAA CATAGCTGTC ACAGTATAGT CACAATCCAC    8760

AAATGATGCA GGTGCAAATG GTTTATAGCC CTGTGAAGTT CTTAAAGTTT AGAGGCTAAC    8820

TTACAGAAAT GAATAAGTTG TTTTGTTTTA TAGCCCGGTA GAGGAGTTAA CCCCAAAGGT    8880

GATATGGTTT TATTTCCTGT TATGTTTAAC TTAATAATCT TATTTTGGCA TTCTTTTCCC    8940

ATTGACTATA TACATCTCTA TTTCTCAAAT GTTCATGGAA CTAGCTCTTT TATTTTCCTG    9000

CTGGTTTCTT CAGTAATGAG TTAAATAAAA CATTGACACA TACAAAAAAA AAAAAAAAAA    9060

AAAAAAAAAA AAAAAAAAA                                                 9080
```

(2) INFORMATION FOR SEQ ID NO:45:

(i) SEQUENCE CHARACTERISTICS:
        (A) LENGTH: 2351 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Met Gln Ile Glu Leu Ser Thr Cys Phe Phe Leu Cys Leu Leu Arg Phe
1               5                   10                  15
```

-continued

```
Cys Phe Ser Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
     50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
        340                 345                 350

Gln Leu Arg Met Lys Asn Asn Glu Glu Ala Glu Asp Tyr Asp Asp Asp
    355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430
```

```
Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
```

-continued

```
                850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Thr Ser Asn Asn Leu Ile Ser Thr Ile Pro Ser Asp Asn
                900                 905                 910
Leu Ala Ala Gly Thr Asp Asn Thr Ser Ser Leu Gly Pro Pro Ser Met
                915                 920                 925
Pro Val His Tyr Asp Ser Gln Leu Asp Thr Thr Leu Phe Gly Lys Lys
                930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Ser Thr Glu Ser Gly Arg Leu Phe
                980                 985                 990
Lys Gly Lys Arg Ala His Gly Pro Ala Leu Leu Thr Lys Asp Asn Ala
                995                 1000                1005
Leu Phe Lys Val Ser Ile Ser Leu Leu Lys Thr Asn Lys Thr Ser Asn
                1010                1015                1020
Asn Ser Ala Thr Asn Arg Lys Thr His Ile Asp Gly Pro Ser Leu Leu
1025                1030                1035                1040
Ile Glu Asn Ser Pro Ser Val Trp Gln Asn Ile Leu Glu Ser Asp Thr
                1045                1050                1055
Glu Phe Lys Lys Val Thr Pro Leu Ile His Asp Arg Met Leu Met Asp
                1060                1065                1070
Lys Asn Ala Thr Ala Leu Arg Leu Asn His Met Ser Asn Lys Thr Thr
                1075                1080                1085
Ser Ser Lys Asn Met Glu Met Val Gln Gln Lys Lys Glu Gly Pro Ile
                1090                1095                1100
Pro Pro Asp Ala Gln Asn Pro Asp Met Ser Phe Phe Lys Met Leu Phe
1105                1110                1115                1120
Leu Pro Glu Ser Ala Arg Trp Ile Gln Arg Thr His Gly Lys Asn Ser
                1125                1130                1135
Leu Asn Ser Gly Gln Gly Pro Ser Pro Lys Gln Leu Val Ser Leu Gly
                1140                1145                1150
Pro Glu Lys Ser Val Glu Gly Gln Asn Phe Leu Ser Glu Lys Asn Lys
                1155                1160                1165
Val Val Val Gly Lys Gly Glu Phe Thr Lys Asp Val Gly Leu Lys Glu
                1170                1175                1180
Met Val Phe Pro Ser Ser Arg Asn Leu Phe Leu Thr Asn Leu Asp Asn
1185                1190                1195                1200
Leu His Glu Asn Asn Thr His Asn Gln Glu Lys Lys Ile Gln Glu Glu
                1205                1210                1215
Ile Glu Lys Lys Glu Thr Leu Ile Gln Glu Asn Val Val Leu Pro Gln
                1220                1225                1230
Ile His Thr Val Thr Gly Thr Lys Asn Phe Met Lys Asn Leu Phe Leu
                1235                1240                1245
Leu Ser Thr Arg Gln Asn Val Glu Gly Ser Tyr Asp Gly Ala Tyr Ala
                1250                1255                1260
Pro Val Leu Gln Asp Phe Arg Ser Leu Asn Asp Ser Thr Asn Arg Thr
1265                1270                1275                1280
```

-continued

```
Lys Lys His Thr Ala His Phe Ser Lys Lys Gly Glu Glu Asn Leu
            1285                1290                1295

Glu Gly Leu Gly Asn Gln Thr Lys Gln Ile Val Glu Lys Tyr Ala Cys
        1300                1305                1310

Thr Thr Arg Ile Ser Pro Asn Thr Ser Gln Gln Asn Phe Val Thr Gln
        1315                1320                1325

Arg Ser Lys Arg Ala Leu Lys Gln Phe Arg Leu Pro Leu Glu Glu Thr
        1330                1335                1340

Glu Leu Glu Lys Arg Ile Ile Val Asp Asp Thr Ser Thr Gln Trp Ser
1345                1350                1355                1360

Lys Asn Met Lys His Leu Thr Pro Ser Thr Leu Thr Gln Ile Asp Tyr
            1365                1370                1375

Asn Glu Lys Glu Lys Gly Ala Ile Thr Gln Ser Pro Leu Ser Asp Cys
            1380                1385                1390

Leu Thr Arg Ser His Ser Ile Pro Gln Ala Asn Arg Ser Pro Leu Pro
            1395                1400                1405

Ile Ala Lys Val Ser Ser Phe Pro Ser Ile Arg Pro Ile Tyr Leu Thr
            1410                1415                1420

Arg Val Leu Phe Gln Asp Asn Ser Ser His Leu Pro Ala Ala Ser Tyr
1425                1430                1435                1440

Arg Lys Lys Asp Ser Gly Val Gln Glu Ser Ser His Phe Leu Gln Gly
            1445                1450                1455

Ala Lys Lys Asn Asn Leu Ser Leu Ala Ile Leu Thr Leu Glu Met Thr
            1460                1465                1470

Gly Asp Gln Arg Glu Val Gly Ser Leu Gly Thr Ser Ala Thr Asn Ser
            1475                1480                1485

Val Thr Tyr Lys Lys Val Glu Asn Thr Val Leu Pro Lys Pro Asp Leu
            1490                1495                1500

Pro Lys Thr Ser Gly Lys Val Glu Leu Leu Pro Lys Val His Ile Tyr
1505                1510                1515                1520

Gln Lys Asp Leu Phe Pro Thr Glu Thr Ser Asn Gly Ser Pro Gly His
            1525                1530                1535

Leu Asp Leu Val Glu Gly Ser Leu Leu Gln Gly Thr Glu Gly Ala Ile
            1540                1545                1550

Lys Trp Asn Glu Ala Asn Arg Pro Gly Lys Val Pro Phe Leu Arg Val
            1555                1560                1565

Ala Thr Glu Ser Ser Ala Lys Thr Pro Ser Lys Leu Leu Asp Pro Leu
1570                1575                1580

Ala Trp Asp Asn His Tyr Gly Thr Gln Ile Pro Lys Glu Glu Trp Lys
1585                1590                1595                1600

Ser Gln Glu Lys Ser Pro Glu Lys Thr Ala Phe Lys Lys Lys Asp Thr
            1605                1610                1615

Ile Leu Ser Leu Asn Ala Cys Glu Ser Asn His Ala Ile Ala Ala Ile
            1620                1625                1630

Asn Glu Gly Gln Asn Lys Pro Glu Ile Glu Val Thr Trp Ala Lys Gln
            1635                1640                1645

Gly Arg Thr Glu Arg Leu Cys Ser Gln Asn Pro Pro Val Leu Lys Arg
            1650                1655                1660

His Gln Arg Glu Ile Thr Arg Thr Thr Leu Gln Ser Asp Gln Glu Glu
1665                1670                1675                1680

Ile Asp Tyr Asp Asp Thr Ile Ser Val Glu Met Lys Lys Glu Asp Phe
            1685                1690                1695
```

-continued

Asp Ile Tyr Asp Glu Asp Glu Asn Gln Ser Pro Arg Ser Phe Gln Lys
                1700                1705                1710

Lys Thr Arg His Tyr Phe Ile Ala Ala Val Glu Arg Leu Trp Asp Tyr
            1715                1720                1725

Gly Met Ser Ser Pro His Val Leu Arg Asn Arg Ala Gln Ser Gly
        1730                1735                1740

Ser Val Pro Gln Phe Lys Lys Val Val Phe Gln Glu Phe Thr Asp Gly
1745                1750                1755                1760

Ser Phe Thr Gln Pro Leu Tyr Arg Gly Glu Leu Asn Glu His Leu Gly
            1765                1770                1775

Leu Leu Gly Pro Tyr Ile Arg Ala Glu Val Glu Asp Asn Ile Met Val
            1780                1785                1790

Thr Phe Arg Asn Gln Ala Ser Arg Pro Tyr Ser Phe Tyr Ser Ser Leu
            1795                1800                1805

Ile Ser Tyr Glu Glu Asp Gln Arg Gln Gly Ala Glu Pro Arg Lys Asn
        1810                1815                1820

Phe Val Lys Pro Asn Glu Thr Lys Thr Tyr Phe Trp Lys Val Gln His
1825                1830                1835                1840

His Met Ala Pro Thr Lys Asp Glu Phe Asp Cys Lys Ala Trp Ala Tyr
            1845                1850                1855

Phe Ser Asp Val Asp Leu Glu Lys Asp Val His Ser Gly Leu Ile Gly
            1860                1865                1870

Pro Leu Leu Val Cys His Thr Asn Thr Leu Asn Pro Ala His Gly Arg
            1875                1880                1885

Gln Val Thr Val Gln Glu Phe Ala Leu Phe Phe Thr Ile Phe Asp Glu
            1890                1895                1900

Thr Lys Ser Trp Tyr Phe Thr Glu Asn Met Glu Arg Asn Cys Arg Ala
1905                1910                1915                1920

Pro Cys Asn Ile Gln Met Glu Asp Pro Thr Phe Lys Glu Asn Tyr Arg
            1925                1930                1935

Phe His Ala Ile Asn Gly Tyr Ile Met Asp Thr Leu Pro Gly Leu Val
            1940                1945                1950

Met Ala Gln Asp Gln Arg Ile Arg Trp Tyr Leu Leu Ser Met Gly Ser
            1955                1960                1965

Asn Glu Asn Ile His Ser Ile His Phe Ser Gly His Val Phe Thr Val
            1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
                2005                2010                2015

Val Glu Cys Leu Ile Gly Glu His Leu His Ala Gly Met Ser Thr Leu
            2020                2025                2030

Phe Leu Val Tyr Ser Asn Lys Cys Gln Thr Pro Leu Gly Met Ala Ser
            2035                2040                2045

Gly His Ile Arg Asp Phe Gln Ile Thr Ala Ser Gly Gln Tyr Gly Gln
            2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
                2085                2090                2095

Pro Met Ile Ile His Gly Ile Lys Thr Gln Gly Ala Arg Gln Lys Phe
            2100                2105                2110

Ser Ser Leu Tyr Ile Ser Gln Phe Ile Ile Met Tyr Ser Leu Asp Gly

-continued

```
              2115                2120                2125
Lys Lys Trp Gln Thr Tyr Arg Gly Asn Ser Thr Gly Thr Leu Met Val
    2130                2135                2140
Phe Phe Gly Asn Val Asp Ser Ser Gly Ile Lys His Asn Ile Phe Asn
2145                2150                2155                2160
Pro Pro Ile Ile Ala Arg Tyr Ile Arg Leu His Pro Thr His Tyr Ser
                2165                2170                2175
Ile Arg Ser Thr Leu Arg Met Glu Leu Met Gly Cys Asp Leu Asn Ser
            2180                2185                2190
Cys Ser Met Pro Leu Gly Met Glu Ser Lys Ala Ile Ser Asp Ala Gln
        2195                2200                2205
Ile Thr Ala Ser Ser Tyr Phe Thr Asn Met Phe Ala Thr Trp Ser Pro
    2210                2215                2220
Ser Lys Ala Arg Leu His Leu Gln Gly Arg Ser Asn Ala Trp Arg Pro
2225                2230                2235                2240
Gln Val Asn Asn Pro Lys Glu Trp Leu Gln Val Asp Phe Gln Lys Thr
                2245                2250                2255
Met Lys Val Thr Gly Val Thr Thr Gln Gly Val Lys Ser Leu Leu Thr
            2260                2265                2270
Ser Met Tyr Val Lys Glu Phe Leu Ile Ser Ser Ser Gln Asp Gly His
        2275                2280                2285
Gln Trp Thr Leu Phe Phe Gln Asn Gly Lys Val Lys Val Phe Gln Gly
    2290                2295                2300
Asn Gln Asp Ser Phe Thr Pro Val Val Asn Ser Leu Asp Pro Pro Leu
305                 2310                2315                2320
Leu Thr Arg Tyr Leu Arg Ile His Pro Gln Ser Trp Val His Gln Ile
                2325                2330                2335
Ala Leu Arg Met Glu Val Leu Gly Cys Glu Ala Gln Asp Leu Tyr
            2340                2345                2350
```

(2) INFORMATION FOR SEQ ID NO:46:

(i) SEQUENCE CHARACTERISTICS:
        (A) LENGTH: 4832 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CTCGAGCTAA AGATATTTTA GAGAAGAATT AACCTTTTGC TTCTCCAGTT GAACATTTGT      60

AGCAATAAGT CATGCAAATA GAGCTCTCCA CCTGCTTCTT TCTGTGCCTT TTGCGATTCT     120

GCTTTAGTGC CACCAGAAGA TACTACCTGG GTGCAGTGGA ACTGTCATGG GACTATATGC     180

AAAGTGATCT CGGTGAGCTG CCTGTGGACG CAAGATTTCC TCCTAGAGTG CCAAAATCTT     240

TTCCATTCAA CACCTCAGTC GTGTACAAAA AGACTCTGTT TGTAGAATTC ACGGATCACC     300

TTTTCAACAT CGCTAAGCCA AGGCCACCCT GGATGGGTCT GCTAGGTCCT ACCATCCAGG     360

CTGAGGTTTA TGATACAGTG GTCATTACAC TTAAGAACAT GGCTTCCCAT CCTGTCAGTC     420

TTCATGCTGT TGGTGTATCC TACTGGAAAG CTTCTGAGGG AGCTGAATAT GATGATCAGA     480

CCAGTCAAAG GGAGAAAGAA GATGATAAAG TCTTCCCTGG TGGAAGCCAT ACATATGTCT     540

GGCAGGTCCT GAAAGAGAAT GGTCCAATGG CCTCTGACCC ACTGTGCCTT ACCTACTCAT     600

ATCTTTCTCA TGTGGACCTG GTAAAAGACT TGAATTCAGG CCTCATTGGA GCCCTACTAG     660
```

-continued

| | | | | |
|---|---|---|---|---|
| TATGTAGAGA | AGGGAGTCTG | GCCAAGGAAA | AGACACAGAC | CTTGCACAAA | TTTATACTAC | 720 |
| TTTTTGCTGT | ATTTGATGAA | GGGAAAAGTT | GGCACTCAGA | AACAAAGAAC | TCCTTGATGC | 780 |
| AGGATAGGGA | TGCTGCATCT | GCTCGGGCCT | GGCCTAAAAT | GCACACAGTC | AATGGTTATG | 840 |
| TAAACAGGTC | TCTGCCAGGT | CTGATTGGAT | GCCACAGGAA | ATCAGTCTAT | TGGCATGTGA | 900 |
| TTGGAATGGG | CACCACTCCT | GAAGTGCACT | CAATATTCCT | CGAAGGTCAC | ACATTTCTTG | 960 |
| TGAGGAACCA | TCGCCAGGCG | TCCTTGGAAA | TCTCGCCAAT | AACTTTCCTT | ACTGCTCAAA | 1020 |
| CACTCTTGAT | GGACCTTGGA | CAGTTTCTAC | TGTTTTGTCA | TATCTCTTCC | CACCAACATG | 1080 |
| ATGGCATGGA | AGCTTATGTC | AAAGTAGACA | GCTGTCCAGA | GGAACCCCAA | CTACGAATGA | 1140 |
| AAAATAATGA | AGAAGCGGAA | GACTATGATG | ATGATCTTAC | TGATTCTGAA | ATGGATGTGG | 1200 |
| TCAGGTTTGA | TGATGACAAC | TCTCCTTCCT | TTATCCAAAT | TCGCTCAGTT | GCCAAGAAGC | 1260 |
| ATCCTAAAAC | TTGGGTACAT | TACATTGCTG | CTGAAGAGGA | GGACTGGGAC | TATGCTCCCT | 1320 |
| TAGTCCTCGC | CCCCGATGAC | AGAAGTTATA | AAGTCAATA | TTTGAACAAT | GGCCCTCAGC | 1380 |
| GGATTGGTAG | GAAGTACAAA | AAAGTCCGAT | TTATGGCATA | CACAGATGAA | ACCTTTAAGA | 1440 |
| CTCGTGAAGC | TATTCAGCAT | GAATCAGGAA | TCTTGGGACC | TTTACTTTAT | GGGGAAGTTG | 1500 |
| GAGACACACT | GTTGATTATA | TTTAAGAATC | AAGCAAGCAG | ACCATATAAC | ATCTACCCTC | 1560 |
| ACGGAATCAC | TGATGTCCGT | CCTTTGTATT | CAAGGAGATT | ACCAAAAGGT | GTAAACATT | 1620 |
| TGAAGGATTT | TCCAATTCTG | CCAGGAGAAA | TATTCAAATA | TAAATGGACA | GTGACTGTAG | 1680 |
| AAGATGGGCC | AACTAAATCA | GATCCTCGGT | GCCTGACCCG | CTATTACTCT | AGTTTCGTTA | 1740 |
| ATATGGAGAG | AGATCTAGCT | TCAGGACTCA | TTGGCCCTCT | CCTCATCTGC | TACAAAGAAT | 1800 |
| CTGTAGATCA | AAGAGGAAAC | CAGATAATGT | CAGACAAGAG | GAATGTCATC | CTGTTTTCTG | 1860 |
| TATTTGATGA | GAACCGAAGC | TGGTACCTCA | CAGAGAATAT | ACAACGCTTT | CTCCCCAATC | 1920 |
| CAGCTGGAGT | GCAGCTTGAG | GATCCAGAGT | TCCAAGCCTC | CAACATCATG | CACAGCATCA | 1980 |
| ATGGCTATGT | TTTTGATAGT | TTGCAGTTGT | CAGTTTGTTT | GCATGAGGTG | GCATACTGGT | 2040 |
| ACATTCTAAG | CATTGGAGCA | CAGACTGACT | TCCTTTCTGT | CTTCTTCTCT | GGATATACCT | 2100 |
| TCAAACACAA | AATGGTCTAT | GAAGACACAC | TCACCCTATT | CCCATTCTCA | GGAGAAACTG | 2160 |
| TCTTCATGTC | GATGGAAAAC | CCAGGTCTAT | GGATTCTGGG | GTGCCACAAC | TCAGACTTTC | 2220 |
| GGAACAGAGG | CATGACCGCC | TTACTGAAGG | TTTCTAGTTG | TGACAAGAAC | ACTGGTGATT | 2280 |
| ATTACGAGGA | CAGTTATGAA | GATATTTCAG | CATACTTGCT | GAGTAAAAAC | AATGCCATTG | 2340 |
| AACCAAGAAG | CTTCTCCCAG | AACCCACCAG | TCTTGAAACG | CCATCAACGG | GAAATAACTC | 2400 |
| GTACTACTCT | TCAGTCAGAT | CAAGAGGAAA | TTGACTATGA | TGATACCATA | TCAGTTGAAA | 2460 |
| TGAAGAAGGA | AGATTTTGAC | ATTTATGATG | AGGATGAAAA | TCAGAGCCCC | CGCAGCTTTC | 2520 |
| AAAAGAAAAC | ACGACACTAT | TTTATTGCTG | CAGTGGAGAG | GCTCTGGGAT | TATGGGATGA | 2580 |
| GTAGCTCCCC | ACATGTTCTA | AGAAACAGGG | CTCAGAGTGG | CAGTGTCCCT | CAGTTCAAGA | 2640 |
| AAGTTGTTTT | CCAGGAATTT | ACTGATGGCT | CCTTTACTCA | GCCCTTATAC | CGTGGAGAAC | 2700 |
| TAAATGAACA | TTTGGGACTC | CTGGGGCCAT | ATATAAGAGC | AGAAGTTGAA | GATAATATCA | 2760 |
| TGGTAACTTT | CAGAAATCAG | GCCTCTCGTC | CCTATTCCTT | CTATTCTAGC | CTTATTTCTT | 2820 |
| ATGAGGAAGA | TCAGAGGCAA | GGAGCAGAAC | CTAGAAAAAA | CTTTGTCAAG | CCTAATGAAA | 2880 |
| CCAAAACTTA | CTTTTGGAAA | GTGCAACATC | ATATGGCACC | CACTAAAGAT | GAGTTTGACT | 2940 |
| GCAAAGCCTG | GGCTTATTTC | TCTGATGTTG | ACCTGGAAAA | AGATGTGCAC | TCAGGCCTGA | 3000 |
| TTGGACCCCT | TCTGGTCTGC | CACACTAACA | CACTGAACCC | TGCTCATGGG | AGACAAGTGA | 3060 |

```
CAGTACAGGA ATTTGCTCTG TTTTTCACCA TCTTTGATGA GACCAAAAGC TGGTACTTCA      3120

CTGAAAATAT GGAAAGAAAC TGCAGGGCTC CCTGCAATAT CCAGATGGAA GATCCCACTT      3180

TTAAAGAGAA TTATCGCTTC CATGCAATCA ATGGCTACAT AATGGATACA CTACCTGGCT      3240

TAGTAATGGC TCAGGATCAA AGGATTCGAT GGTATCTGCT CAGCATGGGC AGCAATGAAA      3300

ACATCCATTC TATTCATTTC AGTGGACATG TGTTCACTGT ACGAAAAAAA GAGGAGTATA      3360

AAATGGCACT GTACAATCTC TATCCAGGTG TTTTTGAGAC AGTGGAAATG TTACCATCCA      3420

AAGCTGGAAT TTGGCGGGTG GAATGCCTTA TTGGCGAGCA TCTACATGCT GGATGAGCA       3480

CACTTTTTCT GGTGTACAGC AATAAGTGTC AGACTCCCCT GGGAATGGCT TCTGGACACA      3540

TTAGAGATTT TCAGATTACA GCTTCAGGAC AATATGGACA GTGGGCCCCA AAGCTGGCCA      3600

GACTTCATTA TTCCGGATCA ATCAATGCCT GGAGCACCAA GGAGCCCTTT TCTTGGATCA      3660

AGGTGGATCT GTTGGCACCA ATGATTATTC ACGGCATCAA GACCCAGGGT GCCCGTCAGA      3720

AGTTCTCCAG CCTCTACATC TCTCAGTTTA TCATCATGTA TAGTCTTGAT GGGAAGAAGT      3780

GGCAGACTTA TCGAGGAAAT TCCACTGGAA CCTTAATGGT CTTCTTTGGC AATGTGGATT      3840

CATCTGGGAT AAAACACAAT ATTTTTAACC CTCCAATTAT TGCTCGATAC ATCCGTTTGC      3900

ACCCAACTCA TTATAGCATT CGCAGCACTC TTCGCATGGA GTTGATGGGC TGTGATTTAA      3960

ATAGTTGCAG CATGCCATTG GGAATGGAGA GTAAAGCAAT ATCAGATGCA CAGATTACTG      4020

CTTCATCCTA CTTTACCAAT ATGTTTGCCA CCTGGTCTCC TTCAAAAGCT CGACTTCACC      4080

TCCAAGGGAG GAGTAATGCC TGGAGACCTC AGGTGAATAA TCCAAAAGAG TGGCTGCAAG      4140

TGGACTTCCA GAAGACAATG AAAGTCACAG GAGTAACTAC TCAGGGAGTA AAATCTCTGC      4200

TTACCAGCAT GTATGTGAAG GAGTTCCTCA TCTCCAGCAG TCAAGATGGC CATCAGTGGA      4260

CTCTCTTTTT TCAGAATGGC AAAGTAAAGG TTTTTCAGGG AAATCAAGAC TCCTTCACAC      4320

CTGTGGTGAA CTCTCTAGAC CCACCGTTAC TGACTCGCTA CCTTCGAATT CACCCCCAGA      4380

GTTGGGTGCA CCAGATTGCC CTGAGGATGG AGGTTCTGGG CTGCGAGGCA CAGGACCTCT      4440

ACTGAGGGTG GCCACTGCAG CACCTGCCAC TGCCGTCACC TCTCCCTCCT CAGCTCCAGG      4500

GCAGTGTCCC TCCCTGGCTT GCCTTCTACC TTTGTGCTAA ATCCTAGCAG ACACTGCCTT      4560

GAAGCCTCCT GAATTAACTA TCATCAGTCC TGCATTTCTT TGGTGGGGGG CCAGGAGGGT      4620

GCATCCAATT TAACTTAACT CTTACCTATT TTCTGCAGCT GCTCCCAGAT TACTCCTTCC      4680

TTCCAATATA ACTAGGCAAA AAGAAGTGAG GAGAAACCTG CATGAAAGCA TTCTTCCCTG      4740

AAAAGTTAGG CCTCTCAGAG TCACCACTTC CTCTGTTGTA GAAAAACTAT GTGATGAAAC      4800

TTTGAAAAAG ATATTTATGA TGTTGCGGCC GC                                   4832
```

(2) INFORMATION FOR SEQ ID NO:47:

(i) SEQUENCE CHARACTERISTICS:
        (A) LENGTH: 1457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30
```

-continued

```
Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                     85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                    165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                    245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                    325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                    405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445
```

-continued

```
Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
```

```
                865                 870                 875                 880
Leu Gly Leu Leu Gly Pro Tyr Ile Arg Ala Glu Val Glu Asp Asn Ile
                    885                 890                 895
Met Val Thr Phe Arg Asn Gln Ala Ser Arg Pro Tyr Ser Phe Tyr Ser
                900                 905                 910
Ser Leu Ile Ser Tyr Glu Glu Asp Gln Arg Gln Gly Ala Glu Pro Arg
                915                 920                 925
Lys Asn Phe Val Lys Pro Asn Glu Thr Lys Thr Tyr Phe Trp Lys Val
        930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
                980                 985                 990
Gly Arg Gln Val Thr Val Gln Glu Phe Ala Leu Phe Phe Thr Ile Phe
                995                 1000                1005
Asp Glu Thr Lys Ser Trp Tyr Phe Thr Glu Asn Met Glu Arg Asn Cys
        1010                1015                1020
Arg Ala Pro Cys Asn Ile Gln Met Glu Asp Pro Thr Phe Lys Glu Asn
1025                1030                1035                1040
Tyr Arg Phe His Ala Ile Asn Gly Tyr Ile Met Asp Thr Leu Pro Gly
                1045                1050                1055
Leu Val Met Ala Gln Asp Gln Arg Ile Arg Trp Tyr Leu Leu Ser Met
                1060                1065                1070
Gly Ser Asn Glu Asn Ile His Ser Ile His Phe Ser Gly His Val Phe
        1075                1080                1085
Thr Val Arg Lys Lys Glu Glu Tyr Lys Met Ala Leu Tyr Asn Leu Tyr
        1090                1095                1100
Pro Gly Val Phe Glu Thr Val Glu Met Leu Pro Ser Lys Ala Gly Ile
1105                1110                1115                1120
Trp Arg Val Glu Cys Leu Ile Gly Glu His Leu His Ala Gly Met Ser
                1125                1130                1135
Thr Leu Phe Leu Val Tyr Ser Asn Lys Cys Gln Thr Pro Leu Gly Met
                1140                1145                1150
Ala Ser Gly His Ile Arg Asp Phe Gln Ile Thr Ala Ser Gly Gln Tyr
                1155                1160                1165
Gly Gln Trp Ala Pro Lys Leu Ala Arg Leu His Tyr Ser Gly Ser Ile
        1170                1175                1180
Asn Ala Trp Ser Thr Lys Glu Pro Phe Ser Trp Ile Lys Val Asp Leu
1185                1190                1195                1200
Leu Ala Pro Met Ile Ile His Gly Ile Lys Thr Gln Gly Ala Arg Gln
                1205                1210                1215
Lys Phe Ser Ser Leu Tyr Ile Ser Gln Phe Ile Ile Met Tyr Ser Leu
                1220                1225                1230
Asp Gly Lys Lys Trp Gln Thr Tyr Arg Gly Asn Ser Thr Gly Thr Leu
                1235                1240                1245
Met Val Phe Phe Gly Asn Val Asp Ser Ser Gly Ile Lys His Asn Ile
        1250                1255                1260
Phe Asn Pro Pro Ile Ile Ala Arg Tyr Ile Arg Leu His Pro Thr His
1265                1270                1275                1280
Tyr Ser Ile Arg Ser Thr Leu Arg Met Glu Leu Met Gly Cys Asp Leu
                1285                1290                1295
```

-continued

```
Asn Ser Cys Ser Met Pro Leu Gly Met Glu Ser Lys Ala Ile Ser Asp
            1300                1305                1310
Ala Gln Ile Thr Ala Ser Ser Tyr Phe Thr Asn Met Phe Ala Thr Trp
        1315                1320                1325
Ser Pro Ser Lys Ala Arg Leu His Leu Gln Gly Arg Ser Asn Ala Trp
    1330                1335                1340
Arg Pro Gln Val Asn Asn Pro Lys Glu Trp Leu Gln Val Asp Phe Gln
1345                1350                1355                1360
Lys Thr Met Lys Val Thr Gly Val Thr Gln Gly Val Lys Ser Leu
                1365                1370                1375
Leu Thr Ser Met Tyr Val Lys Glu Phe Leu Ile Ser Ser Ser Gln Asp
            1380                1385                1390
Gly His Gln Trp Thr Leu Phe Phe Gln Asn Gly Lys Val Lys Val Phe
        1395                1400                1405
Gln Gly Asn Gln Asp Ser Phe Thr Pro Val Val Asn Ser Leu Asp Pro
    1410                1415                1420
Pro Leu Leu Thr Arg Tyr Leu Arg Ile His Pro Gln Ser Trp Val His
1425                1430                1435                1440
Gln Ile Ala Leu Arg Met Glu Val Leu Gly Cys Glu Ala Gln Asp Leu
                1445                1450                1455
Tyr
```

(2) INFORMATION FOR SEQ ID NO:48:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

```
Arg Gly Met Thr Ala Leu Leu Lys Val Ser Ser Cys Asp Lys Asn Thr
1               5                   10                  15
Gly Asp Tyr Tyr Glu Asp Ser Tyr Glu Asp Ile Ser Ala Tyr Leu Leu
            20                  25                  30
Ser Lys Asn Asn Ala Ile Glu Pro Arg Ser Phe Ser Gln Asn Ser Arg
        35                  40                  45
His Pro Ser Thr Arg Gln Lys Gln Phe Asn Ala Thr Pro Pro Thr Pro
    50                  55                  60
Pro Thr Pro Pro Val Leu Lys Arg His Gln Arg Glu Ile Thr Arg Thr
65                  70                  75                  80
Thr Leu Gln Ser Asp Gln Glu Glu Ile Asp Tyr Asp Asp Thr Ile Ser
                85                  90                  95
Val Glu Met Lys
            100
```

(2) INFORMATION FOR SEQ ID NO:49:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
AGAGGCATGA CCGCCTTACT GAAGGTTTCT AGTTGTGACA AGAACACTGG TGATTATTAC       60

GAGGACAGTT ATGAAGATAT TTCAGCATAC TTGCTGAGTA AAAACAATGC CATTGAACCA      120

AGAAGCTTCT CCCAGAATTC TAGACACCCT AGCACTAGGC AAAAGCAATT TAATGCCACC      180

CCTCCTACAC CACCAACCCC ACCAGTACTG AAACGCCATC AACGGAAAT AACTCGTACT       240

ACTCTTCAGT CTGATCAAGA GGAAATTGAC TATGATGATA CCATATCAGT TGAAATGAAG      300
```

(2) INFORMATION FOR SEQ ID NO:50:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Ser Arg His Pro Ser Thr Arg Gln Lys Gln Phe Asn Ala Thr Pro Pro
1               5                   10                  15

Val Leu Lys Arg His Gln Arg Glu Ile Thr Arg
            20                  25
```

(2) INFORMATION FOR SEQ ID NO:51:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
TCGCGACACC CTAGCACTAG GCAAAAGCAA TTTAATGCCA CCCCACCAGT CCTGAAACGC       60

CATCAACGGG AAATAACGCG T                                                81
```

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
ACTACTCTTC AATCTGATCA AGAGGAA                                          27
```

(2) INFORMATION FOR SEQ ID NO:53:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
CGCGCCGCTC GAGTCTACAA TGGCTTTGCC TTTTGCTTTA CTG                        43
```

(2) INFORMATION FOR SEQ ID NO:54:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:54:

GCGCCCATCG ATTTATTCCT TCCTCCTTAA CCTTTCTTGC AAG                43

(2) INFORMATION FOR SEQ ID NO:55:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

CGCGCCGCTC GAGCATCCCA ATGGCCCTGT CCTTTTCTTT ACTGATGG           48

(2) INFORMATION FOR SEQ ID NO:56:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

CCATCGATTC AATCCTTCCT CCTTAATCTT TTTTGCAAG                     39

(2) INFORMATION FOR SEQ ID NO:57:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

CCGGATCCTC TACAATGGCT TTGCCTTTTG CTTTACTG                      38

(2) INFORMATION FOR SEQ ID NO:58:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

CGCGCCGGCG GCCGCTTATT CCTTCCTCCT TAACCTTTCT TGCAAG             46

(2) INFORMATION FOR SEQ ID NO:59:

(i) SEQUENCE CHARACTERISTICS:
        (A) LENGTH: 43 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:59:

CCGGATCCCA TCCCAATGGC CCTGTCCTTT TCTTTACTGA TGG                43

(2) INFORMATION FOR SEQ ID NO:60:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

CGCGCCGGCG GCCGCTCAAT CCTTCCTCCT TAATCTTTTT TGCAAG            46

(2) INFORMATION FOR SEQ ID NO:61:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

AGCTTGCTGT TTGTGTGCTG CCTCTGAAGT CCACACTGAA CAAACTTCAG CCTACTCATG    60

TCCCTAAAAT GGGCAAACAT TGCAAGCAGC                                     90

(2) INFORMATION FOR SEQ ID NO:62:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

AAACAGCAAA CACACAGCCC TCCCTGCCTG CTGACCTTGG AGCTGGGGCA GAGGTCAGAG    60

ACCTCTCTGA                                                           70

(2) INFORMATION FOR SEQ ID NO:63:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

AGCTTCAGAG AGGTCTCTGA CCTCTGCCCC AGCTCCAAGG TCAGCAGGCA GGGAGGGCTG    60

TGTGTTTGCT GTTTGCTGCT TG                                             82

(2) INFORMATION FOR SEQ ID NO:64:

(i) SEQUENCE CHARACTERISTICS:

(A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CAATGTTTGC CCATTTTAGG GACATGAGTA GGCTGAAGTT TGTTCAGTGT GGACTTCAGA      60

GGCAGCACAC AAACAGCA      78

(2) INFORMATION FOR SEQ ID NO:65:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

AATTCGCTGT TTGTGTGCTG CCTCTGAAGT CCACACTGAA CAAACTTCAG CCTACTCATG      60

TCCCTAAAAT GGGCAAACAT TGCAAGCAGC      90

(2) INFORMATION FOR SEQ ID NO:66:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

AAACAGCAAA CACACAGCCC TCCCTGCCTG CTGACCTTGG AGCTGGGGCA GAGGTCAGAG      60

ACCTCTCTGG      70

(2) INFORMATION FOR SEQ ID NO:67:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

AATTCCAGAG AGGTCTCTGA CCTCTGCCCC AGCTCCAAGG TCAGCAGGCA GGGAGGGCTG      60

TGTGTTTGCT GTTTGCTGCT TG      82

(2) INFORMATION FOR SEQ ID NO:68:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

CAATGTTTGC CCATTTTAGG GACATGAGTA GGCTGAAGTT TGTTCAGTGT GGACTTCAGA      60

GGCAGCACAC AAACAGCG                                                      78

(2) INFORMATION FOR SEQ ID NO:69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

CGCGCCGCCC GGGGTAGATC TTGCTACCAG TGG                                      33

(2) INFORMATION FOR SEQ ID NO:70:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

GCGCCCGCGG CCGCCACTGT CCCAGGTCAG TGGTGGTGCC                               40

(2) INFORMATION FOR SEQ ID NO:71:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

CGCGCCGGCG GCCGCTCTAC AATGGCCTTG ACCTTTGCTT TACTGG                        46

(2) INFORMATION FOR SEQ ID NO:72:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

GCGCCCATCG ATTCATTCCT TACTTCTTAA ACTTTCTTGC AAG                           43

(2) INFORMATION FOR SEQ ID NO:73:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

CGCGCCGGCG GCCGCTCTAC AATGGCCTTG ACCTTTGCTT TACTGG                        46

(2) INFORMATION FOR SEQ ID NO:74:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

GCGCCCATCG ATTCATTCCT TACTTCTTAA ACTTTCTTGC AAG      43

(2) INFORMATION FOR SEQ ID NO:75:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Asn Ser Arg His Pro Ser
1               5

(2) INFORMATION FOR SEQ ID NO:76:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Gln Asn Pro Pro Val Leu Lys Arg His Gln Arg Glu Ile Thr
1               5                   10

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

AATTCGCGAC ACCCTAGC      18

(2) INFORMATION FOR SEQ ID NO:78:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

CAAAACCCAC CAGTCTTGAA ACGCCATCAA CGGGAAATAA CG      42

(2) INFORMATION FOR SEQ ID NO:79:

(i) SEQUENCE CHARACTERISTICS:

-continued (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

GCGCTGTGGG ATCGGTTTTG GGTGGTCAGA AC                              32

(2) INFORMATION FOR SEQ ID NO:80:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

TTTGCGGTAG TTGCCCTTTA TTGC                                       24

(2) INFORMATION FOR SEQ ID NO:81:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Arg Thr Leu Gln Ser Asp
1               5

(2) INFORMATION FOR SEQ ID NO:82:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

CGTACTCTTC AGTCT                                                 15

(2) INFORMATION FOR SEQ ID NO:83:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

GCATGAGAAG TCAGACTAG                                             19

(2) INFORMATION FOR SEQ ID NO:84:

(i) SEQUENCE CHARACTERISTICS:
        (A) LENGTH: 16 base pairs
        (B) TYPE: nucleic acid
        (C) STRANDEDNESS: single -continued

```
         (D) TOPOLOGY: linear (xi) SEQUENCE DESCRIPTION: SEQ ID NO:84:

TGCATGCCTG CAGGTC                                                        16
```

METHODS FOR ADMINISTRATION OF RECOMBINANT GENE DELIVERY VEHICLES FOR TREATMENT OF HEMOPHILIA AND OTHER DISORDERS

This application is a continuation-in-part of U.S. Ser. No. 08/869,309, filed Jun. 4, 1997, now abandoned, which is a continuation-in-part of U.S. Ser. No. 08/696,381, filed Aug. 13, 1996, now abandoned, which is a continuation-in-part of U.S. Ser. No. 08/645,601, filed Jul. 3, 1996, now abandoned, which is a continuation-in part of U.S. Ser. No. 08/367,071, filed Dec. 30, 1994 now abandoned, all of which are hereby incorporated by reference.

FIELD OF THE INVENTION

The present invention relates to methods of administration of recombinant gene transfer vehicles for the treatment of hemophilia, thrombosis, and other diseases. The present invention also relates generally to recombinant retroviruses, and more specifically, to high titer recombinant retroviral particle preparations suitable for a variety of applications.

BACKGROUND OF THE INVENTION

A variety of human disorders can be treated by the methods described herein. For example, hemophilia is a genetic disease characterized by a severe blood clotting deficiency. As such, it will be amenable to treatment by gene therapy. In hemophilia A, an X-chromosome linked genetic defect disrupts the gene encoding factor VIII, a trace plasma glycoprotein which acts as a cofactor in conjunction with factor IXa in the activation of factor X. In humans, the factor VIII gene codes for 2,351 amino acids. The protein has six domains, designated from amino to carboxy terminus as A1, A2, B, A3, C1, and C2, respectively (Wood et al., 1984, *Nature* 312:330; Vehar et al., 1984, *Nature* 312:337; and Toole et al., 1984, *Nature* 312:342) with a deduced molecular weight of about 280 kilo Daltons (kD). The 980 amino acid B domain is deleted in the activated procoagulant form of the protein. Additionally, in the native protein two polypeptide chains, the heavy and light chain, flanking the B domain, are bound to a divalent calcium cation.

The genetic defect causing hemophilia A affects about one in every 10,000 males. Due to the resultant clotting deficiency, those afflicted with the disease suffer severe bleeding episodes due to small injuries, internal bleeding, and joint hemorrhage, which leads to arthropathy, the major cause of morbidity in hemophilia. Normal levels of factor VIII average between 50 to 200 ng/ml of blood plasma (Mannucci, P. M. in *Practical Laboratory Hematology*, ed. Koepke, J. A., Churchill Livingstone, N.Y., pp:347–371, 1990); however, patients suffering from mild to moderate hemophilia A typically have plasma levels well below 2–60 ng/ml, while levels below about 2 ng/mL result in severe hemophilia.

Previously, therapy for hemophilia A involved repeated administration off human factor VIII purified from blood products pooled in lots from over 1000 donors. However, because of the low levels of circulating factor VIII, resulting pharmaceutical products using the natural protein typically were highly impure, with an estimated purity by weight (factor VIII to total protein) of approximately 0.04%. Due to the frequency of administration and inability to remove various human pathogens from such preparations, more than 90% of those suffering from hemophilia A were infected in the 1980s with the human immunodeficiency virus (HIV) as a result of their therapy. Many of these HIV infected patients and other HIV negative hemophiliacs have also been infected by Hepatitis B in the same way. Fortunately, recent advances in genetic engineering have lead to the commercial availability of a recombinant form of the protein free from contamination with human pathogens, except for those potentially derived from tissue culture origin of the proteins, or from human serum albumin used in formulation of the recombinant protein. However, this form of therapy is expensive and chronic, and a large proportion of hemophiliacs continue to rely on plasma-derived products due to expense and or shortages of the recombinant product. In addition, most hemophilia A patients in the Unites States do not presently receive factor VIII maintenance therapy, but instead only receive the polypeptide prior to activities or events which might cause bleeding, such as surgery, or to treat spontaneous bleeding. Interestingly, this is despite evidence showing that hemophilic arthropathy can be prevented by administering from an early age prophylactic amounts of factor VIII, typically 24–40 IU per kilogram bodyweight, three times a week. Such therapy kept factor VIII concentrations from falling below 1% of normal (Nillson, et al., *J. Internal Med.* 232:23, 1992). For these reasons, a genetic therapy affording continuous, long term therapeutically effective expression levels or amounts of factor VIII, i.e., to decrease the severity of or eliminate the clotting disorder associated with hemophilia A, would be of great benefit.

A condition clinically indistinguishable from Hemophilia A is Hemophilia B, resulting from the deficiency of clotting factor IX. The incidence of this condition is about 5-fold lower than that of hemophilia A, and presents many of the same therapeutic challenges and difficulties. For similar reasons, it would be of great benefit to provide a gene therapy to these patients.

Factor X deficiency results in a rare but serious bleeding disorder affecting 1 in 500,000 known as Stuart disease. Le et al., 1997, *Blood* 89:1254–9, describes therapeutic levels of functional human factor X in rats after retroviral mediated hepatic gene therapy. As in the case of hemophilia A and B, a genetic therapy affording continuous, long term therapeutically effective expression levels or amounts of factor X, i.e., to decrease the severity of or eliminate the clotting disorder associated with hemophilia B, would be of great benefit.

The present invention also provides for gene therapy delivery of other clotting factors for treatment or prophalaxis of thrombosis. Venous thromboembolism has an annual incidence of 1/1000 in the general population (Dahlback, 1995, *Blood* 85:607). Precipitating factors can include hemostatic challenges such as surgery, fractures, inflammation, immobilization, pregnancy, oral contraceptive use, trauma, cancer, etc. Thrombosis is often familial, and a number of genetic risk factors have been identified. The clinical condition in which recurrent thrombosis occurs has been dubbed thrombophilia. The natural defenses against thrombosis involve two major systems: serpin inhibitors of thrombin, e.g., antithrombin III, the major pathway by which heparin exerts its clinical antithrombin effect, and the protein C system. Gene therapy for thrombosis disorders is needed and is addressed by the instant invention.

The present invention also provides methods for treatment of diseases such as viral hepatitis. Currently, the only approved treatment for chronic hepatitis B, C and D infections is the use of alpha interferon 2a and 2b. However, for patients with hepatitis B infections only about 35% of patients infected as adults responded to such treatment, and in perinatal infectees only about 10% responded to treatment (Perrillo et al., 1990, *New Eng. J. Med.* 323:295–301). For hepatitis C infections, despite apparent short term success utilizing such therapy, six months after termination of treatment half of the patients who responded to therapy had relapsed. (Davis et al., *New Eng. J. Med.* 321:1501–1506). In pilot studies for hepatitis D infections, 25–60% of patients responded to alpha interferon therapy. Sustained responses were rare; 85–90% of patients who responded had relapsed. (di Bisceglie, A. M. D., *Viral Hepatitis A to F: An Update*, 1994). In addition, a further difficulty with alpha interferon therapy is that the composition frequently has toxic side effects which require reduced dosages for sensitive patients. Thus, improved methods for treatment of viral hepatitis are needed and are addressed by the present invention.

The instant invention also relates to the production and use of high titer recombinant retroviruses. Since the discovery of DNA in the 1940s and continuing through the most recent era of recombinant DNA technology, substantial research has been undertaken in order to realize the possibility that the course of disease may be affected through interaction with the nucleic acids of living organisms. Most recently, a wide variety of methods have been described for altering or affecting genes, including for example, viral vectors derived from retroviruses, adenoviruses, vaccinia viruses, herpes viruses, and adeno-associated viruses (see Jolly, 1994, *Cancer Gene Therapy* 1(1):51–64), as well as direct transfer techniques such as lipofection (Felgner et al., 1989, *Proc. Natl. Acad. Sci. USA* 84:7413–7417), direct DNA injection (Acsadi et al., 1991, *Nature* 352:815–818), microprojectile bombardment (Williams et al., 1991, *PNAS* 88:2726–2730), liposomes of several types (see, e.g., Wang et al., 1987, *PNAS* 84:7851–7855) and administration of nucleic acids alone (PCT Patent Publication No. WO 90/11092).

Of these techniques, recombinant retroviral gene delivery methods have been most extensively utilized, in part due to: (1) the efficient entry of genetic material (the vector genome) into cells; (2) an active, efficient process of entry into the target cell nucleus; (3) relatively high levels of gene expression; (4) the potential to target particular cellular subtypes through control of the vector-target cell binding and the tissue-specific control of gene expression; (5) a general lack of pre-existing host immunity; and (6) substantial knowledge and clinical experience which has been gained with such vectors.

Briefly, retroviruses are diploid positive-strand RNA viruses that replicate through an integrated DNA intermediate. In particular, upon infection by the RNA virus, the retroviral genome is reverse-transcribed into DNA by a virally encoded reverse transcriptase that is carried as a protein in each retrovirus. The viral DNA is then integrated pseudo-randomly into the host cell genome of the infecting cell, forming a "provirus" which is inherited by daughter cells.

Wild-type retroviral genomes (and their proviral copies) contain three genes (the gag, pol and env genes), which are preceded by a packaging signal ($\psi$), and two long terminal repeat (LTR) sequences which flank both ends. Briefly, the gag gene encodes the internal structural (nucleocapsid) proteins. The pol gene codes for the RNA-dependent DNA polymerase which reverse transcribes the RNA genome, and the env gene encodes the retroviral envelope glycoproteins. The 5' and 3' LTRs contain cis-acting elements necessary to promote transcription and polyadenylation of retroviral RNA.

Adjacent to the 5' LTR are sequences necessary for reverse transcription of the genome (the tRNA primer binding site) and for efficient encapsidation of retroviral RNA into particles (the $\psi$ sequence). Removal of the packaging signal prevents encapsidation (packaging of retroviral RNA into infectious virions) of genomic RNA, although the resulting mutant can still direct synthesis of all proteins encoded in the viral genome.

Recombinant retroviruses and various uses thereof have been described in numerous references including, for example, Mann et al., 1983, *Cell* 33:153; Cane and Mulligan, 1984, *Proc. Natl. Acad. Sci. USA* 81:6349; Miller et al., 1990, *Human Gene Therapy* 1:5–14; U.S. Pat. Nos. 4,405,712; 4,861,719; 4,980,289 and PCT Patent Publication Nos. WO 89/02468; WO 89/05349 and WO 90/02806. Briefly, a foreign gene of interest may be incorporated into the retrovirus in place of the normal retroviral RNA. When the retrovirus injects its RNA into a cell, the foreign gene is also introduced into the cell, and may then be integrated into the host's cellular DNA as if it were the retrovirus itself. Expression of this foreign gene within the host results in expression of the foreign protein by the host cell.

One disadvantage, however, of recombinant retroviruses is that they principally infect only replicating cells, thereby making efficient direct gene transfer difficult. Indeed, some scientists have suggested that other, more efficient methods of gene transfer, such as direct administration of pure plasmid DNA, be utilized (Davis et al., 1993, *Human Gene Therapy* 4:733–740).

In order to increase the efficacy of recombinant retroviruses, methods which have been suggested for increasing the efficacy of recombinant retroviruses have principally been aimed at inducing the desired target cells to replicate, thereby allowing the retroviruses to infect the cells. Such methods have included, for example chemical treatment with 10% carbon tetrachloride in mineral oil (Kaleko et al., 1991, *Human Gene Therapy* 2:27–32). Alternatively, others have suggested excising large portions of the liver (e.g., 70% in Rettinger et al., 1994 *PNAS* 91:1460–1464; 70% in Moscioni et al., 1993, *Surgery* 113:304–311) in order to stimulate the rapid division of hepatocytes and thereby increase the infection of such cells.

One further disadvantage of recombinant retroviruses, is that serum from primates (e.g., humans) is known to cause inactivation by an antibody independent complement lysis method. In particular retroviruses of avian, murine, feline, and simian origin are all inactivated and lysed by normal human serum. (Welsh et al., 1975, *Nature* 257:612–614; Welsh et al., 1976, *Virology* 74:432–440; Banapour et al., 1986, *Virology* 152:268–271; and Cooper et al., *Immunology of the Complement System*, Pub., American Press, Inc., pp. 139–162, 1986). The scientific literature has also reported that replication competent murine amphotropic retroviruses injected intravenously into primates are cleared within 15 minutes and that the disappearance is mediated, wholly or in part, by primate complement. (Cornetta et al., 1991, *Human Gene Therapy* 2:5–14; Cornetta et al., 1990, *Human Gene Therapy* 1:15–30; and Banapour et al., 1986, *Virology* 152:268–271)

In order to increase the affect of recombinant retroviruses that are delivered in vivo, the present invention provides recombinant retrovirus compositions which are capable of surviving inactivation in human serum. In addition, the present invention provides high titer recombinant retrovirus compositions which allow delivery of therapeutics or palliatives by routes not previously deemed possible, and without the need to induce replication of cells by chemical treatment or by excision of a target organ such as the liver. The present invention provides these, as well as other related advantages.

SUMMARY OF THE INVENTION

This invention provides for preparations of replication defective recombinant retrovirus expressing human factor VIII protein, wherein the recombinant retrovirus is capable of infecting human cells and is resistant to degradation by human complement. The invention also provides for preparations of replication defective recombinant retrovirus expressing human factor VIII protein in which the recombinant retrovirus preparation is resistant to degradation by human complement and is capable of inducing long term systemic expression of human factor VIII when administered intravenously to a human afflicted with hemophilia A. The wherein said long term systemic expression results in a measurable level of recombinant human factor VIII protein being produced in the blood of said human for a period of at least 30 days after the administration of said recombinant retroviral vector preparation and more preferably for at least six months after injection, and yet more preferably for longer periods of time as described herein.

Pharmaceutical compositions and therapeutic methods of the above-described retroviral vectors expressing factor VIII protein are also provided herein as are therapeutic methods for treatment of hemophilia A by intravenous injection of these retroviral vectors. The retroviral vectors of the invention can expresses a B domain-deleted form of factor VIII, which in one embodiment can be the SQN mutation of factor VIII. The retroviral vectors of the invention can have a titer on HT1080 cells of greater than $10^6$, more preferably $10^7$ cfu/ml and more preferably at least $10^8$ cfu/ml, more preferably $10^9$ cfu/ml, more preferably at least $10^{10}$ cfu/ml, and most preferably $10^{11}$ cfu/ml.

In addition, the present invention provides high titer compositions comprising recombinant retroviruses, as well as methods for utilizing these compositions. Within one aspect of the present invention, methods are provided for obtaining measurable levels of a protein, nucleic acid molecule, or enzymatic product in a bodily fluid or cells of a human, comprising the step of administering to a human a recombinant retroviral preparation having a titer on HT1080 cells of greater than $10^5$ cfu/ml, wherein the recombinant retroviral preparation is capable of directing the expression of a protein, nucleic acid molecule, or enzyme which generates an enzymatic product, such that measurable levels of the protein, nucleic acid molecule, or enzymatic product may be obtained in the bodily fluid or cells of said human. Within certain embodiments, the titer may be greater than $10^6$ cfu/ml, $10^7$ cfu/ml, $10^8$ cfu/ml, $10^9$ cfu/ml, $10^{10}$ cfu/ml, or $10^{11}$ cfu/ml.

Within other aspects of the invention, methods are provided for obtaining measurable levels of a protein, nucleic acid molecule, or enzymatic product in a bodily fluid or cells of a human, comprising the steps of administering to a human a recombinant retroviral preparation having a titer in human serum and on HT1080 cells equivalent to its' titer in heat-inactivated serum and on HT1080 cells, wherein the recombinant retroviral preparation is capable of directing the expression of a protein, nucleic acid molecule, or enzyme which generates an enzymatic product, such that measurable levels of the protein, nucleic acid molecule, or enzymatic product may be obtained in the bodily fluid or cells of said human.

As utilized within the context of the present invention, "measurable levels" of a protein, nucleic acid molecule, or enzymatic product refers to a statistically significant level of detection over background, utilizing any suitable technique (e.g., antibody-mediated detection of a protein, PCR analysis for the presence of a nucleic acid molecule, or visualization of enzymatic products). Further, as utilized within the context of the present invention, "equivalent" titers are deemed to be those which are substantially the same within a given assay, generally, within about three-fold of each other.

Within certain embodiments of the invention, the recombinant retrovirus is administered to a site such as the cerebral spinal fluid, bone marrow, joints, arterial endothelial cells, rectum, buccal/sublingual, vagina, the lymph system, to an organ selected from the group consisting of lung, liver, spleen, skin, blood and brain, or to a site selected from the group consisting of tumors and interstitial spaces. Within other embodiments, the recombinant retrovirus may be administered intraocularly, intranasally, sublinually, orally, topically, intravesically, intrathecally, topically, intravenously, intraperitoneally, intracranially, intramuscularly, or subcutaneously.

Within yet other embodiments of the present invention, the protein is a viral antigen obtained from a virus such as influenza virus, respiratory syncytial virus, HPV, HBV, HCV, EBV, HIV, HSV, FeLV, FIV, Hantavirus, HTLV I, HTLV II and CMV. Within other embodiments, the protein is a cytokine such as IL-1, IL-2, IL-3, IL4, IL-5, IL-6, IL-7, IL-8, IL-9, IL-10, IL-11, IL-12, IL-13, IL-14, IL-15, γ-IFN, G-CSF and GM-CSF, or a receptor for any of these cytokines.

Within another embodiment, the nucleic acid molecule may be an antisense sequence, a non-coding non-heterologous sense sequence, and a ribozyme sequence. Within yet another aspect, the protein is a toxin.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety as if each were individually noted for incorporation.

BRIEF DESCRIPTION OF THE DRAWINGS

FIG. 1 is a schematic illustration of p31N2R5(+).

FIG. 3 is a schematic illustration of p31N25.(+).

FIG. 6 is a schematic illustration of p31N25.(+).

FIG. 38: Nucleotide and predicted amino acid sequence linking the light and heavy chains of Factor VIII in pSVF8-tβ2.

FIG. 39: Linker sequences for pSVF8-500 and pc1/1 AGαF8-500.

FIG. 41: Linker sequence for pSVF8-500B.

DETAILED DESCRIPTION OF THE INVENTION

Figure 2:
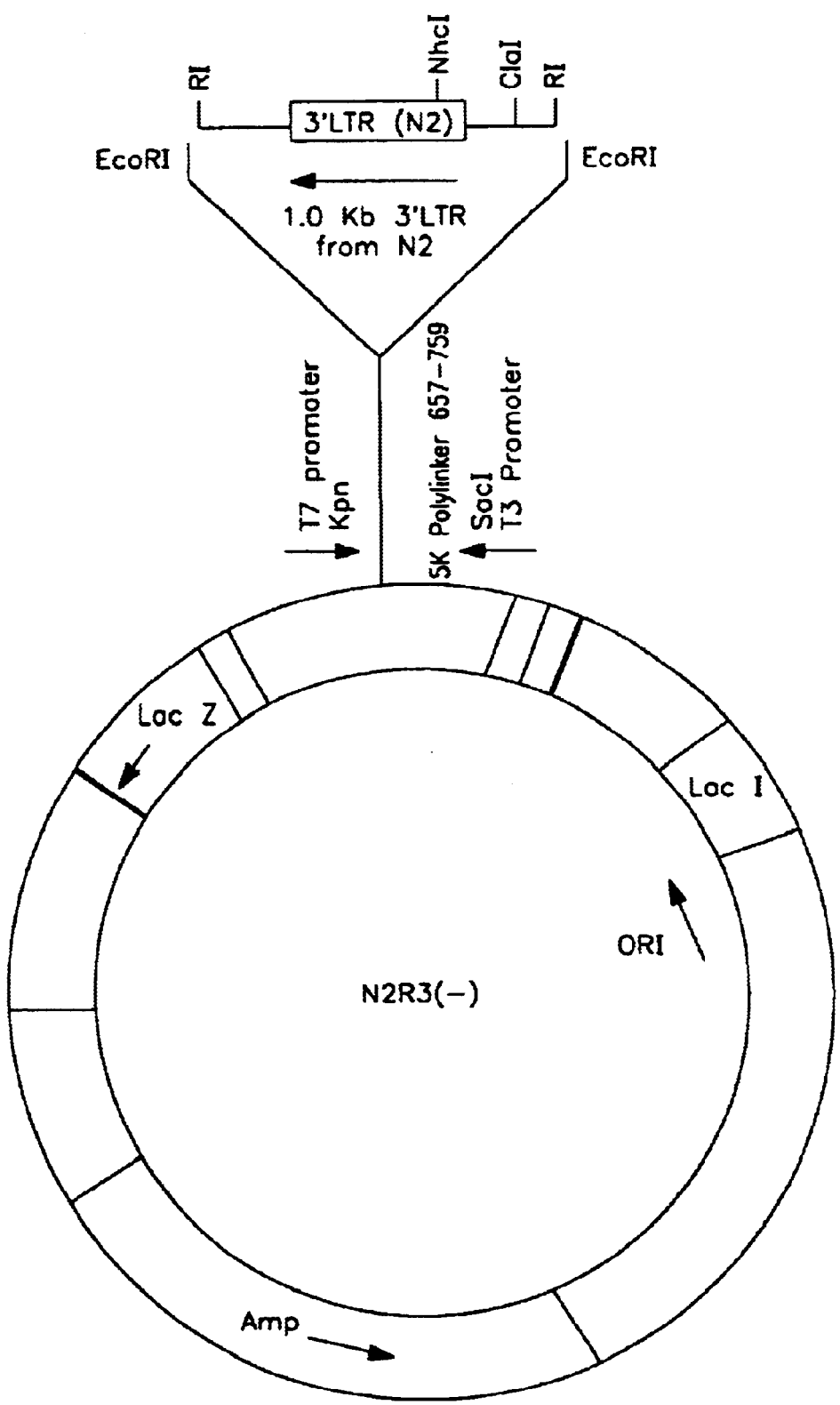
FIG. 2 is a schematic illustration of pN2R3(-).

Prior to setting forth the invention, it may be helpful to an understanding thereof to set forth definitions of certain terms that will be used hereinafter.

"Vector construct", "retroviral vector", "recombinant vector", and "recombinant retroviral vector" refers to a nucleic acid construct which carries, and within certain embodiments, is capable of directing the expression of a nucleic acid molecule of interest. The retroviral vector must include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRs) or portion thereof, and positive and negative strand primer binding sites appropriate to the retrovirus used (if these are not already present in the retroviral vector). Optionally, the recombinant retroviral vector may also include a signal which directs polyadenylation, selectable markers such as Neomycin resistance, TK, hygromycin resistance, phleomycin resistance histidinol resistance, or DHFR, as well as one or more restriction sites and a translation termination sequence. By way of example, such vectors typically include a 5' LTR, a tRNA binding site, a packaging signal, an origin of second strand DNA synthesis, and a 3' LTR or a portion thereof.

"Recombinant retrovirus", "retroviral gene delivery vehicle" and "retroviral vector particle" as utilized within the present invention refers to a retrovirus which carries at least one gene of interest. The retrovirus may also contain a selectable marker. The recombinant retrovirus is capable of reverse transcribing its genetic material into DNA and incorporating this genetic material into a host cell's DNA upon infection.

"Factor VIII" is a nonenzymatic cofactor found in blood in an inactive precursor form. Precursor factor VIII is converted to the active cofactor, factor VIIIa, through limited proteolysis at specific sites by plasma proteases, notably thrombin and factor IXa. The majority of factor VIII circulates as a two-chain heterodimer most likely due to intracellular or pericellular processing of the single chain gene product. The two chains are noncovalently associated in a metal ion dependent manner.

The "biological activity" of factor VIII refers to a function or set of functions performed by the polypeptide or fragments thereof in a biological system or in an in vitro facsimile thereof. The biological activity of factor VIIIa is characterized by its ability to form a membrane binding site for factors IXa and X in a conformation suitable for activation of the latter by the former. This includes standard assays of factor IX or X activation, binding to phospholipids, von Willebrand factor, or specific cell surface molecules, and susceptibility to thrombin, factor IXa, activated protein C, or other specific proteases under appropriate conditions. More particularly biologically active factor VIII corrects the coagulation defect in plasma derived from individuals afflicted with hemophilia A.

A "factor VIII cDNA molecule" is one encoding a full-length factor VIII polypeptide, a B domain deleted factor VIII protein, or other forms of factor VIII protein with biological activity. The human full-length factor VIII coding region is 7,056 nucleotides.

"Biologically active factor IX" encompasses those forms of factor IX which are capable of correcting the coagulation defect in plasma derived from individuals afflicted with hemophilia B as measured in a standard in vitro clotting assay.

As noted above, the present invention provides for method, of administration of recombinant gene delivery vehicles for treatment of hemophilia and a variety of other disorders by gene therapy techniques. The present invention provides high titer complement resistant recombinant retroviral preparations which are suitable for administration to humans. Such preparations provide the unexpected result of providing efficatious gene therapy for a variety of diseases (and by a variety of routes) that were previously not amenable for gene therapy. In addition, the present invention provides recombinant retroviruses which are capable of surviving inactivation in human serum, thereby allowing more efficient gene transfer over prolonged periods of time.
A. Preparation of Recombinant Gene Delivery Vehicles Gene Delivery Vehicles The therapeutic proteins of the present invention may be utilized in a wide variety of gene delivery vehicles. The gene delivery vehicle may be of either viral or non-viral origin (See generally, Jolly, 1994, *Cancer Gene Therapy* 1:51–64; Kimura, 1994, *Human Gene Therapy* 5:845–852; Connelly, 1995, *Human Gene Therapy* 6:185–193; and Kaplitt, 1994, *Nature Genetics* 6:148–153). Gene therapy vehicles for delivery of constructs including a coding sequence of a therapeutic of the invention can be administered either locally or systemically. These constructs can utilize viral or non-viral vector approaches in in vivo or ex vivo modality. Expression of such coding sequence can be induced using endogenous mammalian or heterologous promoters. Expression of the coding sequence in viva can be either constitutive or regulated as is described in detail below.

1. Retroviral Vectors

As noted above, the present invention provides recombinant retroviruses which are constructed to carry or express a selected nucleic acid molecule of interest. Briefly, numerous retroviral gene delivery vehicles may be utilized within the context of the present invention, including for example those described in EP 0,415,731; WO 90/07936; WO 94/03622; WO 93/25698; WO 93/25234; U.S. Pat. No. 5,219,740; WO 9311230; WO9310218; Vile and Hart, 1993, *Cancer Res.* 53:3860–3864; Vile and Hart, 1993, *Cancer Res.* 53:962–967; Ram et al., 1993, *Cancer Res.* 53:83–88, Takamiya et al., 1992, *J. Neurosci. Res.* 33:493–503, Baba et al., 1993, *J. Neurosurg.* 79:729–735 (U.S. Pat. No. 4,777,127, GB 2,200,6511, EP 0,345,242 and WO 91/02805). Particularly preferred recombinant retroviruses include those described in WO 91/02805.

Retroviral gene delivery vehicles of the present invention may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Preferred retroviruses for the preparation or construction of retroviral gene delivery vehicles of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, 1976, *J. Virol.* 19:19–25), Abelson (ATCC No. VR-999), Friend ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Any of the above retroviruses may be readily utilized in order to assemble or construct retroviral gene delivery vehicles given the disclosure provided herein, and standard recombinant techniques (e.g., Sambrook et al., *Molecular Cloning: A Laboratory Manual,* 2d ed., Cold Spring Harbor Laboratory Press, 1989; Kunkle, 1985, *PNAS* 82:488). In addition, within certain embodiments of the invention, portions of the retroviral gene delivery vehicles may be derived from different retroviruses. For example, within one embodiment of the invention, retroviral vector LTRs may be derived from a Murine Sarcoma Virus a tRNA binding site from a Rous Sarcoma Virus, a packaging signal from a Murine Leukemia Virus, and an origin of second strand synthesis from an Avian Leukosis Virus.

Within preferred aspects of the present invention, recombinant retroviruses may be made by introducing a vector construct as discussed above, into a cell (termed a, "packaging cell") which contains those elements necessary for production of infectious recombinant retrovirus which are lacking in the vector construct. A wide variety of retroviral vector constructs may be utilized within the present invention in order to prepare recombinant retroviruses. For example, within one aspect of the present invention retroviral vector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus due to their precise duplication at either end of the genome. As utilized herein, a 5' LTR should be understood to include a 5' promoter element, and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR.

In addition to a 5' and 3' LTR, tRNA binding site, and origin of second strand DNA synthesis, certain preferred retroviral vector constructs which are provided herein also comprise a packaging signal, as well as one or more nucleic acid molecules (e.g., heterologous sequences), each of which is discussed in more detail below.

Within one aspect of the invention, retroviral vector constructs are provided which lack both gag/pol and env coding sequences. As utilized herein, the phrase "lacks gag/pol or env coding sequences" should be understood to mean that the retroviral vector does not contain at least 20, preferably at least 15, more preferably at least 10, and most preferably at least 8 consecutive nucleotides which are found in gag/pol or env genes, and in particular, within gag/pol or env expression cassettes that are used to construct packaging cell lines for the retroviral vector construct.

Packaging cell lines suitable for use with the above-described retroviral vector constructs may be readily prepared (see PCT Patent Publication No. WO 95/30763; see also WO 92/05266), and utilized to create producer cell lines (also termed vector cell lines or "VCLS") for the production of recombinant vector particles. Within particularly preferred embodiments of the present invention packaging cell lines are made from human (e.g., HT1080 cells) or mink parent cell lines, thereby allowing production of recombinant retroviruses that are capable of surviving inactivation in human serum.

Utilizing the methods of the present invention as disclosed herein, packaging cell lines that produce greater than recombinant retroviral particles at titers greater than $10^6$ or $10^7$ cfu/ml (in crude supernatant) may readily be obtained. In addition, it should be noted that such titers are generally obtained from titer assays on HT1080 cells, which produce a threefold lower titer than titers obtained on murine 3T3 cells.

2. Alphavirus and Eucaryotic Layered Vector Gene Delivery Vehicles

The present invention also provides a variety of alphavirus-based vectors which can function as gene delivery vehicles. Such vectors can be constructed from a wide variety of alphaviruses, including for example, Sindbis viruses vectors, Semliki Forest virus (ATCC VR-67; ATCC VR-1247), Ross River virus (ATCC VR-373; ATCC VR-1246) and Venezuelan equine encephalitis virus (ATCC VR923; ATCC VR-1250; ATCC VR-1249; ATCC VR-532).

As an example, the Sindbis virus, which is the prototype member of the alphavirus genus of the togavirus family is an unsegmented genomic RNA (49S RNA) of virus of approximately 11,703 nucleotides in length. This virus contains a 5' cap and a 3' poly-adenylated tail, and displays positive polarity. Infectious enveloped Sindbis virus is produced by assembly of the viral nucleocapsid proteins onto the viral genomic RNA in the cytoplasm and budding through the cell membrane embedded with viral encoded glycoproteins. Entry of virus into cells is by endocytosis through clatharin coated pits, fusion of the viral membrane with the endosome, release of the nucleocapsid, and uncoating of the viral genome. During viral replication the genomic 49S RNA serves as template for synthesis of the complementary negative strand. This negative strand in turn serves as template for genomic RNA and an internally initiated 26S subgenomic RNA. The Sindbis viral nonstructural proteins are translated from the genomic RNA while structural proteins are translated from the subgenomic 26S RNA. All viral genes are expressed as a polyprotein and processed into individual proteins by post translational proteolytic cleavage. The packaging sequence resides within the nonstructural coding region, therefore only the genomic 49S RNA is packaged into virions.

A variety of different alphavirus vector systems may be constructed and utilized within the present invention. Representative examples of such systems include those described in U.S. patent application Ser. Nos. 08/198,450, 08/405,627 and 08/679,640, U.S. Pat. Nos. 5,091,309; 5,217,879 and 5,185,440, PCT Publication Nos. WO 92/10578, WO/94/21792, WO 95/27069, WO 95/27044 and WO 95/07994.

Particularly preferred alphavirus vectors for use within the present invention include those which are described within U.S. application Ser. No. 08/198,450. Briefly, within one embodiment, alphavirus vector constructs are provided comprising a 5' sequence which is capable of initiating in vitro transcription of a alphavirus RNA, a nucleotide sequence encoding alphavirus non-structural proteins, a viral junction region which is active, modified to reduce viral transcription of the subgenomic fragment, or inactivated such that viral transcription of the subgenomic fragment is prevented, and a alphavirus RNA polymerase recognition sequence.

In still further embodiments, the vector constructs described above contain no alphavirus structural proteins in the vector constructs. The selected heterologous sequence may be located downstream from the viral junction region; in the vector constructs having a second viral junction, the selected heterologous sequence may be located downstream from the second viral junction region, where the heterologous sequence is located downstream, the vector construct may comprise a polylinker located between the viral junction region arid said heterologous sequence, and preferably the polylinker does not contain a wild-type Sindbis virus restriction endonuclease recognition sequence.

In addition, within one embodiment of the invention the gene delivery vehicles is a eukarytic layered expression systems (ELVS) (see PCT Patent Publication Nos. WO 95/07994 and WO 96/17072 for a detailed description of eukaryotic layered expression systems). Although initially developed for alphavirus vectors, ELVS vectors may also be developed using other viral and non-viral nucleotide sequences (see PCT Patent Publication Nos:. WO 95/07994 and WO 96/17072.

3. Adeno-associated Viral Vectors

Gene delivery vehicles of the present invention also include parvovirus such as adenovirus associated virus (AAV) vectors. Representative examples of such vectors include the AAV vectors disclosed by Srivastava in WO 93/09239, Samulski et a., 1989, *J. Vir.* 63:3822–3828; Mendelson et al., 1988, *Virol.* 166:154–165; Flotte et al., 1993, *PNAS* 90(22):10613–10617. Particularly preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini, 1993, *Gene* 124:257–262. Another example of such an AAV vector is psub201. See Samulski, 1987, *J. Virol.* 61:3096. Another exemplary AAV vector is the Double-D ITR vector. How to make the Double D ITR vector is disclosed in U.S. Pat. No. 5,478,745. Still other vectors are those disclosed in Carter, U.S. Pat. No. 4,797,368 and Muzyczka. U.S. Pat. No. 5,139,941; Chartejee, U.S. Pat. No. 5,474,935; and Kotin, PCT Patent Publication WO 94/288157. Yet a further example of an AAV vector employable in this invention is SSV9AFABTKneo, which contains the AFP enhancer and albumin promoter and directs expression predominantly in the liver. Its structure and how to make it are disclosed in Su, *Human Gene Therapy* 7:463–470, 1996. Additional AAV gene therapy vectors are described in U.S. Pat. Nos. 5,354,678; 5,173,414; 5,139, 941; and 5,252,479.

4. Other Viral Vector Delivery Systems

In addition to retroviral vectors and alphavirus-based vectors, numerous other viral vectors systems may also be utilized as a gene delivery vehicle. For example, within one embodiment of the invention adenoviral vectors may be employed as a gene delivery vehicle. Representative examples of such vectors include those described by, for example, Berkner, 1988, *Biotechniques* 6:616–627; Rosenfeld et al., 1991, *Science* 252:431–434; WO 93/9191; Kolls et al., 1994, *PNAS* 91(1):215–219; Kass-Eisler et al., 1993, *PNAS* 90(24): 11498–502; Guzman et al., 1993, *Circulation* 88(6):2838–48; Guzman et al., 1993, *Cir. Res.* 73(6) :1202–1207; Zabner et al., 1993, *Cell* 75(2):207–216; Li et al., 1993, *Hum. Gene Ther.* 4(4):403–409; Caillaud et al., 1993, Eur. J. Neurosci. 5(10):1287–1291; Vincent et al., 1993, *Nat. Genet.* 5(2):130–134; Jaffe et al., 1992, *Nat. Genet.* 1(5):372–378; and Levrero et al., 1991, *Gene* 101 (2):195–202; and WO 93/07283; WO 93/06223; and WO 93/07282. Exemplary known adenoviral gene therapy vectors employable in this invention include those described in the above referenced documents and in PCT Patent Publication Nos. WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922 and WO 95/09654. Alternatively, administration of DNA linked to killed adenovirus as described in Curiel, 1992, *Hum. Gene Ther.* 3:147–154, may be employed.

Gene delivery vehicles of the present invention also include herpes vectors. Representative examples of such vectors include those disclosed by Kit in *Adv. Exp. Med. Biol.* 15:219–236, 1989; and those disclosed in U.S. Pat. No. 5,288,641 and EP 0176170 (Roizman). Additional exemplary herpes simplex virus vectors include HFEM/ICP6-LacZ disclosed in WO 95/04139 (Wistar Institute), pHSVlac described in Geller, 1988, *Science* 241:1667–1669, and in WO 90/09441 and WO 92/07945; HSV Us3::pgC-lacZ described in Fink, 1992, *Human Gene Therapy* 3:11–19; and HSV 7134, 2 RH 105 and GAL4 described in EP 0453242 (Breakefield), and those deposited with the ATCC as accession numbers ATCC VR-977 and ATCC VR-260.

Gene delivery vehicles may also be generated from a wide variety of other viruses, including for example, poliovirus (Evans et al., 1989, *Nature* 339:385–388; and Sabin, 1973, *J. Biol. Standardization* 1: 115–118); rhinovirus, pox viruses, such as canary pox virus or vaccinia virus (Fisher-Hoch et al., 1989, *PNAS* 86:317–321; Flexner et al., 1989, *Ann. N.Y. Acad. Sci.* 569:86–103; Flexner et al., 1990, *Vaccine* 8:17–21; U.S. Pat. Nos. 4,603,112, 4,769,330 and 5,017,487; WO 89/01973); SV40 (Mulligan et al., 1979, *Nature* 277:108–114); influenza virus (Luytjes et al., 1989, *Cell* 59:1107–1113; McMicheal et al., 1983, *N. Eng. J. Med.* 309:13–17; and Yap et al., 1978, *Nature* 273:238–239); SV40; HIV (Poznansky, 1991, *J. Virol.* 65:532–536); measles (EP 0 440,219); astrovirus (Munroe et al., 1993, *J. Vir.* 67:3611–3614); and coronavirus, as well as other viral systems (e.g., EP 0,440,219; WO 92/06693; U.S. Pat. No. 5,166,057). In addition, viral carriers may be homologous, non-pathogenic(defective), replication competent virus (e.g., Overbaugh et al., 1988, *Science* 239:906–910), and nevertheless induce cellular immune responses, including CTL.

4. Non-viral Gene Delivery Vehicles

Other gene delivery vehicles and methods that may be employed such as, for example, nucleic acid expression vectors; polycationic condensed DNA linked or unlinked to killed adenovirus alone, for example see U.S. Ser. No. 08/366,787, filed Dec. 30, 1994, and Curiel, 1992, *Hum Gene Ther* 3:147–154; ligand linked DNA, for example see Wu, 1989, *J Biol Chem* 264:16985–16987; eucaryotic cell delivery vehicles cells, for example see U.S. Ser. No. 08/240,030, filed May 9, 1994, and U.S. Ser. No. 08/404, 796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, 1994. *Mol Cell Biol* 14:2411–2418, and in Woffendin, 1994, *Proc. Natl. Acad. Sci.* 91:1581–1585.

Particle mediated gene transfer may be employed, for example, see U.S. provisional application No. 60/023,867. Briefly, the sequence of interest can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialooroso-mucoid. as described in Wu and Wu, 1987, *J. Biol. Chem.* 262:4429–4432, insulin as described in Hucked, 1990, *Biochem Pharmacol* 40:253–263, galactose as described in Plank, 1992, *Bioconjugate Chem* 3:533–539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, PCT Patent Publication Nos. WO 95/13796, WO 94/23697, and WO 91/144445, and European Patent Publication No. 524,968. As described in U.S. provisional application No. 60/023,867, nucleic acid sequences can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., 1994, *Proc. Natl. Acad. Sci. USA* 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

Exemplary liposome and polycationic gene delivery vehicles are those described in U.S. Pat. Nos. 5,422,120 and 4,762,915, in PCT Patent Publication Nos. WO 95/13796, WO 94/23697, and WO 91/14445, in European Patent Publication No. 524,968 and in Starrier, *Biochemistry, pages 236–240* (1975) W. H. Freeman, San Francisco; Shokai, *Biochem Biophys Acct* 600:1, 1980; Bayer, 1979, *Biochem Biophys Acct* 550:464: Rivet, 1987, *Meth Enzyme* 149;119; Wang, 1987, *Proc Natl Acad Sci* 84:7851; Plant, 1989, *Anal Biochem* 176:420.

B. Construction of Recombinant Gene Delivery Vehicles Expressing Therapeutic Proteins The gene delivery vehicles of the invention can be administered by intravenous delivery or by other methods described herein in order to induce long term in vivo expression of a variety of therapeutic proteins. As is demonstrated in Examples 18–24 herein, administration of a retroviral vector intravenously results in sustained, long-term systemic expression of therapeutic genes expressed by the retroviral vector. Thus, methods for obtaining long-term systemic expression in vivo of a variety of proteins known to one of skill in the art are encompassed by the instant invention. Preferably, long-term in vivo systemic expression is obtained by intravenous delivery methods as is described in detail below (see Section H of this application). For long term expression from a retroviral vector in vivo, the action of human complement on the retroviral vector is suppressed. This can be done by a variety of techniques known to one of skill in the art. Preferably, human packaging cell lines are used in order to inhibit the action of human complement on the retroviral vector particles (see PCT publication number US 91/06852, entitled "Packaging Cells"). The terms "human complement resistant" or "resistance to human complement" when applied to a gene delivery vehicle such as a retroviral vector means that the vectors is at least 70% resistant, more preferably 80% resistant and most preferably at least 90% resistant to inactivation by human complement when tested in a standard serum inactivation assay as described in Example 11 herein.

The production of high titer preparations of recombinant retroviral vectors is described in detail herein. The term "high titer retroviral vector preparation" as used herein refers to a retroviral vector preparation that has a titer greater than $10^6$ cfu/ml, more preferably greater than $10^7$ cfu/ml, still more preferably greater than $10^8$ cfu/ml, more preferably greater than $10^9$ cfu/ml, yet more preferably greater than $10^{10}$ cfu/ml, and most preferably greater than $10^{11}$ cfu/ml when tested on HT1080 cells in the assay for colony forming units on HT1080 cells as is described herein. This assay depends on the expression a marker protein to determine cfu/ml. The term "cfu" refers to "colony forming units" when vectors contain a selectable marker. The term refers to identifiable colonies when a phenotypically observable marker is used, such as blue colonies when the marker is beta-galactosidase. In some cases, for example for factor VIII vectors, when no marker gene is present, "cfu" refers to units measured by a PCR-based titer. Briefly, HT1080 cells are transduced with the markerless vector and number of proviral DNA copies are measured by quantitative PCR; HT1080 cells transduced with a retroviral vector containing the neomycin resistance gene are used as a standard (see Section F of the Detailed Description, herein).

The terms "long term systemic expression" or "sustained systemic expression" as used herein in reference to in vivo expression of protein encoded by a retroviral vector mean measurable or biologically active expression into the bloodstream for 30 days, more preferably for 60 days, yet more preferably for 90 days, and more preferably for six months, still for preferably for 1 year, more preferably for at least 5 years after administration of the retroviral vector particle to a host. Most preferably, the expression would be for the life of the patient such that the retroviral vector would only need to be administered to the patient once, or that "booster" injections would have to be delivered to the patient only a few times during the lifetime of the patient. The term "measurable expression" as used herein in reference to in vivo expression of a protein encoded by a retroviral vector means that the protein is produced in sufficient amounts so as to be detectable in biological fluids such as serum by an assay specific for the expressed protein. The term "systemic expression" as used herein means that the proteins are expressed into the circulation and are thus useful for treatment of certain diseases. A variety of diseases discussed in detail below are amenable to treatment by this type of gene therapy.

For example, measurement of human growth hormone can be determined by an ELISA assay specific for human growth hormone protein as described in Example 19 herein. The term "biologically active expression" or "protein expression in biologically or therapeutically active amounts" when used herein in reference to in vivo expression of a protein encoded by a retroviral vector means that protein is produced in sufficient amounts so as to be detectable in a functional assay. For example, expression of factor VIII can be measured in a clotting assay as described in Example 18, herein. Similarly other expressed proteins can be measured by specific assays for each particular protein that are known to those of skill in the art. Long-term in vivo expression of a variety of proteins can be effected by the methods of the invention, preferably by in vivo administration of high titer retroviral vectors as described herein. A large variety of different proteins can be expressed for therapeutic applications in a number of different disease states. Preferred proteins include, cytokines and immune system modulators, hormones, growth factors, vaccine antigens, and proteins for treatment of inherited diseases.

1. Gene Delivery Vehicles Expressing Human Factor VIII and Factor IX for Treatment of Hemophilia Preparation of retroviral vectors expressing a B-domain deleted factor VIII protein are described in detail in the Example section of this application (see Examples 1, 2, 27 and 28 herein). In particular, these examples demonstrate the insertion of a particular factor VIII deletion called the SQN deletion the construction of which is described in Example 2 herein, and which is further described in detail in PCT WO 91/09122.

The B domain separates the second and third A domains of factor FVIII in the newly synthesized single-chain molecule. The B domain extends from amino acids 712 to 1648 according to Wood et al., 1984, Nature 312:330–337. Proteolytic activation of factor VIII involves cleavage at specific Arg residues located at positions 372, 740, and 1689. Cleavages of plasma factor VIII by thrombin or Factor Xa at Arg 372 and Arg 1689 are essential for factor VIII to participate in coagulation. Therefore, activated factor VIII consists of a heterodimer comprising amino acids residues 1–372 (containing the A1 domain) and residues 373–740 (containing the A2 domain), and residues 1690–2332 (containing the A3-C1-C2 domain). An important advantage in using the B domain deleted FVIII molecule is that the reduced size appears to be less prone to proteolytic degradation and therefor, no addition of plasma-derived albumin is necessary for stabilization of the final product. The term "B domain deletion" as used herein with respect to factor VIII protein refers to a factor VIII protein in which some or all removal of some or all of the amino acids between residues 711 and 1694 have been deleted, and which still preserves a biologically active FVIII molecule.

A range of B domain deletions can exist depending on which amino acid residues are in the B domain is deleted and whereby the biological activity of the FVIII molecule is still preserved. A specific B domain deletion called the SQN exists which is created by fusing Ser 743 to Gln 1638 (Lind et al., 1995, Eur J. Biochem 323:19–27, and PCT WO 91/09122). This deletes amino acid residues 744 to 1637 from the B domain creating a Ser-Glu-Asn (SQN) link between the A2 and A3 FVIII domains. When compared to plasma-derived FVIII, the SQN deletion of the B domain of FVIII did not influence its in vivo pharmacokinetics (Fijnvandraat, et. al., P.R.Schattauer Vertagsgesellschatt mbH (Stuttgart) 77:298–302, 1997). The terms "Factor VIII SQN deletion" or "SQN deletion" as used herein refer to this deletion and to other deletions which preserve the single S-Q-N tripeptide sequence and which result in the deletion of the amino acids between the two B-domain SQN sequences (See PCT WO 91/09122 for a description of this amino acid sequence).

There are number of other B-domain deleted forms of factor VIII. cDNA's encoding all of these B-domain deleted factor VIII proteins can be inserted into retroviral vectors by using standard molecular biology techniques similar to those described in Examples 1, 2, 27 and 28 herein. For example cDNA molecules encoding the following B-domain factor VIII deletions can be constructed as described below:

| | |
|---|---|
| Eaton (1986) Biochemistry 25:8343 | des 797–1562 deletion |
| Toole (1986) PNAS 83:5939 | des 760–1639 (LA-FVIII) |
| Meutien (1988) Prot Eng 2:301 | des 771–1666 (FVIII del II: missing one thrombin site) |
| Sarver (1987) DNA 6:553 | des 747–1560 |
| Mertens (1993) Br J Haematol 85:133 | des 868–1562 |
| | des 713–1637 (thrombin resistant) |
| Esmon (1990) Blood 76:1593 | des 797–1562 |
| Donath (1995) Biochem J 312:49 | des 741–1668 |
| Webb (1993) BBRC 190:536 | PCR cloned from mRNA |
| Lind (1995) Eur J Biochem 232:19 | des 748–1648 (partially processed) |
| | des 753–1643 (partially processed) |
| | des 777–1648 (partially processed) |
| | des 744–1637 (FVIII-SQ) |
| | des 748–1645 (FVIII-RH) |
| | des B-domain + 0, 1, 2 Arg (partially processed) |
| | desB, +3Arg (FVIIIR4) |
| | desB, +4Arg (FVIIIR5) |
| Langner (1988) Behring Inst Mitt 16–25 | des 741–1689 des 816–1598 |
| Cheung (199,6) Blood 88:325a | des 746–1639 |
| Pipes (1996) Blood 88:441a | des 795–1688 (thrombin sites mutated) |

Figure 37:
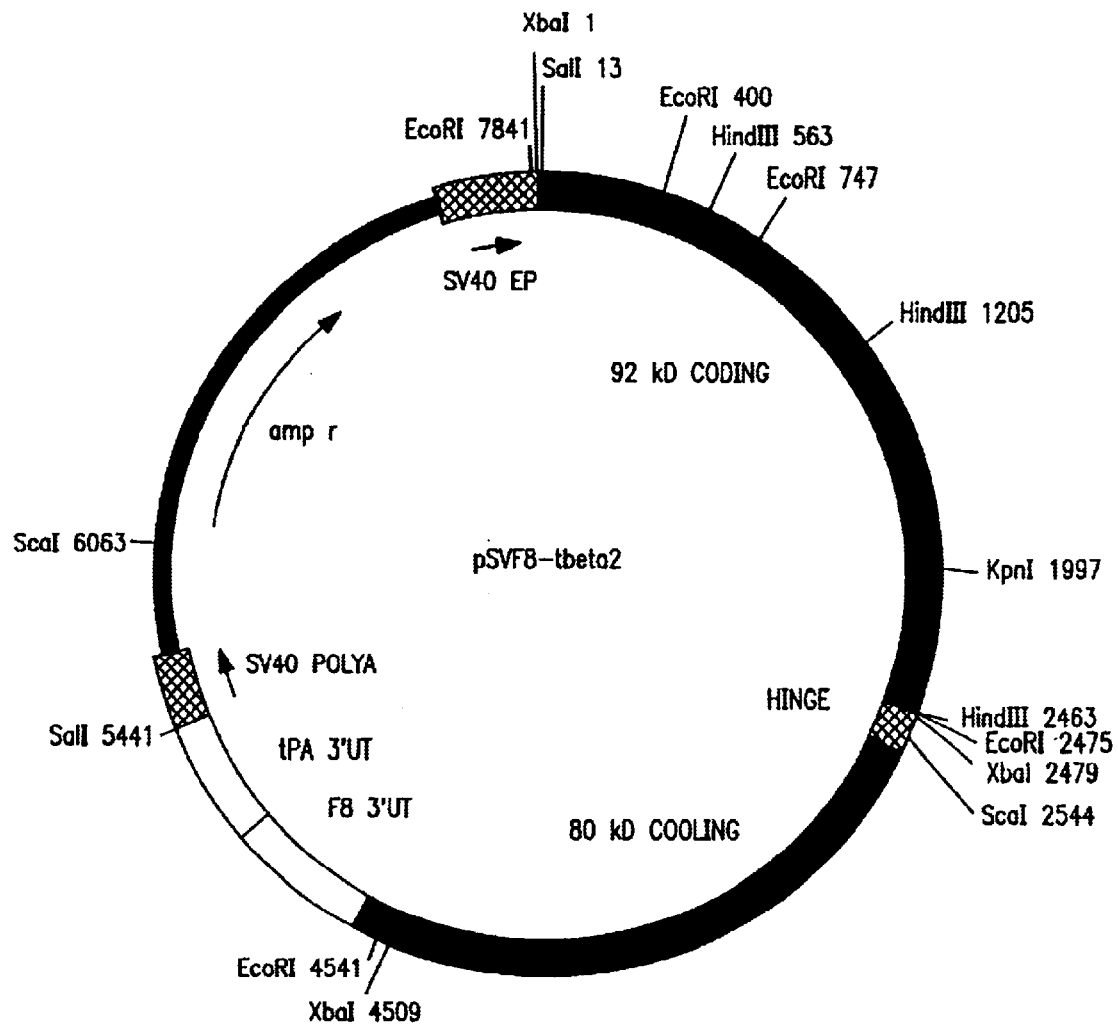
FIG. 37: Schematic representation of pSVF8-tβ2.

A B domain deletion in which an IgG hinge region has been inserted can also be used. For instance, a deletion of this type can be obtained from plasmid PSVF8-tβ2. PSVF8-tβ2 is a plasmid, which was designed to link the heavy and light chains with a short hinge region from immunoglobulin A (see FIG. 37). To obtain cleavage at the end of the heavy chain and to release the light chain, some residues of the β domain were included on either side of the hinge sequence. The 5' untranslated leader and signal peptide are from the human Factor VIII:C cDNA, with the Kozak consensus sequence at the initiation codon as in pSVF8-302. A description of this vector is included in Chapman et al., U.S. Pat. No. 5,595,886. The 3' untranslated region is the same fused Factor VIII and tPA sequence as found in pSVF8-80K.

The construction was completed in two steps: an oligomer with cohesive ends for EcoRI and BclI (117 bp) was cloned into a transfer vector, pF8GM7, the DNA sequence of the oligomer was checked by m13 subcloning and Sanger sequencing.

Next, the final plasmid was assembled by ligation of the following three fragments:

(a) FspI-EcoRI fragment form pSVF8-92S;
(b) EcoRI-NdeI fragment of the transfer vector pF8GM7 with oligomer; and
(c) FspI-NdeI fragment of pSVF8-80K.

Descriptions of pSVF8-92S and pSVF8-80K are included in Chapman et al., U.S. Pat. No. 5,595,886. The sequence linking the heavy and light chains is shown in FIG. 38.

Three additional B domain-deleted factor VIII constructs of particular interest for inclusion in the gene delivery vehicles of the invention can be prepared as follows. Plasmid pSVF8-500 encodes a factor VIII protein with amino acids 770 to 1656 of the full length Factor VIII deleted, according to the nomenclature used in Seq ID No. 45. In addition the threonine at position 1672 of the full-length factor VIII sequence of Seq ID No. 45 was also deleted. The following is a description of the construction of the vector.

The pSVF8-500 plasmid is a derivative of pSVF8-302 in which the regions coding for the 92K and 80K domains are fused with a small connecting β-region of 21 amino acids, retaining the natural proteolytic processing sites. This plasmid was constructed in the following manner:

(1) A SalI-KpnI fragment of 1984 bp containing the region coding for the 92K protein (except for the carboxyl terminal end) and BstXI-SalI fragment of 2186 bp containing the region coding for the carboxyl end of the 80K protein with 3' end untranslated region were isolated by gel electrophoresis after digestion of pSVF8-302 with restriction enzymes.

(2) A BclI-BstXI fragment of 1705 bp containing most of the region coding for the 80K protein was isolated after gel electrophoresis of the BamHI-XbaI fragment of pUC12F8. (pUCF812 is prepared from pF8-102 which is described in U.S. Pat. No. 5,045,455. pF8-102 is digested with Bam-XhaI and ligated into vector pUC12 by in vitro mutagenesis at a BclI site using the following primer: 5' ACT ACT CTT CAA TCT GAT CAA GAG GAA 3' (Seq ID No. 52).

(3) A KpnI-EcoRI fragment containing the carboxyl end of the 92K protein and part of the β region (4 amino acids) was obtained by digestion of the SalI cassette from pSVF8-302 with KpnI and EcoRI.

(4) Ligation of four pieces of synthetic DNA (shown in FIG. 39) to the fragments of steps (2) and (3) and digestion with KpnI.

(5) Final ligation of fragments from steps (1) and (4); digestion with SalI and gel purification of the 6428 bp SalI cassette.

Figure 40A:
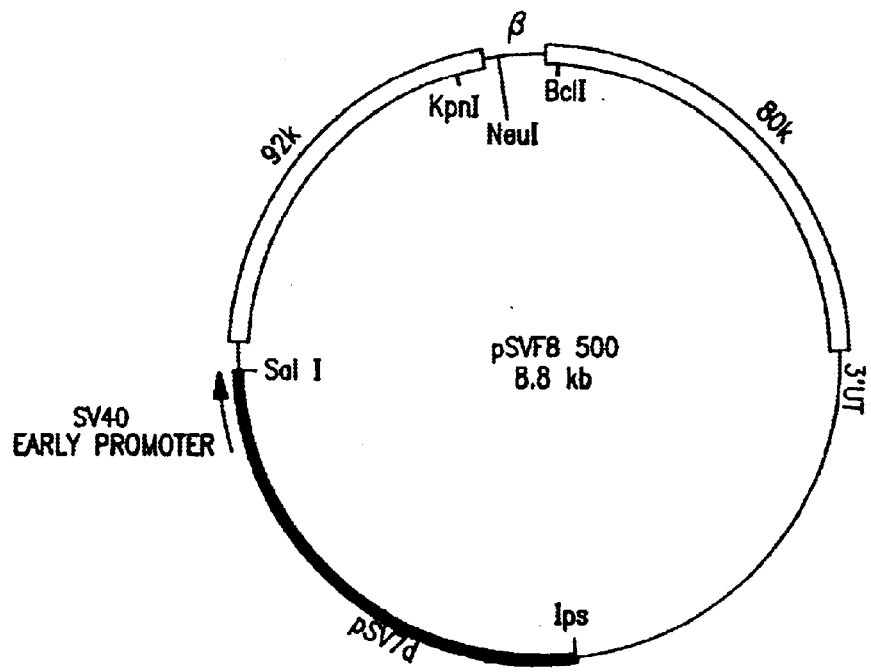
FIG. 40: Schematic representation of pSVF8500 and pc1/1 AGαF8-500.
Figure 40B:
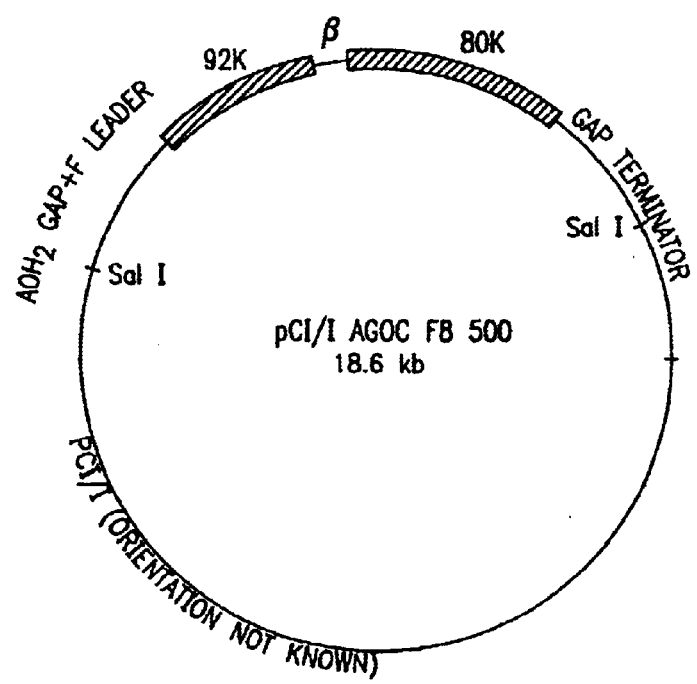

(6) Ligation of the SalI cassette into pSV7d vector; transformation of HB101 and colony hybridization to isolate pSVF8-500 (FIG. 40). The sequence of the junction region coding for 92K-β-80K was verified by DNA sequence after cloning in M13.

Note that the sequence in the linker shown in FIG. 39 is different from wild type human Factor VIII. The sequence was changed to incorporate unique NruI and MluI restriction sites without changing the amino acid sequence. These sites were alsoused to construct other two additional B-domain deleted vectors which are described below.

pSV500BΔThr was constructed from pSVF8-500. The threonine deletion at position 1672 was maintained. The synthetic linker shown in FIG. 41 was used to construct pSV500BΔThr. The linker extends from a unique NruI site at Ser(765) to a unique MluI site at Ile(1659) in the pSVF8-500 vector. This linker was substituted for the corresponding region of pSVF8-500.

A third vector pSVF8-500B was constructed from pSV500BΔThr. This vector is identical to pSVF8-500B except that the codon for threonine 1672 was re-inserted using standard mutagenesis methods. The relationship between, pSVF8-500B, pSVF8-500B, is further illustrated in the table below. Amino acid sequence numbers in the table were determined by reference to full-length factor VIII sequence depicted in Seq. ID No. 45.

| Name | Amino Acids Deleted | Thr at 1672 Deletion |
|---|---|---|
| pSVF8-500 | 770 to 1656 | Yes |
| pSVF8-500BΔThr | 779 to 1658 | Yes |
| PSVF80-500B | 779 to 1658 | No |

In all cases, the BglII-PflI 1.35 kb fragments of each modified cDNA listed above can be inserted into the retroviral vectors described herein using standard molecular biology procedures known to those of skill in the art and described herein. For instance, cDNA clones containing the B domain-deleted factor VIII proteins can be excised and used to replace the BglII to PflI fragment in the retroviral vectors described in examples 27 and 28 herein. A similar procedure can be used to construct other retroviral vectors, including those described in section A, above.

The full-length factor VIII cDNA can also be inserted into the retroviral vectors of the invention as described in Example 2 herein and in WO 96/21035 which is hereby incorporated by reference in its entirety. In addition, the full-length human factor VIII cDNA can be derived from the construct pSV7dF8-200 or pSV7dF8-300 described in Example 28, herein. This can be constructed similarly to the retroviral vector expressing the B-domain deleted factor VIII described in Example 28 where the cDNA fragment is cloned into the BglII/PflI linearized vector. For instance, an AccI to XbaI 5.9 kb fragment can replace the 3.15 kb AccI to XbaI fragment of the modified cDNA in F8:4213. The construction of the retroviral vector can then essentially follow the steps described in Example 28. A variety of Factor VIII deletions, mutations, and polypeptide analogs of Factor VIII can also be introduced into the gene delivery vehicles of the invention including retroviral vectors by modifications of the procedures described herein. These analogs include, for instance, those described in PCT Patent Publication Nos. WO 97/03193, WO 97/03194, WO 97/03195, and WO 97/03191, all of which are hereby incorporated by reference.

Other vectors expressing B domain deleted factor VIII or full-length factor VIII can be constructed using techniques known to those of skill in the art or described herein. For instance, adenoviral vectors expressing B-domain deleted factor VIII molecules can be constructed as described in WO 94/29471. Gene delivery vehicles derived from adenovirus are also provided, in which the factor VIII gene, or its various derivatives as described herein, is inserted into a variety of adenovirus-derived vectors, and subsequently recombinant vector particles are generated as described. The adenovirus vectors of the invention also include the following vectors constructed to express factor VIII proteins.

The prototype recombinant adenovirus vectors were deleted in the early region one, [E1a/E1b, (E1)] region, rendering them replication defective. Following insertion of a gene of interest into the deleted region, propagation of the recombinant E1-deleted adenovirus vector is accomplished in 293 cells, a complementing human embryonic kidney cell line stably transformed with the Ad E1 region, which provide these Ad gene products in trans. Recombinant Ad vectors generated in this fashion can yield preparations with titers between $10^{11}$ to $10^{13}$ particles/ml (Reviewed in Berkner, 1988, *Biotechniques* 6:616–629). However there are several drawbacks to this prototype Ad vector system, including: (1) restriction of heterologous genetic material to approximately 4.5 to 5.0 kb, and (2) partial replication competence of the E1-deleted Ad vectors (Rich, 1993, *Hum.*

*Gen. Ther.* 4:461–476). This later point arises in part to a complementing "E1-like activity" that is expressed in human cells, and results in the expression of other viral gene products present in these vectors, including the highly immunogenic, "late", or structural gene products (e.g. penton protein). As a result of immune responses of the recipient to Ad-specific proteins expressed by the E1-deleted vectors, expression of the heterologous gene, or transgene is transient and associated with the development of pathology at the site of gene transfer.

Thus, second generation Ad vectors have sought to further "cripple" the capacity of the vector to replicate, and express viral-specific gene products, and to increase the capacity of heterolgous genetic material. Such vectors have been of three types: (1) E1 and E3 genes deleted [Bett, *PNAS,* 91:8802–8806, 1994], (2) E1 and E4 genes deleted (Wang, 1995, *Gene Ther.* 2:775–783, and PCT Patent Publication Nos. WO 96/22378 and WO 95/02697), and (3) deletion of all Ad viral genes, or "gutless" (Fisher, 1996, *Virology,* 217:11–22; Hardy, *J. Virol,* 71:1842–1849, and Kochanek, 1996, *PNAS,* 93:5731–5736). The duration of transgene expression in animals inoculated with these second generation recombinant adenovirus vectors has been dramatically increased, as a result of the mitigation of the recipient's immune response.

As expected, increased deletion of viral-specific genes in the second generation Ad vectors has also resulted in an increased capacity for heterologous genetic material, thus extending the usefulness of this system for application to human gene transfer. This capacity for heterologous genetic material is approximately 8 kb in the E1/E3 and E1/E4 vectors, and is greater than 30 kb for the "gutless" Ad vectors, permitting the insertion of entire genes, including relevant gene expression control regions.

Generation of recombinant Ad vectors, including the E1/E3, E1/E4, and "gutless" vectors, harboring the full-length factor VIII gene, or its B-domain derived derivatives, can be accomplished according to methods well-known to those skilled in the art. For example: (1) the full-length factor VIII gene, or its B-domain derived derivatives can be inserted into plasmid pBHG11 (Bett, 1994, *PNAS* 91:8802–8806), and recombinant E1/E3-deleted Ad vectors are generated after transfection of 293 cells and subsequent intracellular homologous recombination, (2) the full-length factor VIII gene, or its B-domain derived derivatives can be first substituted into the E1 region of any of a variety of E1-deleted Ad vectors and co-transfected with Cla I digested H5dl1014, and recombinant E1/E4-deleted Ad vectors are generated after transfection of 293-E4 cells [Wang Gene Ther., 2:775–783, (1995)], and subsequent intracellular homologous recombination, (3) the full-length factor VIII gene, or its B-domain derived derivatives is first inserted into the ΔrAd plasmid [Fisher, 1996, *Virology,* 217:11–22), along with appropriate amounts of "stuffer" sequence derived from, for example, bacteriophage lambda DNA, to permit efficient packaging of recombinant "gutless" adeonvirus vector genomes, transfected onto 293 cells and infected with H5.CBALP helper virus (Yang, 1995, *Virol.* 69:2004–2015). Purification of recombinant "gutless" adeonvirus vector particles from helper virus can be accomplished, for example, by centrifugation over a cesium gradient, as a result of a buoyant density lower than that of helper virus.

In the case of adeno-associated viral vectors, preferably a factor VIII heavy chain and light chain are inserted into separate vectors, as is demonstrated in Examples 29 and 30 herein. Other adenoviral vectors including those described above and in co-owned U.S. serial No. 60/025,649 can be constructed to express factor VIII light chain and heavy chain using the techniques described in Examples 29 and 30. Heavy and light chain constructs for inclusion into the AAV vectors of the invention can be prepared for instance as described in Chapman et al., U.S. Pat. No. 5,595,886.

Hemophilia B can also be treated with systemically administered factor IX-expressing gene delivery vehicles including retroviral vectors. Human factor IX deficiency (Christmas disease or Hemophilia B) affects primarily males because it is transmitted as sex-linked recessive trait. It affects about 2000 people in the US. The human factor gene codes a 416 amino acids of mature protein.

The human factor IX cDNA can be obtained for instance by constructing plasmid pHfIX1, as described by Kurachi and Davie, 1982, *PNAS* 79(21):6461–6464. The cDNA sequence can be excised as a PstI fragment of about 1.5 kb, blunt ended using T4 DNA polymerase. The factor cDNA fragment can be readily inserted, for example into a SrfI site introduced into a retroviral vector. For instance the cDNA fragment can be inserted into the SrfI site of a linearized pMBA retroviral vector using the procedure described in Examples 27 and 28 herein. In this case, the resulting retroviral vector: pMB-F9 will be produced from HA11 cells and its expression will be determined using HT1080 fibroblasts as target cells.

Similarly, the full-length factor IX cDNA fragment can be introduced into other gene delivery vehicles described herein, such as adenoviral vectors and AAV vectors. In the case of adneoviral vectors, vectors expressing factor IX can be produced, for instance, as described in. For instance, adenoviral vectors expressing B-domain deleted factor VIII molecules can be constructed as described in WO 94/29471. Adenoviral vectors expressing factor IX protein can be produced by methods similar to those described above for factor VIII protein.

In the case of AAV vectors, a factor IX cDNA can be inserted into vectors using, for instance, procedures similar to those described in Examples 29 and 30 herein for factor VIII heavy and light chains. Other adenoviral vectors including those described above and in co-owned U.S. provisional application No. 60/025,649 can be constructed to express factor VIII light chain and heavy chain using the techniques similar to those of Examples 29 and 30.

2. Gene Delivery Vehicles Expressing Other Clotting Factors (a) Factor V Vectors For Treatment or Prophylaxis of Thrombosis Due to APC Resistance The present invention provides for needed therapy and prophalaxis of these and other disorders of thrombosis and hypercoagulation by delivery of gene delivery vehicles expressing factor V. Blood coagulation consists of a series of sequential activations of circulating serine protease zymogens, culminating the activation of prothrombin to form thrombin and the subsequent generation of fibrin, the substance of the clot. Two of these reactions, the activation of prothrombin and factor X, require the participation of the large proteinaceous cofactors, factors Va and VIIIa, respectively. The serine protease zymogen, Protein C, exerts its anticoagulant effect when it is cleaved by thrombin to form activated protein C. Activated protein C (APC) destroys the activity of factors Va and VIIIa through cleavage at specific arginine residues. Genetic deficiencies of protein C or its cofactor, protein S, account for ~5–10% of cases of familial thrombophilia. In 1993, Dahlback, 1993, *PNAS* 90:1004. described a new form of thrombophilia, called activated protein C resistance (APC resistance) in which added APC failed to prolong the clotting times of patients' plasmas. This was subsequently shown to account for up to 40% of cases of familial thrombophilia, making it the most common form of inherited disposition to thrombosis (Sun et al., 1994, *Blood* 83:3120). >95% of APC resistance cases result from a single point mutation in factor V, R506Q (Bertina et al., 1994, Nature 369:64, and Greengard et al., 1994, *Lancet* 343:1361). This mutation was subsequently found to be present in various healthy European populations at a level of 1–10% (Svensson et al., 1994, *New Engl J Med* 300:517; Griffin et al., 1993, *Blood* 82:1989; Koster et al., Lancet 342:1503), and presence/absence of symptoms can vary considerably in a family with numerous homozygotes (Greengard et al., 1995, *New Engl J Med* 331:1559), underscoring the multifactorial nature of thrombotic disease. Rosendaal et al., 1995, *Blood* 85: 1504, estimated the relative risk of thrombosis in a heterozygote for APC resistance as seven-fold, and for homozygotes as 80-fold.

Greengard et al. described (*Thromb Haemostas* (1995) 73:1361 (abs)) carrying both a null allele for factor V deficiency and APC resistance. Since these two factor V defects assorted independently, they represented two different factor V alleles. The compound heterozygotes had circulating factor V derived only from the APC resistant factor V allele, and two of the three symptomatic family members had this "pseudohomozygous" genotype. Other family members with only factor V deficiency had no thrombosis. While not wishing to be bound by theory, the risk factor of an APC resistance allele can be compensated in some cases by the mere presence of some normal (APC responsive) factor V. Thus, delivery of factor V by the gene delivery vehicles and the therapeutic methods of the invention to provide normal factor V can be of therapeutic benefit even in the presence of the same amount of resistant factor V, perhaps due to this mechanism.

Gene delivery vehicles, including retroviral vectors can be constructed using molecular biology techniques known to those of skill in the art. For instance, Factor V cDNA is obtained from pMT2-V (Jenny, 1987, *Proc. Natl. Acad. Sci. USA* 84:4846; ATCC deposit #40515) by digestion with SalI. The 7 kb cDNA band is excised from agarose gels and cloned into retroviral vectors, using standard molecular biology techniques. For example, the factor V cDNA insert can be cloned into the SalI site of SalI digested pBA9 vector as described for insertion of a factor VIII fragment in Example 28 herein.

Either a full-length or a B-domain deletion or substitution of the factor V cDNA can be expressed by the gene therapy vectors of the invention. Factor V B-domain deletions such as those reported by Marquette, 1995, *Blood* 86:3026, and Kane, 1990, *Biochemistry* 29:6762, can be made as described by these authors.

(b) Antithrombin III Vectors for Treatment or Prophylaxis of Deficiency or Other Hypercoagulable States The central enzyme of the coagulation pathways, thrombin, acts directly through cleavage of fibrinogen to form fibrin, the substance of the clot, or indirectly through positive feedback mechanisms involving activation of other clotting factors. The most commonly used acute-phase anticoagulant used is heparin, most of whose effects are mediated through augmentation of the inhibition of thrombin. The major thrombin inhibitor in plasma is antithrombin III (ATIII). The frequency of ATIII deficiency is as high as 1:500 (Tait, 1990, *Br J Haematol* 75:141). Although most cases are clinically silent, deficiency may pose a risk factor synergistic with others. Most patients are treated with oral anticoagulants, supplemented by ATIII concentrates for surgery or other major trauma (Winter, 1981, *Br J. Haematol* 49:449–457). Oral anticoagulation is considered an inconvenient and inadequate treatment for hypercoagulable states, while plasma-derived proteins carry the risk of transmittal of infectious agents and other problems. Acquired deficiencies of ATIII are more frequent, such as in premature infants, L-asparaginase therapy for leukemia, DIC, sepsis, nephrotic syndromes, traumatic bleeding, severe burns, malignancies, ARDS, DVT/PE, and enteropathies. Concentrates have been used for animal models of some of these conditions (Emerson, 1994, *Blood Coag Fibrinol* 5:37). The use gene therapy to deliver ATIII using the methods described herein can provide useful therapy, particularly in ATIII deficiency states.

Gene delivery vehicles including retroviral vectors capable of expressing ATIII cDNA can be readily constructed using standard molecular biology techniques known to those of skill in the art. For instance a retroviral vector expressing AT III can be constructed from the vector pKT218 (Prochownik, 1983, *J. Biol. Chem.* 258:8389; ATCC number 57224/57225) by excision with PstI. The 1.6 kb cDNA insert can be recovered from agarose gels and cloned into the PstI site of vector SK–. The insert can be recovered by restriction enzyme digestion and cloned into retroviral vectors described herein by the restriction enzymes. For instance, the AT III insert can be excised by XhoI/NotI digestion and cloned into the XhoI/NotI digested pMBA vector described in Example 27 herein to form pMBA-AT3.

(c) Protein C Vectors for Treatment or Prophylaxis of Deficiency or Other Hyercoapulable States As described above, protein C is a serine protease zymogen that acts to downregulate the coagulation cascade. Its deficiency is associated with increased risk of recurrent thrombosis, purpura fulminans, and warfarin-induced skin necrosis (Bauer, in Disorders of Hemostasis, Ratnoff & Forbes (Eds), W B Saunders, Philadelphia (1996)). The incidence of heterozygosity is as high as 1/200 (Miletich, 1987, *New Engl J. Med.* 317:991). Although most cases are clinically silent, deficiency may pose a risk factor synergistic with others. Recombinant protein C is administered on a compassionate basis to severely affected homozygotes (Minford, 1996, *Br J Haematol* 93:215). Homozygotes and symptomatic heterozygotes could be treated more effectively by retroviral-mediated gene delivery. In addition, there is evidence to suggest that augmenting levels of activated protein C (APC) could play a major role in prevention of thrombosis in patients with other causes (genetic or acquired) of hypercoagulability. Gruber (Blood 79:2340(1992)) showed that low levels of APC circulate in the plasma of normals, and speculated that basal levels of APC serve to downregulate coagulation in response to low-level prothrombotic signals. The ratio of circulating endogenous APC level to protein C zymogen level was lower in protein C-deficient individuals with history of thrombosis than in their thrombosis-free relatives, but in general APC levels overall are proportional to the zymogen protein C levels (Espana, 1996, *Thrombos Haemostas* 75:56–61). While not wishing to be bound by theory, it may be that gene therapy vectors which express protein C in non-deficient individuals at risk for thrombosis from other causes will have a protective effect in individuals with normal levels of protein C due to this mechanism. An artificial variant of protein C, HPC-FLINQ (Richardson, 1992, *Nature* 360:261; Kurz, 1997, *Blood* 89:534) was recently described with an enhanced activation profile in the presence of thrombin without the normally required cofactor, thrombomodulin (see below), so that APC was generated in the presence of thrombin levels attained during the clotting of plasma. In addition, HPC-S460A, a second artificial variant of human protein C, has a normal activation profile but a much lowered propensity for subsequent inhibition by plasma serpins. While not wishing to be bound by theory, since binding to serpins is the major mechanism for removal of APC from the circulation, the nonenzymatic anticoagulant activity demonstrated for this variant (Gale, 1997, *Prot. Sci.* 6:132) may be preferred due to have a significantly prolonged plasma half-life upon activation. Yet another approach was taken by Ehrlich, 1989,*J. Biol. Chem.* 264:14298, who made a variant of protein C that would became activated during the process of secretion, resulting in secretion of the activated enzyme. In particular, delivery of these variants by the means of gene therapy vectors and the gene therapy methods described herein are useful in reducing thrombosis in individuals at risk.

The gene delivery vehicles of the invention, including retroviral vectors, capable of expressing Protein C can be made using techniques known to those of skill in the art. For instance, protein C cDNA will be obtained by restriction enzyme digestion of published vector (Foster, 1984, *Proc. Natl. Acad. Sci. USA* 81:4766; Beckmann, 1985, *Nucleic Acids Res* 13:5233). The 1.6 kb cDNA insert can be recovered from agarose gels and cloned into the multiple cloning site of vector SK- under standard conditions. The insert can be recovered by restriction enzyme digestion and cloned into a retroviral vector; for example, excision by XhoI/NotI digestion followed by cloning into XhoI/NotI digested retroviral vector. For instance, the protein C DNA fragment can be cloned into the XhoI/NotI digested pMBA vector described in Example 27 herein to form pMBA-PC. In some cases, variants of protein C will be constructed prior to cloning into the vector backbone, as described in Ehrlich, Richardson, Kurz, Gale publications cited above.

(d) Prothrombin Vectors for Treatment or Prophylaxis of Hypercoagulable States

As described-above, the normal protein C anticoagulant pathway requires activation by the enzyme thrombin. Thrombin is normally a procoagulant enzyme which cleaves fibrinogen to form fibrin, activates platelets, and performs positive feedback reactions upon components of the coagulation cascade. Its action in the anticoagulant pathway under physiological conditions is dependent upon binding to an endothelial cell surface-bound cofactor, thrombomodulin. Upon binding to this protein, thrombin undergoes a conformational change that greatly reduces its ability to perform the procoagulant reactions mentioned above while greatly increasing the rate of activation of protein C zymogen, thus changing its specificity from a procoagulant to an anticoagulant enzyme. In accordance with this model, infusion of low levels of thrombin has been shown to be antithrombotic (Gruber, 1990, *Circ.* 82:578; Hanson, 1993, *J. Clin. Invest.* 92:2003; McBane, 1995, *Thromb Haemostas* 74:879). Thrombin variants with similar changes in specificity in the absence of thrombomodulin have been developed (Dang, 1997, *Nature Biotech* 15:146; Gibbs, 1995, *Nature* 378:413; (1991) PNAS 88:7371; Wu, 1991, *PNAS* 88:6775; Guinto, 1995, *PNAS* 92:11185). Delivery of these variants by the means of gene delivery vehicles and the therapeutic methods of the invention would be useful in reducing thrombosis in individuals at risk.

Gene delivery vehicles expressing prothrombin and its variants can be constructed by methods known to those of skill in the art, by using variations on the methods described herein. For instance, prothrombin cDNA can be obtained by restriction enzyme digestion of a published vector (Degen (1983) Biochemistry 22:2087). The 1.9 kb cDNA insert can be recovered from agarose gels and cloned into the multiple cloning site of vector SK-. The insert can be recovered by restriction enzyme digestion and cloned into a retroviral vector using restriction enzyme digestion. For instance, excision by ClaI/NotI digestion and cloning into ClaI/NotI digested pBA-9 vector to form pBA9-FII can be performed by using a modification of the procedure similar to that described in Example 28 herein for factor VIII b-domain deletion fragments. In some cases, variants of prothrombin are constructed prior to cloning into the vector backbone, as described in the Dang, Wu, Gibbs, and Guinto publications cited above.

(e) Thrombomodulin Vector for Treatment or Prophylaxis of Hypercoagulable States As described above, the endothelial cell surface protein, thrombomodulin, is a necessary cofactor for the normal activation of protein C by thrombin. A soluble recombinant form has been described (Parkinson, 1990, *J. Biol. Chem.* 265:12602), which was proposed for use as a clinical therapeutic anticoagulant acting by means of the protein C pathway. Delivery of this and other variants by the gene delivery vehicles and the gene therapy methods of the invention is useful in reducing thrombosis in individuals at risk.

Gene delivery vehicles, including retroviral vectors, expressing thrombomodulin and its variants can be constructed using techniques known to those of skill in the art. For instance, thrombomodulin cDNA can be obtained from the vector puc19TM15 (Jackman, 1987, *Proc. Natl. Acad. Sci. USA* 84:6425; Shirai, 1988,*J. Biochem.* 103:281; Wen, 1987, *Biochemistry* 26:4350; Suzuki, 1987, *EMBO J* 6:1891; ATCC number 61348,61349) by excision with SalI. The 3.7 kb cDNA insert will be recovered from agarose gels and cloned into the SalI site of retroviral vector. For instance, the thrombomodulin fragment can be cloned into the SalI site of SalI-digested pBA-9 vector to form pBA9-TM, using a modification of the procedure described in Example 28 herein. Variants of thrombomodulin lacking the cytoplasmic and transmembrane domains can be constructed prior to cloning into the vector backbone, as described by Parkinson.

3. Gene Delivery Vehicles Expressing Therapeutic Agents for Treatment of Viral Hepatitis The gene delivery vehicles including retroviral vectors and the methods of administration described are useful for treatment of viral hepatitis, including hepatitis B and hepatitis C. For instance, the gene delivery vehicles of the invention can be used to express interferon-alpha for treatment of viral hepatitis. While not wishing to be bound by theory, it is shown in Example 24 herein that retroviral vectors injected intravenously preferentially transduce liver cells. Thus, the methods of intravenous delivery described herein for gene delivery vehicles can be used for treatment of liver diseases such as hepatitis and in particular viral hepatitis, in which therapeutic proteins expressed by the gene delivery vehicles such as retroviral vectors can be delivered preferentially to the liver.

Currently, the only approved treatment for chronic hepatitis B, C and D infections is the use of alpha interferon 2a and 2b. Alpha-interferon is a secreted protein induced in B lymphocytes, macrophages and null lymphocytes by foreign cells, virus-infected cells, tumor cells, bacterial cells and products and viral envelopes. The mechanism of antiviral action of interferon is by inducing the synthesis of effector proteins: two of the most important are 2',5'-oligo-adenylate synthetase (OAS) and dsRNA-dependent protein kinase (RDPK). OAS synthesizes adenylate oligomers that activate RNAaseL, which degrades viral single stranded RNA. RDPK phosphorylates initiation factor eIF-2a which results in the inhibition of viral protein translation. In addition to the direct antiviral effect, alpha interferon has immunomodulatory effects that are important against viral infections. These immunomodulatory effects are: enhancement of the expression of both Class I and class II major histocompatibility complex (MHC) molecules, modulation of the expression of the interleukin-2 receptor, TNF-α receptor, transferrin receptor, enhancement of spontaneous natural killer (NK) cell cytotoxicity and modulation of antibody production by B cells. In chronic hepatitis B infection, the beneficial effect of interferon alpha appears to be from the immunomodulatory effects, while in chronic hepatitis C infection, the beneficial effect is dependent on its antiviral activity. (Bresters, D., in *Hepatitis C Virus*, pp121–136, Reesink H W (ed), 1994). The mechanism of action in interferon alpha for treatment of chronic hepatitis D is poorly understood (Rizzetto, M. and Rosina, F. in *Viral Hepatitis*, pp. 363–369, Zuckerman, A. J. and Thomas H. C. (ed), 1993).

Localized expression of interferon alpha in the liver from a gene delivery vehicle such as a retroviral vector can be an effective treatment for hepatitis. While not wishing to bound by theory, delivery of alpha interferon at the site of infection by the gene therapy vectors of the invention, including retroviral vectors, results in high local concentration of the cytokine thereby focusing the antiviral and immunological effects to the adjacent infected hepatocytes. A further advantage of this treatment is that the current systemic mode of systemic alpha interferon therapy may either be unnecessary or be reduced in dose and frequency of treatment. This reduction can reduce the adverse side effects associated with the systemic delivery of alpha interferon. Thus, the gene therapy approaches described herein may be used in combination with administration of alpha-interferon protein formulations.

The construction of a number of different retroviral vectors expressing interferon-alpha is described in detail in Example 33, herein. Other retroviral vectors not specifically listed in Example 33 can also be readily constructed to express interferon-alpha using similar procedures. There are at least 24 different human alpha interferon genes or pseudogenes. There are two distinct families (I and II) mature human alpha interferon (I) are 166 amino acids long (one is 165 amino acids) whereas alpha interferon (II) have 172 amino acids. Eighteen genes are in the alpha interferon I family, including at least four pseudogenes. Six genes are in the alpha interferon II family, including five pseudogenes (Callard, R., and Gearing, A., *Cytokine Facts Book*, Academic Press, 1994 pp. 148–154). In Example 33 herein, we use alpha interferon 2a, 2b, 2c, 54 and 76, all members of the alpha interferon (I) family. Similar techniques can be used for inserting other members of the alpha interferon I family (such as alpha interferon F and N) into retroviral vectors. Thus other biologically active forms of alpha-interferon in addition to 2a, 2b, 2c, 54 and 76 as described herein can also be expressed by the gene delivery vehicles of the invention and used for treatment of viral hepatitis.

Patients with viral hepatitis can be treated a combination gene therapy approach. A gene delivery vehicle expressing a protein drug such as alpha-interferon can be administered intravenously or directly to the liver by methods described herein. This therapeutic approach can be combined with intramusuclar delivery of a gene delivery vehicle expressing a hepatitis B or hepatitis C antigen for inducing a immune response against the hepatitis virus. Specific hepatitis B and C antigens useful in this type of therapy and the construction of retroviral vectors expressing such antigens are described herein and in PCT Patent Publication No. WO 93/15207. In addition, molecularly cloned genomes which encode the hepatitis B virus may be obtained from a variety of sources including, for example, the American Type Culture Collection (ATCC, Rockville, Md.). For example, ATCC No. 45020 contains the total genomic DNA of hepatitis B (extracted from purified Dane particles) (see FIG. 3 of Blum et al., 1989, *TIG* 5(5):154–158) in the Bam HI site of pBR322 (Moriarty et al., 1981, *Proc. Natl. Acad. Sci. USA* 78:2606–2610). (Note that correctable errors occur in the sequence of ATCC No. 45020.)

4. Gene Delivery Vehicles Expressing Cytokines and Immunomodulatory Factors

Genes encoding any of the cytokine and immunomodulatory proteins described herein can be expressed in a retroviral vector to achieve long term in vivo expression. Other forms of these cytokines which are known to those of skill in the art can also be used. For instance, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. As an additional example, nucleic acid sequences encoding the short and long forms of mCSF can be obtained as described in U.S. Pat. Nos. 4,847,201 and 4,879,227, respectively. Retroviral vectors expressing cytokine or immunomodulatory genes can be produced as described herein and in PCT publication number US 94/02951 entitled "Compositions and Methods for Cancer Immunotherapy".

Additional examples of such factors include cytokines, such as IL-1, IL-2 (Karupiah et al., 1990, *J. Immunology* 144:290–298; Weber et al., 1987, *J. Exp. Med.* 166:1716–1733; Gansbacher et al., 1990, *J. Exp. Med.* 172:1217–1224; U.S. Pat. No. 4,738,927), IL-3, IL-4 (Tepper et al., 1989, *Cell* 57:503–512; Golumbek et al., 1991, *Science* 254:713–716; U.S. Pat. No. 5,017,691), IL-5, IL-6 (Brakenhof et al., 1987, *J. Immunol.* 139:4116–4121; WO 90/06370), IL-7 (U.S. Pat. No. 4,965,195), IL-8, IL-9, IL-10, IL-11, IL-12, IL-13 (*Cytokine Bulletin*, Summer 1994), IL-14 and IL-15, particularly IL-2, IL4, IL6, IL-12, and IL-13, alpha interferon (Finter et al., 1991, *Drugs* 42(5):749–765; U.S. Pat. No. 4,892,743; U.S. Pat. No. 4,966,843; WO 85/02862; Nagata et al., 1980, *Nature* 284:316–320; Familletti et al., 1981, *Methods in Enz.* 78:387–394; Twu et al., 1989, *Proc. Natl. Acad. Sca. USA* 86:2046–2050; Faktor et al., 1990, *Oncogene* 5:867–872), beta interferon (Seif et al., 1991, *J. Virol.* 65:664–671), gamma interferons (Radford et al., *The American Society of Hepatology* 20082015, 1991; Watanabe et al., 1989, *PNAS* 86:9456–9460; Gansbacher et al., 1990, *Cancer Research* 50:7820–7825; Maio et al., 1989, *Can. Immunol. Immunother.* 30:34–42; U.S. Pat. Nos. 4,762,791; 4,727,138), G-CSF (U.S. Pat. Nos. 4,999,291 and 4,810,643), GM-CSF (WO 85/04188), tumor necrosis factors (TNFs) (Jayaraman et al., 1990, *J. Immunology* 144:942–951), CD3 (Krissanen et al., 1987, *Immunogenetics* 26:258–266), ICAM-1 (Altman et al., 1989, *Nature* 338:512–514; Simmons et al., 1988, *Nature* 331:624–627), ICAM-2, LFA-1, LFA-3 (Wallner et al., 1987, *J. Exp. Med.* 166(4):923–932), MHC class I molecules, MHC class II molecules, B7.1-.3, $\beta_2$-microglobulin (Parnes et al., 1981, *PNAS* 78:2253–2257), chaperones such as calnexin, MHC linked transporter proteins or analogs thereof (Powis et al., 1991, *Nature* 354:528–531). Within one preferred embodiment, the gene encodes gamma-interferon. Immunomodulatory factors may also be agonists, antagonists, or ligands for these molecules. For example soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including for example depositories such as the American Type Culture Collection (ATCC, Rockville, Md.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains, sequences encoding beta interferon), ATCC No 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Plasmids containing cyokine genes or immunodulatory genes can be digested with appropriate restriction enzymes, and DNA fragments containing the particular gene of interest can be inserted into the gene delivery vector using standard molecular biology techniques. (See Sambrook, et al., Molecular Cloning: A Laboratory Manual ($2^{nd}$ Edition, Vols. 1–3, Cold Spring Harbor Laboratory (1989) or Ausbel, et al. ed. Current Protocols in Molecular Biology, Greene Publishing and Wiley-Interscience, New York (1987). In particular, retroviral vectors expressing cytokine and immunomodulatory molecules can be constructed as described in PCT publication number WO 94/02951 and PCT publication number WO 96/21015, both of which are incorporated by reference in their entirety.

4. Gene Delivery Vehicles Expressing Polypeptide Hormones and Growth Factors

Retroviral vectors producing a variety of known polypeptide hormones and growth factors can be used in the methods of the invention to produce therapeutic long-term expression of these proteins. A large variety of hormones, growth factors and other proteins which are useful for long term expression by the retroviral vectors of the invention are described, for instance, in EP publication number 0437478B1, entitled "Cyclodextrin-Peptide Complexes". Nucleic acid sequences encoding a variety of hormones can be used, including human growth hormone, insulin, calcitonin, prolactin, follicle stimulating hormone, leutinizing hormone, human chorionic gonadotropin, thyroid stimulating hormone. Retroviral vectors expressing polypeptide hormones and growth factors can be prepared by methods known to those of skill in the art and as described herein. For instance, a retroviral vector expressing human growth hormone can be prepared as described in Example 8, herein. As an additional example, nucleic acid sequences encoding different forms of human insulin can be isolated as described in European Patent Publications EP 026598 or 070632, and incorporated into retroviral vectors as described herein.

Any of the polypeptide growth factors described below in section C of this application can also be administered therapeutically by long-term expression in vivo with a retroviral vector. For instance, a variety of different forms of IGF-1 and IGF-2 growth factor polypeptides are also well known the art and can be incorporated into retroviral vectors for long term expression in vivo. See e. g. European Patent No. 0123228B1, grant published on Sep. 19, 1993, entitled "Hybrid DNA Synthesis of Mature Insulin-like Growth Factors". As an additional example, the long term in vivo expression of different forms of fibroblast growth factor can also be effected by the methods of invention. See, e.g. U.S. Pat. No. 5,464,774, issued Nov. 7, 1995, U.S. Pat. Nos. 5,155,214, and 4,994,559, for a description of different fibroblast growth factors.

Plasmids containing cyokine genes or immunodulatory genes can be digested with appropriate restriction enzymes, and DNA fragments containing the particular gene of interest can be inserted into the gene delivery vector using standard molecular biology techniques. (See Sambrook, et al., Molecular Cloning: A Laboratory Manual ($2^{nd}$ Edition, Vols. 1–3, Cold Spring Harbor Laboratory (1989) or Ausbel, et al. ed. Current Protocols in Molecular Biology, Greene Publishing and Wiley-Interscience, New York (1987). In particular, retroviral vectors expressing polypeptide hormones and growth factors can be constructed using procedures similar to those described herein for human growth hormone.

5. Gene Delivery Vehicles Expressing Proteins for Treatment of Hereditary Disorders There are a number of proteins useful for treatment of hereditary disorders that can be expressed in vivo by the methods of invention. Many genetic diseases caused by inheritance of defective genes result in the failure to produce normal gene products, for example, thalassemia, phenylketonuria, Lesch-Nyhan syndrome, severe combined immunodeficiency (SCID), hemophilia, A and B, cystic fibrosis, Duchenne's Muscular Dystrophy, inherited emphysema and familial hypercholesterolemia (Mulligan et al., 1993, Science 260:926; Anderson et al., 1992, Science 256:808; Friedman et al., 1989, Science 244:1275). Although genetic diseases may result in the absence of a gene product, endocrine disorders, such as diabetes and hypopituitarism, are caused by the inability of the gene to produce adequate levels of the appropriate hormone insulin and human growth hormone respectively.

Gene therapy by the methods of the invention is a powerful approach for, treating these types of disorders. This therapy involves the introduction of normal recombinant genes into somatic cells so that new or missing proteins are produced inside the cells of a patient. A number of genetic diseases have been selected for treatment with gene therapy, including adenine deaminase deficiency, cystic fibrosis, $\alpha_1$-antitrypsin deficiency, Gaucher's syndrome, as well as non-genetic diseases. As an example of the present invention, a retroviral vector can be used to treat Gaucher disease. Gaucher disease is a genetic disorder that is characterized by the deficiency of the enzyme glucocerebrosidase. This enzyme deficiency leads to the accumulation of glucocerebroside in the lysosomes of all cells in the body. For a review see Science 256:794, 1992 and The Metabolic Basis of Inherited Disease, 6th ed., Scriver, et al., vol. 2, p. 1677).

As described in detail above, long term expression of Factor VIII or Factor IX is useful for treatment of blood clotting disorders, such as hemophilia. Different forms of Factor VIII, such as the B domain deleted Factor VIII construct described in Example 2 herein can be used to produce retroviral vectors expressing Factor VIII for use in the methods of the invention. In addition to clotting factors, there are a number of proteins which can be expressed in the retroviral vectors of the invention and which are useful for treatment of hereditary diseases. These include lactase for treatment of hereditary lactose intolerance, AD for treatment of ADA deficiency, and alpha-1 antitypsin for treatment of alpha-1 antitrypsin deficiency. See F. D. Ledley, 1987, *J. Pediatics* 110:157–174; I. Verma, Scientific American (November, 1987) pp. 68–94; and PCT Patent Publication WO 95/27512 entitled "Gene Therapy Treatment for a Variety of Diseases and Disorders" for a description of gene therapy treatment of genetic diseases.

One such disorder is familial hypercholesterolemia is a disease characterized clinically by a lifelong elevation of low density lipoprotein (LDL), the major cholesterol-transport lipoprotein in human plasma; Pathologically by the deposition of LDL-derived cholesterol in tendons, skin and arteries leading to premnature coronary heart disease; and genetically by autosomal dominant inherited trait. Hetrozygotes number about 1 in 500 persons worldwide. Their cells are able to bind cholesterol at about half the rate of normal cells. Their plasma cholesterol levels show two fold elevation starting at birth. Homozygotes number 1 in 1 million persons. They have severe cholesterolemia with death occurring usually before age 20. The disease (Arteriosclerosis) depends on geography. It affects 15.5 per 100,000 individuals in the U.S. (20,000 total) and 3.3 per 100,000 individuals in Japan. Gene delivery vehicles expressing the LDL receptor for treatment of disorders manifesting with elevated serum LDL can be constructed by techniques known to those of skill in the art. An example of a retroviral vector expressing LDS receptor is shown in example 32 herein. Other retroviral vectors such as those described herein can readily be constructed using PCR amplication and restriction enzyme treatment methods similar to those described in Example 31.

Similarly, retroviral vectors expressing alpha-1 antitypsin for treatment of alpha-1 antitrypsin deficiency can be constructed by variations of the procedure demonstrated in Example 32, herein.

6. Gene Delivery Vehicles Expressing Other Therapeutic Proteins

There are a variety of other proteins of therapeutic interest that can be expressed in vivo by retroviral vectors using the methods of the invention. For instance sustained in vivo expression of tissue factor inhibitory protein (TFPI) is useful for treatment of conditions including sepsis and DIC and in preventing reperfusion injury. (See PCT Patent Publications Nos. WO 93/24143, WO 93/25230 and WO 96/06637. Nucleic acid sequences encoding various forms of TFPI can be obtained, for example, as described in U.S. Pat. Nos. 4,966,852; 5,106,833; and 5,466,783, and can be incorporated in retroviral vectors as is described herein.

Other proteins of therapeutic interest such as erythropoietin (EPO) and leptin can also be expressed in vivo by retroviral vectors according to the methods of the invention. For instance EPO is useful in gene therapy treatment of a variety of disorders including anemia (see PCT publication number WO 95/13376 entitled "Gene Therapy for Treatment of Anemia".) Sustained gene therapy delivery of leptin by the methods of the invention is useful in treatment of obesity. (See WO 96/05309 entitled "Obesity Polypeptides able to modulate body weight" for a description of the leptin gene and its use in the treatment of obesity. Retroviral vector expressing EPO or leptin can readily he produced using the methods described herein and the constructs described in these two patent publications.

A variety of other disorders can also be treated by the methods of the invention. For example, sustained in vivo systemic production of apolipoprotein E or apolipoprotein A by the retroviral vectors of the invention can be used for treatment of hyperlipidemia. (See Breslow, J. et al. Biotechnology 12, 365 (1994).) In addition, sustained production of angiotensin receptor inhibitor (T. L. Goodfriend, et al., 1996, *N. Engl. J. Med.* 334:1469) can effected by the gene therapy methods described herein. As yet an additional example, the long term in vivo systemic production of angiostatin by the recombinant retroviruses of the invention is useful in the treatment of a variety of tumors. (See O'Reilly et al., 1996, *Nature Med.* 2:689.

Sequences which encode the above-described nucleic acid molecules may be obtained from a variety of sources. For example, plasmids which contain sequences that encode altered cellular products may be obtained from a depository such as the American Type Culture Collection (ATCC, Rockville, Md.), or from commercial sources such as Advanced Biotechnologies (Columbia, Md.). Plasmids containing cyokine genes or immunodulatory genes can be digested with appropriate restriction enzymes, and DNA fragments containing the particular gene of interest can be inserted into the gene delivery vector using standard molecular biology techniques. (See Sambrook, et al., Molecular Cloning: A Laboratory Manual ($2^{nd}$ Edition, Vols. 1–3, Cold Spring Harbor Laboratory (1989) or Ausbel, et al. ed. Current Protocols in Molecular Biology, Greene Publishing and Wiley-lnterscience, New York (1987).

Alternatively, cDNA sequences for use with the present invention may be obtained from cells which express or contain the sequences. Briefly, within one embodiment mRNA from a cell which expresses the gene of interest is reverse transcribed with reverse transcriptase using oligo dT or random primers. The single-stranded cDNA may then he amplified by PCR (see U.S. Pat. Nos. 4,683,202, 4,683,195 and 4,800,159. See also *PCR Technology Principles and Applications for DNA Amplification,* Erlich (ed.), Stockton Press, 1989) utilizing oligonucleotide primers complementary to sequences on either side of desired sequences. In particular, a double-stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Nucleic acid molecules which are carried and/or expressed by the recombinant retroviruses described herein may also be synthesized, for example, on an Applied Biosystems Inc. DNA synthesizer (e.g., APB DNA synthesizer model 392 (Foster City, Calif.).

7. Recombinant Retroviruses of Expressing Therapeutic Genes

A wide variety of nucleic acid molecules may be carried and/or expressed by the recombinant retroviruses of the present invention. Generally, the nucleic acid molecules which are described herein do not occur naturally in the recombinant retrovirus that carries it, and provides some desirable benefit, typically an ability to fight a disease, or other pathogenic agent or condition. As used herein, "pathogenic agent" refers to a cell that is responsible for a disease state. Representative examples of pathogenic agents include tumor cells, autoreactive immune cells, hormone secreting cells, cells which lack a function that they would normally have, cells that have an additional inappropriate gene expression which does not normally occur in that cell type, and cells infected with bacteria, viruses, or other intracellular parasites. In addition, as used herein "pathogenic agent" may also refer to a cell that overexpresses or inappropriately expresses a recombinant retrovirus (e.g., in the wrong cell type), or that has become tumorigenic due to inappropriate insertion into a host cell's genome.

Examples of nucleic acid molecules which may be carried and/or expressed by the recombinant retroviruses of the present invention include genes and other nucleic acid molecules which encode a substance, as well as biologically active nucleic acid molecules such as inactivating sequences that incorporate into a specified intracellular nucleic acid molecule and inactivate that molecule. A nucleic acid molecule is considered to be biologically active when the molecule itself provides the desired benefit without requiring the expression of a substance. For example, the biologically active nucleic acid molecule may be an inactivating sequence that incorporates into a specified intracellular nucleic acid molecule and inactivates that molecule, or the molecule may be a tRNA, rRNA or mRNA that has a configuration that provides a binding capability.

Substances which may be encoded by the nucleic acid molecules described herein include proteins (e.g., antibodies including single chain molecules), immunostimulatory molecules (such as antigens) immunosuppressive molecules, blocking agents, palliatives (such as toxins, antisense ribonucleic acids, ribozymes, enzymes, and other material capable of inhibiting a function of a pathogenic agent) cytokines, various polypeptides or peptide hormones, their agonists or antagonists, where these hormones can be derived from tissues such as the pituitary, hypothalamus, kidney, endothelial cells, liver, pancreas, bone, hemopoetic marrow, and adrenal. Such polypeptides can be used for induction of growth, regression of tissue, suppression of immune responses, apoptosis, gene expression, blocking receptor-ligand interaction, immune responses and can be treatment for certain anemias, diabetes, infections, high blood pressure, abnormal blood chemistry or chemistries (e.g., elevated blood cholesterol, deficiency of blood clotting factors, elevated LDL with lowered HDL), levels of Alzheimer associated amyloid protein, bone erosion/calcium deposition, and controlling levels of various metabolites such as steroid hormones, purines, and pyrimidines.

For palliatives, when "capable of inhibiting a function" is utilized within the context of the present invention, it should be understood that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for cancerous diseases include cell replication, susceptibility to external signals (e.g., contact inhibition), and lack of production of anti-oncogene proteins. Examples of such functions for cardiovascular disease include inappropriate growth or accumulation of material in blood vessels, high blood pressure, undesirable blood levels of factors such as cholesterol or low density lipoprotein that predispose to disease, localized hypoxia, and inappropriately high and tissue-damaging levels of free radicals. Examples of such functions for neurological conditions include pain, lack of dopamine production, inability to replace damaged cells, deficiencies in motor control of physical activity, inappropriately low levels of various peptide hormones derived from neurological tissue such as the pituitary or hypothalamus, accumulation of Alzheimer's Disease associated amyloid plaque protein, and inability to regenerate damaged nerve junctions. Examples of such functions for autoimmune or inflammatory disease include inappropriate production of cytokines and lymphokines, inappropriate production and existence of autoimmune antibodies and cellular immune responses, inappropriate disruption of tissues by proteases and collagenases, inhibition of the normal action of proteases, lack of production of factors normally supplied by destroyed cells, and excessive or aberrant regrowth of tissues under autoimmune attack.

Within one aspect of the present invention, methods are provided for administration of a recombinant retrovirus which directs the expression of a palliative. Within various embodiments, the palliative may be a DNA molecule, an RNA molecule, or some combination of the two.

Representative examples of palliatives that act directly to inhibit the growth of cells include toxins such as ricin (Lamb et al., 1985, Eur. J. Biochem. 148:265–270), abrin (Wood et al., 1991, Eur. J. Biochem. 198:723–732; Evensen et al., 1991, J. of Biol. Chem. 266:6848–6852; Collins et al., 1990, J. of Biol. Chem. 265:8665–8669; Chen et al., 1992, Fed. of Eur. Biochem Soc. 309:115–118), diphtheria toxin (Tweten et al., 1985, J. Biol. Chem. 260:10392–10394), cholera toxin (Mekalanos et al., 1983, Nature 306:551–557; Sanchez and Holmgren, 1989, PNAS 86:481–485), gelonin (Stirpe et al., 1980, J. Biol. Chem. 255:6947–6953), pokeweed (Irvin, 1983, Pharmac. Ther. 21:371–387), antiviral protein (Barbieri et al., 1982, Biochem. J. 203:55–59; Irvin et al., 1980, Arch. Biochem. & Biophys. 200:418–425; Irvin, 1975, Arch. Biochem. & Biophys. 169:522–528), tritin, Shigella toxin (Calderwood et al., 1987, PNAS 84:4364–4368; Jackson et al., 1987, Microb. Path. 2:147–153), and Pseudomonas exotoxin A (Carroll and Collier, 1987. J. Biol. Chem., 262:8707–8711). A detailed description of recombinant retroviruses which express Russel's Viper Venom is provided in PCT Patent Publication No. WO 96/21416.

Within other aspects of the invention, the recombinant retrovirus carries a gene specifying a product which is not in itself toxic, but when processed or modified by a protein, such as a protease specific to a viral or other pathogen, is convened into a toxic form. For example, the recombinant retrovirus could carry a gene encoding a proprotein chain, which becomes toxic upon processing by the HIV protease. More specifically, a synthetic inactive proprotein form of the toxic ricin or diphtheria A chains could be cleaved to the active form by arranging for the HIV virally encoded protease to recognize and cleave off an appropriate "pro" element.

Within yet another aspect of the invention, the recombinant retrovirus directs the expression of a substance capable of activating an otherwise inactive precursor into an active inhibitor of a pathogenic agent, or a conditional toxic palliative, which are palliatives that are toxic for the cell expressing the pathogenic condition. As should be evident given the disclosure provided herein, a wide variety of inactive precursors may be converted into active inhibitors of a pathogenic agent. For example, antiviral nucleoside analogues such as AZT or ddI are metabolized by cellular mechanisms to the nucleotide triphosphate form in order to specifically inhibit retroviral reverse transcriptase, and thus viral replication (Furmam et al., 1986, *Proc. Natl. Acad. Sci. USA* 83:8333–8337). Recombinant retroviruses which direct the expression of a gene product (e.g., a protein) such as Herpes Simplex Virus Thymidine Kinase (HSVTK) or Varicella Zoster Virus Thymidine Kinase (VZVTK) which assists in metabolizing antiviral nucleoside analogues to their active form are therefore useful in activating nucleoside analogue precursors (e.g., AZT or ddC) into their active form. AZT or ddI therapy will thereby be more effective, allowing lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, will be made more efficacious.

Within one embodiment of the invention, the HSVTK gene may be expressed under the control of a constitutive macrophage or T-cell-specific promoter, and introduced into macrophage or T-cells. Constitutive expression of HSVTK results in more effective metabolism of nucleotide analogues such as AZT or ddI to their biologically active nucleotide triphosphate form, and thereby provides greater efficacy, delivery of lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, may also be utilized within the context of the present invention.

Within a related aspect of the present invention, recombinant retroviruses are provided which direct the expression of a substance that activates another compound with little or no cytotoxicity into a toxic product in the presence of a pathogenic agent, thereby effecting localized therapy to the pathogenic agent. In this case, expression of the gene product from the recombinant retrovirus is limited to situations wherein an entity associated with the pathogenic agent, such as an intracellular signal identifying the pathogenic state, is present, thereby avoiding destruction of nonpathogenic cells. This cell-type specificity may also be conferred at the level of infection, by targeting the recombinant retrovirus to cells having or being susceptible to the pathogenic condition.

Within a related aspect of the present invention, recombinant retroviruses are provided which direct the expression of a gene product(s) that activates a compound with little or no cytotoxicity into a toxic product. Briefly, a wide variety of gene products which either directly or indirectly activate a compound with little or no cytotoxicity into a toxic product may be utilized within the context of the present invention. Representative examples of such gene products include HSVTK and VZVTK which selectively monophosphorylate certain purine arabinosides and substituted pyrimidine compounds, converting them to cytotoxic or cytostatic metabolites. More specifically, exposure of the drugs gangicylovir, acyclovir, or any of their analogues (e.g., FIAC, DHPG) to HSVTK, phosphorylates the drug into its corresponding active nucleotide triphosphate form.

For example, within one embodiment of the invention, the recombinant retrovirus directs the expression of the herpes simplex virus thymidine kinasie ("HSVTK") gene downstream, and under the transcriptional control of an HIV promoter (which is known to be transcriptionally silent except when activated by HIV tat protein). Briefly, expression of the tat gene product in human cells infected with HIV and carrying the recombinant retrovirus causes increased production of HSVTK. The cells (either in vitro or in vivo) are then exposed to a drug such as ganciclovir, acyclovir or its analogues (FIAC, DHPG). As noted above, these drugs are known to be phosphorylated by HSVTK (but not by cellular thymidine kinase) to their corresponding active nucleotide triphosphate forms. Acyclovir triphosphates inhibit cellular polymerases in general, leading to the specific destruction of cells expressing HSVTK in transgenic mice (see Borrelli et al., 1988, *Proc. Natl. Acad. Sci. USA* 85:7572). Those cells containing the recombinant retrovirus and expressing HIV tat protein are selectively killed by the presence of a specific dose of these drugs.

Within one embodiment of the invention, expression of a conditionally lethal HSVTK gene may be made even more HIV-specific by including cis-acting elements in the transcript ("CRS/CAR"), which require an additional HIV gene product, rev, for optimal activity (Rosen et al., 1988, *Proc. Natl. Acad. Sci. USA* 85:2071). More generally, cis elements present in mRNAs have been shown in some cases to regulate mRNA stability or translatability. Sequences of this type (i.e., post-transcriptional regulation of gene expression) may be used for event- or tissue-specific regulation of vector gene expression. In addition, multimerization of these sequences (i.e., rev-responsive "CRS/CAR" or tat-responsive "TAR" elements for HIV) may be utilized in order to generate even greater specificity.

In a manner similar to the preceding embodiment, recombinant retroviruses may be generated which carry a gene for phosphorylation, phosphoribosylation, ribosylation, or other metabolism of a purine- or pyrimidine-based drug. Such genes may have no equivalent in mammalian cells, and might come from organisms such as a virus, bacterium, fungus, or protozoan. Representative examples include: *E. coli* guanine phosphoribosyl transferase ("gpt") gene product, which converts thioxanthine into thioxanthine monophosphate (see Besnard et al., 1987, *Mol. Cell. Biol.* 7:4139–4141); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase which will convert 5-fluorocytosine to the toxic compound 5-fluorouracil (Mullen, 1992, *PNAS* 89:33); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds. Conditionally lethal gene products of this type have application to many presently known purine- or pyrimidine-based anticancer drugs, which often require intracellular ribosylation or phosphorylation in order to become effective cytotoxic agents. The conditionally lethal gene product could also metabolize a nontoxic drug, which is not a purine or pyrimidine analogue, to a cytotoxic form (see Searle et al., 1986, *Brit. J. Cancer* 53:377–384).

Additionally, in the instance where the target pathogen is a mammalian virus, recombinant retroviruses vectors may be constructed to take advantage of the fact that mammalian viruses in general tend to have "immediate early" genes, which are necessary for subsequent transcriptional activation of other viral promoter elements. Gene products of this nature are excellent candidates for intracellular signals (or "identifying agents") of viral infection. Thus, conditionally lethal genes transcribed from transcriptional promoter elements that are responsive to such viral "immediate early" gene products could specifically kill cells infected with any particular virus. Additionally, since the human α and α interferon promoter elements are transcriptionally activated in response to infection by a wide variety of nonrelated viruses, the introduction of vectors expressing a conditionally lethal gene product like HSVTK, for example, from these viral-responsive elements (VREs) could result in the destruction of cells infected with a variety of different viruses.

In another embodiment of the invention, recombinant retroviruses are provided that produce substances such as inhibitor palliatives, that inhibit viral assembly. In this context, the recombinant retrovirus codes for defective gag, pol, env or other viral particle proteins or peptides which inhibit in a dominant fashion the assembly of viral particles. Such inhibition occurs because the interaction of normal subunits of the viral particle is disturbed by interaction with the defective subunits.

One way of increasing the effectiveness of inhibitory palliatives is to express inhibitory genes, such as viral inhibitory genes, in conjunction with the expression of genes which increase the probability of infection of the resistant cell by the virus in question. The result is a nonproductive "deadend" event which would compete for productive infection events. In the specific case of HIV, a recombinant retrovirus may be administered that inhibits HIV replication (by expressing anti-sense tat, etc., as described above) and also overexpress proteins required for infection, such as CD4. In this way, a relatively small number of vector-infected HIV-resistant cells act as a "sink" or "magnet" for multiple nonproductive fusion events with free virus or virally infected cells.

In another embodiment of the invention, recombinant retroviruses are provided for the expression substances such as inhibiting peptides or proteins specific for viral protease. Viral protease cleaves the viral gag and gag/pol proteins into a number of smaller peptides. Failure of this cleavage in all cases leads to complete inhibition of production of infectious retroviral particles. The HIV protease is known to be an aspartyl protease, and these are known to be inhibited by peptides made from amino acids from protein or analogues. Recombinant retroviruses that inhibit HIV will express one or multiple fused copies of such peptide inhibitors.

Administration of the recombinant retroviruses discussed above should be effective against many virally linked diseases, cancers, or other pathogenic agents.

Within still other embodiments of the invention, recombinant retroviruses are provided that express a palliative, wherein the palliative has a membrane anchor and acts as an anti-tumor agent(s). Such a palliative may be constructed, for example, as an anti-tumor agent-membrane anchor fusion protein. Briefly, the membrane anchor aspect of the fusion protein may be selected from a variety of sequences, including, for example, the transmembrane domain of well known molecules. Generally, membrane anchor sequences are regions of a protein that bind the protein to a membrane. Customarily, there are two types of anchor sequences that attach a protein to the outer surface of a cell membrane: (1) transmembrane regions that span the lipid bilayer of the cell membrane, and interact with the hydrophobic center region (proteins containing such regions are referred to integral membrane proteins), and (2) domains which interact with an integral membrane protein or with the polar surface of the membrane (such proteins are referred to as peripheral, or extrinsic, proteins).

Membrane anchors for use within the present invention may contain transmembrane domains which span the membrane one or more times. For example, in glycophorin and guanylyl cyclase, the membrane binding region spans the membrane once, whereas the transmembrane domain of rhodopsin spans the membrane seven times, and that of the photosynthetic reaction center of Rhodopseudomonas viridis spans the membrane eleven times (see Ross et al., 1982, *J. Biol. Chem.* 257:4152; Garbers, 1991, *Pharmac. Ther.* 50:337–345; Engelman et al., 1980, *Proc. Natl. Acad. Sci. USA* 77:2023; Heijne and Manoil, 1990, *Prot. Eng.* 4:109–112). Membrane anchors for use in the present invention can also include, for example, phosphoinositol anchors. Regardless of the number of times the protein crosses the membrane, the membrane spanning regions typically have a similar structure. More specifically, the 20 to 25 amino-acid residue portion of the domain that is located inside the membrane generally consists almost entirely of hydrophobic residues (see Eisenberg et al., 1984, *Ann. Rev. Biochem.* 53:595–623). For example, 28 of the 34 residues in the membrane spanning region of glycophorin are hydrophobic (see Ross et al., supra; Tomita et al., 1978, *Biochemistry* 17:4756–4770). In addition, although structures such as beta sheets and barrels do occur, the membrane spanning regions typically have an alpha helical structure, as determined by X-ray diffraction, crystallography and cross-linking studies (see Eisenberg et al., supra; Heijne and Manoil, supra). The location of these transmembrane helices within a given sequence can often be predicted based on hydrophobicity plots. Stryer et al., *Biochemistry*, 3rd. ed. 304, 1988. Particularly preferred membrane anchors for use within the present invention include naturally occurring cellular proteins (that are non-immunogenic) which have been demonstrated to function as membrane signal anchors (such as glycophorin).

Within a preferred embodiment of the present invention, a DNA sequence is provided which encodes a membrane anchor-gamma interferon fusion protein. Within one embodiment, this fusion protein may be constructed by genetically fusing the sequence which encodes the membrane anchor of the gamma-chain of the Fc receptor, to a sequence which encodes gamma-interferon.

In yet another aspect, recombinant retroviruses are provided which have a therapeutic effect by encoding one or more ribozymes (RNA enzymes) (Haseloff and Gerlach, 1989, *Nature* 334:585) which will cleave, and hence inactivate, RNA molecules corresponding to a pathogenic function. Since ribozymes function by recognizing a specific sequence in the target RNA and this sequence is normally 12 to 17 bp, this allows specific recognition of a particular RNA sequence corresponding to a pathogenic state, such as HIV tat, and toxicity is specific to such pathogenic state. Additional specificity may be achieved in some cases by making this a conditional toxic palliative, as discussed above.

In still another aspect, recombinant retroviruses are provided comprising a biologically active nucleic acid molecule that is an antisense sequence (an antisense sequence may also be encoded by a nucleic acid sequence and then produced within a host cell via transcription). In preferred embodiments, the antisense sequence is selected from the group consisting of sequences which encode influenza virus, HIV, HSV, HPV, CMV, and HBV. The antisense sequence may also be an antisense RNA complementary to RNA sequences necessary for pathogenicity. Alternatively, the biologically active nucleic acid molecule may be a sense RNA (or DNA) complementary to RNA sequences necessary for pathogenicity.

More particularly, the biologically active nucleic acid molecule may be an antisense sequence. Briefly, antisense sequences are designed to bind to RNA transcripts, and thereby prevent cellular synthesis of a particular protein, or prevent use of that RNA sequence by the cell. Representative examples of such sequences include antisense thymidine kinase, antisense dihydrofolate reductase (Maher and Dolnick, 1987, *Arch. Biochem. & Biophys.* 253:214–220; Bzik et al., 1987, *PNAS* 84:8360–8364), antisense HER2 (Coussens et al., 1985, *Science* 230:1132–1139), antisense ABL (Fainstein et al., 1989, *Oncogene* 4:1477–1481 ), antisense Myc (Stanton et al., 1984, *Nature* 310:423425) and antisense ras, as well as antisense sequences which block any of the enzymes in the nucleotide biosynthetic pathway.

In addition, within a further embodiment of the invention antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon), due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

In another embodiment, the substances of the invention include a surface protein that is itself therapeutically beneficial. For example, in the particular case of HIV, expression of the human CD4 protein specifically in HIV-infected cells may be beneficial in two ways:

1. Binding of CD4 to HIV env intracellularly could inhibit the formation of viable viral particles much as soluble CD4 has been shown to do for free virus, but without the problem of systematic clearance and possible immunogenicity, since the protein will remain membrane bound and is structurally identical to endogenous CD4 (to which the patient should be immunologically tolerant).
2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monoytes and macrophages, which act as a reservoir for virus production as a result of their relative refractility to HIV-induced cytotoxicity (which, in turn, is apparently due to the relative lack of CD4 on their cell surfaces).

Still further aspects of the present invention relate to recombinant retroviruses capable of immunostimulation. Briefly, the ability to recognize and defend against foreign pathogens is essential to the function of the immune system. In particular, the immune system must be capable of distinguishing "self" from "nonself" (i.e., foreign), so that the defensive mechanisms of the host are directed toward invading entities instead of against host tissues. Cytolytic T lymphocytes (CTLs) are typically induced, or stimulated, by the display of a cell surface recognition structure, such as a processed, pathogen-specific peptide, in conjunction with a MHC class I or class II cell surface protein.

Diseases suitable to treatment include viral infections such as influenza virus, respiratory syncytial virus, HPV, HBV, HCV, EBV, HIV, HSV, FeLV, FIV, Hantavirus, HTLV I, HTLV II and CMV, cancers such as melanomas, renal carcinoma, breast cancer, ovarian cancer and other cancers, and heart disease.

In one embodiment, the invention provides methods for stimulating a specific immune response and inhibiting viral spread by using recombinant retroviruses that direct the expression of an antigen or modified form thereof in susceptible target cells, wherein the antigen is capable of either (1) initiating an immune response to the viral antigen or (2) preventing the viral spread by occupying cellular receptors required for viral interactions. Expression of the protein may be transient or stable with time. Where an immune response is to be stimulated to a pathogenic antigen, the recombinant retrovirus is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogs thereof (e.g., Altmann et al., 1989, *Nature* 338:512).

An immune response can also be achieved by transferring to an appropriate immune cell (such as a T lymphocyte) (a) the gene for the specific T-cell receptor that recognizes the antigen of interest (in the context of an appropriate MHC molecule if necessary), (b) the gene for an immunoglobulin which recognizes the antigen of interest, or (c) the gene for a hybrid of the two which provides a CTL response in the absence of the MHC context. Thus, recombinant retroviruses may also be used as an immunostimulant, immunomodulator, or vaccine, etc.

In the particular case of disease caused by HIV infection, where immunostimulation is desired, the antigen generated from a recombinant retrovirus may be in a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but haplotype-specific epitopes or to present several haplotype-specific epitopes, and allow a response capable of eliminating cells infected with most or all strains of HIV. The haplotype-specific epitopes can be further selected to promote the stimulation of an immune response within an animal which is cross-reactive against other strains of HIV. Antigens from other HIV genes or combinations of genes, such as gag, pol, rev, vif, nef, prot, gag/pol, gag prot, etc., may also provide protection in particular cases.

HIV is only one example. This approach should be effective against many virally linked diseases or cancers where a characteristic antigen (which does not need to be a membrane protein) is expressed, such as in HPV and cervical carcinoma, HTLV-1-induced leukemias, prostate-specific antigen (PSA) and prostate cancer, mutated p53 and colon carcinoma and melanoma, melanoma specific antigens (MAGEs), and melanoma, mucin and breast cancer.

In accordance with the immunostimulation aspects of the invention, substances which are carried and/or expressed by the recombinant retroviruses of the present invention may also include "immunomodulatory factors," many of which are set forth above. Immunomodulatory factors refer to factors that, when manufactured by one or more of the cells involved in an immune response, or, which when added exogenously to the cells, causes the immune response to be different in quality or potency from that which would have occurred in the absence of the factor. The factor may also be expressed from a non-recombinant retrovirus derived gene, but the expression is driven or controlled by the recombinant retrovirus. The quality or potency of a response may be measured by a variety of assays known to one of skill in the art including, for example, in vitro assays which measure cellular proliferation (e.g., $^3$H thymidine uptake), and in vitro cytotoxic assays (e.g., which measure $^{51}$Cr release) (see, Warner et al., 1991, *AIDS Res. and Human Retroviruses* 7:645–655). Immunomodulatory factors may be active both in vivo and ex vivo.

Representative examples of such factors include cytokines, such as IL-1, IL 2 (Karupiah et al., 1990, *J.*

*Immunology* 144:290–298; Weber et al., 1987, *J. Exp. Med.* 166: 1716–1733; Gansbacher et al., 1990, *J. Exp. Med.* 172:1217–1224; U.S. Pat. No. 4,738,927), IL-3, IL-4 (Tepper et al., *Cell* 57:503–512, 1989; Golumbek et al., 1991, *Science* 254:713–716; U.S. Pat. No. 5,017,691), IL-5, IL-6 (Brakenhof et al., 1987, *J. Immunol.* 139:4116–4121; WO 90/06370), IL-7 (U.S. Pat. No. 4,965,195), IL-8, IL-9, IL-10, IL-11, IL-12, IL-13 (*Cytokine Bulletin,* Summer 1994), IL-14 and IL-15, particularly IL-2, IL-4, IL-6, IL-12, and IL-13, alpha interferon (Finter et al., 1991, *Drugs* 42(5):749–765; U.S. Pat. Nos. 4,892,743; 4,966,843; WO 85/02862; Nagata et al., *Nature* 284:316–320, 1980; Familletti et al., 1981, *Methods in Enz.* 78:387–394; Twu et al., 1989, *Proc. Natl. Acad. Sci. USA* 86:2046–2050, 1989; Faktor et al., 1990, *Oncogene* 5:867–872), beta interferon (Seif et al., 199.1, *J. Virol.* 65:664–671), gamma interferons (Radford et al., *The American Society of Hepatology* 20082015, 1991; Watanabe et al., 1989, *PNAS* 86:9456–9460; Gansbacher et al., 1990, *Cancer Research* 50:7820–7825; Maio et al., 1989, *Can. Immunol. Immunother.* 30:34–42; U.S. Pat. Nos. 4,762,791; 4,727,138), G-CSF (U.S. Pat. Nos. 4,999,291 and 4,810,643), GM-CSF (WO 85/04188), tumor necrosis factors (TNFs) (Jayaraman et al., *J. Immunology* 144:942–951, 1990), CD3 (Krissanen et al., 1987, *Immunogenetics* 26:258–266), ICAM-1 (Altman et al., 1989, *Nature* 338:512–514; Simmons et al., 1988, *Nature* 331:624–627), ICAM-2, LFA-1, LFA-3 (Wallner et al., 1987, *J. Exp. Med.* 166(4):923–932), MHC class I molecules, MHC class II molecules, B7.1-.3,$\beta_2$-microglobulin (Parnes et al., *PNAS* 78:2253–2257, 1981), chaperones such as calnexin, MHC linked transporter proteins or analogs thereof (Powis et al., *Nature* 354:528–531, 1991). Within one preferred embodiment, the gene encodes gamma-interferon. Immunomodulatory factors may also be agonists, antagonists, or ligands for these molecules. For example soluble forms of receptors can often behave as antagonists for these types of factors, as can mutated forms of the factors themselves.

An example of an immunomodulatory factor cited above is a member of the B7 family of molecules (e.g., B7.1-.3 costimulatory factor). Briefly, activation of the full functional activity of T cells requires two signals. One signal is provided by interaction of the antigen-specific T cell receptor with peptides which are bound to major histocompatibility complex (MHC) molecules, and the second signal, referred to as costimulation, is delivered to the T cell by antigen presenting cells. The second signal is required for interleukin-2 (IL-2) production by T cells, and appears to involve interaction of the B7.1-.3 molecule on antigen-presenting cells with CD28 and CTLA4 receptors on T lymphocytes (Linsley et al., *J. Exp. Med.,* 173:721–730, 1991a and *J. Exp. Med.,* 174:561–570, 1991). Within one embodiment of the invention, B7.1-.3 may be introduced into tumor cells in order to cause costimulation of CD8$^+$ T cells, such that the CD8$^+$ T cells produce enough IL-2 to expand and become fully activated. These CD8$^+$ T cells can kill tumor cells that are not expressing B7 because costimulation is no longer required for further CTL function. Vectors that express both the costimulatory B7.1-.3 factor, and, for example, an immunogenic HBV core protein, may be made utilizing methods which are described herein. Cells transduced with these vectors will become more effective antigen presenting cells. The HBV core-specific CTL response will be augmented from the fully activated CD8$^+$ T cell via the costimulatory ligand B7.1-.3.

The choice of which immunomodulatory factor to include within a recombinant retrovirus may be based upon known therapeutic effects of the factor, or, experimentally determined. For example, a known therapeutic effector in chronic hepatitis B infections is alpha interferon. This has been found to be efficacious in compensating a patient's immunological deficit, and thereby assisting recovery from the disease. Alternatively, a suitable immunomodulatory factor may he experimentally determined. Briefly, blood samples are first taken from patients with a hepatic disease. Peripheral blood lymphocytes (PBLs) are restimulated in vitro with autologous or HLA matched cells (e.g., EBV transformed cells) that have been transduced with a recombinant retrovirus which directs the expression of an immunogenic portion of a hepatitis antigen and the immunomodulatory factor. These stimulated PBLs are then used as effectors in a CTL assay with the HLA matched transduced cells as targets. An increase in CTL response over that seen in the same assay performed using HLA matched stimulator and target cells transduced with a vector encoding the antigen alone, indicates a useful immunomodulatory factor. Within one embodiment of the invention, the immunomodulatory factor gamma interferon is particularly preferred.

The present invention also includes recombinant retroviruses which encode immunogenic portions of desired antigens including, for example, viral, bacterial or parasite antigens. For example, various immunogenic portions of the HBV S antigens may be combined in order to present an immune response when administered by one of the recombinant retroviruses described herein. In addition, due to the large immunological variability that is found in different geographic regions for the S antigen open reading frame of HBV, particular combinations of antigens may be preferred for administration in particular geographic regions. Briefly, epitopes that are found in all human hepatitis B virus S samples are defined as determinant "a". Mutually exclusive subtype determinants however have also been identified by two-dimensional double immunodiffusion (Ouchterlony, 1958, *Progr. Allergy* 5:1). These determinants have been designated "d" or "y" and "w" or "r" (LeBouvier, 1971, *J. Infect.* 123:671; Bancroft et al., 1972, *J. Immunol.* 109:842; Courouce et al., 1976, *Bibl. Haematol.* 42:1–158). The immunological variability is due to single nucleotide substitutions in two areas of the hepatitis B virus S antigen open reading frame resulting in the following amino acid changes: (1) exchange of lysine-122 to arginine in the hepatitis B virus S antigen open reading frame causes a subtype shift from d to y, and (2) exchange of arginine-160 to lysine causes the shift from subtype r to w. In black Africa, subtype ayw is predominant, whereas in the U.S. and northern Europe the subtype $adw_2$ is more abundant (*Molecular Biology of the Hepatitis B Virus,* McLachlan (ed.), CRC Press, 1991). As will be evident to one of ordinary skill in the art, it is generally preferred to construct a vector for administration which is appropriate to the particular hepatitis B virus subtype which is prevalent in the geographical region of administration. Subtypes of a particular region may be determined by two-dimensional double immunodiffusion or, preferably, by sequencing the S antigen open reading frame of HBV virus isolated from individuals within that region.

Also presented by HBV are pol ("HBV pol"), ORF 5, and ORF 6 antigens. Briefly, the polymerase open reading frame of HBV encodes reverse transcriptase activity found in virions and core-like particles in infected liver tissue. The polymerase protein consists of at least two domains: the amino terminal domain encodes the protein that primes reverse transcription, and the carboxyl terminal domain which encodes reverse transcriptase and RNase H activity.

Immunogenic portions of HBV pol may be administered to a warm-blooded animal by introducing into the animal a recombinant retrovirus which expresses the antigen of interest in order to generate an immune response within the animal. Similarly, other HBV antigens such as ORF 5 and ORF 6, (Miller et al., 1989, *Hepatology* 9:322–327), may be expressed utilizing recombinant retroviruses as described herein.

As noted above, at least one immunogenic portion of a hepatitis B antigen can be incorporated into a recombinant retrovirus. The immunogenic portion(s) which are incorporated into the recombinant retrovirus may be of varying length, although it is generally preferred that the portions be at least 9 amino acids long, and may include the entire antigen. Immunogenicity of a particular sequence is often difficult to predict, although T cell epitopes may be predicted utilizing the HLAA2. 1 motif described by Falk et al., 1991, *Nature* 351:290. From this analysis, peptides may be synthesized and used as targets in an in vitro cytotoxic assay. Other assays, however, may also be utilized, including, for example, ELISA which detects the presence of antibodies against the newly introduced vector, as well as assays which test for T helper cells, such as gamma-interferon assays, EL-2 production assays, and proliferation assays.

Within one embodiment of the present invention, at least one immunogenic portion of a hepatitis C antigen can be incorporated into a recombinant retrovirus. Preferred immunogenic portion(s) of hepatitis C may be found in the C and NS3–NS4 regions since these regions are the most conserved among various types of hepatitis C virus (Houghton et al., 1991, *Hepatology* 14:381–388). Particularly preferred immunogenic portions may be determined by a variety of methods. For example, as noted above for the hepatitis B virus, identification of immunogenic portions of the polypeptide may be predicted based upon amino acid sequence. Briefly, various computer programs which are known to those of ordinary skill in the art may be utilized to predict CTL epitopes. For example, CTL epitopes for the HLA A2.1 haplotype may be predicted utilizing the HLA A2.1 motif described by Falk et al. (*Nature* 351:290, 1991). From this analysis, peptides are synthesized and used as targets in an in vitro cytotoxic assay.

Within another aspect of the present invention, methods are provided for destroying hepatitis B carcinoma cells comprising the step of administering to a warm-blooded animal a recombinant retrovirus which directs the expression of an immunogenic portion of antigen X, such that an immune response is generated. Sequences which encode the HBxAg may readily be obtained by one of skill in the art given the disclosure provided herein. Briefly, within one embodiment of the present invention, a 642 bp Nco I-Taq I is recovered from ATCC 45020, and inserted into recombinant retroviruses as described above for other hepatitis B antigens.

The X antigen, however, is a known transactivator which may function in a manner similar to other potential oncogenes (e.g., E1A). Thus, it is generally preferable to first alter the X antigen such that the gene product is non-tumorigenic before inserting it into a recombinant retrovirus. Various methods may be utilized to render the X antigen non-tumorigenic including, for example, by truncation, point mutation, addition of premature stop codons, or phosphorylation site alteration. Within one embodiment, the sequence or gene of interest which encodes the X antigen is truncated. Truncation may produce a variety of fragments, although it is generally preferable to retain greater than or equal to 50% of the encoding gene sequence. In addition, it is necessary that any truncation leave intact some of the immunogenic sequences of the gene product. Alternatively, within another embodiment of the invention, multiple translational termination codons may be introduced into the gene. Insertion of termination codons prematurely terminates protein expression, thus preventing expression of the transforming portion of the protein.

The X gene or modified versions thereof may be tested for tumorigenicity in a variety of ways. Representative assays include tumor formation in nude mice, colony formation in soft agar, and preparation of transgenic animals, such as transgenic mice.

Within another aspect of the present invention, methods are provided for destroying hepatitis C carcinoma cells comprising the step of administering to a warm-blooded animal a recombinant retrovirus which directs the expression of an immunogenic portion of a hepatitis C antigen. Preferred immunogenic portion(s) of a hepatitis C antigen may be found in the polypeptide which contains the Core antigen and the NS1–NS5 regions (Choo et al., 1991, *Proc. Natl. Acad. Sci. USA* 88:2451–2455). Particularly preferred immunogenic portions may be determined by a variety of methods. For example, as noted above preferred immunogenic portions may be predicted based upon amino acid sequence. Briefly, various computer programs which are known to those of ordinary skill in the art may be utilized to predict CTL epitopes. For example, CTL epitopes for the HLA A2.1 haplotype may be predicted utilizing the HLA A2.1 motif described by Falk et al. (*Nature* 351:290, 1991). Another method that may also be utilized to predict immunogenic portions is to determine which portion has the property of CTL induction in mice utilizing retroviruses (see, Warner et al., 1991, *AIDS Res. and Human Retroviruses* 7:645–655). As noted within Warner et al., CTL induction in mice may be utilized to predict cellular immunogenicity in humans. Preferred immunogenic portions may also be deduced by determining which fragments of the polypeptide antigen or peptides are capable of inducing lysis by autologous patient lymphocytes of target cells (e.g., autologous EBV-transformed lymphocytes) expressing the fragments after vector transduction of the corresponding genes.

Preferred immunogenic portions may also be selected in the following manner. Briefly, blood samples from a patient with a target disease, such as HCV, are analyzed with antibodies to individual HCV polypeptide regions (e.g., HCV core, E1, E2/SNI and NS2–NS5 regions), in order to determine which antigenic fragments are present in the patient's serum. In patients treated with alpha interferon to give temporary remission, some antigenic determinants will disappear and be supplanted by endogenous antibodies to the antigen. Such antigens are useful as immunogenic portions within the context of the present invention (Hayata et al., 1991, *Hepatology* 13:1022–1028; Davis et al., 1989, *N. Eng. J. Med.* 321:1501–1506).

Additional immunogenic portions of a chosen antigen, such as those from the hepatitis B or C virus, may be obtained by truncating the coding sequence. For example, with HBV the following sites may be truncated: Bst UI, Ssp I, Ppu M1, and Msp I (Valenzuela:et al., 1979, *Nature* 280:815–19; Valenzuela et al., *Animal Virus Genetics: ICN/UCLA Symp. Mol. Cell Biol.,* 1980, B. N. Fields and R. Jaenisch (eds.), pp. 57–70, New York: Academic). Further methods for determining suitable immunogenic portions as well as methods are also described below in the context of hepatitis C.

With respect to the treatment of HBV, particularly preferred immunogenic portions for incorporation into recombinant retroviruses include HBeAg, HBcAg, and HBsAgs. Further, more than one immunogenic portion (as well as immunomodulatory factors, if desired) may be incorporated into the recombinant retrovirus. For example, within one embodiment a recombinant retrovirus may be prepared which directs the co-expression of both an immunogenic portion of the hepatitis B antigen, as well as an immunogenic portion of the hepatitis C polypeptide. Such constructs may be administered in order to prevent or treat acute and chronic hepatitis infections of either type B or C. Similarly, within other embodiments, a recombinant retrovirus may be prepared which directs the co-expression of both an immunogenic portion of the hepatitis B X antigen, as well as an immunogenic portion of the hepatitis C polypeptide. Such a construct may similarly be administered in order to treat hepatocellular carcinoma that is associated with either hepatitis B or C. In addition, because those individuals chronically infected with hepatitis B and C are at higher risk for developing hepatocellular carcinoma, such a vector may also be utilized as a prophylactic treatment for the disease.

Immunogenic portions may also be selected by other methods. For example, the HLA A2.1/$K^b$ transgenic mouse has been shown to be useful as a model for human T-cell recognition of viral antigens. Briefly, in the influenza and hepatitis B viral systems, the murine T-cell receptor repertoire recognizes the same antigenic determinants recognized by human T-cells. In both systems, the CTL response generated in the HLA A2.1/$K^b$ transgenic mouse is directed toward virtually the same epitope as those recognized by human CTLs of the HLA A2.1 haplotype (Vitiello et al., 1991, *J. Exp. Med.* 173:1007–1015; Vitiello et al., *Abstract of Molecular Biology of Hepatitis B Virus Symposia*, 1992).

Immunogenic proteins of the present invention may also he manipulated by a variety of methods known in the art, in order to render them more immunogenic. Representative examples of such methods include: adding amino acid sequences that correspond to T helper epitopes; promoting cellular uptake by adding hydrophobic residues; by forming particulate structures; or any combination of these (see generally, Hart, op. cit., Milich et al., 1988, *Proc. Natl. Acad. Sci. USA* 85:1610–1614; Willis, *Nature* 340:323–324, 1989; Griffiths et al., 1991, *J. Virol.* 65:450456).

The present invention also provides recombinant retroviruses capable of immune down-regulation. Briefly, specific down-regulation of inappropriate or unwanted immune responses, such as in autoimmune or pseudo-autoimmune diseases such as chronic hepatitis, diabetes, rheumatoid arthritis, graft vs. host disease and Alzheimer's, or in transplants of heterologous tissue such as bone marrow, can be engineered using immune-suppressive viral gene products, or active portion thereof, which suppress surface expression of transplantation (MHC) antigen. Within the present invention, an "active portion" of a gene product is that fragment of the gene product which must be retained for biological activity. Such fragments or active domains can be readily identified by systematically removing nucleotide sequences from the protein sequence, transforming target cells with the resulting recombinant retrovirus, and determining MHC class I presentation on the surface of cells using FACS analysis or other immunological assays, such as a CTL assay. These fragments are particularly useful when the size of the sequence encoding the entire protein exceeds the capacity of the viral carrier. Alternatively, the active domain of the MHC antigen presentation inhibitor protein can be enzymatically digested and the active portion purified by biochemical methods. For example, a monoclonal antibody that blocks the active portion of the protein can be used to isolate and purify the active portion of the cleaved protein (Harlow et al., *Antibodies: A Laboratory Manual,* Cold Springs Harbor, 1988).

Within one embodiment, the suppression is effected by specifically inhibiting the activation of display of processed peptides in the context of self MHC molecules along with accessory molecules such as CD8, intercellular adhesion molecule-1 (ICAM-1)., ICAM-2, ICAM-3, leukocyte functional antigen-1 (LFA-1) (Altmann et al., 1989, *Nature* 338:521), the B7.1-.3 molecule (Freeman et al., 1989, *J. Immunol.* 143:2714), LFA-3 (Singer, 1992, *Science* 255:1671. Rao, 1991, *Crit. Rev. Immunol.* 10:495), or other cell adhesion molecules. Antigenic peptide presentation in association with MHC class I molecules leads to CTL activation. Transfer and stable integration of specific sequences capable of expressing products expected to inhibit MHC antigen presentation block activation of T-cells, such as $CD8^+$ CTL, and therefore suppress graft rejection. A standard CTL assay may be utilized in order to detect this response. Components of the antigen presentation pathway include the 45 Kd MHC class I heavy chain, $\beta_2$-microglobulin, processing enzymes such as proteases, accessory molecules, chaperones such as calnexin (Gaczynska et al., 1993, *Nature,* 365:264–282), and transporter proteins such as PSF1, TAP1 and TAP 2 (Driscoll et al., 1993, *Nature* 365:262–263).

In an alternative example, recombinant retroviruses are provided which direct the expression of a gene product or an active portion of a gene product capable of binding $\beta_2$-microglobulin. Briefly, transport of MHC class I molecules to the cell surface for antigen presentation requires association with $\beta_2$-microglobulin. Thus, proteins that bind $\beta_2$-microglobulin and inhibit its association with MHC class I indirectly inhibit MHC class I antigen presentation. Suitable proteins include the H301 gene product. Briefly, the H301 gene, obtained from the human cytomegalovirus (CMV) encodes a glycoprotein with sequence homology to the $\beta_2$-microglobulin binding site on the heavy chain of the MHC class I molecule (Browne et al., 1990, *Nature* 347:770). H301 binds $\beta_2$-microglobulin, thereby preventing the maturation of MHC class I molecules, and renders transformed cells unrecognizable by cytotoxic T-cells, thus evading MHC class I restricted immune surveillance.

Within another embodiment, recombinant retroviruses are provided which direct the expression of a protein or active portion of a protein that binds to newly synthesized MHC class I molecules intracellularly. This binding prevents migration of the MHC class I molecule from the endoplasmic reticulum, resulting in the inhibition of terminal glycosylation. This blocks transport of these molecules to the cell surface and prevents cell recognition and lysis by CTL. For instance, one of the products of the E3 gene may be used to inhibit transport of MHC class I molecules to the surface of the transformed cell. More specifically, E3 encodes a 19 kD transmembrane glycoprotein, E3/19K, transcribed from the E3 region of the adenovirus 2 genome. Within the context of the present invention, tissue cells are transformed with a recombinant retrovirus containing the E3/19K sequence, which upon expression produces the E3/19K protein. The E3/19K protein inhibits the surface expression of MHC class I surface molecules, and cells transformed by the recombinant retrovirus evade an immune response. Consequently, donor cells can be transplanted with reduced risk of graft rejection and may require only a minimal immunosuppressive regimen for the transplant patient. This allows an acceptable donor-recipient chimeric state to exist with fewer complications. Similar treatments may be used to treat the range of so-called autoimmune diseases, including systemic lupus erythematosus, multiple sclerosis, rheumatoid arthritis or chronic hepatitis B infection.

Another alternative method of immunosuppression involves the use of antisense message, ribozyme, or other gene expression inhibitor specific for T-cell clones which are autoreactive in nature. These block the expression of the T-cell receptor of particular unwanted clones responsible for an autoimmune response. The anti-sense, ribozyme, or other gene may be introduced using a viral vector delivery system.

Other proteins, not discussed above, that function to inhibit, suppress or down-regulate MHC class I antigen presentation may also be identified and utilized within the context of the present invention. In order to identify such proteins, in particular those derived from mammalian pathogens (and, in turn, active portions thereof), a recombinant retrdvirus that expresses a protein or an active portion thereof suspected of being capable of inhibiting MHC class I antigen presentation is transformed into a tester cell line, such as BC. The tester cell lines with and without the sequence encoding the candidate protein are compared to stimulators and/or targets in the CTL assay. A decrease in cell lysis corresponding to the transformed tester cell indicates that the candidate protein is capable of inhibiting MHC presentation.

Many infectious diseases, cancers, autoimmune diseases, and other diseases involve the interaction of viral particles with cells, cells with cells, or cells with factors. In viral infections, viruses commonly enter cells via receptors on the surface of susceptible cells. In cancers, cells may respond inappropriately or not at all to signals from other cells or factors. In autoimmune disease, there is inappropriate recognition of "self" markers. Within the present invention, such interactions may be blocked by utilizing recombinant retroviruses that produce, in vivo, an analogue to either of the partners in an interaction. Such an analogue is known as a blocking agent.

This blocking action may occur intracellularly, on the cell membrane, or extracellularly. The blocking action of a viral or, in particular, a recombinant retrovirus carrying a gene for a blocking agent, can be mediated either from inside a susceptible cell or by secreting a version of the blocking protein to locally block the pathogenic interaction.

For example, in the case of HIV, the two agents of interaction are the gp 120/gp 41 envelope protein and the CD4 receptor molecule. Thus, an appropriate blocker would be a recombinant retrovirus expressing either an HIV env analogue that blocks HIV entry without causing pathogenic effects, or a CD4 receptor analogue. The CD4 analogue would be secreted and would function to protect neighboring cells, while the gp 120/gp 41 is secreted or produced only intracellularly so as to protect only the vector-containing cell. It may be advantageous to add human immunoglobulin heavy chains or other components to CD4 in order to enhance stability or complement lysis. Delivery of a recombinant retrovirus encoding such a hybrid-soluble CD4 to a host results in a continuous supply of a stable hybrid molecule.

Vector particles leading to expression of HIV env may also be constructed. It will be evident to one skilled in the art which portions are capable of blocking virus adsorption without overt pathogenic side effects (Willey et al., 1988, *J. Virol.* 62:139; Fisher et al., 1986, *Science* 233:655).

C. Tissue-specific Promoters

Although not an absolute requirement for the practice of the invention, in a further embodiment, the gene delivery vehicles of the invention can contain a liver specific promoter to maximize the potential for liver specific expression of the exogenous DNA sequence contained in the vectors. Preferred liver specific promoters include the hepatitis B X-gene promoter and the hepatitis B core protein promoter. These liver specific promoters are preferably employed with their respective enhancers. The enhancer element can be linked at either the 5' or the 3' end of the nucleic acid encoding the therapeutic molecule. The hepatitis B X gene promoter and its enhancer can be obtained from the viral genome as a 332 base pair EcoRV-NcoI DNA fragment employing the methods described in Twu, 1987, *J. Virol.* 61:3448–3453. The hepatitis B core protein promoter can be obtained from the viral genome as a 584 base pair BamHI-BglII DNA fragment employing the methods described in Gerlach, 1992, *Virol* 189:59≅66. It may be necessary to remove the negative regulatory sequence in the BamHI-BglII fragment prior to inserting it. Other liver specific promoters include the AFP (alpha fetal protein) gene promoter and the albumin gene promoter, as disclosed in EP Patent Publication 0 415 731, the −1 antitrypsin gene promoter, as disclosed in Rettenger, 1994, *Proc. Natl. Acad. Sci.* 91:1460–1464, the fibrinogen gene promoter, the APO-A1 (Apolipoprotein A1) gene promoter, and the promoter genes for liver transference enzymes such as, for example, SGOT, SGPT and -glutamyle transferase. See also PCT Patent Publications WO 90/07936 and WO 91/02805 for a description of the use of liver specific promoters in retroviral vectors.

For the retroviral vectors described herein, such as those described in Examples 1 and 27 herein, a liver specific promoter as described in this section can be introduced into the vector to operably linked to gene of interest (for example factor VIII) in order to induce more liver specific expression of the protein. In the case of AAV vectors, the promoter is operably linked to the nucleic acid encoding the therapeutic molecule upstream from the latter and between the AAV vector sequences (for example between the inverted terminal repeats in psub201 or downstream of the Double D ITR sequence).

Examples of the construction of retroviral vectors expressing a interferon under the control of liver-specific promoters is shown in Example 33 herein. Similar techniques can be used to construct retroviral vectors expressing other proteins under control of liver-specific promoters.

D. Use of Gene Delivery Vectors Co-expressing Therapeutic Protein and a Prodrug-converting Enzyme The gene delivery vehicles and the therapeutic methods of delivery are useful for the long term expression of therapeutic proteins for treatment of a variety of disorders described herein. Particularly, because of the long term treatment made possible by the present invention, it can be desirable for the gene delivery vehicles of the invention to co-express a prodrug converting enzyme which converts a non-cytotoxic compound into its cytotoxic counterpart. The protype of such enzymes is herpes simplex thymidine kinase (HSVTK) which converts the prodrug gancyclovir into a toxic compound.

Techniques for introducing HSVTK or other prodrug converting enzymes into gene delivery vehicles, particularly retroviral vectors are well known to those of skill in the art. (See e.g. WO 91/02805, WO 90/07936, and WO 95/14091). Procedures for preparing gene delivery vehicles, particularly retroviral vectors which co-express a therapeutic protein and HSVTK or other prodrug converting enzymes are described herein and are also described in number of publications (See, e.g. WO 93/10218.) These procedures can readily be used by those of skill in the art to introduce the HSVTK gene or a gene encoding another prodrug converting enzyme into the gene delivery vehicles of the invention. In addition, the pro-drug converting enzyme can be introduced into a second vector particle which is then co-administered with the gene delivery vehicle expressing the therapeutic protein. An example of this approach is described in WO 96/21015.

E. Pretreatment of Target Tissues

Retroviral vectors are known to preferentially infect dividing cells. (See Miller et al., 1990, *Molecular Cell Biol.* 10:4239.) There are variety of techniques that may be used to increase the number of dividing cells in target tissues and thereby enhance the efficiency of target cell infection by the retroviral vectors of the invention. For example, growth factors may be used to stimulate target tissues to enter the portion of the cell cycle in which retroviral vector integration can take place. Such growth factors and their target tissues include, but are not limited to, the following:

Protein S and Gas6 acting on nervous system cells and smooth muscle cells; thrombin acting on smooth muscle cells, gastrointestinal epithelium, liver fat storage cells, dental pulp cells, fibroblasts, endothelial cells, mesangial cells, and astrocytes; coagulation Factor Xa acting on smooth muscle cells; nerve growth factor acting on nervous system cells; CSF-1 acting on placenta and endometrium; IGF-1 acting on kidney, bone, skin, adipose tissue, airway smooth muscle cells, gastrointestinal epithelium, neural tissue, muscle, and follicular cells; insulin acting on gastrointestinal epithelium, skin, and adipose tissue; KGF acting on urothelium. mammary epithelium, skin, liver, and gastrointestinal epithelium; TGF acting on gastrointestinal epithelium, dental pulp, neural tissue, fibroblasts, connective tissue, inner ear sensory epithelium, colon, bone, pneumocyte type II cells, cornea, and smooth muscle cells; endothelin acting on kidney, smooth muscle cells, melanocytes, cardiac muscle, and astrocytes; PDGF acting on kidney, airway smooth muscle cells, gastrointestinal epithelium, neural tissue, and connective tissue; EGF acting on kidney, skin, neural tissue, inner ear sensory epithelium, connective tissue, fibroblasts, endometrium, liver, and intestine; HGF acting on liver, kidney, mammary epithelium, gastrointestinal epithelium, alveolar epithelium, melanocytes, placenta, and alveolar type II cells; PSA acting on prostate, breast, lung, colon, ovary, liver, and kidney; injurin and HGF-activators acting on liver, kidney, and mammary epithelium, FGF acting on neural cells, kidney, endothelium, fibroblasts, skin, skeletal muscle, connective tissue, melanocytes, cornea, bone marrow, dental pulp cells, liver, melanocytes, smooth muscle cells, and thyroid follicular cells; VEGF acting on endothelial cells; Arg-vasopressin acting on liver, kidney, and fibroblasts; thyroid hormones acting on bone; azoxymethane acting on the colon; prostaglandins acting on liver and dental pulp; IL1 acting on fibroblasts; IL2 acting on T cells; IL15 acting on muscle; triiodothyronine acting on liver; LIF acting on muscle and bone; amphiregulin acting on the skin; soluble thrombomodulin acting on fibroblasts; stem cell factor acting on erythroid progenitors; osteogenic protein 1 acting on chondrocytes, and bone; bone morphogenic protein acting on liver; MGF acting on melanocytes; MGSA acting on melanocytes; heregulins acting on mammary epithelium, keratinocytes, and Schwann cells; and melanotropin acting on melanocytes. Growth factors can also be used in combination, particularly but not limited to mixtures consisting of one or several of EGF, IGF, PDGF, FGF, or KGF. In particular, multiple growth factors known to stimulate cell division of a particular target tissue can used in comination to increase the proportion of dividing cells in the tissue. The actions of the above and other growth factors can also be potentiated with substances including but not limited to dextran sulfate, heparin, and other sulfated glycosanimoglycans, FBP; leukotrienes, prostaglandins, oleic acid, HGF activators, androgens, estrogens, ethanol, PF4, and TGF beta antagonists. Treatment with growth factors or the other substances described above can occur by administering the substances in vivo or can also be used in other treatment modalities such as ex vivo treatment.

The polypeptide growth factors described herein can be administered in a variety of forms including full-length growth factors, growth factor fragments, truncated growth factors, growth factor fusion proteins and growth factor analogues. Growth factor fusion proteins include fusion proteins with the full-length growth factor, truncated growth factor, growth factor analogue, and growth factor fragment. As used herein the term "growth factor fragment" refers to any growth factor polypeptide that contains less than a full-length sequence, and which retains sufficient biological activity to be used in the methods of the invention. The term "growth factor analogue" as used herein refers to growth factors, truncated growth factors and growth factor fragments with amino acid substitutions, deletions, additions, and modifications; and retaining the biological activity of the growth factor. Thus, the term "growth factor analogue" as used herein includes splice variants, truncations, variants, alleles and derivatives of the mature protein. Analogues possess one or more of the bioactivities of the full length protein. Thus, polypeptides that are identical or contain at least 60%, preferably 70%, more preferably 80%, and most preferably 90% amino acid sequence homology to the amino acid sequence of the mature protein wherever derived, from human or nonhuman sources, are included within this definition.

Growth factor analogues include variants of the growth factors described herein. Growth factor variants contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to minimize misfolding by substitution or deletion of one or more cysteine residues that are not necessary for function. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Thr/Cys and Phe/Trp/Tyr. The analogs herein further include peptides having one or more peptide mimics, also known as peptoids, that possess the bioactivity of the protein. Included within the definition are also polypeptides containing one or more analog amino acid (including, for example, unnatural amino acids, etc.), polypeptides with substituted linkages, as well as other modifications known in the art, both naturally occurring and non-naturally occurring. The term polypeptide also does not exclude post-expression modifications of the polypeptide, for example, glycosylations, acetylations, phosphorylations and the like A large variety of different forms of the various growth factors described above are known to those of skill in the art and can be used in the methods of the invention. For example, a variety of PDGF polypeptides are known in the art. For instance, nucleic acid vectors encoding naturally occurring PDGF and the production of recombinant PDGF are described in U.S. Pat. No. 5,219,759, issued Jun. 15, 1993, entitled "Recombinant DNA encoding PDGF A-chain Polypeptide Expression Vectors". In addition to the naturally occurring PDGF polypeptides, a variety of PDGF analogues are known in the art and can be used in the methods described herein. (See e.g. U.S. Pat. No. 5,149,792, issued Sep. 22, 1992, entitled "Platelet-Derived Growth Factor B Chain Analogues"; U.S. Pat. No. 5,128,321, issued Jul. 7, 1992, entitled "PDGF Analogues and Methods of Use"; and U.S. Pat. No. 4,849,407, issued Jul. 18, 1989, and entitled "Biologically Active Mosaic Proteins".

Different forms of IGF-1 and IGF-2 growth factor polypeptides are also well known the art. For example, recombinant human, as well as specific DNA sequences and expression vectors for the production of human IGF-1 are described in European Patent No. 0123228B1, grant published on Sep. 19, 1993, entitled "Hybrid DNA Synthesis of Mature Insulin-like Growth Factors". A variety of other forms of IGF-1 polypeptides are known in the art and can readily be produced for use in the methods of the invention. See e.g. U.S. Pat. No. 5,019,500, entitled "59 Valine Insulin-Like Growth Factor I and Process for Production Thereof"; PCT Patent Publication No. WO 93/23067 entitled "IGF-1 Analogues"; European Patent No. EP0128733B1, entitled "Human Insulin-Like Growth Factor (IGF) Produced from a Human Host, Process, Expression Vector and Recombinant Host Therefor., and IGF-containing Pharmaceutical Composition".

FGF growth factors encompass two families of growth factors found in a variety of different tissues and which are mitogenic factors for a number of different tissues. These two families of polypeptides have been termed acidic FGF and basic FGF. A large variety of different FGF polypeptides, analogues and fragments are known in the art an can be used in the methods of the present invention. See, e.g. U.S. Pat. No. 5,464,774, issued Nov. 7, 1995, entitled "Bovine Basic Fibroblast Growth Factor"; U.S. Pat. No. 5,155,214, entitled Basic Fibroblast Growth Factor, and U.S. Pat. No. 4,994,559, entitled "Human Fibroblast Growth Factor".

Different forms of keratinocyte growth factor that are useful in the methods of the invention are also known to those of skill in the art. See, for example, a preferred truncated form of KGF which is described in PCT Patent Publication No. 95/10434, published Jan. 12, 1995, and entitled "A Truncated Form of KGF Having Increased Biological Activity". Similarly, different forms of EGF polypeptides are known in the art. See e.g. PCT publication No. WO 90/08771 and U.S. Pat. No. 5,096,825, issued Mar. 17, 1992, entitled Gene for Human Epidermal Growth Factor and Synthesis of Expression Thereof.

The growth factor polypeptides, fragments and analogues used in the instant invention can be produced in a variety of ways, including isolation of PDGF polypeptide from naturally occurring sources, polypeptide chain synthesis by peptide synthesis methods and production of recombinant proteins. These methods are well known to those of skill in the art and are further described herein. For examples of the production of recombinant PDGF polypeptides and analogues, see U.S. Pat. No. 5,045,633, issued Sep. 3, 1991, entitled "Expression of Biologically Active PDGF Analogues in Eucaryotic Cells"; U.S. Pat. No. 4,769,328, issued Sep. 6, 1988, entitled "Expression of Biologically Active PDGF Analogues in Yeast"; and U.S. Pat. No. 4,801,542, issued Jan. 31, 1989, entitled "Expression of Biologically Active PDGF Analogues in Eucaryotic Cells". For examples of the production of FGF polypeptides see e.g. U.S. Pat. No. 5,229,501, entitled "Expression and Production of Human Firbroblast Growth Factor Receptor", U.S. Pat. No. 5,331, 095, entitled "Process for Purification and Production of Basic Fibroblast Growth Factor"; and U.S. Pat. No. 5,143,829, entitled High Level Expression of Basic FGF Having a Homogeneous N-terminus".

Liver is an attractive organ for gene therapy because it is easily accessible via the circulation and is the source of a variety of proteins involved in genetic disorders, including factor VIII. Gene therapy targeting the liver using the retroviral vectors of the invention can be performed with or without pretreatment to include benign hyperplasia of the liver. Pretreatment to induce benign liver hyperplasia can be effected, for example, by treatment with hepatocyte growth factor (HGF) and/or transforming growth factor alpha. (See e.g. Liu, et al. (1994) Hepatology 19:1521.)

A variety of different forms of HGF useful to induce liver cell proliferation are known in the art. See e.g. European Patent Publication No. EP 461560, published Dec. 12, 1991, and entitled "Recombinant Human Leukocyte Derived Heaptacyte Growth Factor—with DNA encoding it, Recombinant Expression Vectors, and Transformant Cells Expressing it." HGF can also be produced and administered to induce liver proliferation in vivo as is described in Joplin et al., 1992, *J. Clin. Invest.* 90:1284.

Liver cells can also be stimulated by administration of agents that mediate or potentiate the activation of endogenous HGF. HGF is produced as a single chain protein that is inactive as a growth factor. Single chain HGF is subsequently cleaved into a two-chain form which is the biologically active growth factor. Enzymes which are shown to convert single-chain HGF to its biologically active form are useful for inducing liver cell proliferation. Therefore, these enzymes can be administered either alone or in combination with exogenous HGF to enhance liver proliferation. Examples of such enzymes are coagulation factor XIIa (see Shiomura et al., 1995, *European J. of Biochem* 229:257); HGF activator (see Shiomura et al., 1992, Cytotechnology 8:219); HGF converting enzyme (Mizuno et al., 1994, *Biochem. Biophys. Res. Comm.* 198:1161); and urokinase and tissue plasminogen activators (Mars et al., 1993, *Am J. Pathol.* 143:949). For example, urokinase can be co-administered with HGF. HGF and urokinase could be either be co-formulated or mixed immediately prior to injection. If HGF and urokinase were co-formulated, they could, for example, be stored at low pH in order to minimize the activity of urokinase.

The effects of either HGF or TGFalpha on liver stimulation have also been shown to be enhanced by prior administration of collagenase (Liu, 1994, *Hepatology* 19:1521). Agents that stimulate release of collagenase-like materials from monocytic cell types, such as LPS or endotoxin-like substances (Beauchamp, 1994, *Surgery* 116:637) may also be used. Nonenzymatic adjuncts and costimulants of growth factors may also be used, including estrogens with HGF (Ni, 1994, *Hepatology* 19:183), heparin or other sulfated glycosaminoglycans with HGF (Yamakazi, 1996, *Cytokine* 8:178; Matsumoto, 1996, *Biochem Biophys Res Commun* 227:455), spermine or spermidine with HGF (Higaki, 1994, *Gastroenterology* 106:1024), nicotinamide with EGF (Wu (1994) Cancer Res 54:5964), or choline (Tessitore, 1997, *Biochem J.* 322:151). The phosphofetuin/phospho-alpha-2-HS glycoprotein pathway downregulates liver regeneration. Inhibitors of this pathway may be used to upregulate liver proliferation. Such inhibitors include IL6, ILlaipha, or anti-fetuin antibodies (Ohnishi, 1997, *Eur. J. Biochem.* 243:753). Combinations of these agents can also be applied along with the various growth factors described above.

In addition to growth factor therapy, liver cell growth can also be stimulated by nutritional minipulation. A variety of different nutritional regimines can be used. For instance, a period of protein deprivation followed by consumption of a high protein meal can be used to stimulate DNA synthesis and cell division. (See Mead et al., 1990, *Cancer Res.* 50:7023–7030.)

Another example of stimulation of cell division in a particular tissue is the use of cyclooxigenase inhibitors, such as indomethacin, to induce hyperplasia in the gastric mucosa. In particular, indomethacin is known to increase DNA synthesis and cell clearance in duodenal and jejunal mucusa (see Uribe et al., 1992, *Dig. Dis. Sci.* 37:403–408). Thus, pretreatment with indomethacin or other non-steroidal anti inflammatory drugs can be used to increase cell proliferation in the gastric mucosa. In addition, prostaglandins, in particular, prostraglandin E2 can be used after introduction of the gene therapy vehicle in order to increase the retention of the transduced intestinal cells.

Yet another example of a method to increase the number of dividing cells in gastric mucusa is the administration omeprazole. Omeprazole can be obtained and administered as described in Kakei et al., 1995, *Biochem. Biophys. Res. Comm.* 214:861–867.

An additional class of drugs that is known to induce liver proliferation is the peroxisome proliferators. These are a set of structurally diverse drugs that cause an increase in the number of peroxisomes present in hepatocytes, but which also lead to hepatocyte mitosis mimicking regeneration through unknown mechanism(s). Some of these have found clinical utility as hypolipidemic drugs, particularly clofibrate (Reddy and Lalwai, 1983, *CRC Crit Rev Toxicol* 12:1–58), and act through activation of members of the superfamily of nuclear steroid receptors known as PPAR (peroxisome proliferator-activated receptors) and subsequent increased transcription of peroxisomal beta-oxidative enzymes (Isseman and Green, 1990, *Nature* 347:645–650), and possibly through down-regulation of the endoplasmic reticulum protein, BiP (Motojima & Goto, 1992, *FEBS Lett* 308:207–210). These drugs include clofibrate (Sigma Chemical Compan, St. Louis, Mo., USA), WY 16463 (Chem Syn, Lenexa, Kans., USA), DEHP (Aldrich, Milwaukee Wis., USA), DHEA (Sigma). PFDA (Aldrich), PFOA (Aldrich), fenofibrate (Laboratories Fournier, Daix, France), gemfibrozil (Lopid, Warner-Lambert, Ann Arbor Mich.), (Sigma), clofibric acid (Sigma), bezafibrate (Sigma), methyl clofenapate, tibric acid, BR 931(4-chloro-6(2,3-xylidino)2-pyrimidinylthio-(N-beta-hydroxy-ethyl)acetamide), DEHA (di(2ethylhexyl)adipate), nafenopin, clinofibrate.

Other classes of nonproteinaceous substances known to stimulate liver proliferation may be employed. These include 9-cis-retinoic acid (Ohmura, 1996, *Life Sciences* 58:PL211), the glycolipid, hepatopoietin B, (Michalopoulos, 1990, *FASEB J.* 4:176), cyclosporine A (Masuhara, 1993, *Carcinogenesis* 14:1579), phosphatidylethanolamine N-methyltransferase inhibitors such as 3-deazaadenosine or other methylation inhibitors (Chiang, 1979, *Biochem Pharmacol* 28:1897), nonsteroidal antiinflammatory drugs that activate PPAR such as flufenamic acid, fenoprofen, and ibuprofen (Lehmann, 1997, *J. Biol. Chem.* 272:3406); or apoptosis-inducing molecules (Busch, 1984, *Carcinogenesis* 5:453; Colambano, 1985, *Lab Invest* 52:670) such as anti-Fas antibody, dexamethasone, etoposide, canptothecin, staumsporin, hypericin, S-nitrosoglutathione, taxol, 4-hydroxyphenyl retinamide, prostaglandin A2, delta-12-PGJ2, sulindac sulfone, actinomycin D, beta-lapachone, TPEN, vinblastine, vincristine, and A23187. Triiodothrone can also be administered as a stimulatory compound. Combinations of these substances can also be applied along with the peptide growth factors described herein.

D. Cell Culture

As noted above, the present invention provides high titer recombinant retroviral preparation suitable for administration to humans. In order to produce such high titer preparations, cell culture methods as described below are provided in order to enable the production of high titer recombinant retroviruses. Briefly, a wide variety of methods may be utilized, including for example, the use of fermenters or bioreactors, roller bottles, cell hotels or cell factories, and hollow fiber culture.

In particular, for bioreactors or fermenters, cells are preferably grown on microcarriers (i.e., Cytodex 1 or Cytodex 2; Pharmacia, Piscataway. N.J. at concentrations ranging from 3 to 15 g/L microcarrier. Suitable media, and growth conditions are described by way of a representative illustration in Example 17.

For roller bottles, suitable conditions include those described above for bioreactors, with the exception that microcarrier beads are not utilized. Generally, cells are grown in 850 $cm^2$ roller bottles ("FALCON" Corning, Corning N.Y.) containing DMEM media, along with 15%–20% FBS. Preferably, the bottles are sealed to avoid contamination, although "open" bottles may also be utilized under appropriate conditions (e.g., 5% $CO_2$). Generally, the roller bottles are incubated at a temperature of 37° C., with a rotation speed of 0.5 rpm/minute.

Cell factories may also be utilized for the large scale cell culture and production of recombinant retroviruses. Briefly, cell factories (also termed "cell hotels") typically contain 2, 10, or 40 trays, are molded from virgin polystyrene, treated to provide a Nuclon D surface, and assembled by sonic welding one to another. Generally, these factories have two port tubes which allow access to the chambers for adding reagents or removing culture fluid. A 10-layer factory provides 6000 $cm^2$ of surface area for growing cells, roughly the equivalent of 27 T-225 flasks. Cell factories are available from a variety of manufacturers, including for example Nunc.

Most cell types are capable of producing high titer vector into the media for 3–6 days, allowing for multiple harvests. Each cell type is tested to determine the optimal harvest time after seeding the culture and optimal number of harvest days. Cells are typically initially grown in DMEM supplemented with 2–20% FBS in roller bottles until the required number of cells for seeding a cell factory is obtained. Cells are then seeded into the factories and 2 liters of culture supernatant containing vector is harvested from each day for four days. Fresh DMEM/FBS is used to replenish the cultures.

Within other aspects of the present invention, hollow fiber culture methods are provided for the production of recombinant retroviruses. Briefly, high titer retroviral production using hollow fiber cultures is based on increasing viral concentration as the cells are being cultured to a high density in a reduced volume of media. Cells are fed nutrients and waste products are diluted using a larger volume of fresh media which circulates through the lumen of numerous capillary fibers. The cells are cultured on the exterior spaces of the capillary fibers in a bioreactor chamber where cell waste products are exchanged for nutrients by diffusion through 30,000 Dalton pores in the capillary fibers. Retroviruses which are produced from the cell lines are too large to pass through the 30,000 Dalton pore membrane, and thus concentrate in the hollow fiber bioreactor along side of the cells. The volume of media being cultured on the cell side is approximately 10 to 100 fold lower then volumes required for equivalent cell densities cultured in tissue culture dishes or flasks. This decrease fold in volume inversely correlates with the fold induction of titer when hollow fiber retroviral liters are compared to tissue culture dishes or flasks. This 10–100 fold induction in titer is seen when an individual retroviral producer cell line is amiable to hollow fiber growth conditions. To achieve maximum cell density, the individual cells must be able to grow in very close proximity and on top of each other. Many cell lines will not grow in this fashion and retroviral packaging cell lines based on these types of cell lines may not achieve 10 fold increases in titer. Cell lines which would grow very well would be non-adherent cell line and it is believed that a retroviral producer line based on a non-adherent cell line may reach 100 fold increases in titer compared to tissue culture dishes and flasks.

The harvest procedure, in its original design, is a procedure which uses syringes to evacuate and replace culture sups to harvest the produced vector. This syringe procedure has an associated high risk of possible contamination, which requires a significant number manual connections and disconnection's of media flow paths. However a convenient procedure has been devised which will reduce the risk of contaminating the cultures, increase the daily volumes which can harvested and reduce the time required to handle the culture system. The harvesting procedure is now performed using a batch peristaltic pump drive to deliver precise volumes of fresh media to replace equal volumes of harvest material which is then delivered through thin line tubing into a collection bottle stored at 4° C. The pump batch sequence is activated by a timer which can be set at specific time points and the pump can be adjusted to harvest any set volume of harvest material, twenty-four hours a day. The collected supernatant can then be frozen, pooled with earlier harvests, or processed as described elsewhere. This collection procedure can be used for any hollow fiber system including the Cellco (Rockville, Md.), Unisyn (Tustin, Calif.), or Cellex (Coon Rapids, Minn.) systems including ceramic matrix high density culture systems.

E. Concentration and Purification of Recombinant Retroviral Particles

As noted above, the present invention provides methods for concentrating and purifying recombinant retroviruses, in order to increase the purity of therapeutic preparation, as well as to increase the titer of recombinant retrovirus that may be given. A wide variety of methods may be utilized for increasing viral concentration and purity, including for example, precipitation of recombinant retroviruses with ammonium sulfate, polyethylene glycol ("PEG") concentration, concentration by centrifugation (either with or without gradients such as PERCOLL, or "cushions" such as sucrose, use of concentration filters (e.g., Amicon filtration), and 2-phase separations. Each of these methods will be discussed in more detail below.

Briefly, in order to accomplish concentration by precipitation of recombinant retroviruses with ammonium sulfate, ammonium sulfate is added slowly to an appropriate concentration, followed by centrifugation and removal of the ammonium sulfate either by dialysis or by separation on a hydrophobic column. One difficulty with this method however, is that in addition to concentration of recombinant retroviruses, other proteinaceous debris may also be concentrated.

Alternatively, recombinant retroviruses may be concentrated from culture medium with PEG (Green et al., 1970, *PNAS* 67:385–393; Syrewicz et al., 1972, *Appl. Micro.* 24:488–494). Such methods are rapid, simple, and inexpensive. However, like ammonium sulfate precipitation, use of PEG also concentrates other proteins from solution.

Within other embodiments, recombinant retroviruses may be concentrated by centrifugation, and more particularly, low speed centrifugation. Briefly, low speed centrifugation allows concentration of recombinant retroviruses, while avoiding the difficulties associated with pelleting that accompanies high speed centrifugation (e.g., virus destruction or inactivation). Particularly preferred methods for concentrating viruses by low-speed centrifugation are described below in more detail in Example 15.

Within yet other aspects of the invention, recombinant retroviruses may be concentrated by an aqueous two-phase separation method. Briefly, polymeric aqueous two-phase systems may be prepared by dissolving two different non-compatible polymers in water. Many pairs of water-soluble polymers may be utilized in the construction of such two-phase systems, including for example polyethylene glycol ("PEG") or methylcellulose, and dextran or dextran sulfate (see Walter and Johansson, 1986, *Anal. Biochem.* 155:215–242; Albertsson, "Partition of Cell Particles and Macromolecules" Wiley, New York, 1960). As described in more detail below in Example 13, utilizing PEG at concentrations ranging from 5% to 8% (preferably 6.5%), and dextran sulfate at concentrations ranging from 0.4% to 1% (preferably 0.4%), an aqueous two-phase system may be established suitable for purifying recombinant retroviruses. Utilizing such procedures, approximately 1.4 liters of crude research grade supernatant may be reduced to a 10 mL volume, while recovering approximately 50% of the total starting retrovirus.

For purposes of illustration, one representative concentration process which combines several concentration steps is set forth below. Briefly, recombinant retroviruses may be prepared either from roller bottles, cell factories, or bioreactors prior to concentration. Preferably, daily harvests of recombinant retroviruses from producer cells is preferred, followed by addition of fresh media Removed media containing the recombinant retrovirus may be frozen at −70° C., or more preferably, stored at 2° C. to 8° C. in large pooled batches prior to processing.

For material obtained from a bioreactor, the recombinant retrovirus pool is first clarified through a 0.8 um filter (1.2 um glass fiber pre-filter, 0.8 um cellulose acetate) connected in series with a 0.65 um filter (Sartorious). This filter arrangement provides approximately 2 square feet of filter, and allows processing of about 15–20 liters of pooled material before clogging. For material obtained from roller bottles or cell factories, a single 0.65 um cartridge (2 sq. ft.) normally suffices for volumes up to 40 liters. For 80 liter cell factory processes, a 5 sq. ft. filter may be required.

Preferably, after clarification, the filter is rinsed with buffer (150 mM NaCl, 25 mM Tris, pH 7.2–7.5). This step has allowed recoveries of recombinant retrovirus ranging from 80% to 120%.

Following clarification, recombinant retroviruses are concentrated by tangential flow ultrafiltration utilizing Filtron units and Sigma Screen cassettes with a 300,000 mw cut off. For bioreactor material (containing 12% to 16% FBS), 4 to 5 liters of material may be concentrated per cassette. For roller bottles or cell factories at 12–16% FBS, 5–6 liters of material may be concentrated per cassette. Finally, for cell factories containing 10% FBS, 8 to 9 liters of material may be concentrated per cassette. Utilizing a pressure differential of 2 psi between filtrate (8 psi) and retentate (10 psi), up to 80 liters of material may be concentrated to a volume of less than 500 ml in under two hours. This process also provides a yield of about 80%.

Following the ultrafiltration step, DNAse is added to a concentration of 50 U/ml, and recirculated at a lower pump speed with the filtrate line closed for 30 minutes. If retroviruses have been trapped within a gel layer formed during the ultrafiltration, this step will break down trapped retrovirus, and improve recovery.

Discontinuous diafiltration is then accomplished by addition of 4 liters of additional buffer, and utilizing the same cross differential pressure set forth above. Generally, recovery after this step is approximately 70%.

Concentrated material is then subjected to column chromatography on a Pharmacia S-500 HG size exclusion gel, utilizing 50 mM NaCl and 25 mM Tris pH 7.2–7.5 as minimum salt and ionic strength concentrations. Generally, recombinant retroviruses elute off in the first peak.

Tangential flow filtration may once again be utilized in order to further reduce the volume to under 200 ml. Finally, the concentrated material is sterilized by filtration through a 0.2 um Millipore filter (PVDF, or Sterivex).

F. Assays

Within other aspects of the present invention, methods are provided for quantitating retroviral particles utilizing non-denaturing gels (e.g., 4–15% gradient polyacrylamide gels), along with methods for estimating or quantitating the resultant products such as, for example, staining with coomassie blue or silver stain, followed by densitometry scanning. Such methods, while not capable of discriminating between viable and non-viable vector particles, are advantageous because they are relatively simple and quick. One representative example of such methods is set forth below in Example 10 in more detail.

Within other aspects of the present invention, assays are provided for titering recombinant retrovirus in a sample. Typically, such assays may be based upon presence of a selectable marker, or formation of blue colonies. However, within certain embodiments recombinant retroviruses are provided which do not include a gene coding for a selectable marker. Therefore, antibody and PCR assays, the latter of which is described below, may be employed in order to determine retrovirus titer. To use PCR to amplify sequences unique to the recombinant retroviruses described herein. various primers are required. Such primers can readily be designed by those skilled in the art and will depend on the retroviral vector backbone employed and the components thereof, the particular region(s) desired to be amplified, etc. Representative examples of particular primer pairs include those specific for LTR sequences, packaging signal sequences or other regions of the retroviral backbone, include primers specific for the nucleic acid molecule (ie., non-heterologous sequence) of interest.

Briefly, within one embodiment of the invention a PCR titering assay is performed by growing a known number of cells, transduced with a recombinant retrovirus on 6-well plates for at least 16 hr. before harvest. One well per plate is sacrificed for counting. Cells. from the other wells are lysed and their contents isolated. DNA is prepared using a QUIAmp DNA isolation kit (QUIAgen, Inc.,Chatsworth, Calif.). DNAs are resuspended in $5 \times 10^6$ cell equivalents/$\mu$l per sample.

To calculate titer, a standard curve is generated using DNA isolated from $5 \times 10^6$ untransduced HT1080 cells (negative control) and $5 \times 10^6$ HT1080 cells transduced with a known vector and having one copy of that vector per cell genome (positive control), such as may be prepared from packaging cell lines transduced with a recombinant retrovirus encoding a selectable marker, e.g., neomycin resistance. The standard curve is generated by combining different amounts of the positive and negative control DNA and amplifying specific sequences therefrom by PCR using primers specific to a particular region of the recombinant retrovirus. A representative group of mixtures for generating a standard curve is:

| Tube | 100% | 75% | 50% | 25% | 10% | 5% | 0% | Blank |
|---|---|---|---|---|---|---|---|---|
| Positive Control ($\mu$l) | 50 | 37.5 | 25 | 12.5 | 5 | 2.5 | 0 | 0 |
| Negative Control ($\mu$l) | 0 | 12.5 | 25 | 37.5 | 45 | 47.5 | 50 | 0 |
| Distilled water ($\mu$l) | 0 | 0 | 0 | 0 | 0 | 0 | 0 | 50 |

Five microliters from each tube is placed into one of eight reaction tubes (duplicates are also prepared), with the remainder bring stored at $-20°$ C. Five microliters from each sample DNA preparations are placed into their own reaction tubes in duplicate. PCR reactions (50 $\mu$l total volume) are then initiated by adding 45.0 $\mu$l of a reaction mix containing the following components per tube to be tested: 24.5 $\mu$l water, 5 $\mu$l 10×reaction PCR buffer, 4 $\mu$l of 25 mM MgCl$_2$, 4 $\mu$l dNTPs (containing 2.5 mM of each of dATP, dGTP, dCTP, and dTTP), 5 $\mu$l of primer mix (100 ng or each primer), 0.25 $\mu$L TaqStart monoclonal antibody (Clontech Laboratories, Inc., Palo Alto, Calif.), 1.00 $\mu$L TaqStart buffer (Clontech Labs, Inc.), and 0.25 $\mu$L AmpliTaq DNA polymerase (Perkin-Elmer, Inc., Norwalk, Conn.). Just prior to aliquoting the reaction mix to the reaction tubes, 1 $\mu$L of $\alpha$-$^{32}$P dCTP (250 $\mu$Ci; 3000 C/mmol, 10 mCi/mL, Amersham Corp., Arlington Heights, Ill.) is added into the reaction mix. After adiquoting 45.0 $\mu$L the reaction mix into each of the reaction tubes, the tubes are capped and placed into a thermocycler. The particular denaturation, annealing, elongation times and temperatures, and number of thermocycles will vary depending on size and nucleotide composition of the primer pair used. 20–25 amplification thermocycles are then performed. 5 $\mu$L of each reaction is then spotted on DE81 ion exchange chromatography paper (Whatman, Maidstone, England) and air dried for 10 min. The filter is then washed five times, 100 mL per wash, in 50 mM Na$_2$PO$_4$, pH 7, 200 mM NaCl, after which it is air dried and then sandwiched in Saran Wrap. Quantitation is performed on a PhosphoImager SI (Molecular Dynamics, Sunnyvale, Calif.). Filters are typically exposed to a phosphor screen, which stores energy from ionizing radiation, for a suitable period, typically about 120 min. After exposure, the phosphor screen is scanned, whereby light is emitted in proportion to the radioactivity on the original filter. The scanning results are then downloaded and plotted on a log scale as cpm (ordinate) versus percent positive control DNA (abscissa). Titers (infectious units/mL) for each sample are calculated by multiplying the number of cells from which DNA was isolated by the percentage (converted to decimal form) determined from the standard curve based on the detected radioactivity, divided by the volume of recombinant retrovirus used to transduce the cells. As will be appreciated by those in the art, other methods of detection, such as colorimetric methods, may also be employed to label the amplified products.

G. Formulation

Within other aspects of the present invention, methods are provided for preserving an infectious recombinant retrovirus, such that the recombinant retrovirus is capable of infecting mammalian cells upon reconstitution (see U.S. Ser. No. 08/153,342). Briefly, recombinant retrovirus which has been purified or concentrated as described above may be preserved by first adding a sufficient amount of a formulation buffer to the media containing the recombinant retrovirus, in order to form an aqueous suspension. The formulation buffer is an aqueous solution that contains a saccharide, a high molecular weight structural additive, and a buffering component in water. As utilized within the context of the present invention, a "buffering compound" or "buffering component" should be understood to refer to a substance that functions to maintain the aqueous suspension at a desired pH. The aqueous solution may also contain one or more amino acids.

The recombinant retrovirus can also be preserved in a purified form. More specifically, prior to the addition of the formulation buffer, the crude recombinant retrovirus described above may be clarified by passing it through a filter, and then concentrated, such as by a cross flow concentrating system (Filtron Technology Corp., Nortborough, Mass.). Within one embodiment, DNase is added to the concentrate to digest exogenous DNA. The digest is then diafiltrated to remove excess media components and establish the recombinant retrovirus in a more desirable buffered solution. The diafiltrate is then passed over a Sephadex S-500 gel column and a purified recombinant retrovirus is eluted. A sufficient amount of formulation buffer is added to this eluate to reach a desired final concentration of the constituents (see, e.g., Example 9) and to minimally dilute the recombinant retrovirus, and the aqueous suspension is then stored, preferably at −70° C. or immediately dried. As noted above, the formulation buffer is an aqueous solution that contains a saccharide, a high molecular weight structural additive, and a buffering component in water. The aqueous solution may also contain one or more amino acids.

The crude recombinant retrovirus can also be purified by ion exchange column chromatography. This method is described in more detail in U.S. patent application Ser. No. 08/093,436. In general, the crude recombinant retrovirus is clarified by passing it through a filter, and the filtrate loaded onto a column containing a highly sulfonated cellulose matrix. The recombinant retrovirus is eluted from the column in purified form by using a high salt buffer. The high salt buffer is then exchanged for a more desirable buffer by passing the eluate over a molecular exclusion column. A sufficient amount of formulation buffer is then added, as discussed above, to the purified recombinant retrovirus and the aqueous suspension is either dried immediately or stored, preferably at −70° C.

The aqueous suspension in crude or purified form can be dried by lyophilization or evaporation at ambient temperature. Specifically, lyophilization involves the steps of cooling the aqueous suspension below the glass transition temperature or below the eutectic point temperature of the aqueous suspension, and removing water from the cooled suspension by sublimation to form a lyophilized retrovirus. Briefly, aliquots of the formulated recombinant retrovirus are placed into an Edwards Refrigerated Chamber (3 shelf RC3S unit) attached to a freeze dryer (Supermodulyo 12K). A multistep freeze drying procedure as described by Phillips et al. (Cryobiology 18:414, 1981) is used to lyophilize the formulated recombinant retrovirus, preferably from a temperature of −40° C. to 45° C. The resulting composition contains less than 10% water by weight of the lyophilized retrovirus. Once lyophilized, the recombinant retrovirus is stable and may be stored at −20° C. to 25° C., as discussed in more detail below.

Within the evaporative method, water is removed from the aqueous suspension at ambient temperature by evaporation. Within one embodiment, water is removed through spray drying (EP 520,748). Within the spray drying process, the aqueous suspension is delivered into a flow of preheated gas, usually air, whereupon water rapidly evaporates from droplets of the suspension. Spray drying apparatus are available from a number of manufacturers (e.g., Drytec, Ltd., Tonbridge, England; Lab-Plant, Ltd., Huddersfield, England). Once dehydrated, the recombinant retrovirus is stable and may be stored at −20° C. to 25° C. Within the methods described herein, the resulting moisture content of the dried or lyophilized retrovirus may be determined through use of a Karl-Fischer apparatus (EM Science Aquastar™ V1B volumetric titrator, Cherry Hill, N.J.), or through a gravimetric method.

The aqueous solutions used for formulation, as previously described, are composed of a saccharide, high molecular weight structural additive, a buffering component, and water. The solution may also include one or more amino acids. The combination of these components act to preserve the activity of the recombinant retrovirus upon freezing and lyophilization, or drying through evaporation. Although a preferred saccharide is lactose, other saccharides may be used, such as sucrose, mannitol, glucose, trehalose, inositol, fructose, maltose or galactose. In addition, combinations of saccharides can be used, for example, lactose and mannitol, or sucrose and mannitol. A particularly preferred concentration of lactose is 3%–4% by weight. Preferably, the concentration of the saccharide ranges from 1% to 12% by weight.

The high molecular weight structural additive aids in preventing viral aggregation during freezing and provides structural support in the lyophilized or dried state. Within the context of the present invention, structural additives are considered to be of "high molecular weight" if they are greater than 5000 m.w. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight. Preferably, the concentration of the high molecular weight structural additive ranges from 0.1% to 10% by weight.

The amino acids, if present, function to further preserve viral infectivity upon cooling and thawing of the aqueous suspension. In addition, amino acids function to further preserve viral infectivity during sublimation of the cooled aqueous suspension and while in the lyophilized state. A preferred amino acid is arginine, but other amino acids such as lysine, omithine, serine, glycine, glutamine, asparagine, glutamic acid or aspartic acid can also be used. A particularly preferred arginine concentration is 0.1% by weight. Preferably, the amino acid concentration ranges from 0.1% to 10% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. A particularly preferred pH of the recombinant retrovirus formulation is 7.4, and a preferred buffer is tromethamine.

In addition, it is preferable that the aqueous solution contain a neutral salt which is used to adjust the final formulated recombinant retrovirus to an appropriate iso-osmotic salt concentration. Suitable neutral salts include sodium chloride, potassium chloride or magnesium chloride. A preferred salt is sodium chloride.

Aqueous solutions containing the desired concentration of the components described above may be prepared a concentrated stock solutions.

A particularly preferred method of preserving recombinant retroviruses in a lyophilized state for subsequent reconstitution comprises the steps of (a) combining an infectious recombinant retrovirus with an aqueous solution to form an aqueous suspension, the aqueous suspension including 4% by weight of lactose, 0.1% by weight of human serum albumin, 0.03% or less by weight of NaCl, 0.1% by weight of arginine, and an amount of tromethamine buffer effective to provide a pH of the aqueous suspension of approximately 7.4, thereby stabilizing the infectious recombinant retrovirus; (b) cooling the suspension to a temperature of from 40° C. to 45° C. to form a frozen suspension; and (c) removing water from the frozen suspension by sublimation to form a lyophilized composition having less than 2% water by weight of the lyophilized composition, the composition being capable of infecting mammalian cells upon reconstitution. It is preferred that the recombinant retrovirus be replication defective and suitable for administration into humans upon reconstitution.

Figure 4:
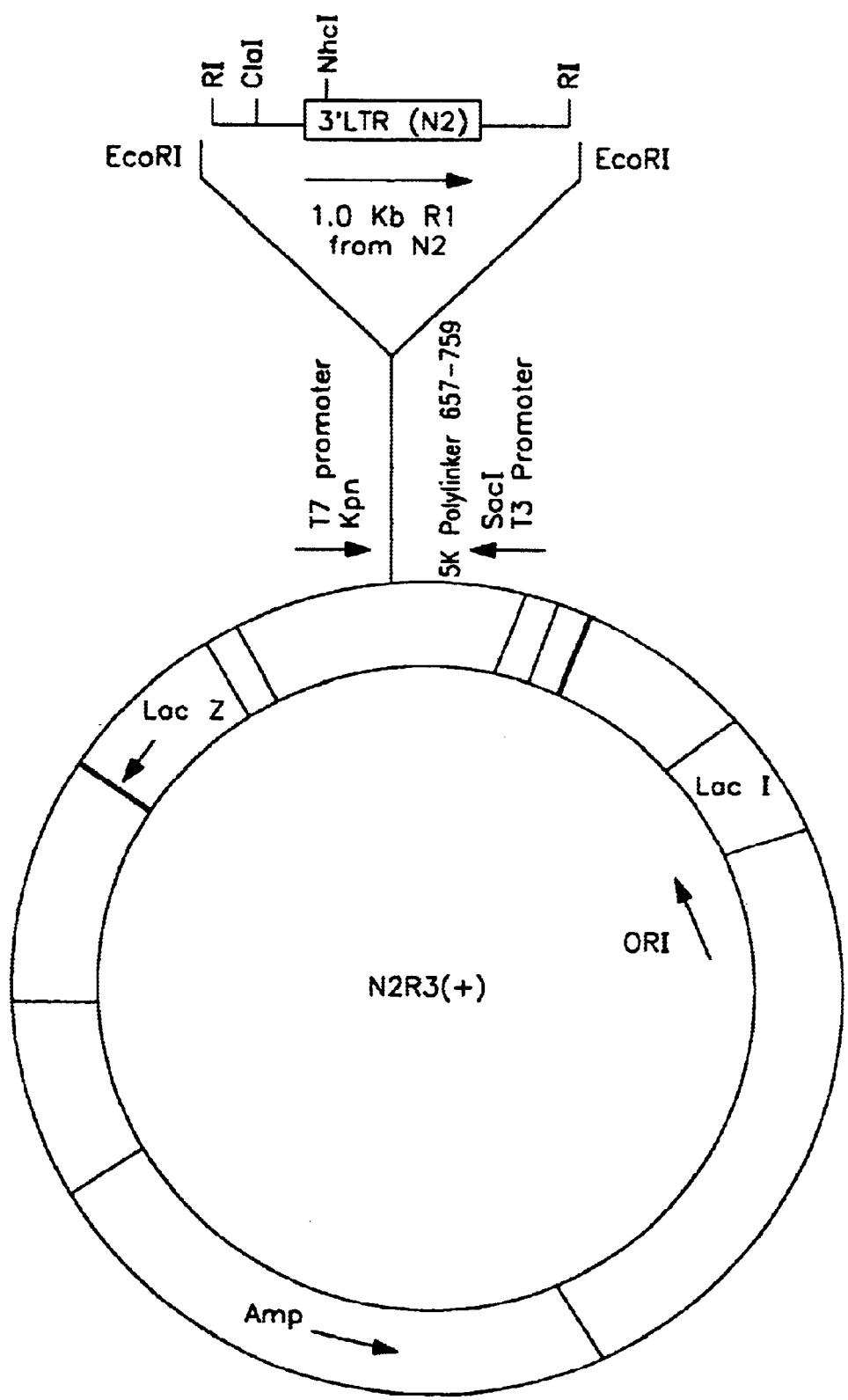
FIG. 4 is a schematic illustration of pN2R3(+).
Figure 5:
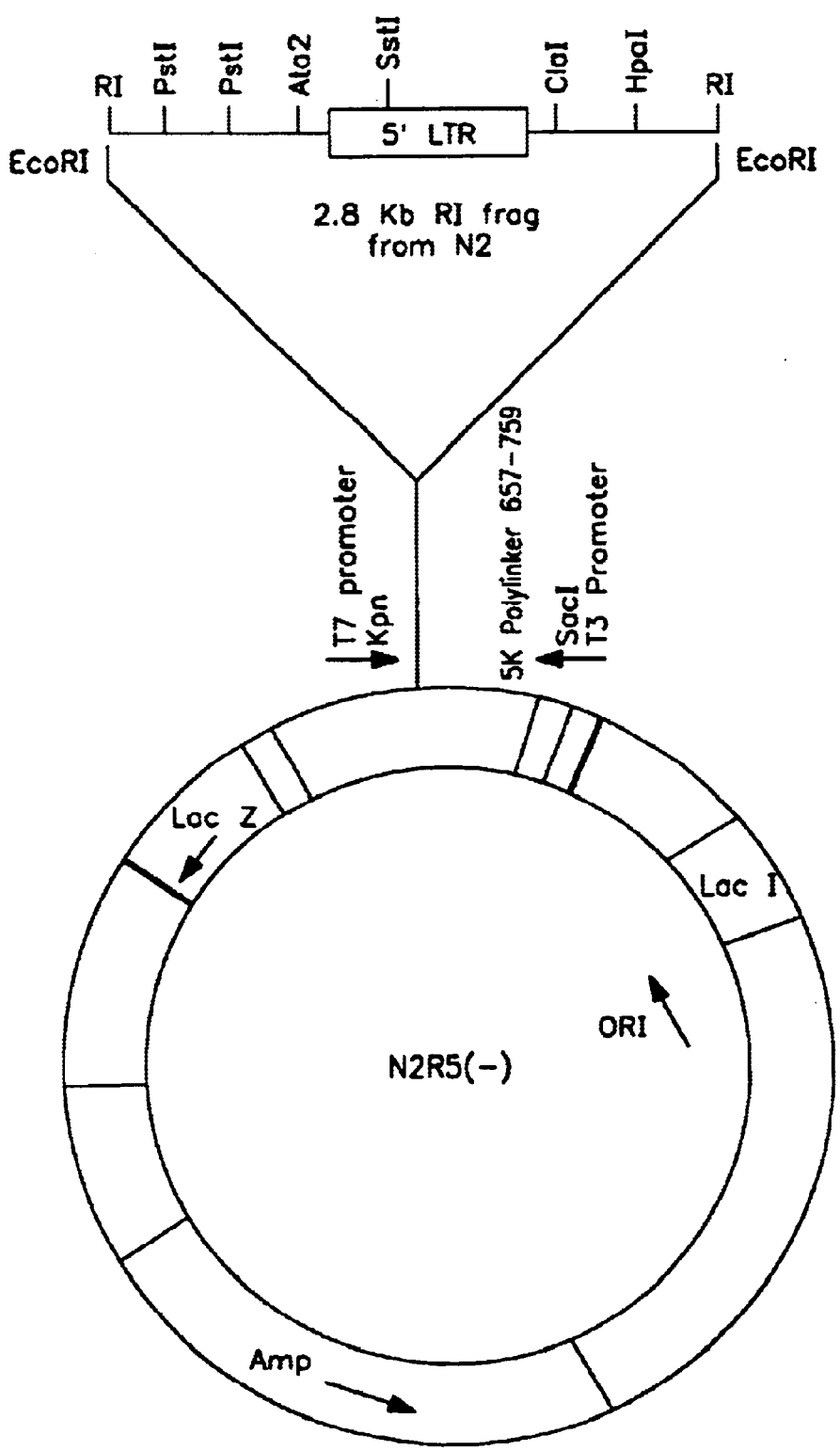
FIG. 5 is a schematic illustration of pN2R5(-).

As illustrated in FIGS. 1 and 2, mannitol and lactose lyophilized recombinant retrovirus formulations were assayed for preservation of viral activity under various storage temperatures as a function of time. Similarly, FIG. 3 illustrates the results of assays of trehalose recombinant retrovirus formulations for preservation of viral activity under various storage temperatures as a function of time. FIG. 4 depicts a comparison of the viral infectivity of frozen formulated recombinant retrovirus (−80° C.) as a liquid and the viral infectivity of lyophilized recombinant retrovirus stored at −20° C. Mannitol formulations may lose considerable activity upon lyophilization (5–6 fold), but appear to remain stable subsequent to the lyophilization event. Although not preferable, such a loss is acceptable assuming sufficient amounts of retrovirus are present in the aqueous solution.

It will be evident to those skilled in the art given the disclosure provided herein that it may be preferable to utilize certain saccharides within the aqueous solution when the lyophilized retrovirus is intended for storage at room temperature. More specifically, it is preferable to utilize disaccharides, such as lactose or trehalose, particularly for storage at room temperature.

The lyophilized or dehydrated retroviruses of the subject invention may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted retrovirus. Such components include cytokines, such as IL-2, polycations, such as protamine sulfate, or other components which enhance the transduction efficiency of the reconstituted retrovirus. Lyophilized or dehydrated recombinant retrovirus may be reconstituted with any convenient volume of water or the reconstituting agents noted above that allow substantial, and preferably total solubilization of the lyophilized or dehydrated sample.

H. Administration

As noted above, high titer recombinant retroviral particles of the present invention may be administered to a wide variety of locations including, for example, into sites such as the cerebral spinal fluid, bone marrow, joints, arterial endothelial cells, rectum, buccal/sublingual, vagina, the lymph system, to an organ selected from the group consisting of lung, liver, spleen, skin, blood and brain, or to a site selected from the group consisting of tumors and interstitial spaces. Within other embodiments, the recombinant retrovirus may be administered intraocularly, intranasally, sublinually, orally, topically, intravesically, intrathecally, topically, intravenously, intraperitoneally, intracranially, intramuscularly, or subcutaneously. Other representative routes of administration include gastroscopy, ECRP and colonoscopy, which do not require full operating procedures and hospitalization, but may require the presence of medical personnel.

Considerations for administering the compositions of the present invention include the following:

Intravenous (IV) administration can occur under a variety of protocols known to those of skill in the art. For instance, retroviral vector particles can be formulated for IV administration as described above and administered as a single injection. Alternatively, the retroviral vector particles can be delivered in a multiple injection protocol. An example of a multiple injection protocol is administration for three times a day for several consecutive days or on alternate days. The multiple injection schedule can be carried out over a number of days for example a week or 10 days or two weeks. The injection schedule can also be repeated. The total number of vector particles delivered can dispersed in varying amounts of formulation buffer. Depending on the volume delivered, the retroviral vectors can be delivered as an injection or as an IV formulation such as an IV drip which can be delivered over a longer period of time. Similarly, the rate of administration can vary. Details of the administration protocol such as the single or multiple injection schedule and volume and time of delivery can be determined experimentally by those of skill in the an, and will also vary depending on the particular gene of interest to be delivered. IV administration is a preferred route of administration for retroviral vectors expressing secretory proteins such as Factor VIII and human growth hormone (see e.g. examples 18–21 herein).

Oral administration is easy and convenient, economical (no sterility required), safe (over dosage can be treated in most cases), and permits controlled release of the active ingredient of the composition (the recombinant retrovirus). Conversely, there may be local irritation such as nausea, vomiting or diarrhea, erratic absorption for poorly soluble drugs, and the recombinant retrovirus will be subject to "first pass effect" by hepatic metabolism and gastric acid and enzymatic degradation. Further, there can be slow onset of action, efficient plasma levels may not be reached, a patient's cooperation is required, and food can affect absorption. Preferred embodiments of the present invention include the oral administration of recombinant retroviruses that express genes encoding erythropoietin, insulin, GM-CSF cytokines, various polypeptides or peptide hormones, their agonists or antagonists, where these hormones can be derived from tissues such as the pituitary, hypothalamus, kidney, endothelial cells, liver, pancreas, bone, hemopoetic marrow, and adrenal. Such polypeptides can be used for induction of growth, regression of tissue, suppression of immune responses, apoptosis, gene expression, blocking receptor-ligand interaction, immune responses and can be treatment for certain anemias, diabetes, infections, high blood pressure, abnormal blood chemistry or chemistries (e.g., elevated blood cholesterol, deficiency of blood clotting factors, elevated LDL with lowered HDL), levels of Alzheimer associated amaloid protein, bone erosion/calcium deposition, and controlling levels of various metabolites such as steroid hormones, purines, and pyrimidines. Preferably, the recombinant retroviruses are first lyophilized, then filled into capsules and administered.

Buccal/sublingual administration is a convenient method of administration that provides rapid onset of action of the active component(s) of the composition, and avoids first pass metabolism. Thus, there is no gastric acid or enzymatic degradation, and the absorption of recombinant retroviruses is feasible. There is high bioavailability, and virtually immediate cessation of treatment is possible. Conversely, such administration is limited to relatively low dosages (typically about 10–15 mg), and there can be no simultaneous eating, drinking or swallowing. Preferred embodiments of the present invention include the buccal/sublingual administration of recombinant retroviruses that contain genes encoding self and/or foreign MHC, or immune modulators, for the treatment of oral cancer; the treatment of Sjogren's syndrome via the buccal/sublingual administration of such recombinant retroviruses that contain IgA or IgE antisense genes; and, the treatment of gingivitis and periodontitis via the buccal/sublingual administration of IgG or cytokine antisense genes.

Rectal administration provides a negligible first pass metabolism effect (there is a good blood/lymph vessel supply, and absorbed materials drain directly into the inferior vena cava), and the method is suitable of children, patients with emesis, and the unconscious. The method avoids gastric acid and enzymatic degradation, and the ionization of a composition will not change because the rectal fluid has no buffer capacity (pH 6.8; charged compositions absorb best). Conversely, there may be slow, poor or erratic absorption, irritation, degradation by bacterial flora, and there is a small absorption surface (about $0.05m^2$). Further, lipidophilic and water soluble compounds are preferred for absorption by the rectal mucosa, and absorption enhancers (e.g., salts, EDTA, NSAID) may be necessary. Preferred embodiment6 of the present invention include the rectal administration of recombinant retroviruses that contain genes encoding colon cancer antigens, self and/or foreign MHC, or immune modulators.

Nasal administration avoids first pass metabolism, and gastric acid and enzymatic degradation, and is convenient. In a preferred embodiment, nasal administration is useful for recombinant retrovirus administration wherein the recombinant retrovirus is capable of expressing a polypeptide with properties as described herein. Conversely, such administration can cause local irritation, and absorption can be dependent upon the state of the nasal mucosa.

Pulmonary administration also avoids first pass metabolism, and gastric acid and enzymatic degradation, and is convenient. Further, pulmonary administration permits localized actions that minimize systemic side effects and the dosage required for effectiveness, and there can be rapid onset of action and self-medication. Conversely, at times only a small portion of the administered composition reaches the brochioli/alveoli, there can be local irritation, and overdosing is possible. Further, patient cooperation and understanding is preferred, and the propellant for dosing may have toxic effects. Preferred embodiments of the present invention include the pulmonary administration of recombinant retroviruses that express genes encoding IgA or IgE for the treatment of conditions such as asthma, hay fever, allergic alveolitis or fibrosing alveolitis, the CFTR gene for the treatment of cystic fibrosis, and protease and collagenase inhibitors such as α-1-antitrypsin for the treatment of emphysema. Alternatively, many of the same types of polypeptides or peptides listed above for oral administration may be used.

Ophthalmic administration provides local action, and permit prolonged action where the administration is via inserts. Further, avoids first pass metabolism, and gastric acid and enzymatic degradation, and permits self-administration via the use of eye-drops or contact lens-like inserts. Conversely, the administration is not always efficient, because the administration induces tearing. Preferred embodiments of the present invention include the ophthalmic administration of recombinant retroviruses that express genes encoding IgA or IgE for the treatment of hay fever conjunctivitis or vernal and atomic conjunctivitis, and ophthalmic administration of recombinant retroviruses that contain genes encoding melanoma specific antigens (such as high molecular weight-melanoma associated antigen), self and/or foreign MHC, or immune modulators.

Transdermal administration permits rapid cessation of treatment and prolonged action leading to good compliance. Further, local treatment is possible, and avoids first pass metabolism, and gastric acid and enzymatic degradation. Conversely, such administration may cause local irritation, is particularly susceptible to tolerance development, and is typically not preferred for highly potent compositions. Preferred embodiments of the present invention include the transdermal administration of recombinant retroviruses that express genes encoding IgA or IgE for the treatment of conditions such as atopic dermatitis and other skin allergies; and transdermal administration of recombinant retroviruses encoding genes encoding melanoma specific antigens (such as high molecular weight-melanoma associated antigen), self and/or foreign MHC, or immune modulators.

Vaginal administration provides local treatment and one preferred route for hormonal administration. Further, such administration avoids first pass metabolism, and gastric acid and enzymatic degradation, and is preferred for administration of compositions wherein the recombinant retroviruses express peptides. Preferred embodiments of the present invention include the vaginal administration of recombinant retroviruses that express genes encoding self and/or foreign MHC, or immune modulators. Other preferred embodiments include the vaginal administration of genes encoding the components of sperm such as histone, flagellin, etc., to promote the production of sperm-specific antibodies and thereby prevent pregnancy. This effect may be reversed, and/or pregnancy in some women may be enhanced, by delivering recombinant retroviruses vectors encoding immunoglobulin antisense genes, which genes interfere with the production of sperm-specific antibodies.

Intravesical administration permits local treatment for urogenital problems, avoiding systemic side effects and avoiding first pass metabolism, and gastric acid and enzymatic degradation. Conversely, the method requires urethral catheterization and requires a highly skilled staff. Preferred embodiments of the present invention include intravesical administration of recombinant retrovirus encoding antitumor genes such as a prodrug activation gene such thymidine kinase or various immunomodulatory molecules such as cytokines.

Endoscopic retrograde cystopancreatography (ERCP) (goes through the mouth; does not require piercing of the skin) takes advantage of extended gastroscopy, and permits selective access to the biliary tract and the pancreatic duct. Conversely, the method requires a highly skilled staff, and is unpleasant for the patient.

Many of the routes of administration described herein (e.g., into the CSF, into bone marrow, into joints, intravenous, intra-arterial, intracranial intramuscular, subcutaneous, into various organs, intra-tumor, into the interstitial spaces, intra-peritoneal, intralymphatic, or into a capillary bed) may be accomplished simply by direct administration using a needle, catheter or related device. In particular, within certain embodiments of the invention, one or more dosages may be administered directly in the indicated manner: into the cerebral spinal fluid at dosages greater than or equal to $10^5$, $10^6$, $10^7$, $10^8$, $10^9$, $10^{10}$ or $10^{11}$ cfu; into bone marrow at dosages greater than or equal to $10^5$, $10^6$, $10^7$, $10^8$, $10^9$, $10^{10}$ or $10^{11}$ cfu; into joint(s) at dosages greater than or equal to $10^5$, $10^6$, $10^7$, $10^8$, $10^9$, $10^{10}$ or $10^{11}$ cfu; intravenously at dosages greater than or equal to $10^8$, $10^9$, $10^{10}$ or $10^{11}$ cfu; intra-arterially at dosages greater than or equal to $10^5$, $10^6$, $10^7$, $10^8$, $10^9$, $10^{10}$ or $10^{11}$ cfu; intra-cranially at dosages greater than or equal to $10^9$, $10^{10}$ or $10^{11}$ cfu; intra-muscularly at dosages greater than or equal to $10^{10}$ or $10^{11}$ cfu; intra-ocularly at dosages greater than or equal to $10^5$, $10^6$, $10^7$, $10^8$, $10^9$, $10^{10}$ or $10^{11}$ cfu; pulmonarily at dosages greater than or equal to $10^5$, $10^6$, $10^7$, $10^8$, $10^9$, $10^{10}$ or $10^{11}$ cfu; nasally at dosages greater than or equal to $10^5$, $10^6$, $10^7$, $10^8$, $10^9$, $10^{10}$ or $10^{11}$ cfu; sub-lingually at dosages greater than or equal to $10^5$, $10^6$, $10^7$, $10^8$, $10^9$, $10^{10}$ or $10^{11}$ cfu; rectally at dosages greater than or equal to $10^5$, $10^6$, $10^7$, $10^8$, $10^9$, $10^{10}$ or $10^{11}$ cfu; orally at dosages greater than or equal to $10^5$, $10^6$, $10^7$, $10^8$, $10^9$, $10^{10}$ or $10^{11}$ cfu; topically at dosages greater than or equal to $10^5$, $10^6$, $10^7$, $10^8$, $10^9$, $10^{10}$ or $10^{11}$ cfu; vaginally at dosages greater than or equal to $10^5$, $10^6$, $10^7$, $10^8$, $10^9$, $10^{10}$ or $10^{11}$ cfu; sub-cutaneously at dosages greater than or equal to $10^9$, $10^{10}$ or $10^{11}$ cfu; inter-vesically at dosages greater than or equal to $10^5$, $10^6$, $10^7$, $10^8$, $10^9$, $10^{10}$ or $10^{11}$ cfu; into an organ such as the lung, liver, spleen, skin, blood or brain at dosages greater than or equal to $10^5$, $10^6$, $10^7$, $10^8$, $10^9$, $10^{10}$ or $10^{11}$ cfu; intra-tumor at dosages greater than or equal to $10^8$, $10^9$, $10^{10}$ or $10^{11}$ cfu; intra-peritoneally at dosages greater than or equal to $10^8$, $10^9$, $10^{10}$ or $10^{11}$ cfu; into interstitial spaces at dosages greater than or equal to $10^{10}$ or $10^{11}$ cfu; intra-lymphatically at dosages greater than or equal to $10^5$, $10^6$, $10^7$, $10^8$, $10^9$, $10^{10}$ or $10^{11}$ cfu; into a capillary bed at dosages greater than or equal to $10^5$, $10^6$, $10^7$, $10^8$, $10^9$, $10^{10}$ or $10^{11}$ cfu; or intrathecally at dosages greater than or equal to $10^5$, $10^6$, $10^7$, $10^8$, $10^9$, $10^{10}$ or $10^{11}$ cfu.

Recombinant retrovirus may be delivered to the target from outside of the body (as an outpatient procedure) or as a surgical procedure, where the vector is administered as part of a procedure with other purposes, or as a procedure designed expressly to administer the vector. Other routes and methods for administration include the non-parenteral routes as well as administration via multiple sites.

As demonstrated in Example 23 herein, viral vectors and particularly retroviral vectors preferentially infect liver cells and spleen cells in order to effect sustained expression of proteins such as factor VIII and human growth hormone. Furthermore, as described herein expression of proteins in the liver is useful therapeutically, for example, for production of proteins secreted by the liver, and for localized production of therapeutic proteins in the liver which can be used in the treatment of liver diseases.

As described above, the gene delivery vehicles of the invention, including recombinant retroviruses are preferentially administered intravenously, generally in a peripheral vein which is readily accessible. However, the gene delivery vehicles of the invention may also be delivered into the hepatic artery or in the portal vein in order to have more effective delivery to the liver. There are many methods available for placing catheters into the human hepatic artery or portal vein which are known to those of skill in the art. For instance, cannulation of the portal vein can be accomplished by a simple dissection of the umbilical vein, thereby eliminating a laparotomy (Storer et al., 1966, *Am J. Surg* 111:56–68, and Weigand et al., 1983, *Rec Res Cancer Res* 86:90–92). For example, the ligamentum teres is cut 4 to 5 cm above the umbilicus and a polyethlyene catheter is threaded into the umbilical vein until reaching the junction with the left branch of the portal vein. Following the exertion of firm pressure on the catheter to break through the vessel wall, a brisk return of blood through the catheter indicates the proper entry into the portal system.

As an additional example, an alternative procedure is described by Beart et al., 1990, *Arch Surg* 125:897–901. In this procedure, a 5F catheter is placed through a hole in the abdominal wall which then extends through a mesenteric vein and into the portal vein. The catheter is flushed with saline and fixed to the exterior of the abdominal wall. These and other procedures may used to deliver the gene delivery vehicles of the invention to the liver.

In addition, the gene delivery vehicles of the invention can be delivered by direct injection into the liver using standard medical procedures.

I. Formulation and Administration of Growth Factors

As is described herein, the recombinant viruses of the invention can be administered after induction of cell proliferation by a growth factor, or may be co-administered with a growth factor. The growth factors of the invention are administered by parenteral, topical, oral or by local administration. For example, the growth factors are administered parenterally, e.g. intravenously, subcutaneously, intradermally, or intramuscularly. Preferably, the growth factors are administered intravenously. Administration of the therapeutic agent of the invention can be accomplished by, for example, injection, catheterization, laser-created perfusion, channels, cannulization, a particle gun, and a pump.

The growth factors of the invention are typically administered with a pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier. The term "liposomes" refers to, for example, the liposome compositions described in U.S. Pat. No. 5,422,120, WO 95/13796, WO 94/23697, WO 91/14445 and EP 524,968 B1. Liposomes may be pharmaceutical carriers for the polypeptides of the invention.

The growth factors of the invention are administered in therapeutically effective amounts. The term "therapeutically effective amount" as used herein and applied to polypeptide growth factors refers to an amount of a growth factor that is capable of stimulating cell division in a target tissue in vivo.

Stimulation of cell proliferation in a target tissue means that the number of dividing cells in the target tissue is greater than in the absence of treatment. The precise effective amount for a subject will depend upon the subject's size and health, the nature and extent of the condition being treated, recommendations of the treating physician, and particular growth factor that is used. The effective amount for a given situation can be determined by routine experimentation and will vary from growth factor to growth factor. For example, for HGF, a dose of 1 ug/kg to 2 mg/kg body weight, and more preferably from 10 ug/kg to 200 ug/kg body weight is used. In the case of KGF, a dose of 100 ug/kg to 5 mg/kg body weight, or more preferably a dose of 1 mg/kg to 50 mg/kg body weight is used. Dose amounts for the other growth factors used in the claimed methods are known to those of skill in the art or can readily be determined experimentally.

Clofibrate, or the other proxisome proliferators, can be administered by IP injection (5–500 mg/kg), or orally (5–500 mg/kg). More preferably the dosages are 10–100 mg/kg. A typical dosing schedule is daily administration for 3–10 days. A tapered dosing can alternatively be employed. Following clofibrate dosing, retroviral vectors can be administered, preferably intravenously, at doses ranging from 1E5 to 1E11 cfu per injection. Injection schedules of one to three times daily, for one to ten days, will be employed. Repeat administrations of retroviral vector with or without repeat clofibrate or growth factor dosing can be performed.

Collagenase can be administered at a dosage of from 0.05–5 U/kg. more preferably 0.5–2 U/kg) (Liu (994) Hepatology 19:1521). Estrogens with HGF or other growth factors can be administered at a dosage of 0.01–20 ug/g, and more preferably 0.5–2 ug/g. Heparin or other sulfated glycosaminoglycans administered with HGF or other growth factors can be administered at a dose of 100–10,000 U/kg, more preferably 2000–6000 U/kg.

9-cis-retinoic acid is administered at dosages of 10–200 mg/kg, more preferably 60–100 mg/kg. Cyclosporine A is delivered at a dose of 0.1–100 mg/kg, more preferably 10–50 mg/kg. Prostaglandins E1and/or I1; isoproterenol can be administered at dosages of 0.5–100 ug/kg; more preferably 1–10 ug/kg with or without glucagon at a dose of 0.1.1–10 mg/kg, more preferably 0.5–2 mg/kg. Phosphatidylethanolamine N-methyltransferase inhibitors such as 3-deazaadenosine or other methylation inhibitors are administered at a dose of 1–50 mg/kg. more preferably 5–15 mg/kg. Liver mitogen nafenopin can be administered at a dose of 0.1–1000 mg/kg, more preferably 50–300 mg/kg. Cyproterone acetate can be administered at a dose of (0.1–600 mg/kg, more preferably 10–100 mg/kg. Triiodothyrone can be administered at at dose of 0.1–10 mg/kg, more preferably 0.5–5.0 mg/kg.

The following examples are offered by way of illustration, and not by way of limitation.

EXAMPLE 1
Preparation of Retroviral Vector Backbones
A. Preparation of Retroviral Backbones KT-1 and KT-3B The Moloney murine leukemia virus (MoMLV) 5' long terminal repeat (LTR) EcoR I-EcoR 1 fragment, including gag sequences, from the N2 vector (Armentano et al., 1987, *J. Vir.* 61:1647–1650; Eglitas et al., 1985, *Science* 230:1395–1398) is ligated into the plasmid SK$^+$ (Stratagene, La Jolla, Calif.). The resulting construct is designated N2R5. The N2R5 construct is mutated by site-directed in vitro mutagenesis to change the ATG start codon to ATT preventing gag expression. This mutagenized fragment is 200 base pairs (bp) in length and flanked by Pst I restriction sites. The Pst I-Pst I mutated fragment is purified from the SK$^+$ plasmid and inserted into the Pst I site of N2 MoMLV 5' LTR in plasmid pUC31 to replace the non-mutated 200 bp fragment. The plasmid pUC31 is derived from pUC19 (Stratagene, La Jolla, Calif.) in which additional restriction sites Xho I, Bgl II, BssH II and Nco I are inserted between the EcoR I and Sac I sites of the polylinker. This construct is designated pUC31/N2R5gM.

A 1.0 kilobase (Kb) MoMLV 3' LTR EcoR I-EcoR I fragment from N2 is cloned into plasmid SK$^+$ resulting in a construct designated N2R3$^-$. A 1.0 Kb Cla I-Hind III fragment is purified from this construct.

The Cla I-Cla I dominant selectable marker gene fragment from pAFVXM retroviral vector (Kriegler et al., 1984, *Cell* 38:483; St. Louis et al., 1988, *PNAS* 85:3150–3154), comprising a SV40 early promoter driving expression of the neomycin (neo) phosphotransferase gene, is cloned into the SK$^+$ plasmid. This construct is designated SK$^+$ SV$_2$-neo A 1.3 Kb Cla I-BstB I gene fragment is purified from the SK$^+$ SV$_2$-neo plasmid.

KT-3B or KT-1 vectors are constructed by a three part ligation in which the Xho I-Cla I fragment containing the gene of interest and the 1.0 Kb MoMLV 3' LTR Cla I-Hind III fragment are inserted into the Xho I-Hind III site of pUC31/N2R5gM plasmid. This gives a vector designated as having the KT-1 backbone. The 1.3 Kb Cla I-BstB I neo gene fragment from the pAFVXM retroviral vector is then inserted into the Cla I site of this plasmid in the sense orientation to yield a vector designated as having the KT-3B backbone.

EXAMPLE 2
Oral Administration of Recombinant Retroviruses Expressing Factor VIII
A. Construction of Full-Length and B Domain Deleted Factor VIII cDNA Retroviral Vector The following is a description of the construction of several retroviral vectors encoding a full-length factor VIII cDNA. Further discussion is also provided in PCT Patent Publication No. WO 96/21035. Due to the packaging constraints of retroviral vectors and because selection for transduced cells is not a requirement for therapy, a retroviral backbone, e.g., KT-1, lacking a selectable marker gene is employed.

1. Production of Plasmid Vectors Encoding Full-Length Factor VIII

A gene encoding full-length factor VIII can be obtained from a variety of sources. One such source is the plasmid pCIS-F8 (see EP 0 260 148), which contains a full-length factor VIII cDNA whose expression is under the control of a CMV major immediate-early (CMV MIE) promoter and enhancer. The factor VIIi cDNA contains approximately 80 bp of 5' untranslated sequence from the factor VIII gene and a 3' untranslated region of about 500 bp. In addition, between the CMV promoter and the factor VIII sequence lies a CMV intron sequence, or "cis" element. The cis element, spanning about 280 bp, comprises a splice donor site from the CMV major immediate-early promoter about 140 bp upstream of a splice acceptor from an immunoglobulin gene.

More specifically, a plasmid, designated pJW-2, encoding a retroviral vector for expressing full length factor VIII is constructed using the KT-1 backbone from pKT-1. Briefly, in order to facilitate directional cloning of the factor VIII cDNA insert into pKT-1, the unique Xho I site is converted to a Not I site by site directed mutagenesis. The resultant plasmid vector is then opened with Not I and Cla I. pCIS-F8 is digested to completion with Cla I and Eag I, for which there are two sites, to release the fragment encoding full-length factor VIII. This fragment is then ligated into the Not I/Cla I restricted vector to generate a plasmid designated pJW-2.

2. Construction of a Truncated Factor VIII Retroviral Vector (ND-5)

A plasmid vector encoding a truncation of about 80% (approximately 370 bp) of the 3' untranslated region of the factor VIII cDNA, designated pND-5, is constructed in a pKT-1 vector as follows: As described for pJW-2, the pKT-1 vector employed has its Xho I restriction site replaced by that for Not I. The factor VIII insert is generated by digesting pCIS-F8 with Cla I and Xba I, the latter enzyme cutting 5' of the factor VIII stop codon. The approximately 7 kb fragment containing all but the 3' coding region of the factor VIII gene is then purified. pCIS-F8 is also digested with Xba I and Pst I to release a 121 bp fragment containing the gene's termination codon. This fragment is also purified and then ligated in a three way ligation with the larger fragment encoding the rest of the factor VIII gene and Cla I/Pst I restricted BLUESCRIPT® KS$^+$ plasmid (Stratagene, supra) to produce a plasmid designated pND-2.

The unique Sma I site in pND-2 is then changed to a Cla I site by ligating Cla I linkers (New England Biolabs, Beverly, Mass.) under dilute conditions to the blunt ends created by a Sma I digest. After recircularization and ligation, plasmids containing two Cla I sites are identified and designated pND-3.

The factor VIII sequence in pND-3, bounded by Cla I sites and containing the full length gene with a truncation of much of the 3' untranslated region, is cloned as follows into a plasmid backbone derived from a Not I/Cla I digest of pKT-1 (a pKT-1 derivative by cutting at the Xho I site, blunting with Klenow, and inserting a Not I linker (New England Biolabs)), which yields a 5.2 kb Not I/Cla I fragment. pCIS-F8 is cleaved with Eag I and Eco RV and the resulting fragment of about 4.2 kb, encoding the 5' portion of the full-length factor VIII gene, is isolated. pND-3 is digested with Eco RV and Cla I and a 3.1 kb fragment is isolated. The two fragments containing portions of the factor VIII gene are then ligated into the Not I/Cla I digested vector backbone to produce a plasmid designated pND-5.

3. Construction of the B-Domain Deleted Vector

The precursor DNA for the B-deleted FVIII is obtained from Miles Laboratory. This expression vector is designated p25D and has the exact backbone as pCISF8 above. The Hpa I site at the 3' of the FVIII8 cDNA in p25D is modified to Cla-I by oligolinkers. An Acc I to Cla I fragment is clipped out from the modified p25D plasmid. This fragment spans the B-domain deletion and includes the entire 3' two-thirds of the cDNA. An Acc I to Cla I fragment is removed from the retroviral vector JW-2 above, and replaced with the modified B-domain deleted fragment just described. This is designated B-del-1.

B. Assay for Factor VIII Expression

1. Assay of KT-ND5 Vector Expression by Transient Packaging and Transduction of Murine Cells Cell lines, L33, (Dennert, USC Comprehensive Cancer Center, Los Angeles, Calif., Patek, et. al., 1979, *Int. J. of Cancer* 24:624–628) BC10ME (Patek et al., 1982, Cell Immuno 72:113, ATCC# TIB85) L33env, and BCenv (L33env and BCenv express HIV-1 IIIBenv, Warner et al., 1991, *AIDS Res. and Human Retrovirus* 7:645), transduced with the KT-ND5 vector, carrying the amphotropic or VSVG envelope protein are examined for the expression of factor VIII. Non-transduced cells are also analyzed for factor VIII expression and compared with KT-ND5 transduced cells to determine the effect of transduction on protein expression.

Murine cell lines, L33-KT-ND5, L33env-KT-ND5, L33env, L33, BC10ME, BC10ME-KT-ND5, BCenv, and BCenv-KT-ND5, are tested for expression of the KT-ND5 molecule. Cells are grown to subconfluent density and the supernatant is removed following centrifugation at 200×g. The samples are diluted and assayed by the Coamatic® Factor VIII assay (KabiVitrum Diagnostica, Molndal, Sweden).

The assay is performed as follows: 100 $\mu$l of culture media are mixed with 200 $\mu$l of 1×working buffer diluted according to the maufacturer's instructions. Fifty $\mu$l of the mixture are prewarmed at 37° C. for 3–4 minutes in wells of a microtiter plate. The 50 $\mu$l of factor reagent from the kit, prewared to 37° C. are added, and the mixture incubated at 37° C. for 4 min., after which 50 $\mu$l of chromogenic substrate (7.7 mg S2765 plus 0.2 mg of thrombin inhibitor 12581 in a mannitol carrier, diluted to a total of 6.0 ml with sterile water) are added. After a 10 minute incubation at 37° C., 50 $\mu$l of 20% acetic acid are added to stop the reaction. Absorbance at 405 nm is determined against buffer. A standard curve using dilutions of pooled normal human plasma (1.0 IU factor VIII/ml) is used. Serum levels of factor VIII in non-hemophilic patients are in the range of 200 ng/mL.

When this assay is used for patient samples, 9 volumes of blood are mixed with one volume of 0.1 M sodium citrate, at a neutral pH, and centrifuged at 2,000×g for 5–20 min. at 20–25° C. to pellet cells. Due to heat lability of factor VIII, plasma samples should be tested within 30 min. of isolation or stored immediately at −70° C., although as much as 20% of factor VIII activity may be lost during freezing and thawing.

2. Assay of KT-ND5 Vector Expression by Transient Packaging and Transduction of Human Cells Cell lines transduced with KT-ND5 are examined for expression of factor VIII. Non-transduced cells are analyzed to compare with KT-ND5 transduced cells and determine the effect that transduction has on expression.

Two human cell lines, JY and JY-KT-ND5 are tested for expression of KT-ND5. Suspension cells grown to $10^6$ cells/ml are removed from culture flasks by pipet and pelleted by centrifugation at 200×g. The supernatant is removed, diluted, and assayed by the Coamatic$^R$ Factor VIII assay as described above in Example 2B 1.

C. Transient Transfection and Transduction of Packaging Cell Lines HX and DA with the Vector Construct KT-ND5

1. Plasmid DNA Transfection

The packaging cell line, HX (WO92/05266), are seeded at $5.0\times10^5$ cells on a 10 cm tissue culture dish on day 1 with Dulbecco's Modified Eagle Medium (DMEM) and 10% fetal bovine serum (FBS). On day 2, the media is replaced with 5.0 ml fresh media 4 hours prior to transfection. A standard calcium phosphate-DNA co-precipitation is performed by mixing 40.0 $\mu$l 2.5 M $CaCl_2$, 10 $\mu$g plasmid DNA, and deionized $H_2O$ to a total volume of 400 $\mu$l. Four hundred microliters of the DNA-$CaCl_2$ solution is added dropwise with constant agitation to 400 $\mu$l precipitation buffer (50 mM HEPES-NaOH, pH 7.1; 0.25 M NaCl and 1.5 mM $Na_2HPO_4$-$NaH_2PO_4$). This mixture is incubated at room temperature for 10 minutes. The resultant fine precipitate is added to a culture dish of cells. The cells are incubated with the DNA precipitate overnight at 37° C. On day 3, the media is aspirated and fresh media is added. The supernatant is removed on day 4, passed through a 0.45 $\mu$l filter, and stored at −80° C.

Alternatively, 29 2 3 cells (WO 92/05266) (these are 293 cells expressing gag and pol) are transfected with the vector DNA and the plasmid pMLP-VSVG (or other VSVG encoding plasmids) to yield VSVG psuedotyped vector particles that are harvested and stored as described above.

2. Packaging Cell Line Transduction

DA (an amphotropic cell line derived from a D17 cell line ATCC No. 183, WO 92/05266) cells are seeded at $5.0 \times 10^5$ cells/10 cm tissue culture dish in 10 ml DMEM and 10% FBS, 4 µg/ml polybrene (Sigma, St. Louis, Mo.) on day 1. On day 2, 3.0 ml, 1.0 ml and 0.2 ml of the freshly collected virus-containing HX media is added to the cells. The cells are incubated with the virus overnight at 37° C. On day 3, the media is removed and 1.0 ml DMEM, 10% FBS with 800 µg/ml G418 is added to the plate. Only cells that have been transduced with the vector and contain the neomycin selectable marker will survive. A G418 resistant pool is generated over a period of a week. The pool of cells is dilution cloned by removing the cells from the plate and counting the cell suspension, diluting the cells suspension down to 10 cells/ml and adding 0.1 ml to each well (1 cell/well) of a 96 well plate (Corning, Corning, N.Y.). Cells are incubated for 14 days at 37° C., 10% $CO_2$. Twenty-four clones are selected and expanded up to 24 well plates, 6 well plates then 10 cm plates at which time the clones are assayed for expression and the supernatants are collected and assayed for viral titer.

The titer of the individual clones is determined by infection of HT1080 cells, (ATCC No. CCL 121). On day 1, $5.0 \times 10^5$ HT1080 cells are plated on each well of a 6 well microtiter plate in 3.0 ml DMEM, 10% FBS and 4 µg/ml polybrene. On day 2, the supernatant from each clone is serially diluted 10 fold and used to infect the HT1080 cells in 1.0 ml aliquots. The media is replaced with fresh DMEM, 10% FBS media, and the cells incubated with the vector overnight at 37° C., 10% $CO_2$. On day 3, selection of transduced cells is performed by replacing the media with fresh DMEM, 10% FBS media containing 800 µg/ml G418. Cells are incubated at 37° C., 10% $CO_2$ for 14 days at which time G418 resistant colonies are scored at each dilution to determine the viral titer of each clone as colony forming units(cfu)/ml.

Using these procedures, cell lines are derived that produce greater than or equal to $10^6$ cfu/ml in culture.

The packaging cell line HX is transduced with vector generated from the DA vector producing cell line in the same manner as described for transduction of the DA cells from HX supernatant.

Transduction of the DA or HX cells with vectors lacking a neo selectable marker (Example 1) was performed as described above. However, instead of adding G418 to the cells on day 3, the cells are cloned by limiting dilution. Titer is analyzed as described above.

3. Generation of Producer Cell Line via One Packaging Cell Line

In some situations it may be desirable to avoid using more than one cell line in the process of generating producer lines. In this case, DA cells are seeded at $5.0 \times 10^5$ cells on a 10 cm tissue culture dish on day 1 with DMEM and 10% irradiated (2.5 megarads minimum) FBS. On day 2, the media is replaced with 5.0 ml fresh media 4 hours prior to transfection. A standard calcium phosphate-DNA coprecipitation is performed by mixing 60 µl 2.0 M $CaCl_2$, 10 µg MLP-G plasmid, 10 µg KT-ND5 retroviral vector plasmid, and deionized water to a volume of 400 µl. Four hundred microliters of the DNA-$CaCl_2$ solution is added dropwise with constant agitation to 400 µl 2×precipitation buffer (50 mM HEPES-NaOH, pH 7.1, 0.25 M NaCl and 1.5 mM $Na_2HPO_4$-$NaH_2PO_4$). This mixture is incubated at room temperature for 10 minutes. The resultant fine precipitate is added to a culture dish of DA cells plated the previous day. The cells are incubated with the DNA precipitate overnight at 37° C. On day 3, the medium is removed and fresh medium is added. The supernatant containing G-pseudotyped virus is removed on day 4, passed through a 0.45 µl filter and used to infect the DA packaging cell.

DA cells are seeded at $5.0 \times 10^5$ cells on a 10 cm tissue culture dish in 10 ml DMEM and 10% FBS, 4 mg/ml polybrene (Sigma, St. Louis, Mo.) on day 1. On day 2, 2.0 ml, 1.0 ml or 0.5 ml of the freshly collected and filtered G-pseudotyped virus containing supernatant is added to the cells. The cells are incubated with the virus overnight at 37° C. On day 3 the medium is removed and 10 ml DMEM, 10% irradiated FBS with 800 µg/ml G418 is added to the plate. Only cells that have been transduced with the vector and contain the neo selectable marker will survive. A G418 resistant pool is generated over the period of 1–2 weeks. The pool is tested for expression and then dilution cloned by removing the cells from the plate, counting the cell suspension, diluting the cell suspension down to 10 cells/ml and adding 0.1 ml to each well (1 cell/well) of a 96-well plate. Cells are incubated for 2 weeks at 37° C. 10% $CO_2$ Twenty-four clones are selected and expanded up to 24-well plates, then 6-well plates, and finally 10 cm plates, at which time the clones are assayed for expression and the supernatants are collected and assayed for viral titer as described above.

D. Detection of Replication Competent Retroviruses (RCR)

1. The Extended $S^+L^-$ Assay

The extended $S^+L^-$ assay determines whether replication competent, infectious virus is present in the supernatant of the cell line of interest. The assay is based on the empirical observation that infectious retroviruses generate foci on the indicator cell line $MiCl_1$ (ATCC No. CCL 64.1). The $MiCl_1$ cell line is derived from the Mv1Lu mink cell line (ATCC No. CCL 64) by transduction with Murine Sarcoma Virus (MSV). It is a non-producer, non-transformed, revertant clone containing a replication defective murine sarcoma provirus, $S^+$, but not a replication competent murine leukemia provirus, $L^-$. Infection of $MiCl_1$ cells with replication competent retrovirus "activates" the MSV genome to trigger "transformation" which results in foci formation.

Supernatant is removed from the cell line to be tested for presence of replication competent retrovirus and passed through a 0.45µ filter to remove any cells. On day 1, Mv1Lu cells are seeded at $1.0 \times 10^5$ cells per well (one well per sample to be tested) of a 6 well plate in 2 ml DMEM, 10% FBS and 8 µg/ml polybrene. Mv1Lu cells are plated in the same manner for positive and negative controls on separate 6 well plates. The cells are incubated overnight at 37° C., 10% $CO_2$. On day 2, 1.0 ml of test supernatant is added to the Mv1Lu cells. The negative control plates are incubated with 1.0 ml of media. The positive control consists of three dilutions (200 focus forming units (ffu), 20 ffu and 2 ffu each in 1.0 ml media) of MA virus (referred to as pAM in Miller et al., *Molec. and Cell Biol.* 5:431, 1985) which is added to the cells in the positive control wells. The cells are incubated overnight. On day 3, the media is aspirated and 3.0 ml of fresh DMEM and 10% FBS is added to the cells. The cells are allowed to grow to confluency and are split 1:10 on day 6 and day 10, amplifying any replication competent retrovirus. On day 13, the media on the Mv1Lu cells is aspirated and 2.0 ml DMEM and 10% FBS is added to the cells. In addition, the $MiCl_1$ cells are seeded at $1.0 \times 10^5$ cells per well in 2.0 ml DMEM, 10% FBS and 8 µg/ml polybrene. On day 14, the supernatant from the Mv1Lu cells is transferred to the corresponding well of the MiCl₁ cells and incubated overnight at 37° C., 10% $CO_2$. On day 15, the media is aspirated and 3.0 ml of fresh DMEM and 10% FBS is added to the cells. On day 21, the cells are examined for focus formation (appearing as clustered, refractile cells that overgrow the monolayer and remain attached) on the monolayer of cells. The test article is determined to be contaminated with replication competent retrovirus if foci appear on the MiCl₁ cells. Using these procedures, it can be shown that the HBV core producer cell lines are not contaminated with replication competent retroviruses.

2. Cocultivation of Producer Lines and MdH Marker Rescue Assay

As an alternate method to test for the presence of RCR in a vector-producing cell line, producer cells are cocultivated with an equivalent number of *Mus dunni* (NIH NIAID Bethesda, Md.) cells. Small scale cocultivations are performed by mixing of $5.0 \times 10^5$ *Mus dunni* cells with $5.0 \times 10^5$ producer cells and seeding the mixture into 10 cm plates (10 ml standard culture media/plate, 4 µg/ml polybrene) at day 0. Every 3–4 days the cultures are split at a 1:10 ratio and $5.0 \times 10^5$ *Mus dunni* cells are added to each culture plate to effectively dilute out the producer cell line and provide maximum amplifcation of RCR. On day 14, culture supernatants are harvested, passed through a 0.45µ cellulose-acetate filter, and tested in the MdH marker rescue assay. Large scale cocultivations are performed by seeding a mixture of $1.0 \times 10^8$ *Mus dunni* cells and $1.0 \times 10^8$ producer cells into a total of twenty T-150 flasks (30 ml standard culture media/flask, 4 µg/ml polybrene). Cultures are split at a ratio of 1:10 on days 3, 6, and 13 and at a ratio of 1:20 on day 9. On day 15, the final supernatants are harvested, filtered and a portion of each is tested in the MdH marker rescue assay.

The MdH marker rescue cell line is cloned from a pool of *Mus dunni* cells transduced with LHL, a retroviral vector encoding the hygromycin B resistance gene (Palmer et al., 1987, *PNAS* 84: 1055–1059). The retroviral vector can be rescued from MdH cells upon infection of the cells with RCR. One ml of test sample is added to a well of a 6-well plate containing $10^5$ MdH cells in 2 ml standard culture medium (DMEM with 10% FBS, 1% 200 mM L-glutamine, 1% non-essential amino acids) containing 4 µg/ml polybrene. Media is replaced after 24 hours with standard culture medium without polybrene. Two days later, the entire volume of MdH culture supernatant is passed through a 0.45µ cellulose-acetate filter and transferred to a well of a 6-well plate containing $5.0 \times 10^4$ *Mus dunni* target cells in 2 ml standard culture medium containing polybrene. After 24 hours, supernatants are replaced with standard culture media containing 250 µg/ml of hygromycin B and subsequently replaced on days 2 and 5 with media containing 200 µg/ml of hygromycin B. Colonies resistant to hygromycin B appear and are visualized on day 9 post-selection, by staining with 0.2% Coomassie blue.

F. Transduction of Human Cells with KT-ND5 Vector Construct

On day one, HT1080 cells are set up at $2 \times 10^4$ cells per well in six well tissue culture plates containing 2 mls standard growth media (DME+10% FBS ). On day two, ND-5 FVIII retroviral vector particles from a confluent vector producing cell line are harvested as a HX-ND-5 clone. They are filtered through 0.45 µm syringe filters prior to testing the supernatants. (Alternatively the filtered media supernatants may be frozen at 80 in aliquots for later use.) Polybrene is added to each well such that the final concentration is 8 µg per ml. Thirty minutes later, either diluted or undiluted retroviral vector supernatant is added to duplicate wells. Typical volumes and dilutions are 0.5 ml per well and four or more 1:3 serial dilutions in growth media. As a control, two wells are transduced with the same volume of growth media only. On day three, the wells are refeed with 2 mls of fresh media and the cells allowed to reach confluence, which may typically be about day four or five. On this day, the cells are again refeed with one ml per well fresh growth media. Twenty four hours later the media is harvested and filtered as above.

G. Expression of Transduced Vector for FVIII

The expression of vector transduced human cells for FVIII is detected by the Coamatic$^R$ assay as described above in Example 2B1. Activity is assayed relative to supernatant from the control wells by counting the cells per well from the two control wells and normalizing FVIII expression data per $1 \times 10^6$ cells per 24 hours.

H. Administration of Vector Construct

1. Animal Administration Protocol

The intestinal epithelium is an attractive site for gene delivery due to its rapidly proliferating tissue mass and the known location of stem cells in the crypts of Lieberkuhn. The deep location of the stem cells in the crypts and the protective role of the mucus gel layer, makes the retrovirus relatively inaccessible to the tissue cells. However, the accessibility of the retroviral vector to these stem cells can be improved in animal models by the in vivo mucus removal method of Sandberg et al., 1994, *Human Gene Therapy* 5:3232–329.

Male Sprague-Dawley rats obtained from Charles River Breeding Laboratories (Portage, Md.) are anesthetized and the cecum is identified upon opening the peritoneal cavity. A 3 cm ileal segment is isolated from the last Peyer's patch in the terminal ileum and ligated at each end. A plastic catheter attached to a syringe is inserted into the segment and two milliliters of the mucolytic agents dithiotireitol and N-acetyl-cysteine is instilled under mild pressure for two minutes, then removed. This procedure is repeated once again before filling the segment with 0.2 to 2.0 ml of retroviral vector particles at $10^6$ to $10^{10}$ cfu/ml. The ligatures are removed 1 to 4 hours later and the abdominal cavity is sutured. Control animals are instilled with formulation buffer only.

Blood is collected from the tail vein and assayed for factor VIII production by a sandwich ELISA specific for human factor VIII (according to the modified procedure of Zatloukal, K., et al., *PNAS* 91:5148–5152, 1994). The ELISA is based on two Diagnostica). ESH 4 (25 µg/ml in 1.0 M NaHCO₃/0.5 M NaCl, pH 9.0) is coupled to the ELISA plates overnight at 4° C., washed with 0.1% Tween 20 in PBS, and blocked with 1% BSA in PBS. The samples are applied in 0.05 M Tris-HCl/1 M NaCl/2% BSA, pH 7.5, over 4 hr at room temperature, the plates are washed, and ESH 8 (2.5 µg/ml in 0.05 M Tris-HCl/1 M NaCl/2% BSA, pH 7.5,) which has been biotinylated with N-hydroxysuccinimidobiotin (Pierce, Rockford, Ill.) is added for 2 hr at room temperature. The color reaction is performed with peroxidase-conjugated streptavidin (Boehringer Mannheim, Indianapolis, Ind.) and o-phenylenediamine dihydrochloride as substrate. The human factor VIII:c standard (from the National Institute for Biological Standards and Control, Hertfordshire, U.K.) and normal rat plasma are used as references.

2. Human Administration Protocol

Lyophilized recombinant retrovirus containing the gene for Factor VIII expression is formulated into an enteric coated tablet or gel capsule according to known methods in the art. These are described in the following patents: U.S.

Pat. No. 4,853,230, EP 225,189, AU 9,224,296, AU 9,230,801, and WO 92144,52.

The capsule is administered orally to be targeted to the jejunum. At 1 to 4 days following oral administration of the recombinant retrovirus, expression of Factor VIII is measured in the plasma and blood by the Coamatic$^R$ Factor VIII assay as described in Example 2B1.

EXAMPLE 3

Intravesical Administration of Recombinant Retroviruses Expressing TK

A. Construction of TK Vector Constructs

1. Construction of plasmids Containing Vector LTR Sequences

All of the following retroviral vectors are based on the N2 vector (Keller et al., Nature 318:149–154, 1985). Briefly, 5' and 3' Eco RI LTR fragments (2.8 and 1.0 Kb, respectively) (Armentano, J. Vir. 61:1647, 1987; Eglitis, Science 230:1395, 1985) are initially subcloned into the Eco RI site of plasmids SK$^+$ (Stratagene, San Diego, Calif.) and pUC31. pUC31 is a modification of pUC19 (Stratagene, San Diego, Calif.) carrying additional restriction sites (Xho I, Bgl II, BssH II, and Nco I) between the Eco RI and Sac I sites of the polylinker. Plasmid N2R3+/− is thereby created from ligation of the SK$^+$ plasmid with the 1.0 Kb 3' LTR fragment. The plasmids p31 N2R5+/− and p31N2R3+/− are constructed from the ligation of pUC31 with the 2.8 Kb 5' LTR and packaging signal (Y) or the 1.0 Kb 3' LTR fragment, respectively. In each case N2 refers to the vector source, R refers to the fact that the fragment is an Eco RI fragment, 5 and 3 refer to 5' or 3' LTRs, and +or − refers to the orientation of the insert (see FIGS. 1–6 for examples of LTR subclones).

In one case, a 1.2 Kb Cla I/Eco RI 5' LTR and W fragment from N2 is subcloned into the same sites of an SK$^+$ vector. This vector is designated pN2CR5. In another case, the 5' LTR containing a 6 bp deletion of the splice donor sequence (Yee et al., Cold Spring Harbor, Quantitative Biology, 51:1021, 1986) is subcloned as a 1.8 Kb Eco RI fragment into pUC31. This vector is designated p31N25D[+], FIG. 6.

2. Construction of Plasmids Containing HSVTK

The coding region and transcriptional termination signals of HSV-1 thymidine kinase gene (HSVTK) are isolated as a 1.8 Kb Bgl II/Pvu II fragment from plasmid 322TK (3.5 kb Bam HI fragment of HSV-1 (McKnight et al.) cloned into Bam HI of pBR322 (ATCC No. 31344)) and cloned into Bgl II/Sma I-digested pUC31. This construct is designated pUCTK. For constructs which require deletion of the terminator signals, pUCTK is digested with Sma I and Bam HI and the 0.3 Kb fragment containing the (A)$_n$ signal is removed. The remaining coding sequences and sticky-end Bam HI overhang are reconstituted with a double-stranded oligonucleotide made from the following oligomers:

5' GAG AGA TGG GGG AGG CTA ACT
    GAG 3' (SEQUENCE ID. NO. 1)

5' GAT CCT CAG TTA GCC TCC CCC
    ATC TCT C 3' (SEQUENCE ID. NO. 2)

Figure 7:
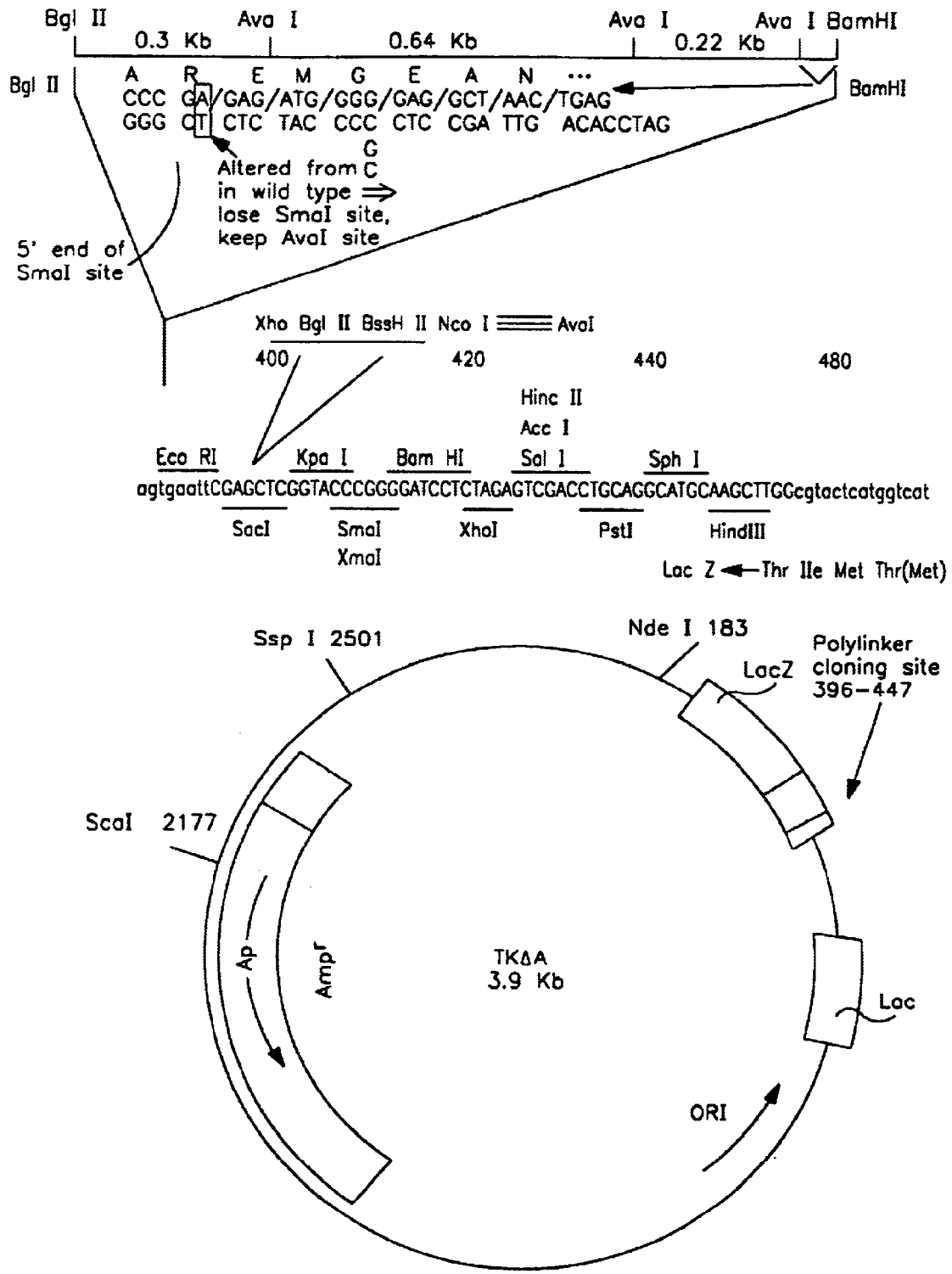
FIG. 7 is a schematic illustration of pTK.A with SEQ ID NOS: 8, 9, 10, 7 and 11.

The resulting construct is designated pTKD A, FIG. 7.

For diagnostic purposes, the oligonucleotides are designed to destroy the Sma I site while maintaining the Ava I site without changing the translated protein.

The plasmid pPrTKDA (FIG. 8), which contains the HSVTK promoter and coding sequence (lacking an (A)$_n$ signal), is constructed as follows.

1. pTKD A is linearized with Bgl II treated with alkaline phosphatase, and gel purified.

2. A 0.8 Kg fragment contained the HSVTK transcriptional promoter is isolated as a Bam HI/Bgl II fragment from p322TK.

Figure 8:
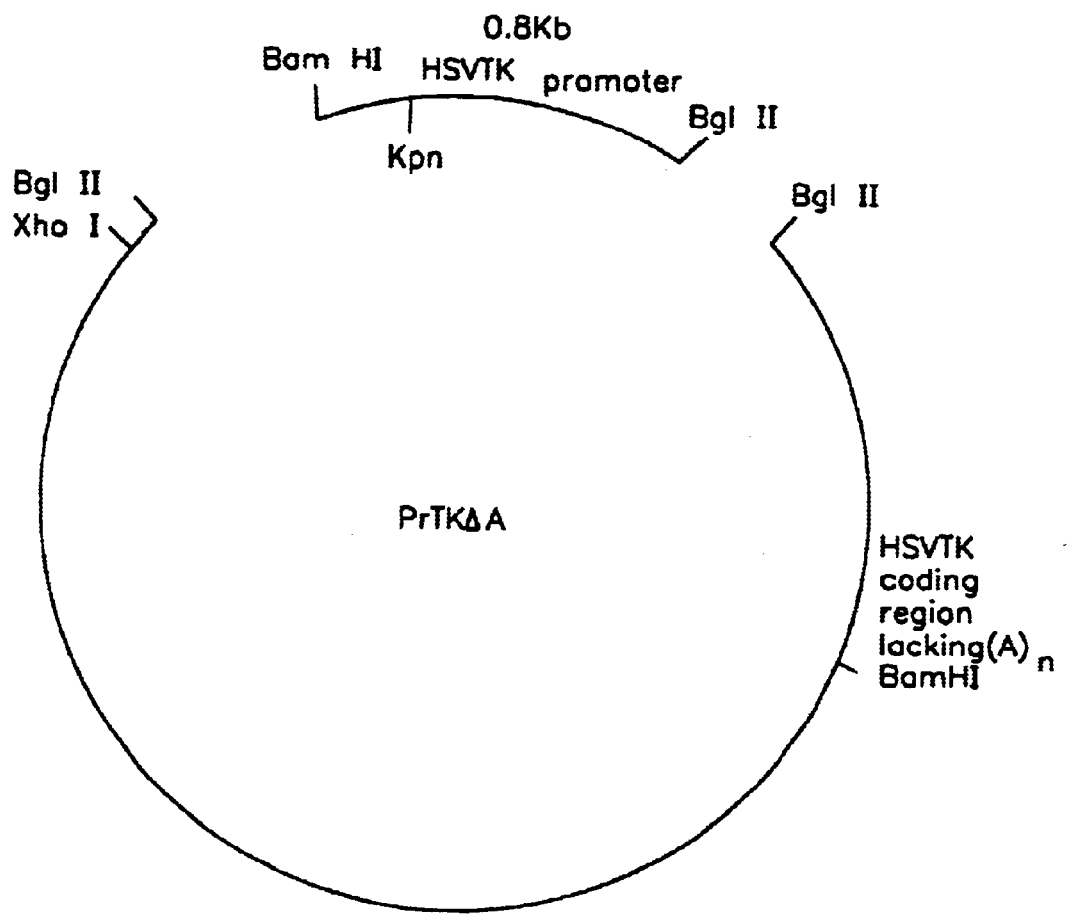
FIG. 8 is a schematic illustration of pPrTK.A.

3. Products from (1) and (2) are ligated, transformed into bacteria, and positive clones are screened for the proper orientation of the promoter region. A resultant clone is designated pPrTKDA (FIG. 8).

3. Construction of Retroviral Provectors Expressing HSVTK from a Constitutive Promoter The retroviral provectors pTK-1 and pTK-3 are constructed essentially as described below.

1. The 5 Kb Xho I/Hind III 5' LTR and plasmid sequences are isolated from p31N2R5(+) (FIG. 1).

2. HSVTK coding sequences lacking transcriptional termination sequences are isolated as a 1.2 Kb Xho I/Bam HI fragment from pTKDA (FIG. 2).

3. 3' LTR sequences are isolated as a 1.0 Kb Bam HI/Hind III fragment from pN2R3(−) (FIG. 2).

Figure 9:
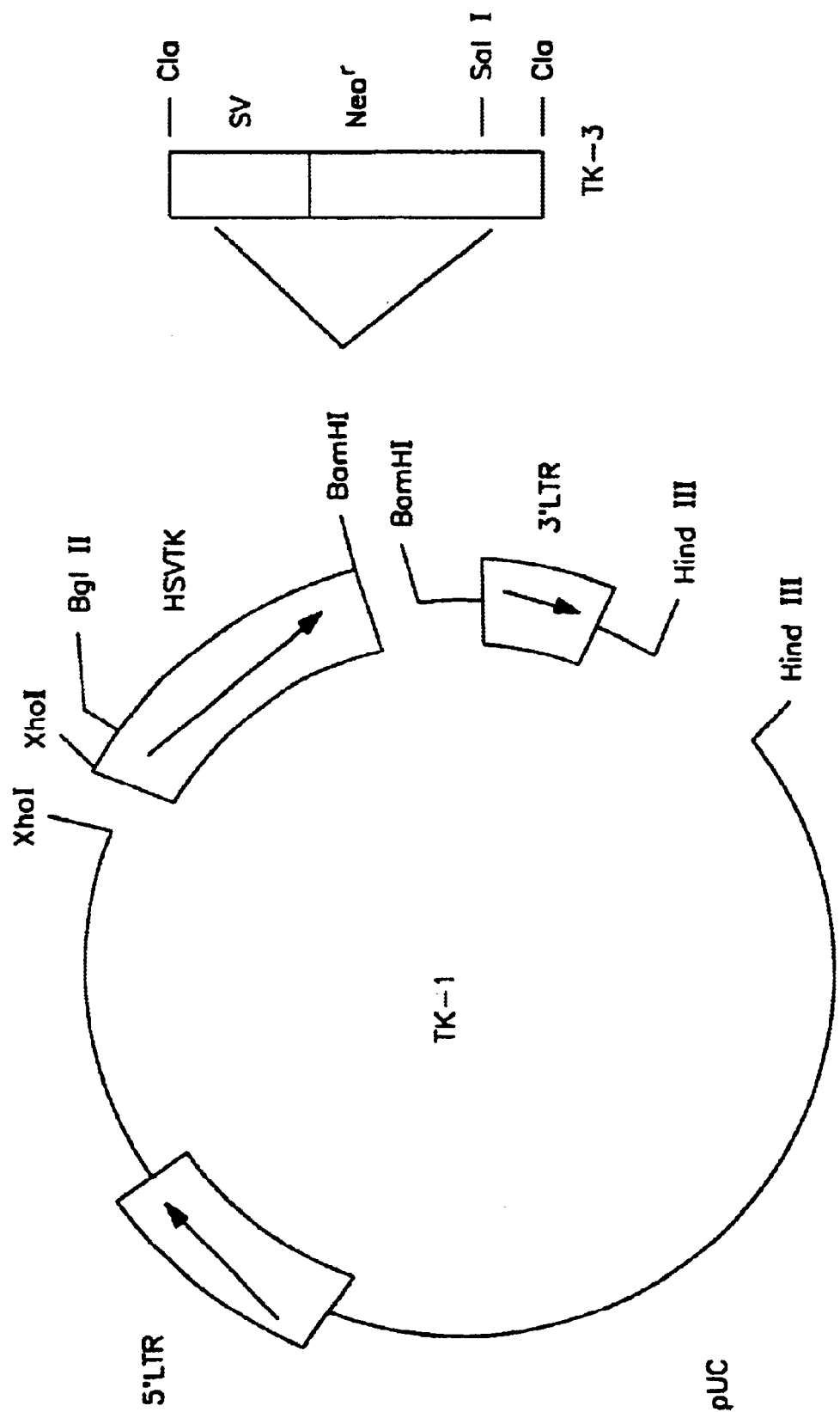
FIG. 9 is a schematic illustration of pTK-1 and pTK-3.

4. The fragments from steps 1–3 are mixed, ligated, transformed into bacteria, and individual clones identified by restriction enzyme analysis. The construct is designated TK-1 (FIG. 9).

5. pTK-3 is constructed by linearizing TK-1 with Bam HI, filling in the 5' overhang and blunt-end ligating a 5'-filled Cla I/Cla I fragment containing the bacterial lac UV5 promoter, SV40 early promoter, plus Tn5 neo$^r$ gene obtained from pAFVXM retroviral vector (Krieger et al., 1984, Cell 39:483; St. Louis et al., 1988, PNAS 85:3150). Kanamycin-resistant clones are isolated and individual clones are screened for the proper orientation by restriction enzyme analysis (FIG. 9).

These constructs were used to generate infectious recombinant vector particles in conjunction with a packaging cell line, such as DA as described above.

Figure 10:
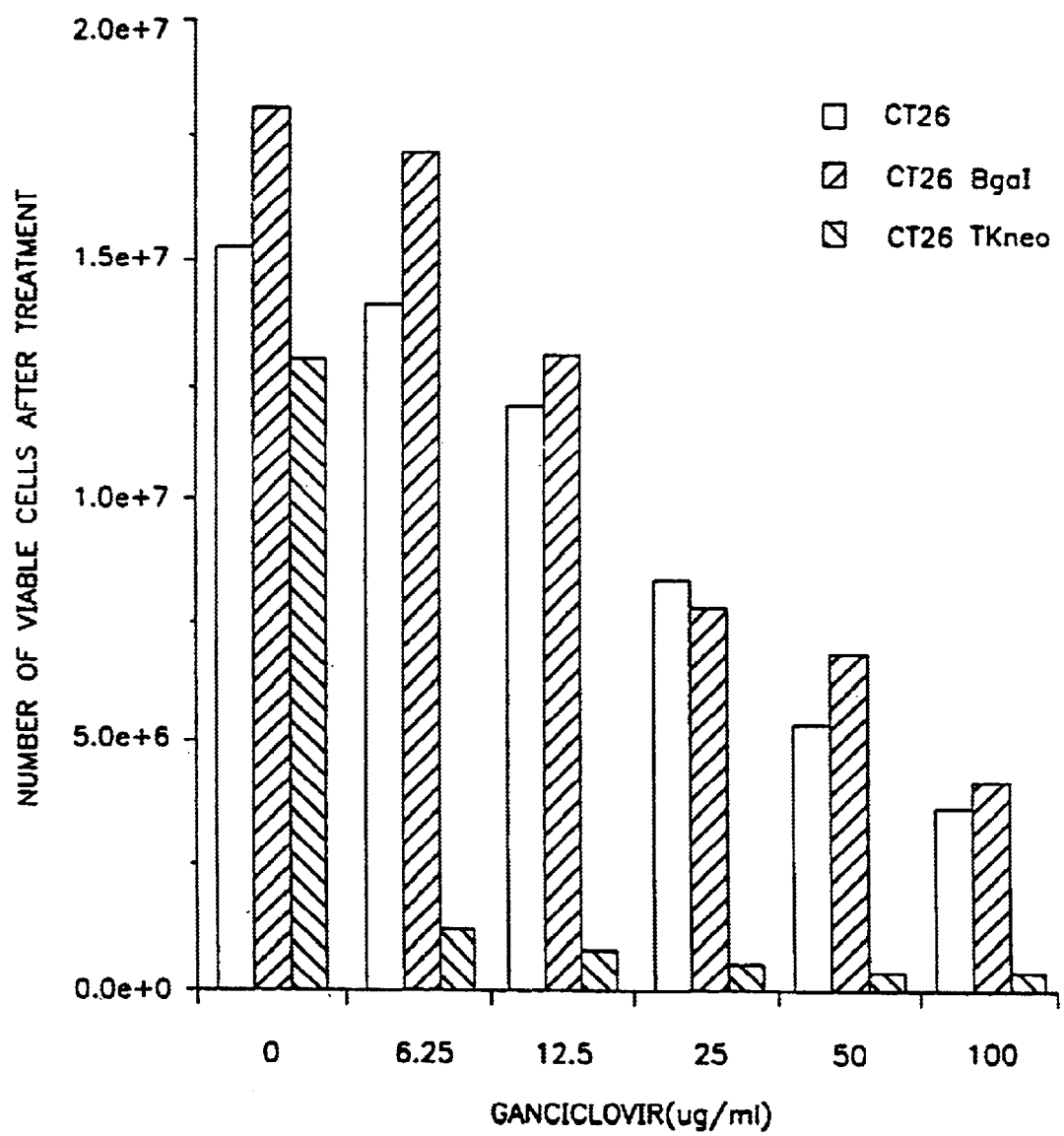
FIG. 10 is a bar graph which illustrates the effect of Ganciclovir on CT26, CT26 bgal and CT26TK Neo cells.

B. Determination of the Effect of Ganciclovir on Mouse Colon Carcinoma Cells with or without TK-3 Vector An experiment was performed to determine whether or not ganciclovir had an effect on CT26 cells (colon tumor 26, Brattain, Baylor College of Medicine, Houston, Tex.) that were transduced with DA/TK-3. CT26 cells are transduced with G-pseudotyped TK-3 vector. Twenty-four hours after adding the viral supernatant, the CT26 cells are placed under G-418 selection (450 lg/ml). After 10 days incubation, a G-418 selected pool is obtained and designated CT26TK Neo. CM26 TK Neo cells were seeded into six 10 cm$^2$ plates at a density of 2.5×10$^6$ per plate. As controls, each of two other cell types, CT26 and CT26 beta-gal (this cell line was transduced with a retroviral vector carrying the reporter gene β-galactosidase from E. coli.), were also seeded into six 10 cm$^2$ plates as controls. Five plates of each cell type were treated twice per day for four consecutive days with medium containing ganciclovir concentrations of 100 µg/ml, 50 µg/ml, 25 µg/ml, 12.5 µg/ml and 6.25 µg/ml. One plate of each cell type was left untreated. Afterwards, the cells were removed from each dish using trypsin-EDTA, resuspended in DMEM with 10% FBS and counted. The data in FIG. 10 shows that even the lowest dose of ganciclovir had a dramatic cytotoxic effect on the CT26 TKneo cells. This dose of ganciclovir (6.25 µg/ml) or even the next higher dose (12.5 µg/ml) did not have an effect on either the CT26 or CT26 beta-gal cells. However, beginning at a ganciclovir dose of 25 ug/ml, a dose-dependent decrease in cell growth could be seen, although CT26 TK Neo cells were always more sensitive to the drug.

C. Determination of a Ganciclovir Dose for the Treatment of Mice Injected with CT26 TK Neo Cells In order to test whether in vivo transduction of a murine tumor could be used to treat the disease, an experiment was performed to determine the optimal concentration of ganciclovir necessary to eliminate a tumor that was transduced and selected in vitro to assure 100% transduction. Twelve groups of 3 mice each are injected with $2\times10^5$ CT26TK Neo cells. Six groups of mice are injected with these cells intraperitoneally (I.P.) and six groups of mice are injected subcutaneously (S.C.). Two other groups of 3 mice each are injected with $2\times10^5$ unmodified CT26 cells (as a control) either I.P. or S.C.

Ten days after the injection of the CT26 or CT26TK Neo cells into these groups of mice, several concentrations of ganciclovir treatment are initiated. Each dose regimen consists of 2 daily AM and PM I.P. injections of ganciclovir. The experiment is summarized in Table A below.

TABLE A

| Group | Innoculum | Injection Route | Concentration of Ganciclovir (Mg/Kg) |
|---|---|---|---|
| 1 | CT26 I.P. | | 0 |
| 2 | CT26 TKneo | I.P. | 0 |
| 3 | CT26 TKneo | I.P. | 15.63 |
| 4 | CT26 TKneo | I.P. | 31.25 |
| 5 | CT26 TKneo | I.P. | 62.5 |
| 6 | CT26 TKneo | I.P. | 125.0 |
| 7 | CT26 TKneo | I.P. | 250.0 |
| 8 | CT26 TKneo | I.P. | 500.0 |
| 9 | CT26 Subq. | | 0 |
| 10 | CT26 TKneo | Subq. | 0 |
| 11 | CT26 TKneo | Subq. | 15.63 |
| 12 | CT26 TKneo | Suhq. | 31.25 |
| 13 | CT26 TKneo | Subq. | 62.5 |
| 14 | CT26 TKneo | Subq. | 125.0 |
| 15 | CT26 TKneo | Subq. | 250.0 |
| 16 | CT26T Kneo | Subq. | 500.0 |

Figure 11:
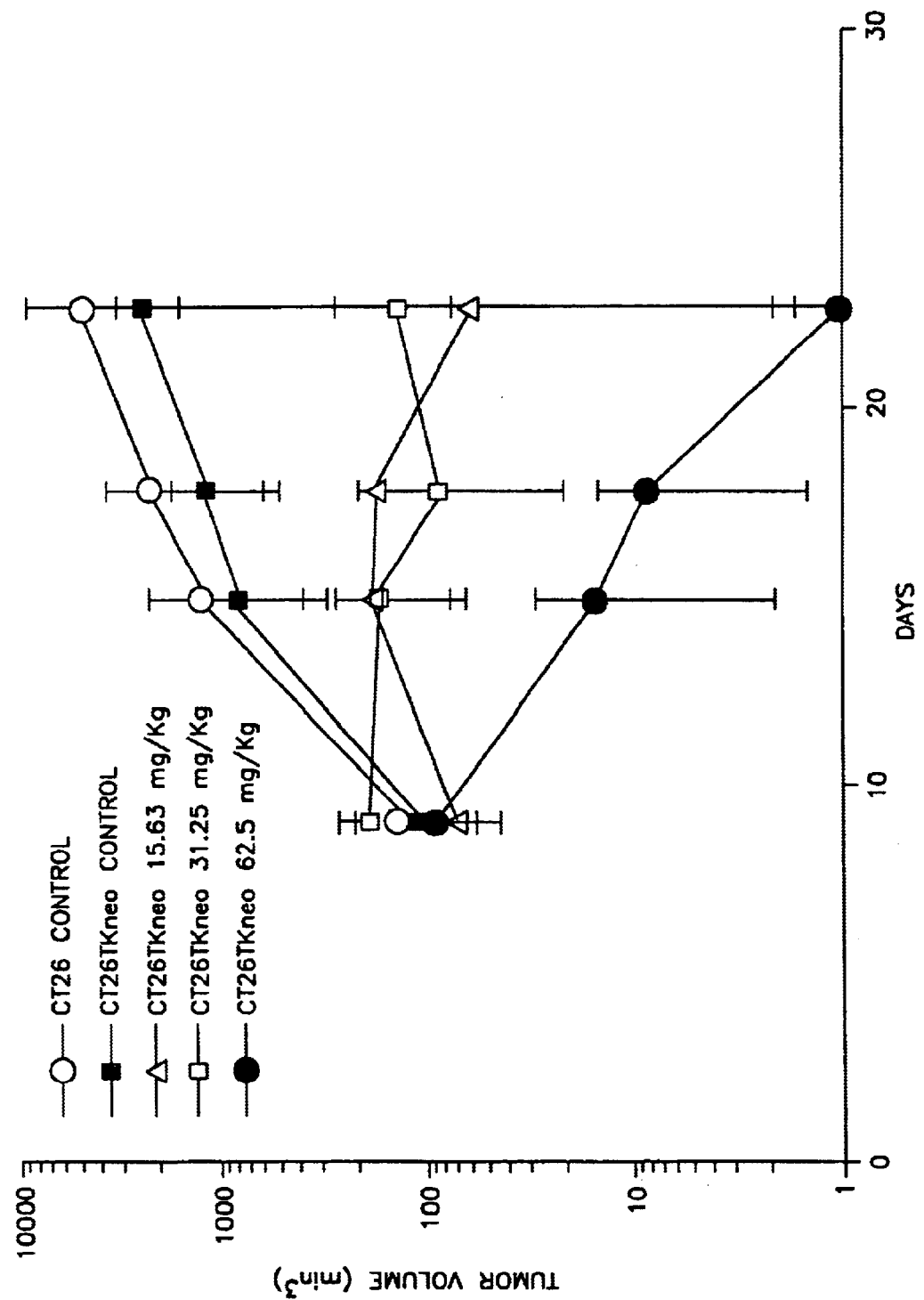
FIG. 11 is a graph which illustrates the effect of tumor volume over time in a Ganciclovir dose study of mice injected with CT26TK Neo.

After 5 days, all of the mice in the 125 mg/Kg, 250 mg/Kg and 500 mg/Kg treated groups were dead due to the toxic effects of ganciclovir. Mice in the 15.63 mg/Kg, 31.25 mg/Kg and 62.5 mg/Kg treated groups were treated for an additional 7 days and were able to tolerate the treatment. Tumor measurements were made for 23 days FIG. 11). CT26TK Neo grew only slightly slower than unmodified CT26 in the absence of ganciclovir. Complete tumor regression was seen in the groups of mice treated with the 62.5 mg/Kg regimen. Partial tumor regression was seen in the 31.25 mg/Kg treated groups. Little or no effect was seen in the 15.63 mg/Kg treated groups as compared to the 2 untreated control groups. Even though there was some toxicity observed in the 62.5 mg/Kg groups, it was not life threatening and reversible upon the discontinuation of the treatments so this concentration was used for future studies (FIG. 11). After 24 days, the I.P. injected animals were sacrificed and evaluated. The optimal concentration for anti-tumor effect was similar whether the tumor was grown I.P. or S.C.

D. Comparison of Cytotoxicity on CT26 and CT26TK Neo In Vivo Tumor Growth

Figure 12:
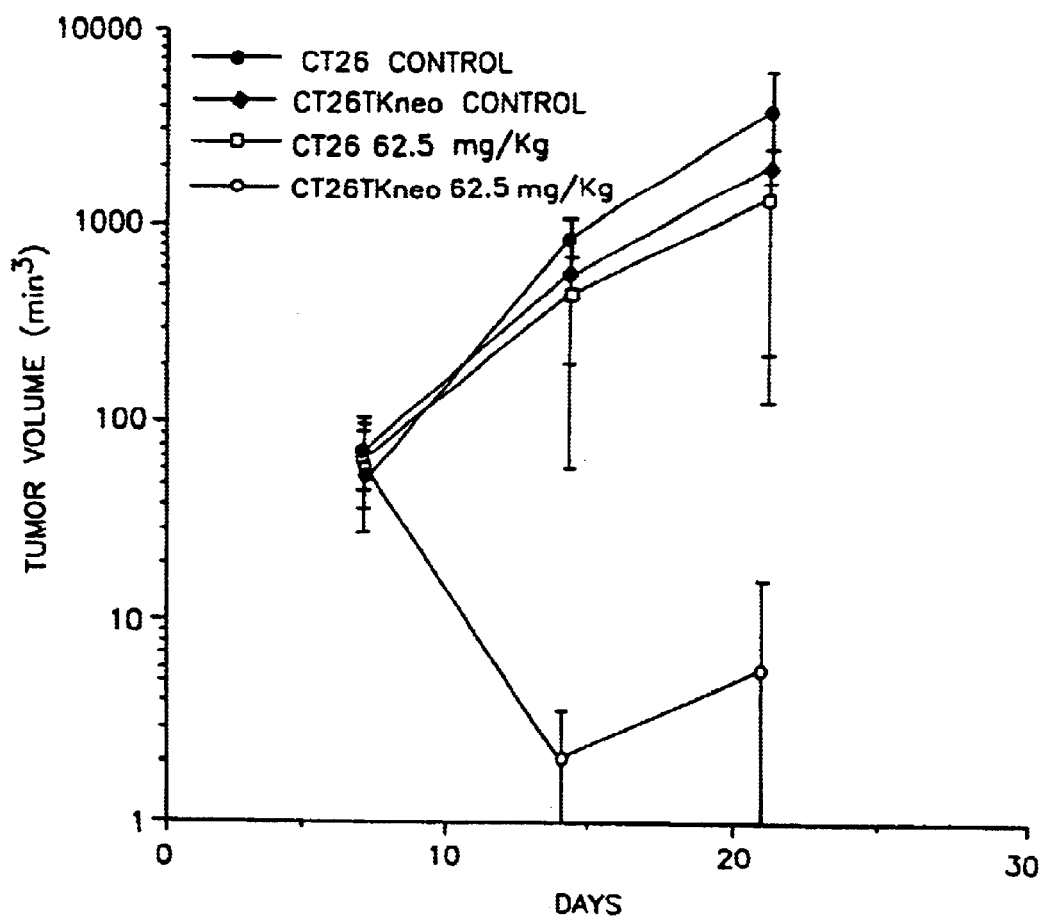
FIG. 12 is a graph illustrating the effect of Ganciclovir in CT26 versus CT26TK Neo cells.

In order to determine whether ganciclovir has an effect on the growth of unmodified CT26 tumor cells in vivo, 2 groups of 7 mice are injected S.C. with $2\times10^5$ unmodified CT26 cells and 2 groups of 7 mice are injected S.C. with $2\times10^5$ CT26TK Neo cells. Seven days after tumor implantation, one group of CT26 injected mice and one group of CT26TK Neo injected mice are placed on a twice daily (AM and PM) regimen of I.P. ganciclovir at 62.5 mg/Kg. These mice are treated for 12 days or until the CT26TK Neo injected animals have no detectable tumor burden. Tumor growth is monitored over a three week period. Mice injected with CT26 and treated with ganciclovir had tumors that were somewhat smaller than untreated mice injected with CT26, indicating a small HSVTK-independent inhibition of tumor growth (FIG. 12). However, a dramatic decrease in tumor burden was observed if, and only if, CT26 TKneo containing mice were treated with ganciclovir (FIG. 12).

E. Determination of the Effect of Ganciclovir on AY-27 Rat Carcinoma Cells with or without the TK-3 Vector An experiment is performed to determine whether or not ganciclovir has an effect on AY-27 cells that are transduced with DA/TK-3. AY-27 cells are rat carcinoma cells which have been induced by N-[4-(5-nitro-2-furyl)-2-thiazolyl] formamide (Selman et al., 1986, *J. Urol* 136:141, 1986). The AY-27 cells are transduced with G-pseudotyped TK-3 vector. Twenty-four hours after adding the viral supernatant, the AY-27 cells are placed under G-418 selection (450 µg/ml). After 10 days incubation, a G-418 selected pool is obtained and designated AY-27TK Neo. AY-27TK Neo cells are seeded into six 10 cm² plates at a density of $2.5\times10^6$ per plate. As controls, each of two other cell types, AY-27 and AY-27beta-gal (this cell line is transduced with a virus carrying the reporter gene β-galactosidase from *E. coli.*), are also seeded into six 10 cm² plates as controls. Five plates of each cell type are treated twice per day for four consecutive days with medium containing ganciclovir concentrations of 100 µg/ml, 50 µg/ml, 25 µg/ml, 12.5 µg/ml and 6.25 µg/ml. One plate of each cell type is left untreated. Afterwards, the cells are removed from each dish using trypsin-EDTA, resuspended in DMEM with 10% FBS and counted. The data generated can be used to determine the concentration which has the most cytotoxic effect o the AY-27, AY-27 beta-gal, or AY-27 TK Neo cells.

F. Determination of a Ganciclovir Dose for the Treatment of Rats Injected with AY-27 TK Neo Cells In order to test whether in vivo transduction of a murine tumor could be used to treat the disease, an experiment was performed to determine the optimal concentration of ganciclovir necessary to eliminate a tumor that was transduced and selected in vitro to assure 100% transduction. Twelve groups of 3 rats each are injected with $2\times10^5$ AY-27TK Neo cells. Six groups of rats are injected with these cells intravesically. Six other groups of 3 rats each are injected intravesically with $2\times10^5$ unmodified AY-27 cells (as a control).

Ten days after the injection of the AY-27 or AY-27TK Neo cells into these groups of rats, several concentrations of ganciclovir treatment are initiated. Each dose regimen consists of 2 daily AM and PM I.P. injections of ganciclovir. The experiment is summarized in Table B below.

TABLE B

| Group | Innoculum | Injection Route | Concentration of Ganciclovir (Mg/Kg) |
|---|---|---|---|
| 1 | AY-27 | | 0 |
| 2 | AY-27 TKneo | intravesically | 0 |
| 3 | AY-27 TKneo | intravesically | 15.63 |
| 4 | AY-27 TKneo | intravesically | 31.25 |
| 5 | AY-27 TKneo | intravesically | 62.5 |
| 6 | AY-27 TKneo | intravesically | 125.0 |
| 7 | AY-27 TKneo | intravesically | 250.0 |
| 8 | AY-27 TKneo | intravesically | 500.0 |

Rats are treated for 12 days, eliminating those that die due to the higher concentrations of ganciclovir. Tumor measurements are made for 20 days, assessing tumor regression in order to determine an optimal ganciclovir concentration.

G. Administration Protocol

1. Rat Administration Protocol

AT-27 rat bladder carcinoma cells are transplanted into the bladders of 20 male Fischer 344 rats (Charles River Breeding Laboratories, Portage, Md.). One to fourteen days following transportation, tumor-bearing rats weighing between 200 to 300 grams are anesthetized, their bladders are surgically exteriorized and evacuated of urine with a 27-gauge needle. Viral vector particles are instilled into the bladders of 5 rats at $10^6$ to $10^{10}$ in cfu 200 to 2,000 µl of formulation buffer. The addition of 4 to 8 µg/ml of polybrene increases the efficiency of transduction. In order to prevent leakage, the cystotomy is repaired with 7-zero nonabsorbable suture. The virus is allowed to incubate to incubate in the presence of the tumor cells for 0.5 to 1.0 hour by keeping the animal anesthetized and thereby preventing voiding. Ten control rats receive 500 µl of formulation buffer only.

Alternatively, 200 to 2,000 µl of vector can be instilled directly into the bladder by catheterization through the urethra following urine evacuation and rinsing with saline.

At 24 to 72 hours after vector treatment, the rats are placed on twice daily (AM and PM) injections of I.P. ganciclovir at the previously determined optimum dose (e.g. 62.5 mg/Kg body weight) for 4 to 12 days. Finally, the rats receive a single daily dose of ganciclovir until the end of the experiment (1 to 10 weeks). Whole bladders are removed and tumor growth is measured.

2. Human Administration Protocol

A urinary (Foley) catheter is inserted through the urethra into the bladder and secured in place. The bladder is evacuated of urine and washed with 100 to 500 mls of sterile saline. Recombinant retroviruses containing the gene for thymidine kinase expression are instilled through the catheter into the bladder at $10^5$ to $10^{11}$ cfu in 10 to 500 ml of formulation buffer preferably containing 4 to 8 µg/ml of polybrene, or other enhancing excipients. The viral particles are allowed to incubate for 0.25 to 12 hours prior to removal of the catheter. After 1 to 7 days, ganciclovir is administered at 1 to 5 mg/Kg I.V. (at a constant rate over 1 hour) every 12 hours for 2 to 21 days. The vector can be readministered multiple times (2 to 20), followed by ganciclovir administration. Due to the frequency of granulocytopenia and thrombocytopenia in patients receiving ganciclovir, it is recommended that neutrophil and platelet counts be performed every two days during the dosing of the drug. Tumor regression is monitored by x-ray and/or biopsy and the treatment repeated if required.

EXAMPLE 4

Pulmonary Administration of Recombinant Retroviruses Expressing Factor VIII

A. Construction of Full-Length and B Domain Deleted Factor VIII cDNA Retroviral Vector The construction of the full-length and B domain deleted Factor VIII retroviral vectors are described in Example 2A.

B. Aerosolization of Recombinant Retroviruses Expressing Factor VIII

The KT-ND5 viral supernatant in formulation buffer, with 4 to 8 µg/ml of polybrene or other transduction enhancing excipient, is nebulized using a DeVilbiss #15 Atomizer (DeVilbiss Health Care Division, Somerset, Pa.) designed to produce 0.3 to 0.5 µm particles (Rousculp, 1992, *Human Gene Therapy* 3:471–477). The aerosol produced by this nebulizer uses compressed air in a laminar flow hood. The mist is directed into a polypropylene tube, and the condensed vapor, as well as the control viral supernatant, is resterilized by 0.22 µm filtration. Retroviral particles pass through this filter without any significant loss of functional activity.

C. Administration of Vector Construct

1. Rat Administration Protocol

Rats are anesthetized and the trachea is exposed by anterior midline incision. Recombinant retroviral particles expressing the factor VIII gene product are diluted in 300 µl of formulation buffer, with or without 4 to 8 µg/ml of polybrene or other transduction enhancing excipient, at $10^5$ to $10^{10}$ cfu/ml and instilled into the trachea though a small gauge needle. Control animals are administered 300 µl of formulation buffer only. The incision is sutured and the rats are allowed to recover. Two to fourteen days following viral instillation, blood is drawn from the tail vein and examined for factor VIII production as described in Example 2Hi.

2. Human Administration Protocol

The recombinant retrovirus is administered using a DeVilbiss #15 Atomizer (as described above) for 2 to 60 minutes. Two to fourteen days following administration of the recombinant retroviruses, expression of Factor VIII is measured in the blood and plasma by the Coamatic$^R$ Factor VIII assay (as described in Example 2B1).

EXAMPLE 5

Transdermal Administration of Recombinant Retroviruses

A. Construction of TK-3 Vector Construct

Construction and verification of the TK-3 vector construct and recombinant retroviruses are described in Examples 3A through 3F.

B. Administration of Vector Construct

1. Animal Administration Protocol

Cottontail rabbit papillomavirus (CRPV) provides an animal model for the highly oncogenic human papillomavirus (HPV). Papillomas can be induced in the cottontail rabbit and virus infection leads to three different outcomes in the rabbit (Lin, Y. et et., *J Virol* 67:382, 1993). First, papillomas appear and persist for the lifetime of the rabbit, second, papillomas spontaneously regress 2 to 3 months after infection; and third, papillomas progress to carcinomas after 8 to 15 months.

In this experiment, twelve cottontail rabbits (E. Johnson, Rago, K A) are injected with the B strain of CRPV (Stevens, J. et al., *J Virol* 30:891, 1979) by intradermal injection as described by Stevens, J., et al., (*J Virol* 30:891, 1979). Four to six months after infection, when papillomas form, the animals are divided into two groups. In the first group, papillomas of 6 animals are injected with 25 to 100 µl of formulation buffer, with or without 4 to 8 µg/ml of polybrene or other transduction enhancing excipient, at $10^5$ to $10^{10}$ cfu/ml though a small gauge needle. In the second group, control animals are administered 25 to 100 µl of formulation buffer only. At 24 to 72 hours after vector treatment, the rabbits are placed on twice daily (AM and PM) injections of I.P. ganciclovir at the previously determined optimum dose (e.g. 62.5 mg/Kg body weight) for 4 to 12 days. Finally, the rabbits receive a single daily dose of ganciclovir until the end of the experiment (1 to 10 weeks). Papilloma regression is visually monitored for 2 to 14 days.

2. Human Administration Protocol

The clinical cutaneous lesions that result from the human papillomavirus (HPV) include common warts, filiform warts, plantar warts, and anogenital warts (reviewed in Cobb et al., 1990, *J. Am. Acad. Derm.* 22:547). In this experiment, patients are divided into two groups. In the first group, 100 to 500 µl of recombinant retrovirus particles at a concentration of $10^9$ cfu/ml in a formulated ointment, preferably containing 4 to 8 µg/ml of polybrene or other enhancing excipients, are applied to the warts using a transdermal delivery system (TDS).

Transdermal delivery systems (TDS) are capable of delivering a drug through intact skin so that it reaches the systemic circulation in sufficient quantity to be therapeutically beneficial. TDS provides a variety of advantages including elimination of gastrointestinal absorption problems and hepatic first pass effect, reduction of dosage and dose intervals, and improved patient compliance. The major components of TDS are a controlled release device composed of polymers, the drug to be administered, excipients, and enhancers, and a fastening system to fix the device to the skin. A number of polymers have been described which include gelatin, gum arabic, paraffin waxes, and cellulose acetate phthalate (Sogibayasi, K., et al., *J. Controlled Release,* 29:177–185, 1994).

The second group receives 100 to 500 μl of vector particle in formulation buffer only. The areas are covered and the viral particles are allowed to incubate for 0.25 to 12 hours prior to removal of the TDS. After 1 to 7 days, ganciclovir is administered at 1 to 5 mg/Kg I.V., preferably at a constant rate over 1 hour) every 12 hours for 2 to 21 days. The vector can be readministered multiple times (2 to 20), followed by ganciclovir administration. Due to the frequency of granulocytopenia and thrombocytopenia in patients receiving ganciclovir, it is recommended that neutrophil and platelet counts be performed every two days during the dosing of the drug. The regression of the wart is visually monitored for 2 to 14 days.

EXAMPLE 6

Ocular Administration of Recombinant Retroviruses for E3/19K

A. Cloning of E3/19K Gene into KT-3B

1. Isolation and Purification of Adenovirus

The isolation and purification of adenovirus is described by Green et al. (*Methods in Enzymology* 58: 425, 1979). Specifically, five liters of Hela cells (3–6.0×10$^5$ cells/ml) are infected with 100–500 plaque forming units (pfu) per ml of adenovirus type 2 (Ad2) virions (ATCC No. VR-846). After incubation at 37° C. for 30–40 hours, the cells are placed on ice, harvested by centrifugation at 230×g for 20 minutes at 4° C., and resuspended in Tris-HCl buffer (pH 8.1). The pellets are mechanically disrupted by sonication and homogenized in trichlorotrifluoroethane prior to centrifugation at 1,000×g for 10 min. The upper aqueous layer is removed and layered over 10 mls of CsCl (1.43 g/cm$^3$) and centrifuged in a SW27 rotor for 1 hour at 20,000 rpm. The opalescent viral band is removed and adjusted to 1.34 g/cm$^3$ with CsCl and further centrifuged in a Ti 50 rotor for 16–20 hours at 30,000 rpm. The visible viral band in the middle of the gradient is removed and stored at 4° C. until purification of adenoviral DNA.

2. Isolation and Purification of Adenovirus DNA

The adenovirus band is incubated with protease for 1 hour at 37° C. to digest proteins. After centrifugation at 7,800×g for 10 minutes at 4° C., the particles are solubilized in 5% SDS at room temperature for 30 minutes before being extracted with equal volumes of phenol. The upper aqueous phase is removed, re-extracted with phenol, extracted three times with ether, and dialyzed in Tris buffer for 24 hours. The viral Ad2 DNA is precipitated in ethanol, washed in ethanol, and resuspended in Tris-EDTA buffer (pH 8.1). Approximately 0.5 mg of viral Ad2 DNA is isolated from virus produced in 1.0 L of cells.

3. Isolation of E3/19K Gene

The viral Ad2 DNA is digested with EcoR I and separated by electrophoresis on a 1% agarose gel. The resulting 2.7 Kb Ad2 EcoR I D fragments, located in the Ad2 coordinate region 75.9 to 83.4, containing the E3/19K gene (Herisse et al., *Nucleic Acids Research* 8:2173, 1980, Cladaras et al., *Virology* 140:28, 1985) are eluted by electrophoresis, phenol extracted, ethanol precipitated, and dissolved in Tris-EDTA (pH 8.1).

4. Cloning of E3/19K Gene into KT-3B

The E3/19K gene is cloned into the EcoR I site of PUC1813. PUC1813 is prepared as essentially described by Kay et al. (*Nucleic Acids Research* 15:2778, 1987) and Gray et al. (*PNAS* 80:5842, 1983). The E3/19K is retrieved by EcoR I digestion and the isolated fragment is cloned into the EcoR I site of phosphatase-treated pSP73 plasmid. This construct is designated SP-E3/19K. The orientation of the SP-E3/19K cDNA is verified by using appropriate restriction enzyme digestion and DNA sequencing. In the sense orientation, the 5' end of the cDNA is adjacent to the Xho I site of the pSP73 polylinker and the 3' end adjacent to the Cla I site. The Xho I-Cla I fragment containing the E3/19K cDNA in either sense or antisense orientation is retrieved from the SP-E3/19K construct and cloned into the Xho I-Cla I site of the KT-3BB retroviral. This construct is designated KT-3B/E3/19K.

B. Cloning of PCR Amplified E3/19K Gene into KT-3B

1. PCR Amplification of E3/19K Gene

The Ad2 DNA E3/19K gene, including the amino terminal signal sequence, followed by the intraluminal domain and carboxy terminal cytoplasmic tail which allow the E3/19K protein to embed itself in the endoplasmic reticulum (ER), is located between viral nucleotides 28,812 and 29,288. Isolation of the Ad2 E3/19K gene from the vira genomic DNA is accomplished by PCR amplification, with the primer pair shown below:

The forward primer corresponds to the Ad2 nucleotide sequences 28,812 to 28,835.

5'-TATATCTCCAGATGAGGTACATGATTTTAG
    GCTTG-3'                            (Seq ID No. 3)

The reverse primer corresponds to the Ad2 nucleotide sequences 29,241 to 29,213.

5'-TATATATCGATTCAAGGCATTTTCTTTTCATCAATAAAAC-
    3'                                 (Seq ID No. 4)

In addition to the Ad2 complementary sequences, both primers contain a five nucleotide "buffer sequence" at their 5' ends for efficient enzyme digestion of the PCT amplicon products. This sequence in the forward primer is followed by the Xho I recognition site and by the Cla I recognition site in the reverse primer. Thus, in the 5' to 3' direction, the E3/19K gene is flanked by Xho I and Cla I recognition sites. Amplification of the E3/19K gene from Ad2 DNA is accomplished with the following PCR cycle protocol:

| Temperature ° C. | Time (min) | No. Cycles |
|---|---|---|
| 94 | 2.0 | 0 |
| 94 | 0.5 | |
| 55 | 0.17 | 5 |
| 72 | 3.5 | |
| 94 | 0.5 | 30 |
| 70 | 3.5 | |
| 72 | 10.0 | 10 |

2. Ligation of PCR Amplified E3/19K Gene into KT-3B

The E3/19K gene from the SP-E3/19K construct, approximately 780 bp in length, is removed and isolated by 1% agarose/TBE gel electrophoresis. The Xho I-Cla I E3/19K fragment is then ligated into the KT-3B retroviral backbone. This construct is designated KT-3B/E3/19K. It is amplified by transforming *E. coli,* DH5 alpha bacterial strain (Bethesda Research Labs, Gaithersburg, Md.) with the KT-3B/E3/19K construct. Specifically, the bacteria is transformed with 1–100 ng of ligation reaction mixture DNA.

The transformed bacteria cells are plated on LB plates containing ampicillin. The plates are incubated overnight at 37° C., bacterial colonies are selected and DNA prepared from them. The DNA is digested with Xho I and Cla I. The expected endonuclease restriction cleavage fragment sizes for plasmids containing the E3/19K gene are 780 and 1,300 bp.

C. Transduction of Packaging Cell Line DA with the Recombinant Retroviral Vector KT-3B/E3/19K 1. Plasmid DNA Transfection 293 2–3 cells (a cell line derived from 293 cells ATCC No. CRL 1573, (WO 92/05266) $5.0 \times 10^5$ cells are seeded at approximately 50% confluence on a 6 cm tissue culture dish. The following day, the media is replaced with 4 ml fresh media 4 hours prior to transfection. A standard calcium phosphate-DNA coprecipitation is performed by mixing 10.0 μg of KT-3B/E3/19K plasmid and 10.0 μg MLP G plasmid with a 2M $CaCl_2$ solution, adding a 1×HEPES buffered saline solution, pH 6.9, and incubating for 15 minutes at room temperature. The calcium phosphate-DNA coprecipitate is transferred to the 293 2–3 cells, which are then incubated overnight at 37° C., 5% $CO_2$. The following morning, the cells are rinsed three times in 1×PBS. pH 7.0. Fresh media is added to the cells, followed by overnight incubation at 37° C., 10% $CO_2$. The following day, the media is collected off the cells and passed through a 0.45μ filter. This supernatant is used to transduce packaging and tumor cell lines. Transient vector supernatant for other vectors are generated in a similar fashion.

2. Packaging Cell Line Transduction

Packaging cell line transduction is performed as described in Example 2C.

3. Detection of Replication Competent Retroviruses

Detection of replication competent retroviruses is performed as described in Example 2D D. Transduction of Cell Lines with the Recombinant Retroviral Vector KT-3B/E3/19K The following adherent human and murine cell lines are seeded at $5 \times 10^5$ cells/10 cm dish with 4 μg/ml polybrene: HT 1080, Hela, and BC10ME. The following day, 1.0 ml of filtered supernatant from the DA E3/19K pool is added to each of the cell culture plates. The following day, 800 μg/ml G418 is added to the media of all cell cultures. The cultures are maintained until selection is complete and sufficient cell numbers are generated to test for gene expression. The transduced cell lines are designated HT 1080-E3/19K, Hela-E3/19K and BC10ME-E3/19K, respectively.

EBV transformed cell lines (BLCL), and other suspension cell lines, are transduced by co-cultivation with irradiated producer cell line, such as DA-E3/19K. Specifically, irradiated (10,000 rads) producer line cells are plated at $5.0 \times 10^5$ cells/6 cm dish in growth media containing 4 μg/ml polybrene. After the cells have been allowed to attach for 2–24 hours, $10^6$ suspension cells are added. After 2–3 days, the suspension cells are removed, pelleted by centrifugation, resuspended in growth media containing 1 mg/ml G418, and seeded in 10 wells of a round bottom 96 well plate. The cultures were expanded to 24 well plates, then to T-25 flasks.

E. Expression of E3/19K in the Recombinant Retroviral Vector Construct KT3B-E3/19K 1. Western Blot Analysis Radio-immuno precipitation assay (RIPA) lysates are made from selected cultures for analysis of E3/19K expression. RIPA lysates are prepared from confluent plates of cells. Specifically, the media is first aspirated off the cells. Depending upon the size of the culture plate containing the cells, a volume of 100 to 500 ml ice cold RIPA lysis buffer (10 mM Tris, pH 7.4; 1% Nonidet P40; 0.1% SDS; 150 mM NaCl) is added to the cells. Cells are removed from plates using a micropipet and the mixture is transferred to a microfuge tube. The tube is centrifuged for 5 minutes to precipitate cellular debris and the supernatant is transferred to another tube. The supernatants are electrophoresed on a 10% SDS-polyacrylamide gel and the protein bands are transferred to an Immobilon membrane in CAPS buffer (10 mM CAPS (Aldrich, Milwaukee, Wis.) pH 11.0; 10% methanol) at 10 to 60 volts for 2 to 18 hours. The membrane is transferred from the CAPS buffer to 5% Blotto (5% nonfat dry milk; 50 mM Tris, pH 7.4; 150 mM NaCl; 0.02% Na azide, and 0.05% Tween 20) and probed with a mouse monoclonal antibody to E3/19K (Severinsson et al., 1985, *J. Cell. Biol.* 101:540–547). Antibody binding to the membrane is detected by the use of $^{125}$I-Protein A.

2. FACS Analysis of KT3B-E3/19k-Vector Transduced Cells to Demonstrate Decreased Levels of Class I Expression Compared to Non-Transduced Cells Cell lines transduced with the KT3b-E3/19K-vector are examined for MHC class I molecule expression by FACS analysis. Non-transduced cells are also analyzed for MHC class I molecule expression and compared with E3/19K transduced cells to determine the effect of transduction on MHC class I molecule expression.

Murine cell lines, BC10ME, BC10ME-E3/19K, P815 (ATCC No. TIB 64), and P815-E3/19K, are tested for expression of the $H-2D^d$ molecule on the cell surface. Cells grown to subconfluent density are removed from culture dishes by treatment with Versene and washed two times with cold (4° C.) PBS plus 1% BSA and 0.02% Na-azide (wash buffer) by centrifugation at 200 g. Two million cells are placed in microfuge tubes and pelleted in a microfuge at 200 g before removing the supernatant. Cell pellets are resuspended with the $H-2D^d$-specific Mab 34-2-12s (50 ml of a 1:100 dilution of purified antibody, ATCC No. HB 87) and incubated for 30 min at 4° C. with occasional mixing. Antibody labeled cells are washed two times with 1 ml of wash buffer (4° C.) prior to removing the supernatant. Cells are resuspended with a biotinylated goat anti-mouse kappa light chain Mab (50 ml, of a 1:100 dilution of purified antibody) (Amersham, Arlington Height, Ill.) and incubated for 30 min at 4° C. Cells are washed, resuspended with 50 ml of avidin conjugated FTTC (Pierce, Rockford, Ill.), and incubated for 30 min at 4° C. The cells are washed once more, resuspended in 1 ml of wash buffer, and held on ice prior to analysis on a FACStar Analyzer (Becton Dickinson, Los Angeles, Calif.). The mean fluorescence intensity of transduced cells is compared with that of non-transduced cells to determine the effect E3/19K protein has on surface MHC class I molecule expression.

F. Administration of Vector Construct

1. Rat Administration Protocol

Rats are anesthetized and one eye is instilled with 5 to 100 μl of recombinant retroviral particles at a concentration of $10^5$ to $10^{10}$ cfu/ml in formulation buffer, with or without 4 to 8 μg/ml of polybrene or other transduction enhancing excipient, Five to one hundred μl of solution containing formulation buffer only is added to the other eye to be used as a control. The solution is allowed to incubate for 1 hour before each eye is rinsed 3 times with 100 μl of saline. Two to seven days following the treatment, the rat is sacrificed, the cornea is removed, and homogenized in 2 ml ice cold RIPA lysis buffer. Expression of E3/19K is detected by Western blot analysis as described in Example 6E1.

2. Human Administration Protocol

Although the rate of corneal transplant rejection is relatively low, the current therapy for those with rejection requires continuous treatment of steroid compounds. This eventually leads to cataract formation, requiring surgery. Therefore, the introduction of a recombinant retrovirus expressing the E3/19K would prevent the need for such a steroid regimen. Ten to five hundred µl of recombinant retroviruses at a concentration of $10^5$ to $10^{10}$ cfu/ml in formulation buffer, with or without 4 to 8 µg/ml of polybrene or other transduction enhancing excipient in formulation buffer, are administered to the eye of a patient lying in a prone position. The solution is allowed to incubate for 15 to 30 minutes before being washed with saline.

Alternatively, the cornea may be incubated for 1 hour in 1 ml of retroviral vector particles at a concentration of $10^5$ to $10^{10}$ cfu/ml in formulation buffer, with or without 4 to 8 µg/ml of polybrene or other transduction enhancing excipient, just prior to surgical attachment. In either of the above cases, the progress of the transplant is monitored by visually observing tissue viability.

EXAMPLE 7
Intranasal Administration of Recombinant Retroviruses Expressing Factor VIII A. Construction of Full-Length and B Domain Deleted Factor VIII cDNA Retroviral Vector The construction of the full-length and B domain deleted Factor VIII retroviral vectors are described in Example 2A B. Administration of Vector Construct 1. Rat Administration Protocol The nasal route has been shown to be effective for the administration of a number of molecules due to the extensive network of capillaries located under the nasal mucosa. This facilitates effective systemic absorption and when the drug is administered with absorption promoters, absorption occurs rapidly with high bioavailability (review in Gizurarson et al., 1990, *Acta Pharm* 2:105).

One group of six Fischer-344 rats are used for nasal administration of the retroviral vector particles for Factor VIII. One to fifty µl of retroviral vector particles at $10^9$ cfu/ml in formulation buffer, with or without 4 to 8 µg/ml of polybrene or other transduction enhancing excipients are applied with a pipette inserted about 3 to 5 mm into each nostril. Another group is administered formulation buffer without vector in the same manner. Blood samples are collected from the jugular or tail vein 1 to 14 days later and assayed for factor VIII production as described in Example 2Hi.

2. Human Administration Protocol

Several types of drug delivery devices for the nasal cavity exists (reviewed in Chien et al., 1987, *Crit Rev Therap Drug Carr Sys* 4:67). These systems include nasal spray, nose drops, saturated cotton pledget, aerosol spray, and insufflator. The metere-dose nebulizer can deliver a predetermined volume of the formulation to the nasal cavity.

Two groups of patients are used in this study. One group of patients receives 100 to 500 µl of retroviral vector particles at $10^9$ cfu/ml in formulation buffer, with or without 4 to 8 µg/ml of polybrene or other transduction enhancing excipients, applied to each nostril via nasal spray or nasal drops. Another group receives formulation buffer only applied in the same manner. Blood samples are collected 1 to 14 days later and assayed for factor VIII production as described in Example 2B1.

EXAMPLE 8
Preparation of Recombinant Retrovirus for Delivery of Human Growth Hormone A. Preparation of hGH Containing Vectors Vector pDHF828 containing the full-length human growth hormone gene is constructed essentially as follows. Briefly, plasmid pDHF811, was constructed by removing the XhoI-ClaI fragment of the KT-1 retroviral vector described above, and inserting the following oligonucleotide linkers by ligation of the cohesive ends:

Linker sequences:

5' TCGAGGATCC GCCCGGGCGG CCGCATCGAT GTCGACG
    3'     (SEQUENCE ID# 5)

5' CGCGTCGA CATCGATGCG GCCGCC
    CGGG CGGATCC 3'     (SEQUENCE ID# 6)

In particular, the linkers were annealed at 65° C. for 20 minutes, 42° C. for 20 minutes, 37° C. for 20 minutes, and room temperature for 2 hours. The concentrations of both oligonucleotides was 18 mM and the salt concentration was 100 mM NaCl. After annealing, 50 ml of 1.8 mM annealed linker was digested with ClaI overnight to generate ClaI ends. For ligation, 3 nM of KT-1 XhoI-ClaI fragment was mixed with 90 nM of linker, and the resultant mixture incubated at 15° C. for 3 hours. The ligated DNA sample was transformed into DH-5α competent cells, followed by screening of transformants.

Plasmid chGH 800 containing the full length cDNA of the hGH gene (Martial et al., 1979, *Science* 205:602) was digested with Hind III, blunt-ended with the Klenow fragment enzyme, and cloned into the SrfI site of pDHF811. The resultant plasmid was designated pDHF828.

B. Preparation of hGH Expressing Recombinant Retrovirus

The pDHF828 plasmid was then introduced into the HX packaging cell, using standard procedures and assayed using the HGH Chemiluminescence Kit (HGH 100T) (Nichols Institute, San Juan Capistrano, Calif.), according to a preferred modification of the kit protocol. On day 1, the kit components were warmed to room temperature and gently mixed by inversion before opening any vials. Test samples were centrifuged for 5' at top speed in a microfuge before using them in order to remove fibrin and other debris. All samples were measured in quadruplicate, including the standards. The incubations are performed in 12×17 polypropylene tubes that have been stored in the dark. One hundred fifty ul of sample or standard were aliquoted into each tube and ul of antibody is added and the samples were mixed gently. One bead was added to each well using the forceps provided in the kit. The tubes were capped, covered with foil, and shaken on an orbital shaker for 24 hr at room temperature. Standards contain 530 pg/ml (STD D), and serial dilutions were made in zero standard of Std D of 250, 100, 50, 25, 10, 5, and 2.5 pg/ml.

After 24 hours, the tubes were uncapped and 0.5 ml of wash buffer were added. These wash solution was added with enough force to make the bead bounce up off the bottom of the tube. The samples were washed three times with 2.0 ml nanopure water, and aspirated completely each time. The luminometer determinations were done in 12×75 polycarbonate (clear plastic) tubes stored in the dark. The luminometer was pretested with performance control standards.

Using this assay, HX/HGH retroviral vector producing cell lines were generated with titers of $4.8 \times 10^6$ cfu/ml. Introduction of the plasmid into DX packaging cells resulted in production of clonal producer cells with a titer of $1.6 \times 10^7$ cfu/ml.

EXAMPLE 9
Preservation of a Recombinant Retrovirus

A. Lactose Formulation of a Recombinant Retrovirus

Crude recombinant retrovirus is obtained from a Celligan bioreactor (New Brunswick, New Brunswick, N.J.) containing DA cells transformed with the recombinant retrovirus bound to the beads of the bioreactor matrix. The cells release the recombinant retrovirus into the growth media that is passed over the cells in a continuous flow process. The media exiting the bioreactor is collected and passed initially through a 0.8 micron filter then through a 0.65 micron filter to clarify the crude recombinant retrovirus. The filtrate is concentrated utilizing a cross flow concentrating system (Filtron, Boston, Mass.). Approximately 50 Units of DNase (Intergen, New York, N.Y.) per ml of concentrate is added to digest exogenous DNA. The digest is diafiltrated using the same cross flow system to 150 mM NaCl, 25 mM tromethamine, pH 7.2. The diafiltrate is loaded onto a Sephadex S-500 gel column (Pharmacia Piscataway, N.J.), equilibrated in 50 mM NaCl, 25 mM tromethamine, pH 7.4. The purified recombinant retrovirus is eluted from the Sephadex S-500 gel column in 50 mM NaCl, 25 mM tromethamine, pH 7.4.

The formulation buffer containing lactose was prepared at a 2×concentrated stock solution. The formulation buffer contains 25 mM tromethamine, 70 mM NaCl, 2 mg/ml arginine, 10 mg/ml HSA, and 100 mg/ml lactose in a final volume of 100 mls at a pH 7.4.

The purified recombinant retrovirus is formulated by adding one part 2×lactose formulation buffer to one part S-500 purified recombinant retrovirus. The formulated recombinant retrovirus can be stored at −70° C. to −80° C. or dried.

The formulated retrovirus is lyophilized in an Edwards Refrigerated Chamber (3 Shelf RC3S unit) attached to a Supermodulyo 12K freeze dryer (Edwards High Vacuum, Tonawanda, N.Y.). When the freeze drying cycle is completed, the vials are stoppered under a vacuum following a slight nitrogen gas bleeding. Upon removal, vials are crimped with aluminum seals.

Figure 13:
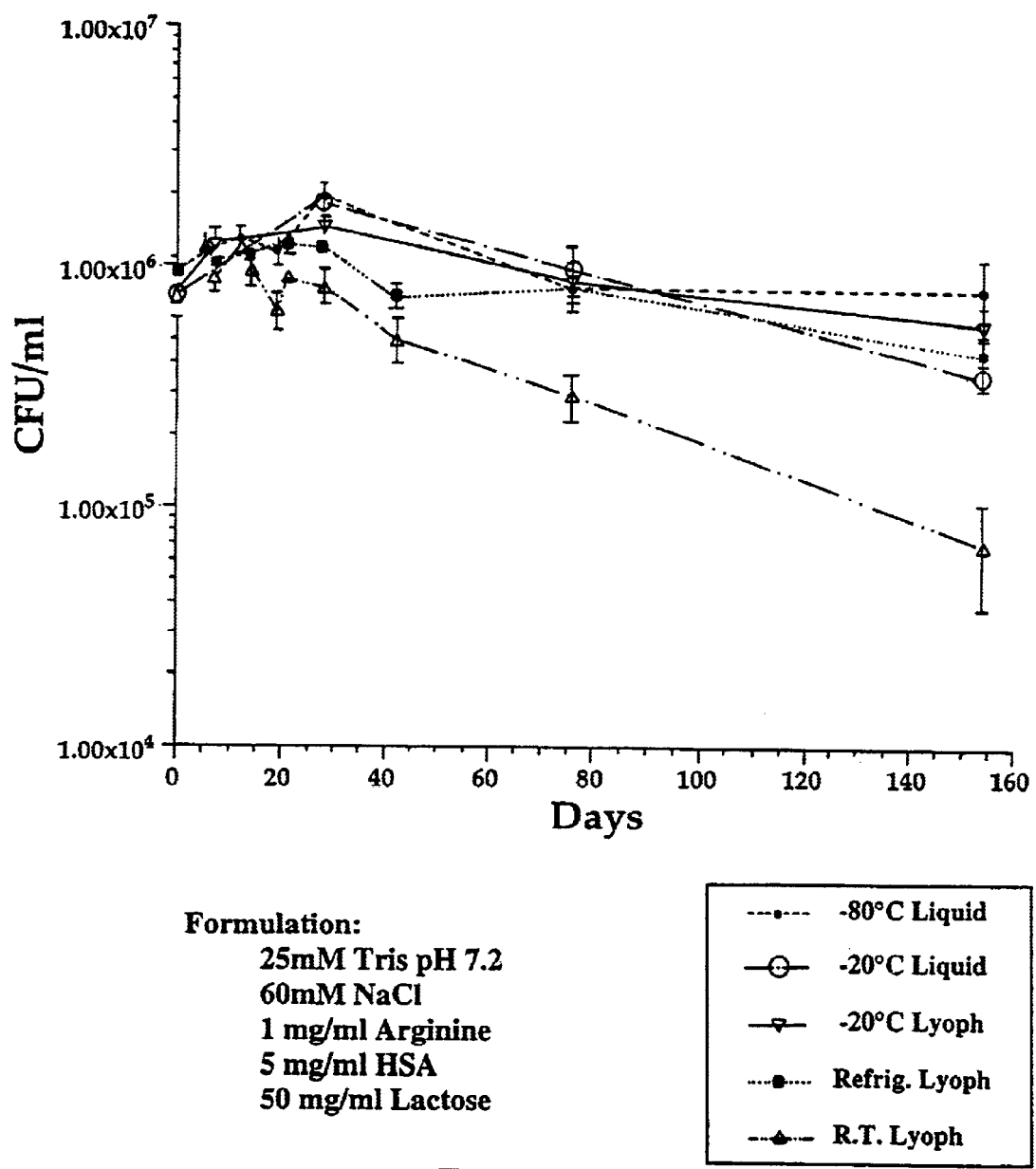
FIG. 13 is a graph demonstrating retention of viral activity upon reconstitution of a representative recombinant retrovirus lyophilized in a formulation buffer containing mannitol.

In the given lactose study, formulated liquid product was stored at both −80° C. and at −20° C. cycling freezer. In FIG. 13 viral infectivity of these samples were compared to the viral infectivity of lyophilized samples. The lyophilized samples were stored at −20° C., refrigerator temperature and room temperature. Activity of the samples upon reconstitution are determined by titer assay.

The lyophilized recombinant retrovirus is reconstituted with 1.0 ml water. The infectivity of the reconstituted recombinant retrovirus is determined by a titer activity assay. The assay is conducted on HT 1080 fibroblasts or 3T3 mouse fibroblast cell line (ATCC No. CCL 163). Specifically, $1\times10^5$ cells are plated onto 6 cm plates and incubated overnight at 37° C., 10% $CO_2$. Ten microliters of a dilution series of reconstituted recombinant retroviruses are added to the cells in the presence of 4 mg/mL polybrene (Sigma, St. Louis, Mo.) and incubated overnight at 37° C., 10% $CO_2$. Following incubation, cells are selected for neomycin resistance in G418 containing media and incubated for 5 days at 37° C., 10% $CO_2$. Following initial selection, the cells are re-fed with fresh media containing G418 and incubated for 5–6 days. After final selection, the cells are stained with Commassie blue for colony detection. The titer of the sample is determined from the number of colonies, the dilution, and the volume used.

FIG. 13 demonstrates that storage in lyophilized form at −20° C. to refrigerator temperatures retains similar viral activity as a recombinant retrovirus stored in liquid at −80 to −20° C. permitting less stringent temperature control during storage.

B. Mannitol Formulation of a Recombinant Retrovirus

The recombinant retrovirus utilized in this example was purified as described in Example 9A.

The formulation buffer containing mannitol was prepared as a 2×concentrated stock solution. The formulation buffer contains 25 mM tromethamine, 35 mM NaCl, 2 mg/ml arginine, 10 mg/ml HSA and 80 mg/ml mannitol at a final volume of 100 mls at a pH 7.4.

The purified recombinant retrovirus is formulated by adding one part mannitol formulation buffer to one part S-500 purified recombinant retrovirus. The formulated recombinant retrovirus can be stored at this stage at −70° C. to −80° C. or dried.

The formulated retrovirus is dried in an Edwards Refrigerated Chamber (3 Shelf RC3S unit) attached to a Supermodulyo 12K freeze dryer. When the freeze drying cycle is completed, the vials are stoppered under a vacuum following nitrogen gas bleeding to 700 mbar. Upon removal, vials are crimped with aluminum seals.

In the given mannitol study, formulated liquid product was stored at both −80° C. and at −20° C. in cycling freezers. The viral infectivity of these samples were compared to the viral infectivity of lyophilized samples, FIG. 14. The lyophilized samples were stored at −20° C., refrigerator temperature and room temperature. Activity of the samples upon reconstitution are determined using the titer assay described in Example 9A.

Figure 14:
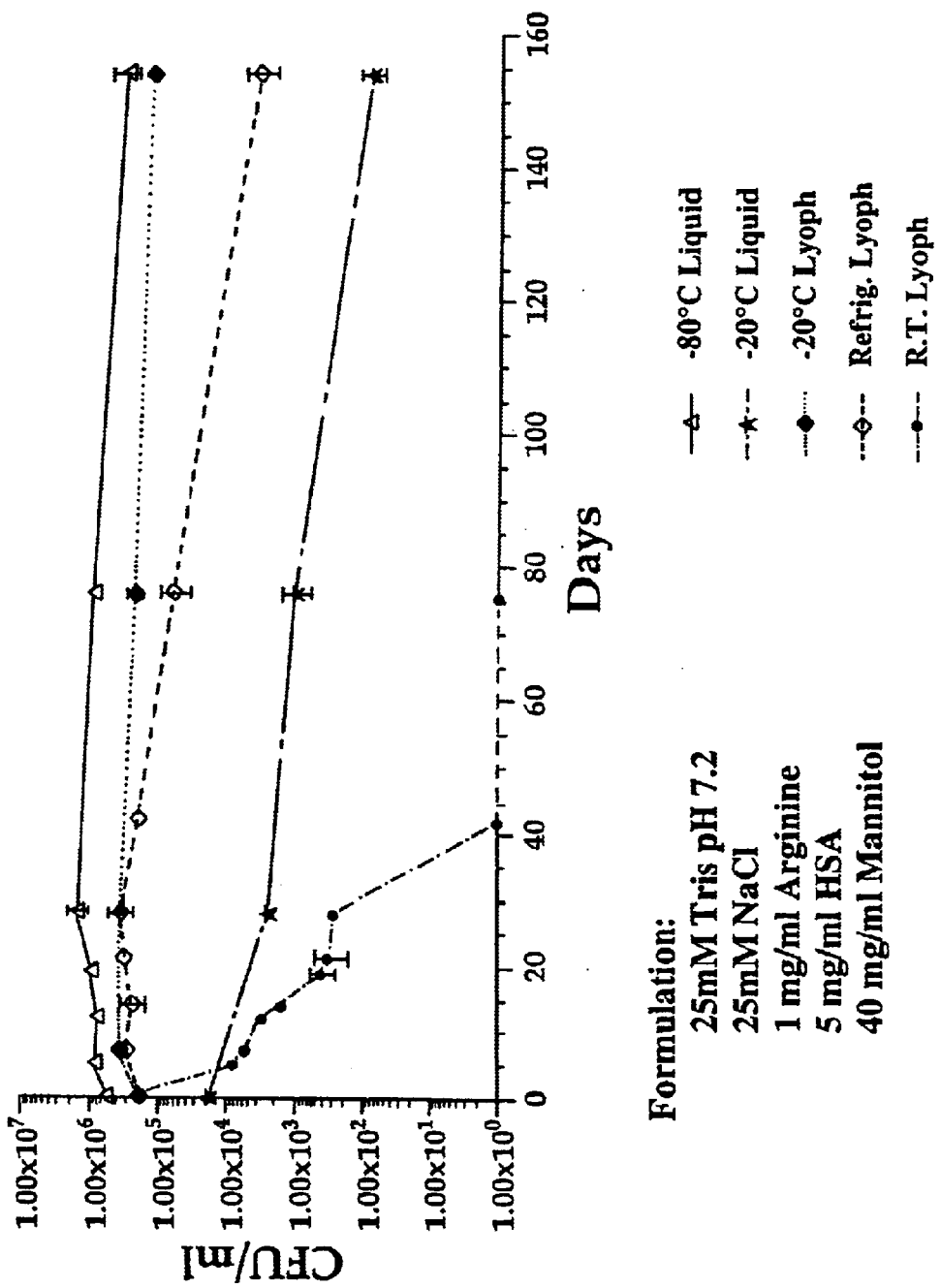
FIG. 14 is a graph demonstrating retention of viral activity upon reconstitution of a representative recombinant retrovirus lyophilized in a formulation buffer containing lactose.

FIG. 14 demonstrates that storage in lyophilized form at −20° C. to refrigerator temperature retains significant viral activity as compared to recombinant retrovirus stored in liquid at −80° C. or −20° C., permitting less stringent temperature control during storage.

C. Trehalose Formulation of a Recombinant Retrovirus

The recombinant retrovirus utilized in this example was purified as described in Example 9A.

The formulation buffer containing trehalose was prepared as a 2×concentrated stock solution. The formulation buffer contains 25 mM tromethamine, 70 mM NaCl, 2.0 mg/ml arginine, 10.0 mg/ml HSA and 100 mg/ml trehalose at a final volume of 100 mls at a pH 7.2.

The purified recombinant retrovirus is formulated by adding one part trehalose formulation buffer to one part S-500 purified recombinant retrovirus. The formulated recombinant retrovirus can be stored at this stage at −70° C. to −80° C. or dried.

The formulated retrovirus is dried in an Edwards Refrigerated Chamber (3 Shelf RC3S unit) attached to a Supermodulyo 12K freeze dryer. When the freeze drying cycle is completed, the vials are stoppered under a vacuum following nitrogen gas bleeding to 700 mbar. Upon removal, vials are crimped with aluminum seals.

In the given trehalose study, formulated liquid product was stored at both −80° C. and at −20° C. in cycling freezers. The viral infectivity of these samples was compared to the viral infectivity of lyophilized samples, FIG. 15. The lyophilized samples were stored at −20° C., refrigerator temperature and room temperature. Activity of the samples upon reconstitution are determined using the titer assay as described in Example 9A.

Figure 15:
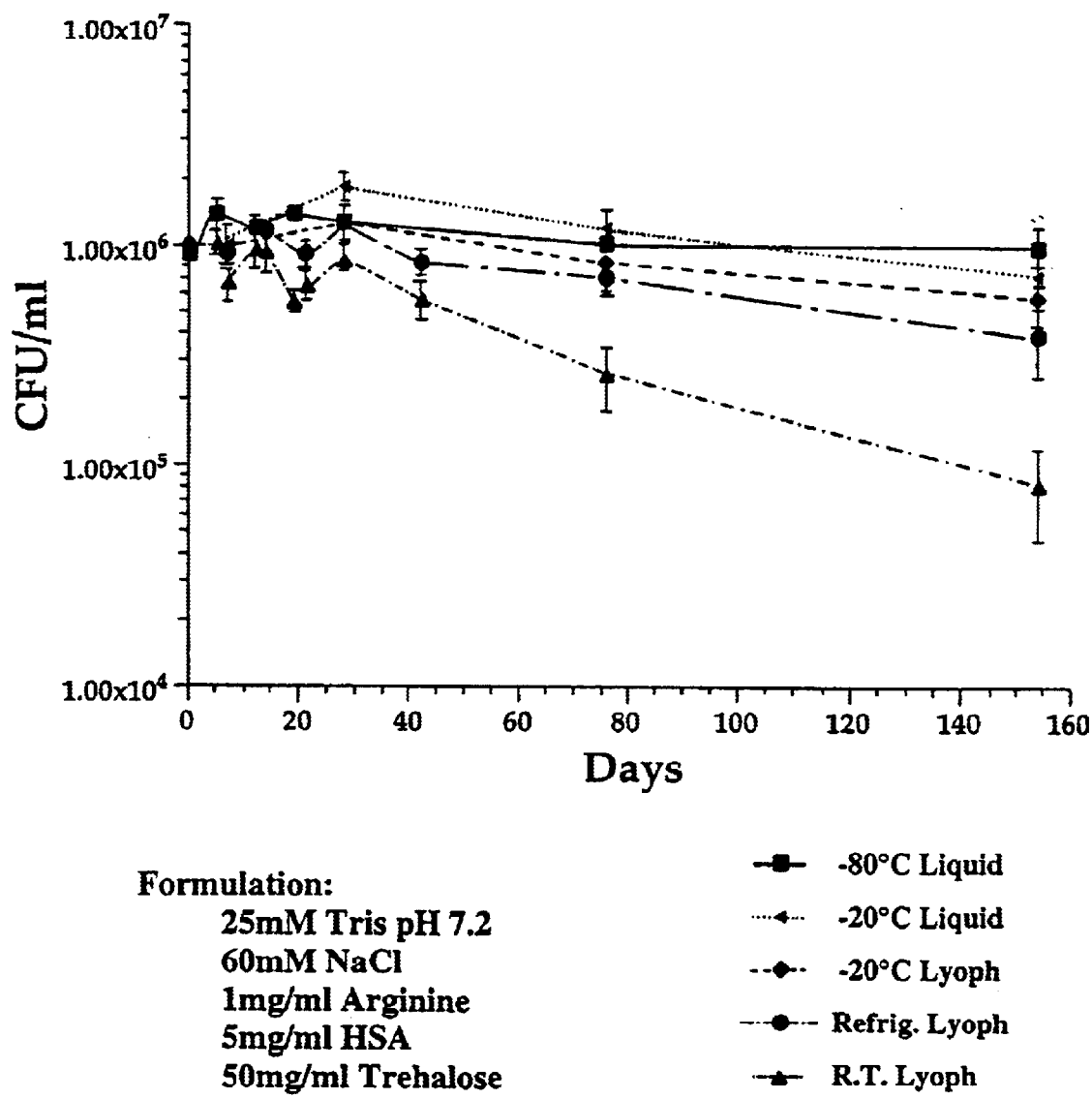
FIG. 15 is a graph demonstrating retention of viral activity upon reconstitution of a representative recombinant retrovirus lyophilized in a formulation buffer containing trehalose.
Figure 16A:
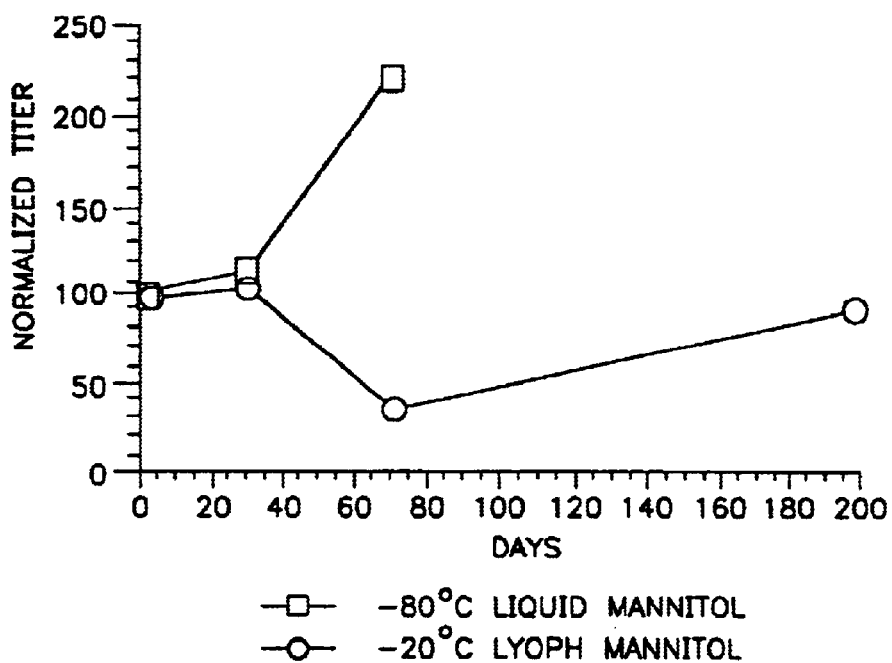
FIGS. 16A–16D are representative graphs comparing stability of liquid non-lyophilized recombinant retrovirus stored at −80° C. versus lyophilized formulated recombinant retrovirus stored at −20° C., using various saccharides.
Figure 16B:
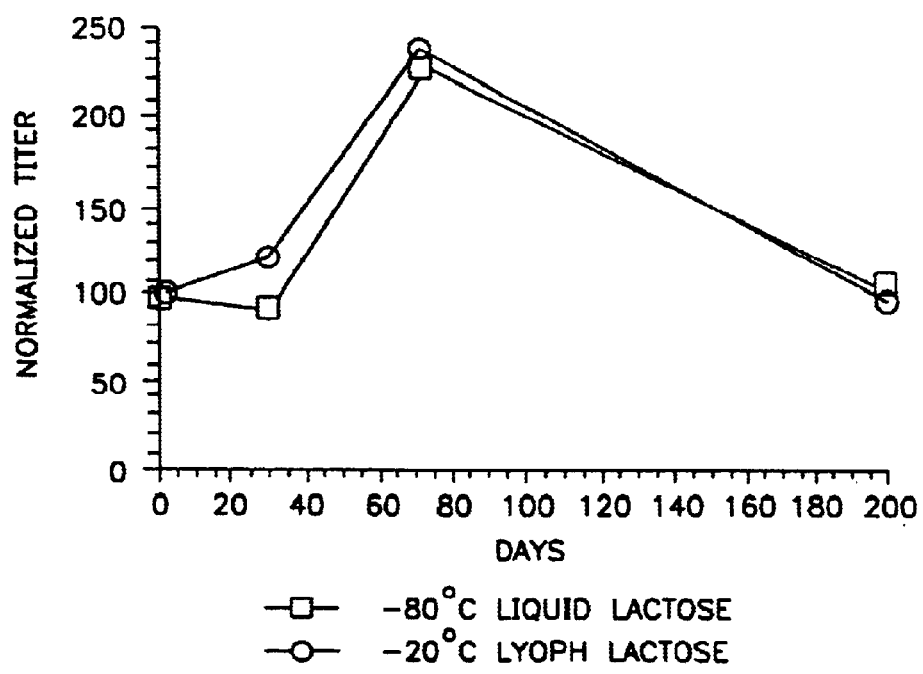
Figure 16C:
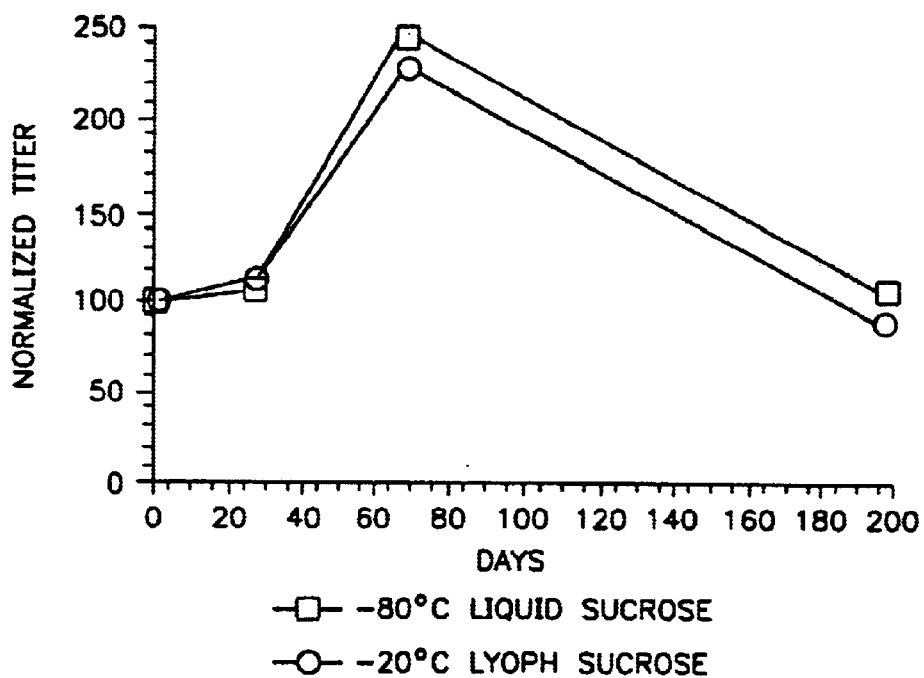
Figure 16D:
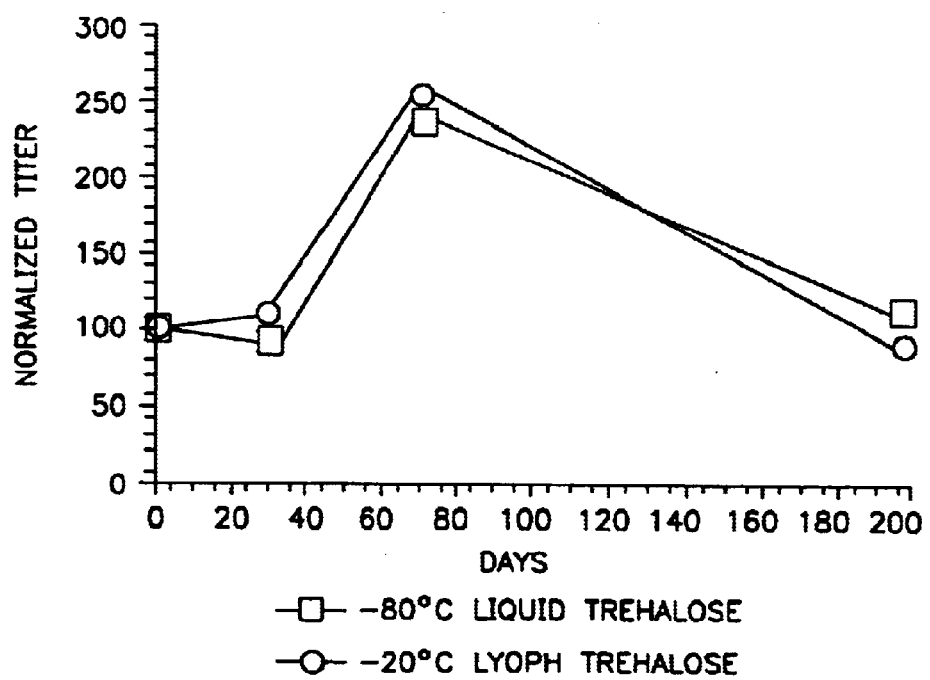
Figure 17:
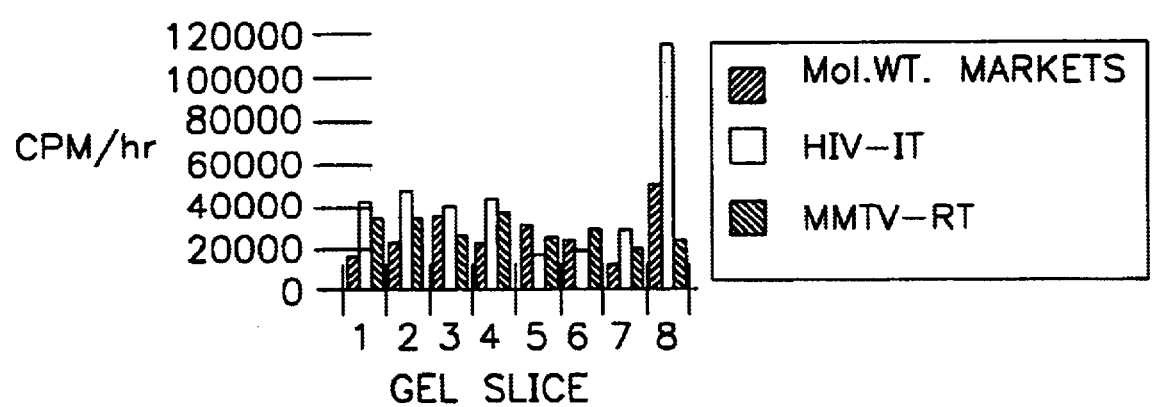
FIG. 17 is a bar graph which depicts the results of a reverse transcriptase assay on samples sliced from a gel. Slice 1 is from the lowest part of the gel, and slice 8 from the highest.
Figure 18:
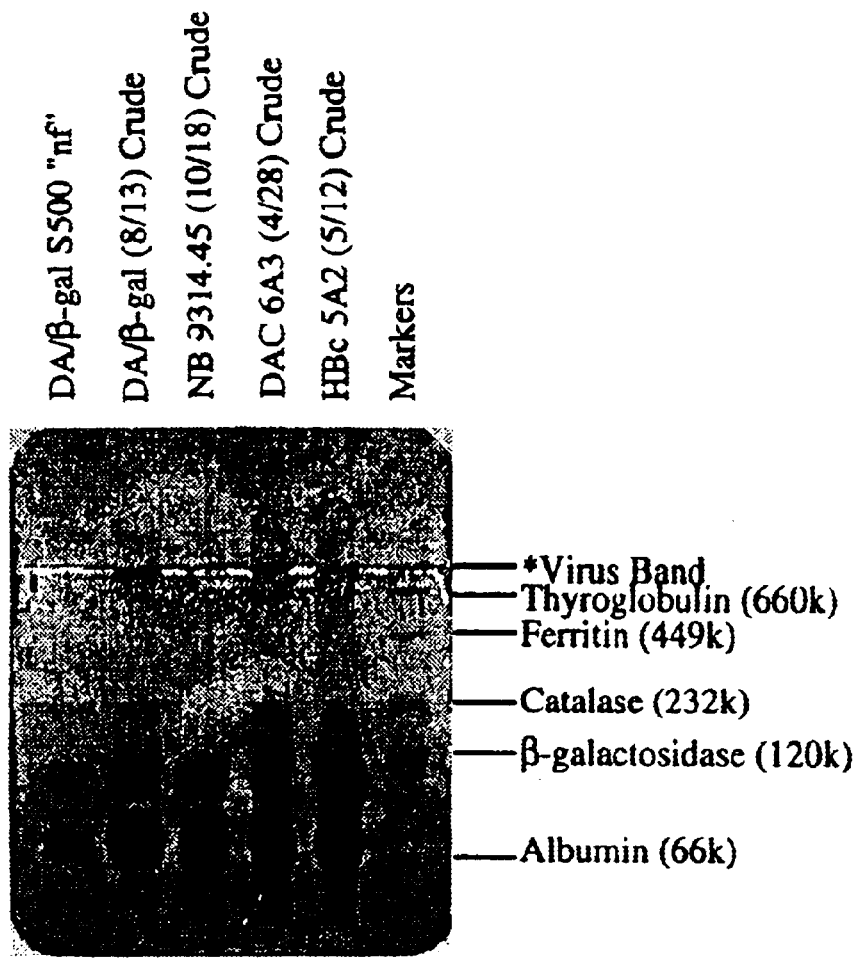
FIG. 18 depicts a 8% to 25% gradient polyacrylamide gel. Lane 1 is DA/βgal S-500 purified; Lane 2 is DA/βgal crude supernatant; Lane 3 is HIV-IT crude supernatant: lane 4 is DAC 6A3 crude supernatant; Lane 5 is HBc/SA2 crude supernatant; and Lane 5 is molecular weight markers.
Figure 19:
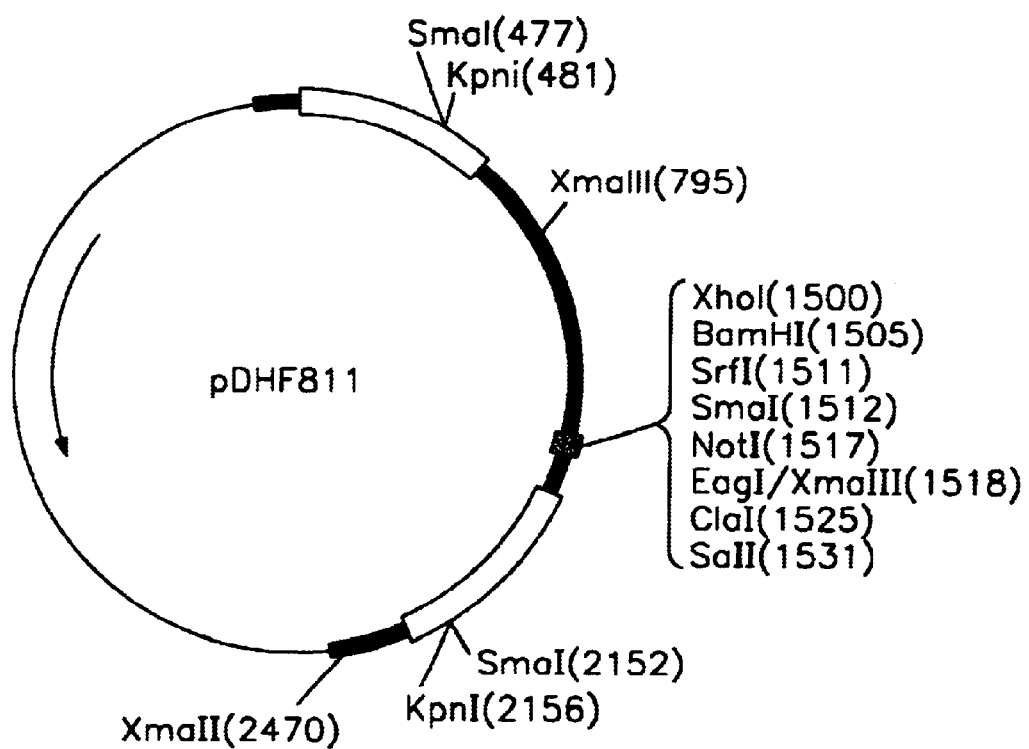
FIG. 19 is a schematic illustration of pDHF811.
Figure 20A:
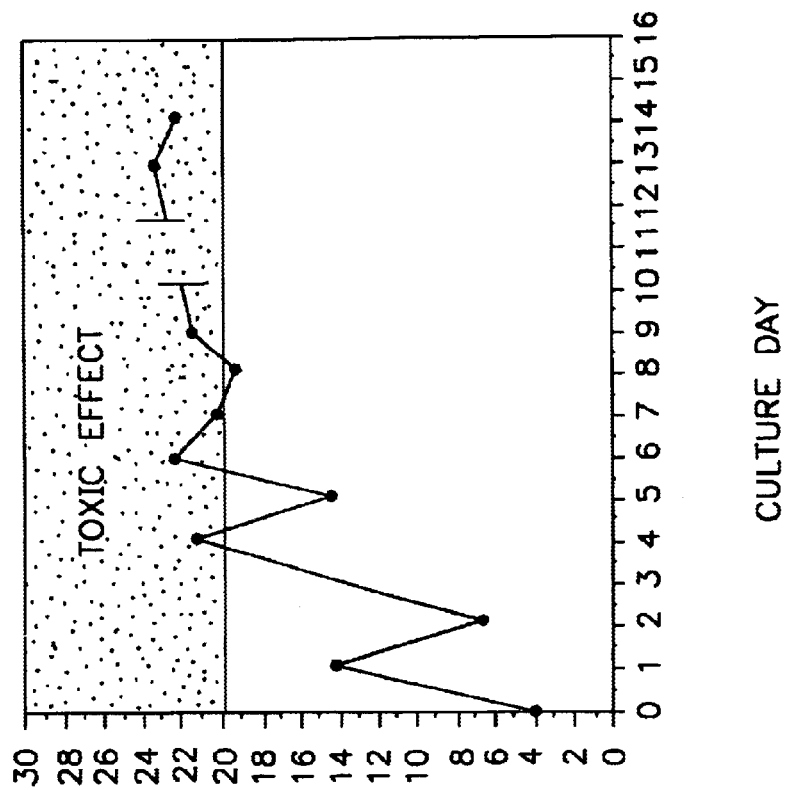
FIGS. 20A–D are graphs which indicate the total quantity of lactate in low seed and high seed cultures (FIGS. 20A and 20B, respectively) and the level of lactate production per day in low seed and high seed cultures (FIGS. 22C and 22D, respectively).
Figure 20B:
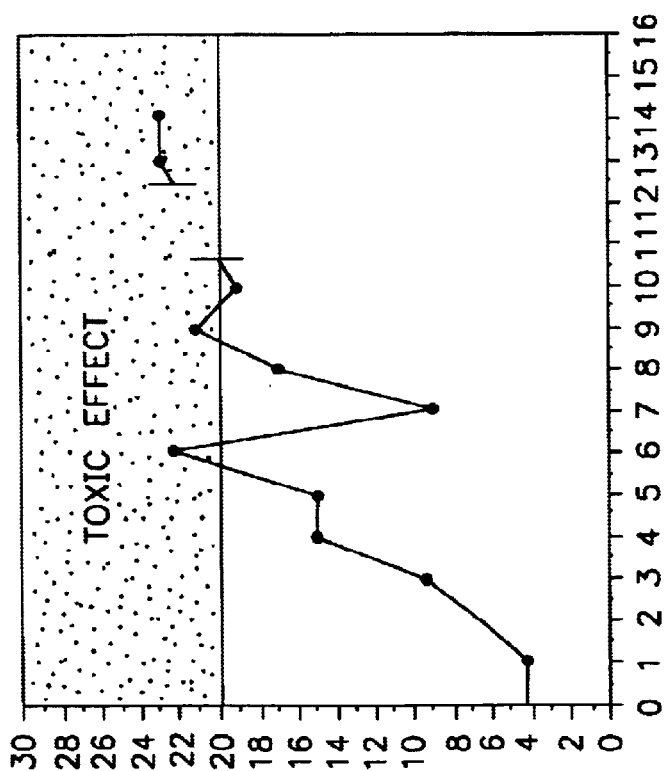
Figure 20D:
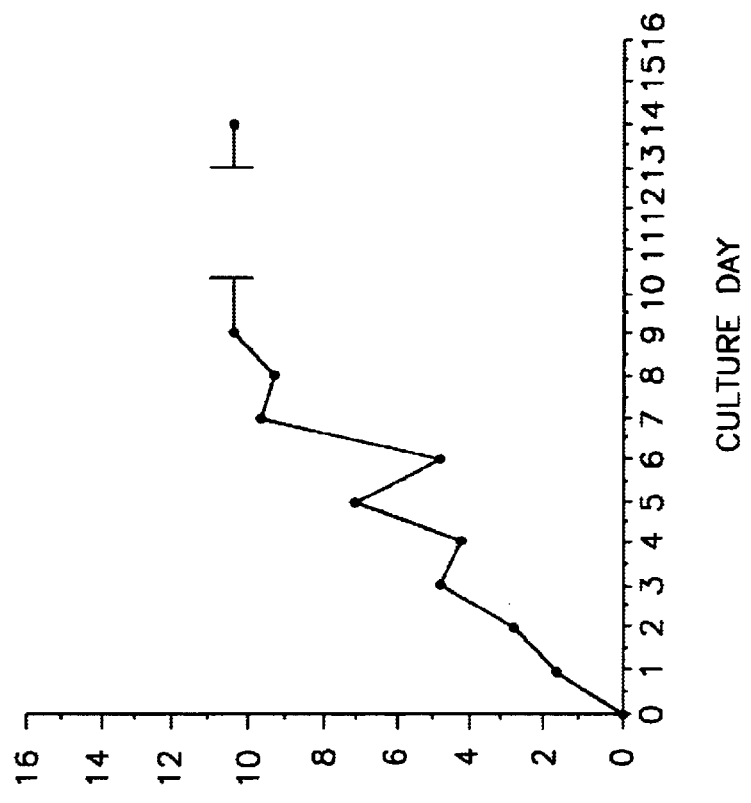
Figure 20C:
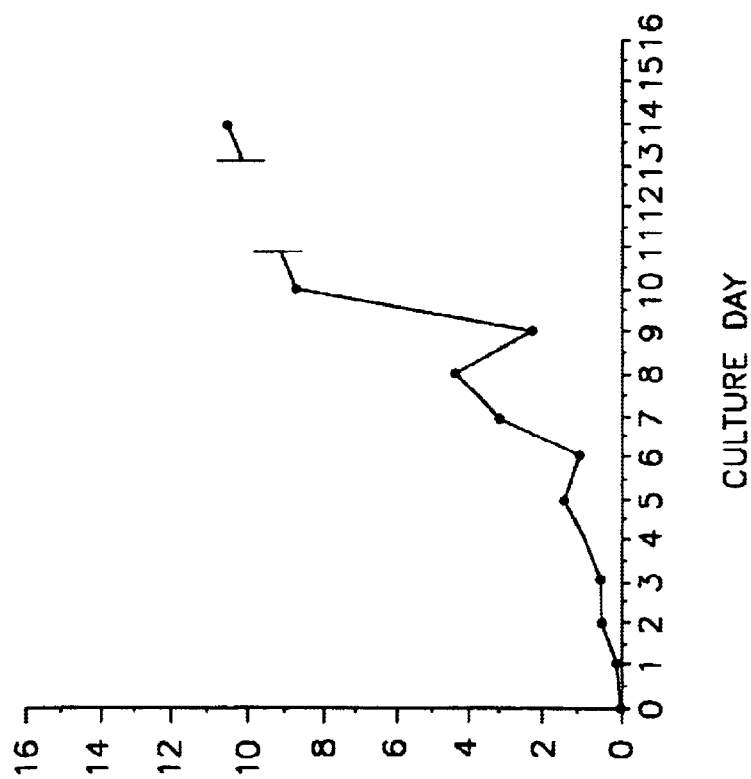

FIG. 15 demonstrates that storage in lyophilized form at −20° C. to refrigerator temperature retains similar viral activity as compared to recombinant retrovirus stored in liquid at −80° C. to −20° C. permitting less stringent temperature control during storage.

Viral infectivity of liquid formulated recombinant retrovirus samples stored at −80° C. was compared to viral infectivity of lyophilized formulated recombinant retrovirus stored at −20° C. Initially, a bulk of recombinant retrovirus was received and formulated in four different ways as shown below. The formulated recombinant retrovirus was then frozen in bulk for 1.5 months subsequent to being quick thawed and freeze dried. Positive controls were stored at −80° C. for comparison with lyophilized samples which were stored at −20° C. after freeze-drying. The formulations are listed below:

| Formulation | Sugar Concentration (mg/ml) | Buffer Concentration (mM tromehamine) | Salt Concentration (mM NaCl) | Arginine Concentration (mg/ml) | Human Serum Albumin Concentration (mg/ml) |
|---|---|---|---|---|---|
| Mannitol | 40 | 25 | 25 | 1 | 5 |
| Lactose | 40 | 25 | 75 | 1 | 5 |
| Sucrose | 50 | 25 | 60 | 1 | 5 |
| Trehalose | 50 | 25 | 60 | 1 | 5 |

In the graphs of FIG. 16, the y-axis on each of the 4 graphs (A, B, C, D) represent the normalized titer. At an initial time point after lyophilization, t=0, a titer value was established for both the −80° C. liquid sample and the −20° C. lyophilized sample. At each time point of the stability study, the titer obtained was divided by the zero time point titer value and the % of original entered onto the graph.

The data demonstrates that post-lyphilization activity is maintained in the lyophilized sample (stored at −20° C.) relative to the liquid sample (stored at −80° C.). The formulated lyophilized recombinant retrovirus was stored in a −20° C. freezer (a frost-free cycling freezer). Comparison to the formulated liquid recombinant retrovirus stored at −80° C. indicates the lyophilized form permits less stringent control of storage conditions.

EXAMPLE 10
Analysis of Crude and Purified Recombinant Retrovirus

Crude and purified solutions of recombinant retrovirus particles may be separated on gradient polyacrylamide gels utilizing, for example, the PHASTGEL system (Pharmacia Biotech). Briefly, samples are place on 4–15% polyacrylamide gels without pretreatment and electrophoresed for 35 minutes at 250V. The gels are then removed and stained with coomassie blue in order to detect virus and other protein components. The gels are then scanned by laser densitometry in order to determine the content of virus and other components.

Virus bands may be identified by their relative molecular weight and by reverse transcriptase activity (RT). The purpose of this assay is to quantify the activity of reverse transcriptase (RT), an enzyme exclusively associated with all retroviruses. The relative amount of retrovirus in a sample can be determined by measuring the activity of this enzyme in a given preparation.

Briefly, moloney murine leukemia virus reverse transcriptase (Pharmacia, Newark, N.J.) is diluted to a concentration of 1 $\mu$g/ml by addition of 1×Tris/EDTA buffer solution containing 10 mM Tris-HCl and 1 mM EDTA, pH 8.0. One hundred microliters of this solution is added 6.84 ml of sterile dH$_2$O, 500 $\mu$l of 1M Tris HCl pH 8.0, 10 $\mu$l of 0.1M MnCl$_2$, 200 $\mu$l of 1M dithiothreitol 50 $\mu$l of 10% Nonidet P40 (NP40), 2 $\mu$l of 100 $\mu$M dNTP (Pharmacia, Newark, N.J., dNTP Ultrapure Kit™), and 300 $\mu$l Methyl-$^3$H Thymidine 5'-Triphosphate (30–50 Ci/mmol). This mixture is incubated for 1 hour at 37° C. in a water bath. Following incubation the sample is placed on ice. Approximately 1.0 ml of 2N HCl is added to the cooled sample. The precipitated radiolabled DNA fragments are vacuum filtered onto glass fiber filters using a Millipore sampling manifold (Millipore, Philadelphia, Pa.). The filters are washed, dried, placed in scintillation cocktail, and counted in a Beckman LS5000TD scintillation counter (Beckman, Dallas, Tex.).

EXAMPLE 11
Analysis of Complement Resistance in Various Packaging Cell Lines
A. Packaging Cell Line Preparation and Transduction Four different packaging cell lines were used to package pCBβ-gal into infectious virions. Two cell lines were derived from D17 dog cells ("D") (ATCC CCL 183), and two were derived from the human embryonic kidney cell line 293 ("2") (ATCC CRL 1573). In the case of both dog and human packaging cells, one cell line expressed the amphotropic envelope from the 4070A virus (ie., DA and 2A, respectively) and the other expressed the xenotropic envelope from the NZB9-1 virus (i.e., DX and 2X, respectively). All packaging cells were grown in DMEM media (Irvine Scientific, Santa Ana, Calif.) supplemented with 10% heat inactivated fetal bovine serum (Hyclone, Salt Lake City, Utah).

Each of the four packaging cell lines was transduced with a G-pseudotyped pCBβ-gal (see Burns et al., 1993, Proc. Nat'l. Acad. Sci. USA 90:8033–8037, for a pseudotyping procedure). After G418 selection, the selected cell pools were dilution cloned (except for the amphotropic vector producing human cell line which was maintained as a non-clonal pool). Vector producing cell lines producing the highest titer on HT1080 cells (ATCC No. CCL 121) were selected. Titers were determined approximately 2 days after transduction by G418 colony forming units or by X-gal staining of the monolayers. (See Current Protocols in Molecular Biology, Ed. Ausubel et al., for more details on the titering assays.)

Retrovirus containing supernatants were collected from each of the confluent monolayers of the individual amphotropic envelope (DA and 2A) or xenotropic envelope (DX or 2X) vector producing cell lines and filtered through a 0.45 $\mu$m filter prior to aliquoting and storage at −70° C.

B. Serum Inactivation Assay

Serum inactivation titer assays were performed as follows: Serum was drawn from at least two different human volunteers, chimpanzees, baboons, and macaque monkeys. Approximately 20–70 mL of blood was collected from each donor into serum separating tubes (Becton Dickinson, Los Angeles, Calif.). Blood was allowed to clot for 20–30 minutes at room temperature, after which time the samples were centrifuged at 2000×g for 10 minutes at 4° C. Serum was frozen in approximately 1.1 mL aliquots and stored at −80° C. Vials from each batch were tested for total classical complement activity (Quantiplate, Kallestad Labs, Inc., Chaska, Minn.), and only batches with "normal" levels of complement activity were used. 1 mL aliquots of fresh, 100% serum were used for each inactivation assay. Complement inactivated controls of each serum were prepared by heat inactivation for 30 minutes at 56° C. Undiluted and diluted preparations of supernatants containing recombinant retroviral particles (BCFU greater than or equal to $10^3$ per mL sera) were mixed 1:10 with medium control, sera, or heat inactivated sera. These mixtures were then incubated at 37° C. for 30 minutes. Treated vector particles were then titered by a standard blue colony forming unit assay (*Current Protocols in Molecular Biology*, supra).

The results of this experiment are presented below in Table 1 as BCFU/ml.

TABLE 1

| | Packaging Cell Line | | | |
| Serum source | DA | DX | 2A | 2X |
| --- | --- | --- | --- | --- |
| HUMAN | | | | |
| control | 19,000 | 110,000 | 5,700 | 6,700 |
| 100% sera | 400 | 0 | 6,100 | 7,600 |
| H.I. sera | 18,000 | 100,000 | 10,500 | 8,800 |
| CHIMP | | | | |
| control | 16,200 | 31,600 | 27,800 | 22,400 |
| 100% sera | 900 | 1,700 | 21,500 | 48,500 |
| H.I. sera | 28,300 | 47,000 | 42,700 | |
| BABOON | | | | |
| control | 16,000 | 13,000 | 8,000 | 7,200 |
| 100% sera | 0 | 0 | 1,800 | 1,000 |
| H.I. sera | 24,000 | 9,600 | 15,000 | 9,400 |
| MACAQUE | | | | |
| control | 170,000 | 13,000 | 2,500 | 2,300 |
| 100% sera | 0 | 0 | 0 | 10 |
| H.I. sera | 270,000 | 12,000 | 3,000 | 2,200 |

H.I. = heat inactivated
control = DMEM + 10% H.I. fetal bovine serum + Sodium pyruvate
Note: zero's indicate that no blue colonies were detected in 0.1 or 0.2 ml undiluted volumes, therefore indicating that titers were conservatively less than 20–40 BCFU/ml.

Briefly, these results demonstrate that recombinant retroviruses which are made in human packaging cell lines exhibit no detectable sensitivity to inactivation by a heat labile component of human serum, presumably complement, in in vitro assays. In contrast, they show partial sensitivity to inactivation by chimp, and then increasing sensitivity to baboon and macaque serum, in order of increasing phylogenetic distance from man. In addition, these in vitro results demonstrate that recombinant retroviruses produced in D17 derived packaging cell lines exhibit near total sensitivity to inactivation by a heat labile component, presumably complement, of human, chimp, baboon and macaque serum.

Other experiments which were conducted employing another recombinant retroviral genome packaged in either of two of the above-described cell lines (dog cell line DA, and human cell line 2A), as well as a different human cell line (HX, a HT1080-derived packaging cell line; confirm that the conclusions drawn from the above results are not vector dependent. Moreover, human producer cell lines derived from 293 and HT1080 generated equally complement resistant vector.

Additional experimental data which was generated using recombinant retroviral particles made in human HT1080- derived packaging cells expressing a different murine envelope tropism, poly, similarly showed insensitivity to heat labile human serum components, further confirming the conclusions above.

EXAMPLE 12

Recombinant Retrovirus Production from Hollow Fiber Cultures

A. Culture Initiation

To initiate a hollow fiber culture, first condition the hollow fiber bioreactor (HFB) for 48 hours prior to seeding by simulating a run condition with 100–200 mL of complete growth media at 37° C. The growth media should be what ever the cell line has been adapted to. All liquids in the HFB when originally shipped should be aspirated and replaced with the complete growth media. When seeding the bioreactor, the cells should not have been split more than 48 hours earlier and should be in log growth phase at the time of harvest for the seeding of the HFB. The cells are harvested by trypsinazation and pelleted by centrifugation. The cell pellet is then resuspended in 4 mL of 25% preconditioned media and delivered to the extra-capillary space by syringe using the side syringe ports found on the HFB. After seeding the HFB, allow the cells to adhere for 20 to 30 minutes before starting the circulation pump. During this time replace the media used to condition the HFB with 100–200 ml using 25% pre-conditioned media. The circulation feed pump is initiated with the starting flow rate set at 25 mL/min. (selling 5 with 2 long pump pins). After 1 hour from the time of switching the pump on, a one mL sample of media is collected in order to record the initial levels of lactate and ammonia. On a daily schedule, 1 ml samples are collected every 24 hours to assay for the daily production of lactate and ammonia The initial 100–200 ml of old is exchanged media with fresh media when lactate levels begin to reach 2.0 g/l (or the equivalent to 22 mM/L). The same volume of media is replaced until the culture approaches daily levels of 20 mmol/L. When daily levels of lactate reach 20 mmol/L increase your reservoir bottle size to a 500 mL bottle containing 500 mL of fresh media. The flow feed rate is then increased to 50 mL/min. when the culture begins to produce 2.2 mmol/day of lactate. When daily 500 mL volumes reach 20 mmol/L of lactate, the original Cellco supplied reservoir feeding cap is exchanged for the larger reservoir cap (Unisyn-vender part #240820) adapted for the Cellco system with the addition of tubing and male luer lock fittings. This reservoir cap will accommodate the large 2 Liter Corning bottles. (To avoid the exchange of the reservoir caps during a culture run, initiate the culture run with the larger reservoir cap which can also support smaller bottle sizes.) When daily lactate readings are assayed and recorded, one can calculate the daily levels of lactate production of the culture in order to determine when the culture reaches maximum cell density when the rate of lactate decreases and levels off.

B. Seeding Density for the 2X-β-gal

In order to establish specific seeding requirements, two hollow fiber runs are established. One run is seeded with a low number of cells and one with a high number of cells. Progress of the culture is tracked by analyzing the daily glucose consumption and lactate production levels. FIG. 20 is a representative graph of data generated over a two week period of the vector producer cell line 2X-β-GAL$_{17-14}$.

In this experiment, one HFB was seeded with $1.3 \times 10^7$ cells (to represent the low seed culture) the other seeded with $1.6 \times 10^8$ cells. In this experiment, the cell line (2x-β-GAL$_{17-14}$) was able to initiate a good hollow fiber run under low and high seeding conditions. Being able to incubate the HFB with fewer cells, is only convenient for reducing the effort required for generating the number of cells required to start a culture However a low seed start also extends the time it takes to reach optimal cell densities which usually yield the highest titers. In this experiment, the cell line used, adapted very well to hollow fiber cultures which eventually required daily media changes of 500 ml per day.

C. Cell Culture Health and Maximum Cell Densities

In the original Cellco design, it was observed that the original media reservoir cap was not suited to fit larger bottles other than the standard 100 and 500 ml media bottles. This is a problem when aggressive growth cultures require greater than 500 ml daily exchanges of media. Daily multiple changes of media increases the likelihood of culture contamination by increasing the daily handling time of the system. If one does not opt to perform multiple daily exchanges of media then one exposes the culture to daily toxic levels of waste products which can affect the cell expansion of the system along with the length at which the culture run will survive. FIG. 20-B demonstrates lactate concentrations of a culture which required daily 500 mL exchanges of fresh media after reaching day 7 of culture. FIG. 20-D is one indication of the health of the culture by tracking the amount of lactate being produced on a daily basis. The graphs indicate that the culture was no longer allowed to expand based on the plateauing of daily production of lactate. Another indicator of the health of the cell culture was the drop in peak titer production which also correlated with the daily exposure of high levels of lactate (See FIG. 21). These findings would indicate that optimal titers can be correlated with the maximum cell densities and the relative health of the culture.

Figure 21:
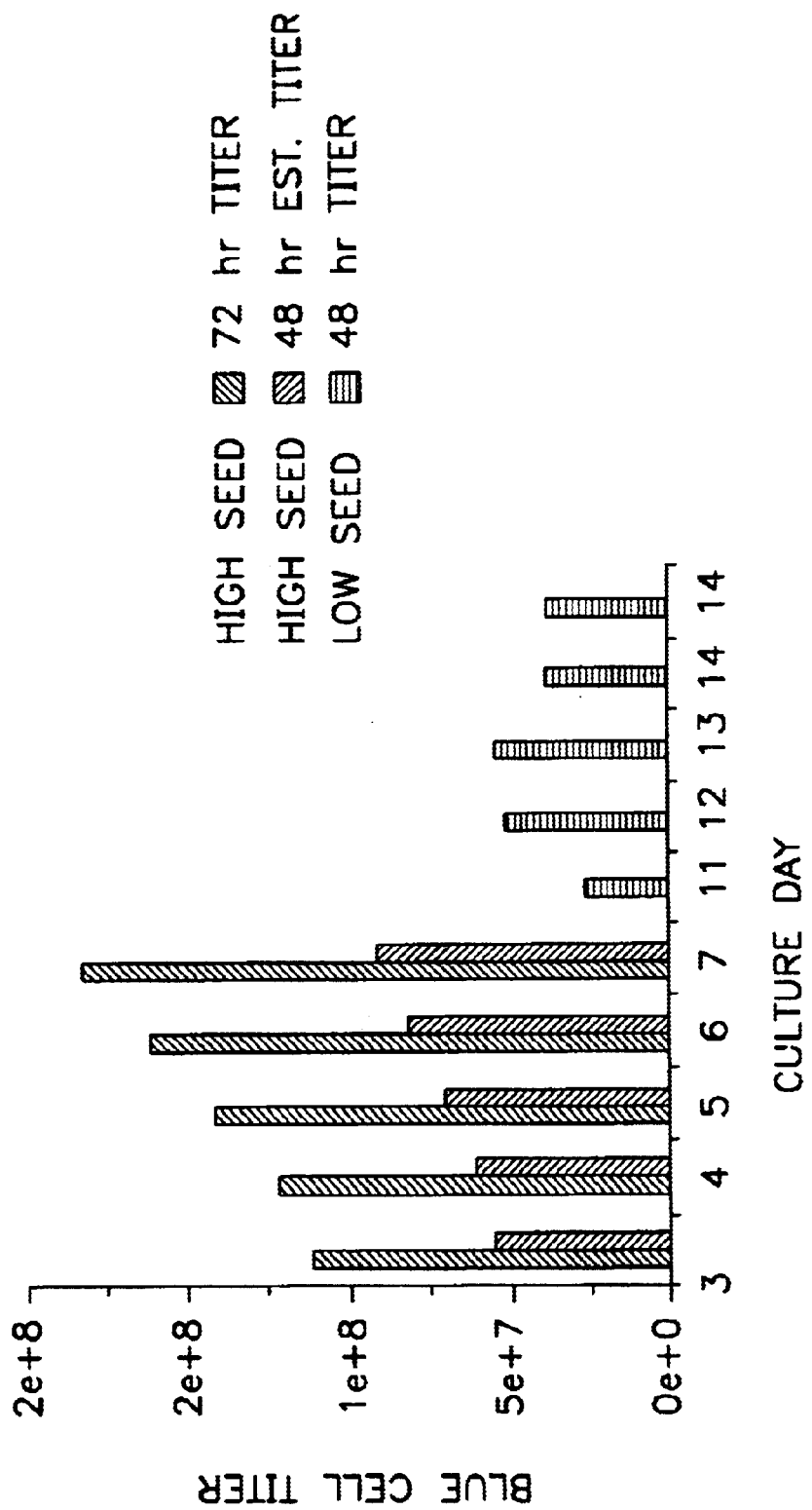
FIG. 21 is a bar graph which depicts the titer of the cell line 2X-β-gal under different initial seeding conditions.

D. Optimal Titer Concentrations, Frequency of Harvests and Total Harvest Amounts β-gal titers for the above experiment were determined from frozen samples and were titered on 293 cells assayed 48 or 72 hours after transduction. The transduced cells were stained for β GAL activity and individual cells counted on a hemocytometer giving a titer based on the number of blue cells/mL (BCT/mL). As shown in FIG. 21, optimum titers were obtained on day 7 of the high seed culture at $1.8 \times 10^8$ BCT/mL from a 72 hour blue cell titer on 293 cells. The duplicate culture initially seeded with a 10 fold lower seeding density, peaked at $5.2 \times 10^7$ BCT/mL from a 48 hour blue cell titer. Previous flat stock cultures of 2X b-$GAL_{17-14}$ cultures have been titered using 48 hour blue cell titers on HT1080 cells and have been calculated to be $5 \times 10^6$ BCT/mL. If one uses the values obtained from 48 hour blue cell titers, the increase in titer by using hollow fiber systems is ten fold higher than crude supernatants obtained from tissue culture dishes or flasks. These maximum titers were reached prior to hitting the daily 20 mmol/L toxic levels lactate which appeared to reduce the titer produced the following week. Crude supernatants can be harvested every 9 hours with out any loss of titer (See FIG. 2). It is predicted that 3 harvests per day can be achieved with minimum loss of titers. In addition, continuous hollow fiber cultures can be maintained for several weeks. When titers were compared between the low and the high seed culture, there was little differences by day 11 between the two seed cultures averaging $4 \times 10^7$ BCT/mL.

EXAMPLE 13
Two-Phase Purification of Recombinant Retroviruses

A. Concentration of DA/ND-7 Recombinant Particles

Five milliliters of formulated DX/ND-7 recombinant retroviral particles at a titer of $3.5 \times 10^8$ cfu/ml (total of $1.75 \times 10^9$ cfu) is diluted in 1400 ml of media (DMEM containing 5% Fetal Bovine Serum). Three hundred milliliters of two-phase partitioning components (PEG-8000 (autoclaved), dextran-sulfate, and NaCl) are added to a final concentration of 6.5% PEG, 0.4% dextran-sulphate, and 0.3 M NaCl. The resultant solution is placed into a two-liter separatory funnel, and left in a cold room for 24 hours (including two mixing steps approximately 6 to 16 hours apart).

Following the 24 hour period, the bottom layer (approximately 20 mL) is carefully eluted, and the interphase (approximately 1 mL) is collected in a 15 mL conical FALCON tube. The interphase containing vector is diluted to 10 mL by addition of PBS, and incubated at 37° C. in order to bring the solution to room temperature and destabilize the micelles.

To one-half of the diluted interphase, KCl is added to a final concentration 0.4 M, and mixed well. The tube is then placed on ice for ten minutes, and spun for 2 minutes at 2,000 rpm in a bench-top centrifuge. The supernatant is removed and filtered through a 0.45 um syringe filter.

The other half of the interphase containing vector is separated by S-500 Sephadex chromatography in 1×PBS.

The results of these concentration processes, as determined in a BCFU assay, are shown below in Table 1:

TABLE 2

| PHASE | CONCENTRATION |
| --- | --- |
| Crude | $1.1 \times 10^9$ bcfu |
| Separation: Top phase | $1.4 \times 10^8$ bcfu |
| Separation: Interphase | $7(+/-3) \times 10^8$ bcfu |
| Separation: Bottom phase | $2 \times 10^6$ bcfu |
| Final step: KCl separation | $*6(+/-3) \times 10^8$ bcfu |
| Final step: S-500 separation | $*1.8(+/-0.3) \times 10^{8 \text{ bcfu}}$ |

*Note that since the sample was split into two halves, that these numbers were doubled in order to represent the level of purification that would be expected if the entire 1 mL interphase was separated as indicated.

In summary, 1.4 liters of crude research grade supernatant containing recombinant retroviral particles may be reduced to a 10 ml volume, with approximately 50% (+/-20%) being recovered when KCl separation is utilized as the final step. When S-500 chromatography is utilized as the final step, only about 10% of the initial recombinant retroviral particles are recovered in a 14 ml.

In order to complete concentration of the retroviral vector particles, the vector-containing solution may be further subjected to concentration utilizing an MY-membrane Amicon filter, thereby reducing the volume from 10 to 14 mL, down to less than 1 mL.

EXAMPLE 14
Production of Vector From DX/ND7 βgal Clone 87 Utilizing a Cell Factory DX/ND7 βgal clone 87, an expression vector, was grown in cell factories. Cells were grown in DMEM supplemented with Fetal Bovine Serum in roller bottles until enough cells to seed 20 10-layer cell factories (NUNC) at a 1:3 dilution were obtained. Each 10-layer cell factory is seeded with approximately 0.8 liters of cell medium.

Cells were seeded into the cell factory by pouring media containing cells into the factory so that the suspensions evenly fill the 10 layers. The factory is then carefully tilted away from the port side to prevent the suspension from redistribution in the common tube. Finally, the cell factory is rotated into its final upright position. A hepavent filter is attached to each port. The factory was then placed in a $CO_2$ incubator.

In three days, and for each of the next three days, supernatant containing vector was harvested. The cell factory is placed in a tissue culture hood. One filter is removed and sterile transfer tubing is connected to the open port. The factory is lifted so that supernatant drains into the tubing. Approximately 2 liters of supernatant is harvested from each factory. Fresh DMEM/FBS is used to replenish the lost medium. The transfer tubing is removed and the factory replaced in the incubator. From 20 cell factories, approximately 90 liters of crude vector containing supernatant were obtained.

Verification of the vector was performed by transduction of HT1080 cells. These cells were harvested 2 days later and stained for β-gal protein. The titer of the supernatant was determined to be $2\times10^7$/ml.

EXAMPLE 15
Concentration of Recombinant Retroviruses by Low-Speed Centrifugation
A. Retroviral Vector Supernatant Preparation Producer cell lines DA/βgal and HX/DN-7 were cultured in a culture flask and a roller bottle, respectively, containing Dulbecco's Modified Eagle's Medium (DMEM) supplemented with 10% fetal bovine serum plus 1 mM L-Glutamine, Sodium pyruvate, non-essential amino acids and antibiotics. Viral supernatant was harvested from the flask and roller bottle, and were filtered through a 0.45 um syringe filter. The filtered supernatants were stored either at 4° C. (HX/ND7), or frozen at −70° C. (DAβ-gal).
B. Virus Concentration Viral supernatant was aliquoted into 50 ml sterile OAKRIDGE screw cap tubes, and placed into an SS34 rotor for use in a Sorvall centrifuge. The tubes were spun for 1 hour at 16,000 rpm (25,000 g-force) at 4° C. Upon completion of the spin, the tubes were removed, the supernatant decanted and a small opaque pellet resuspended in the DMEM media described above.
C. Virus Titration Concentrated virus was titered on HT1080 cells plated 24 hours earlier at a cell density of $2\times10^5$ cells per well in a six well plate+4 ug/ml polybrene. Briefly, virus preps were diluted from 1/10 to 1/10,000 and 50 ul of each dilution was used to infect one well from the six well plate. Plates were incubated overnight at 37° C. Forty-eight hours later, cells were fixed and stained with X-gal. The results are set forth below in Table 1.

As is evident from Table 1, virus recovery ranged from 30% to 99%, with the best recovery being obtained from human producer cells (HX/ND7; recovery ranged from 91% to 99%).

EXAMPLE 16
Concentration of Recombinant Retroviruses by Ultrafiltration

S-500 purified supernatant containing the β-gal expressing recombinant retrovirus DX/CB-βgal and partially concentrated supernatant containing the same virus were each filtered through a 0.45 um filter, and loaded into a CENTRIPREP-100 filter (product #4308, Amicon, Mass.). The supernatants were kept at a temperature of 4° C. throughout this procedure, including during centrifugation. The CENTRIPREP filters were spun three times each for 45 to 60 minutes at 500×G. Between each spin the filtrate was decanted. The retentate was thus sequentially reduced, such that the initial 15 ml (or 10 ml) volume was reduced to approximately 0.6 mL per unit.

The resultant titer was determined by assaying HT 1080 target cells set up at a concentration of $1\times10^5$ cells per well 24 hours prior to transduction of the viral sample. Cells were transduced in the presence of 8 ug/ml polybrene and 2 mL growth media (DMEM plus 10% FBS) per well. As shown in Table 1 below, approximately one hundred percent of the virus was recovered utilizing this procedure (note that titers are in BCFU/ml).

M TABLE 4

|  | Pre-centriprep titer/volume. | Final titer volume |
| --- | --- | --- |
| S-500 | $4 \times 10^7$/15 ml | $1.3 \times 10^9$/0.6 ml |
| part. conc. | $3 \times 10^8$/10 ml | $1 \times 10^{10}$/0.6 ml |

EXAMPLE 17
Preparation of Recombinant Retrovirus in a Bioreactor
A. Freezing Protocol Producer cells are frozen in DMEM media containing 10% to 20% FBS, and 5 to 15% DMSO, at a concentration of $1\times10^7$ cells/ml/vial. Cells are frozen in a controlled rate freezer (Series PC, Controlled Rate Freezing System, Custom Biogenic Systems, Warren Mich.) at a rate of from 1 to 10° C. per minute. Frozen cells are stored in liquid nitrogen.
B. Bioreactor Protocol Cells are thawed from frozen vials at 37° C., washed once with media to remove DMSO, and expanded into 850 cm²

TABLE 3

Virus Concentration through Low Speed Centrifugation

| Parameter description | Experiment number | | | | |
| --- | --- | --- | --- | --- | --- |
|  | 1 | 2 | | 3 | |
| Virus source | DAβ-gal | DAβ-gal | HX/ND7 | DAβ-gal | HX/ND7 |
| Titer of normal harvest | $4.4 \times 10^6$ | $2.1 \times 10^6$ | $3.2 \times 10^5$ | $5 \times 10^6$ | $5 \times 10^5$ |
| Titer of virus concentrate | $6 \times 10^8$ | $7.4 \times 10^7$ | $3.2 \times 10^7$ | $2.9 \times 10^8$ | $3.9 \times 10^7$ |
| Starting volume | 80 ml | .39 ml | 39 ml | 118 ml | 40 ml |
| Final concentrate volume | .5 ml | .36 ml | .36 ml | .78 ml | .28 ml |
| Fold virus concentration | 136X | 34X | 100X | 58X | 78X |
| Virus recovery | 87% | 30% | 91% | 50% | 99% |

"FALCON" roller bottles (Corning, Corning, N.Y.) Expanded cell culture is used to inoculate a "CELLIGEN PLUS" bioreactor (5 liter working volume; New Brunswick, Edison, N.J.). The cells are grown on microcarriers (i.e., Cytodex 1 or Cytodex 2; Pharmacia, Piscataway, N.J.) at a concentration of 3 to 15 g/L microcarrier. Initial inoculation densities are from 4 to 9 cells/bead at half to full volume for 2 to 24 hours. The media constituents for virus production are DMEM-high glucose (Irvine Scientific, Santa Ana, Calif.) basal media supplemented with FBS (10 to 20%), Glutamine (8 to 15 mM), glucose (4.5 to 6.5 g/L), Nonessential amino acids (1×), RPMI 1640 amino acids (0.2 to 9.6×), 10 mM HEPES, RPMI 1640 Vitamins (0.2 to 5×).

During culture, pH (6.9 to 7.6) and dissolved oxygen ("DO" 5 to 90%) are controlled by the use of a four gas system which includes air, oxygen, nitrogen, and carbon dioxide. After several days of batch growth the culture is then continuously perfused with fresh media with concurrent continuous harvesting in an escalating perfusion rate of 0.5 to 2.5 volumes/day. Cell retention is the result of differential sedimentation of cell covered beads in a decanting column.

During operation the bioreactor is monitored for viable cells, titer, glucose lactate, ammonia levels, and lack of contamination. Viable cells and titer range from $1\times10^5$ cells/ml to $1\times10^7$ cells/ml. Glucose ranges from 6 to 0.25 g/L, Lactate from 1 to 25 mM, and Ammonia ranges from 0.5 to 30 mM. Cells are incubated in the bioreactor for 5 to 25 days.

EXAMPLE 18
Long Term Expression of Human Factor VIII in Rabbits Following Intravenous Expression of Vector Recombinant retroviral vector expressing B domain deleted factor VIII was constructed, packaged, and expressed as described in Example 2 herein. Large scale production was carried out in Cell Factories as described for DX/ND7 in Example 14. The retroviral vector was then lactose formulated as described in Example 9 herein. High titer formulated retroviral vector was injected into 500 g juvenile rabbits according to the following schedule: 1.5E8 vector particles were injected into the ear vein at 2.5 hr intervals, three times per day for three days (Day 0, 1, and 2). On days 3, 4, 5, 6, 7, 56, and every 7 days subsequently, citrated plasma was obtained by venipuncture of the ear vein and analyzed for human factor VIII antigen as follows. Day 1: Coat Immulon IV plates (Dynatech, Chantilly, Va., USA). Plate 1 was coated with 200 ul anti-factor VIII light chain monoclonal ESH8 (American Diagnostica, Grenwich, Conn., USA) at 3 ug/ml in coating buffer (0.1 M bicarbonate, pH 9.2) at 4 degrees overnight. Plate 2 and 3 were coated with 300 ul Sigma fractionated ascites anti-beta galactosidase (Sigma #G4644, Sigma Chemical Company, St. Louis, Mo., USA) at 8 ug/ml. These are the "absorption" plates.

Day 2: Plates were washed once with buffer DB2 (1000 ml=7.8 g Tris HCl/58.4 g NaCl/20 g BSA/1 ml Tween 20, pH 7.5), then blocked with 300 ul DB2, covered with parafilm, and incubated at room temperature for at least 90 min. on an orbital shaker at 80 rpm. Plates were then washed in DB2. 200 ul samples in duplicate were diluted in DB2 (plasma samples were diluted at least 1:3), centrifuged for 5' at room temperature at 14,000 rpm in an Eppendorf microfuge, and added to plate 1. Plate 1 was covered with parafilm and incubated two hours at room temperature shaking at 80 rpm.

00 ul of polyclonal anti-FVIII:C at 20 ug/ml in buffer DB2 (Enzyme Research Labs, South Bend, Ind., USA) was placed on absorption plate 2, covered with parafilm, and incubated at room temperature shaking at 80 rpm. Likewise, 300 ul donkey anti-sheep IgG conjugated to alkaline phosphatase (Sigma Chemical Company, St Louis Mo., USA) was absorbed on absorption plate 3 at 1:30,000 in DB2, covered and incubated at room temperature shaking at 80 rpm.

After two hours at room temperature, plate 1 was washed and 200 ul of absorbed sheep anti-VIII:C was transferred from plate 2 to plate 1. Plate 1 was covered with parafilm and incubated at room temperature for 1–2 hrs, shaking at 80 rpm.

After 2 hr, plate 1 was washed and 200 ul absorbed donkey anti-sheep conjugate was transferred from plate 3 to plate 1. Plate 1 was covered and incubated 1 hr at room temperature shaking at 80 rpm.

Plate 1 was washed, and freshly prepared Attophos substrate (JBL Scientific, Huntingdon, England, UK) prepared as recommended by the manufacturer was added at 200 ul per well, the plate was read at 2 min intervals (30 cycles) on Cytofluor II fluorometer, excitation 450, emission 580 filters; mix=1; gain=65.

Readings were compared to a standard curve using duplicate dilutions of NHP (pooled normal plasma, George King, Overland Park, Kans., USA) as a factor VIII source diluted in 1:3 rabbit plasma at 3-fold dilutions starting at 1:10 NHP.

Figure 22:
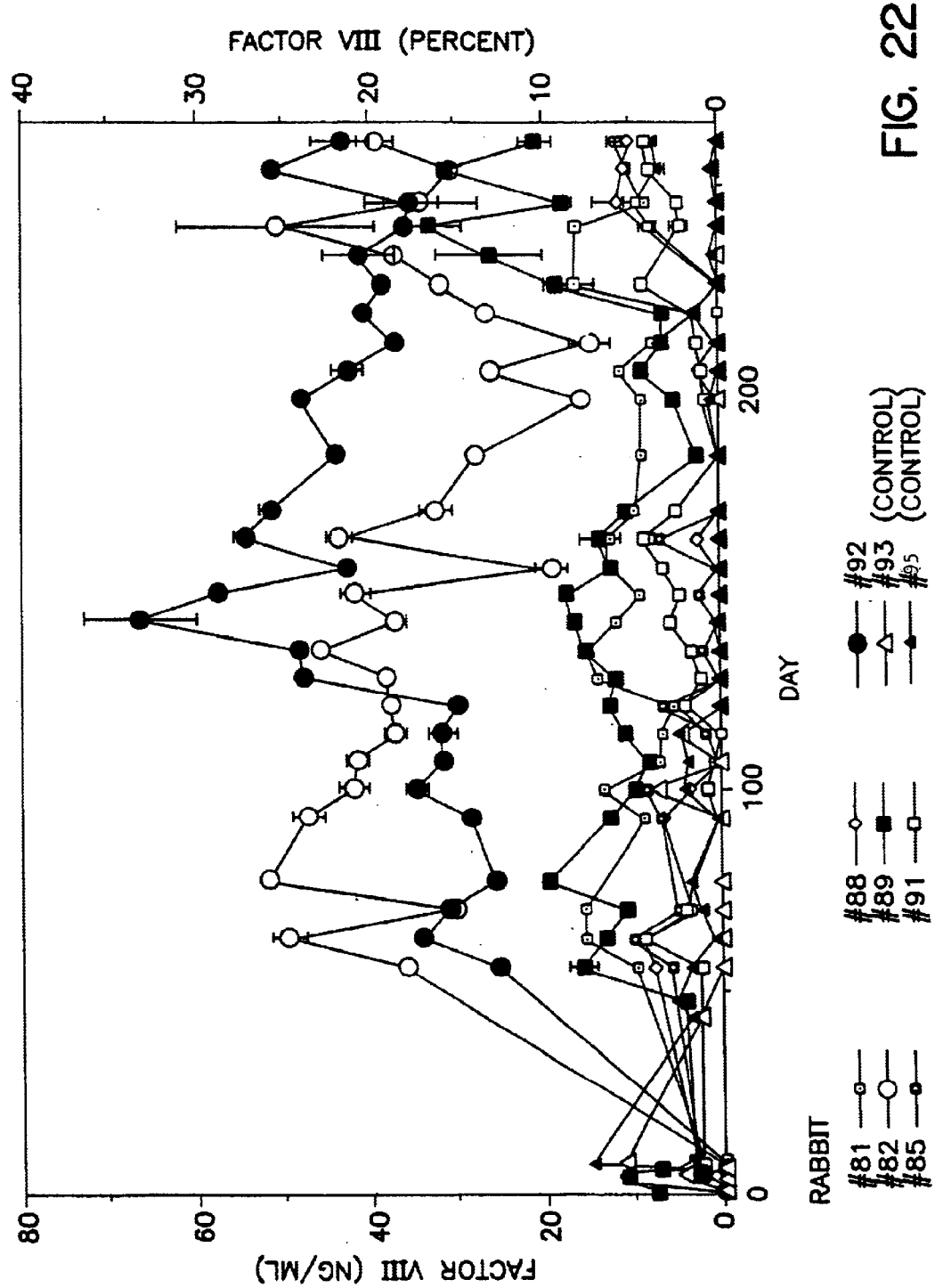
FIG. 22: Factor VIII antigen was determined in citrated blood samples drawn on the indicated days. Antigen determined by a standard curve obtained using normal pooled human plasma is plotted on the left y axis; the per cent of normal human levels is indicated on the right y axis.

Data from Day 0 (prebleeds) to day 261 from 7 experimental and two control rabbits are shown in FIG. 22. Levels remained low during the first 7 days, with no significant differences being seen between the experimental and control groups (p>0.25). On Day 56 and subsequent days, two rabbits displayed 30–50 ng/ml human factor VIII antigen in their plasmas. These levels, with slight fluctuations, were maintained at least until Day 261 (8 months later), the last time point tested. The experimental group as a whole over the entire time course was significantly different from the controls (p<0.03). Therefore, rabbits injected via ear vein with high titer formulated retroviral vectors displayed high level systemic expression of factor VIII following a lag phase of 7–56 days.

Figure 23:
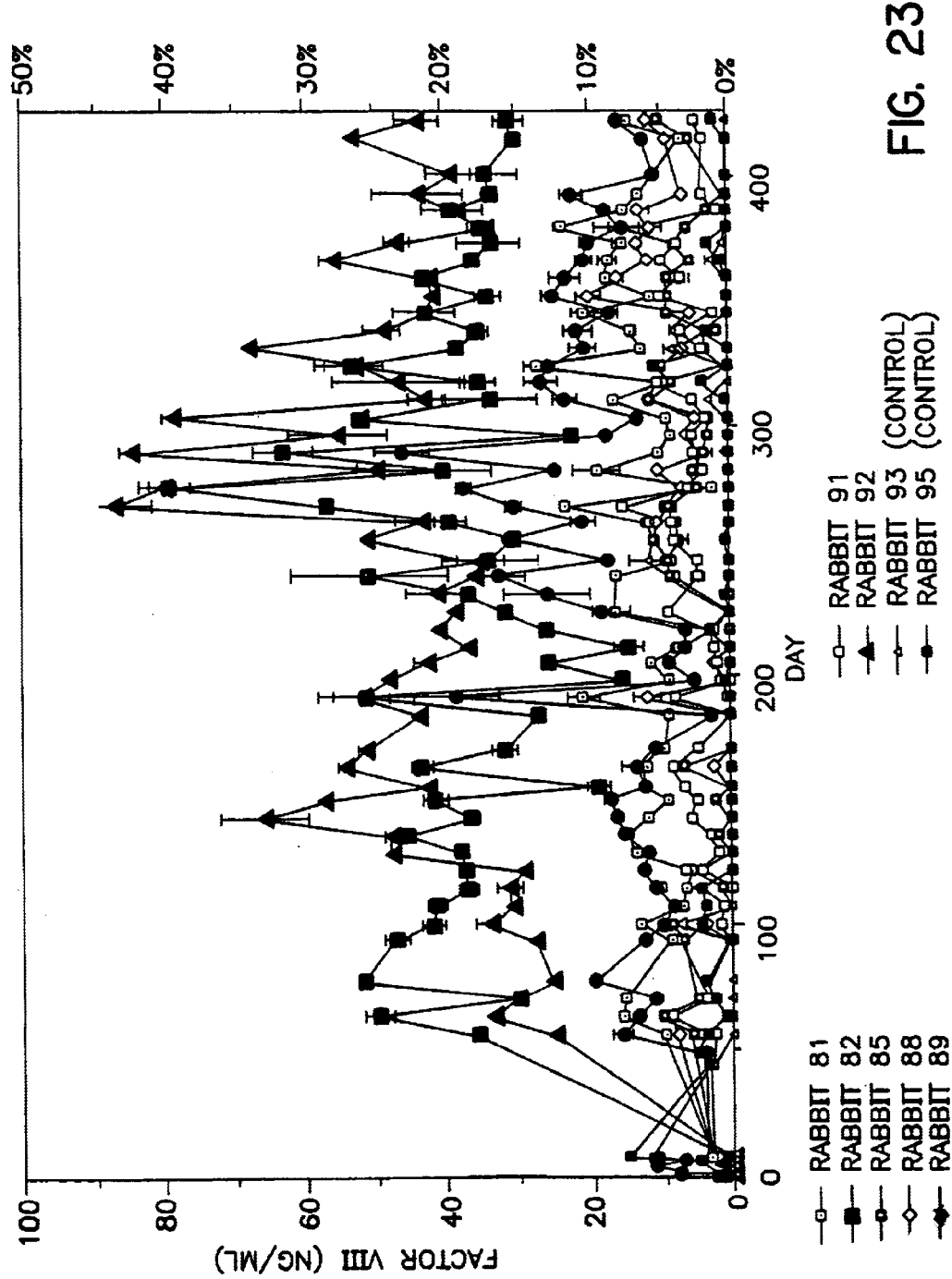
FIG. 23: Factor VIII expression in rabbits. Juvenile rabbits were injected with a total of $10^9$ cfu of the factor VIII vector B-del-1 in a total of 9 injections over days 0,1, and 2. Citrated plasma samples were obtained at the indicated times and human factor VIII antigen levels determined by ELISA. Rabbits 93 and 95 (controls) received formulation buffer in lieu of vector.

FIG. 23 shows the data in this experiment extended through Day 429. The two high-expressing rabbits described above maintain their expression levels through day 429. Medium-level expressing rabbits do as well, while the control rabbits remain negative. Thus, expression is observed at least from Day 56–429, indicating >373 days of expression from a single course of vector administration.

Figure 24:
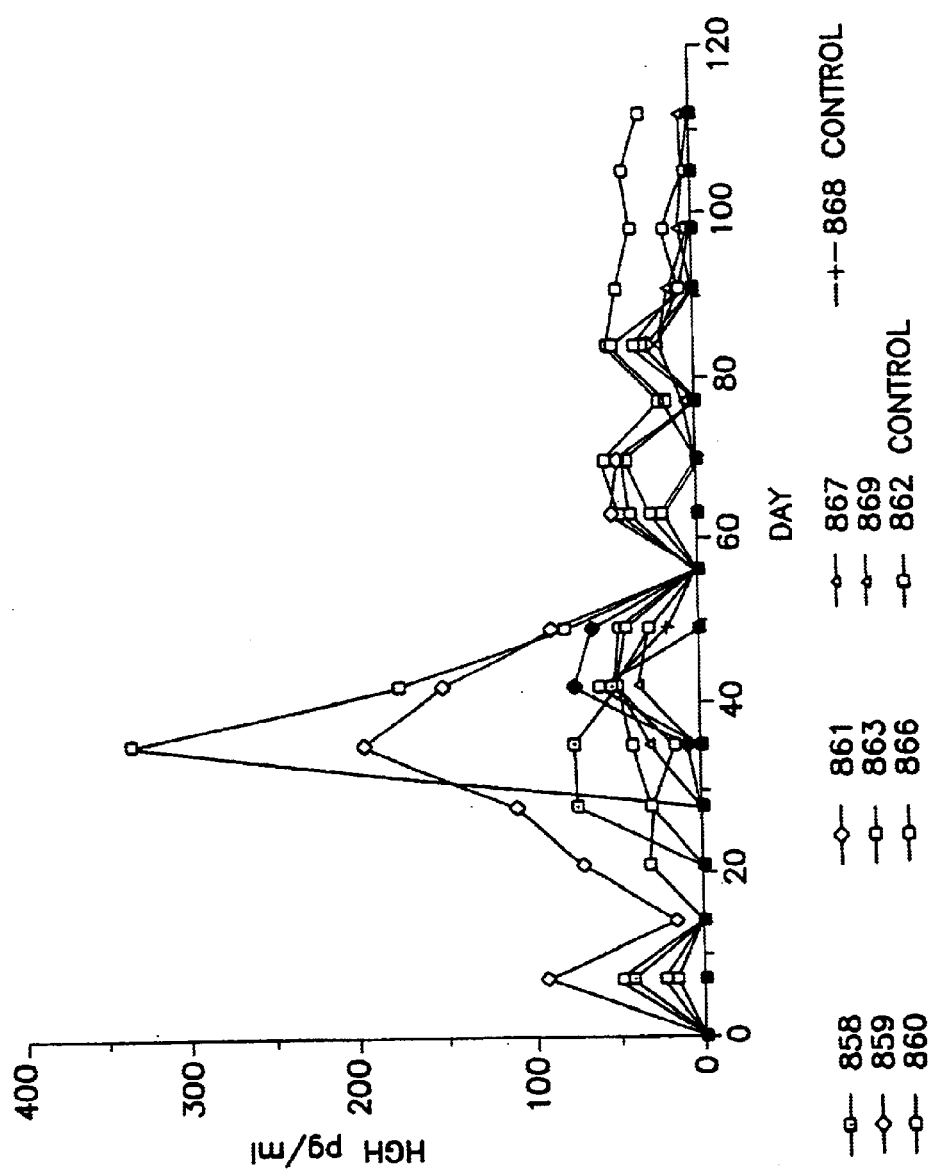
FIG. 24: Serum samples were obtained from rabbits on indicated days, and human growth hormone antigen was measured using ELISA.

EXAMPLE 19
High Level Expression of Human Growth Hormone with a Lag Phase in Rabbits Following Intravenous Injection of Retroviral Vector Human growth hormone-expressing retroviral vectors were produced as described in Example 8 herein. Large scale production in Cell Factories was performed as described for DX/ND7 in Example 14 herein. The retroviral vector was lactose formulated as described in Example 9 herein. The titer was 8E8. Vector was diluted 5-fold in formulation buffer, and 1 ml injections were given to 500 g juvenile rabbits 3 time per day for three days as described in Example 18 for factor VII vector. Serum was collected on days 0 (prebleed), 7, 4 and every 7 days thereafter. Serum was analyzed for human growth hormone content using a commercial ELISA kit (Boehringer Mannheim Biochemicals, Indianapolis, Ind., USA) according to the directions of the manufacturer. The results are shown in FIG. 24. A modest degree of expression (100 pg/ml) was observed in rabbit #861 at Day 7. Several other rabbits displayed smaller initial expression. Expression in all rabbits declined, to zero except for rabbit #861, by Day 14. Unexpectedly, expression in several rabbits (#861, 863, 858, 866) began to rise between Day 21 and Day 36. Two rabbits (#863 and 861) displayed peak expression levels at Day 36 of 200–350 pg/ml. Expression in all rabbits subsequently declined to zero at Day 56. A periodic small rise and decline was seen thereafter, reaching a low steady state of approximately 50 pg/ml in one rabbit (#863) after Day 84. Therefore, rabbits injected via ear vein with high titer formulated retroviral vector displayed a high level systemic expression of humanly growth hormone with a lag phase of 20–36 days.

EXAMPLE 20

Figure 25:
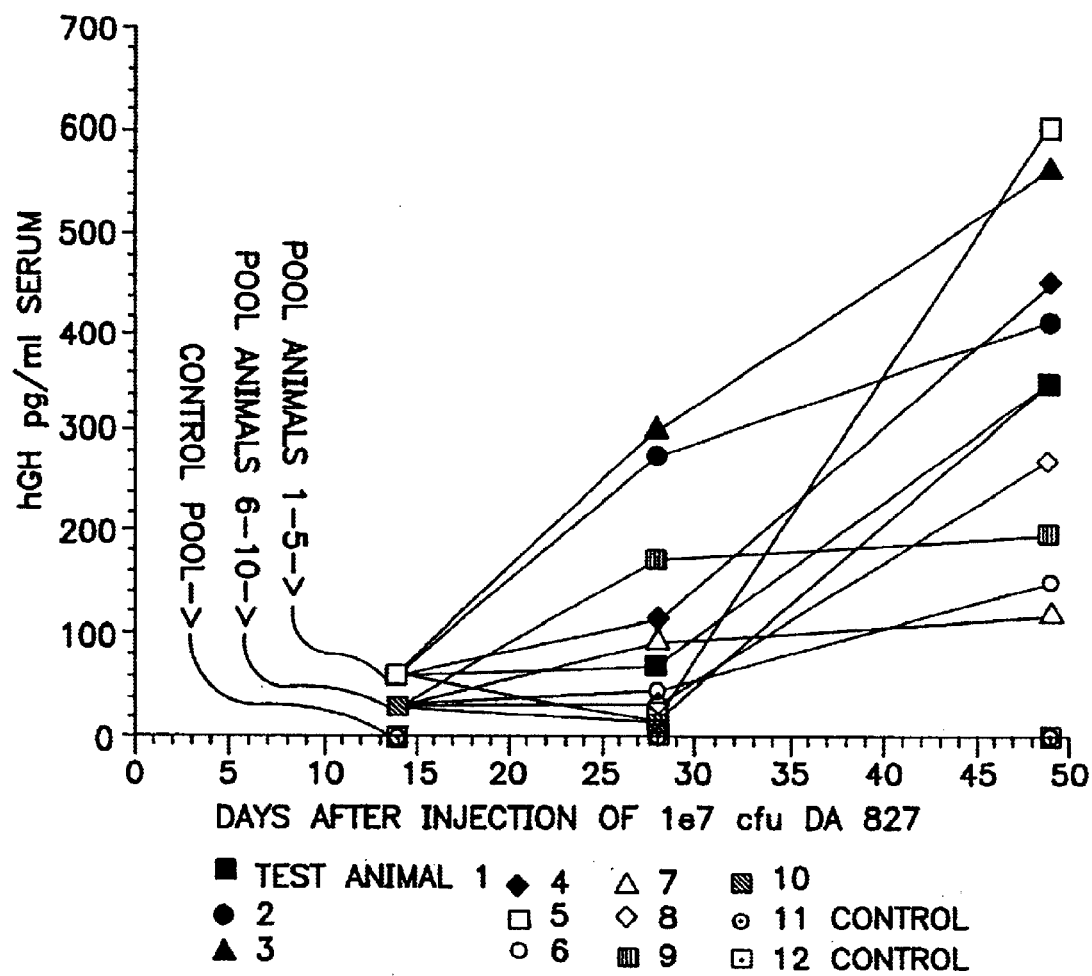
FIG. 25: Serum samples were obtained from mice on indicated days and human growth hormone antigen was determined by ELISA. Since the animals were too small on Day 14 to yield sufficient sample for the ELISA measurement, sera from test animals 1–5, test animals 6–10, and control animals 11 and 12 were respectively pooled prior to measurement. Data from subsequent days were obtained from individual animals.

High Level Expression of Human Growth Hormone with a Lag Phase in Mice Following Intravenous Injection of Retroviral Vector Human growth hormone-expressing retroviral vectors were produced as described in Example 8, herein. Large scale production in Cell Factories was performed as described for DX/ND7 in Example 14, herein. The retroviral vector was then lactose formulated as described in Example 9, herein. The titer was 8E8. Three week old mice were given a single injection of 200 ul vector via the tail vein. Human growth hormone was analyzed in mouse serum using a commercial ELISA kit (Boehringer Mannheim Biochemicals) according to the instructions of the manufacturer. The results are shown in FIG. 25. Due to the low serum volumes that could be obtained from young mice relative to the volumes required for ELISA analysis, pooled test mice were tested on Day 14, and therefore the results shown on this date represent the average value for the indicated animals. All three pools (two test, on control) yielded values of <50 pg/ml on Day 14. By Day 28, animals had grown sufficiently that individual animals could be tested. Animals 2 and 3 displayed hGH levels of approximately 300 pg/ml on Day 28; animal 9 showed a level; of 200 pg/ml. All other mice were <100 pg/ml. The two controls, Animals #11 and 12, were 0 throughout the test period. By day 48, all 10 test animals displayed increasing levels of hGH, and all were clearly above 100 pg/ml, with animals #1, 2, 3, 4, 5, and 10 showing levels of 300–600 pg/ml. Therefore, mice injected a single time with high-titer formulated retroviral vector expressed human growth hormone at high levels for at least 20 days following a lag phase of 14–48 days.

EXAMPLE 21

High Level Expression of Human Growth Hormone in Adult Mice

Figure 26:
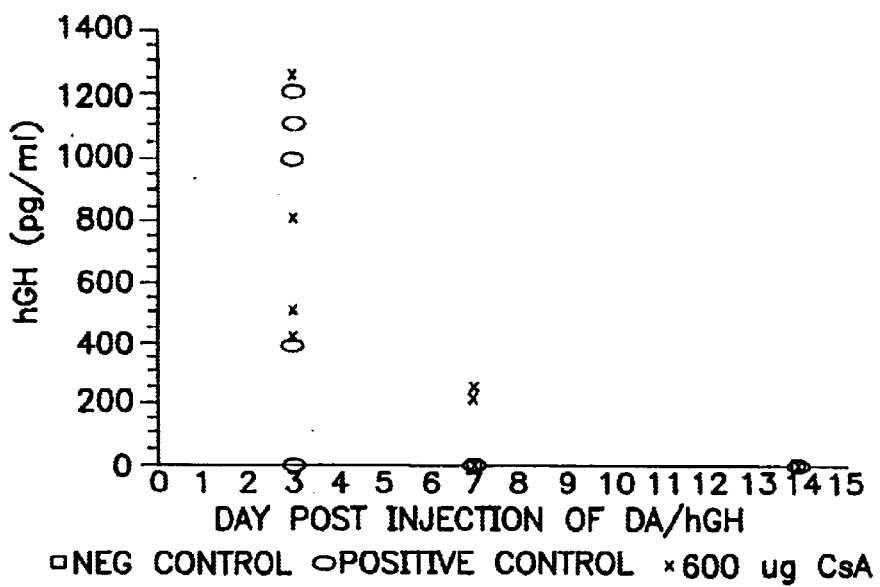
FIG. 26: Sera were obtained from adult mice on the indicated days. Human growth hormone antigen was measured by ELISA. Each point represents an individual animal. Negative controls had been injected with formulation buffer; positive controls with 1E7 cfu retroviral vector; "600 ug CsA" with both vector and cyclosporin A as described in the text.

Human growth hormone-expressing retroviral vectors were produced as described in Example 8 herein. Large scale production was carried out in Cell Factories as described for DX/ND7 in Example 14 herein. The retroviral vectors were then lactose formulated as described in Example 9, herein. The titer was 8E8 Adult mice were given a single injection of 100 µl vector via the tail vein. One group of mice also received 600 µg cyclosporin A once daily i.m. starting 1 day prior to injection of vector and continuing through Day 13. Human growth hormone was analyzed in mouse serum using a commercial ELISA kit (Boehringer Mannheim Biochemicals) according to the instructions of the manufacturer. The results are shown in FIG. 26. "Positive control" refers to mice that received no cyclosporin. High level (400–1200 pg/ml) human growth hormone was observed on Day 3, declining to zero by Day 14. Negative controls (formulation buffer-injected) expressed no human growth hormone. The injection of cyclosporin A using the above schedule neither augmented nor diminished the growth hormone response. Therefore, intravenous injection of high titer formulated retroviral vectors induces high level expression of growth hormone in adult animals with no lag phase.

EXAMPLE 22

Use of Peroxisome Proliferators to Induce Liver Mitosis and Retroviral Transduction In Vivo Balb/C mice were treated IP (500 µl) or via gavage (200 µl) with the peroxisome proliferator WY 14643 (Chem Syn, Lenexa, Kans., USA) (15 mg/ml) once per day for 4 days. On day 4, 200 ul beta galactosidase retroviral vector (1E9 cfu/ml, DA-Bengal) was injected via tail vein. On day 7, the mice were sacrificed, tissues were fixed in 2% formaldehyde/PBS for 24 hr, and blocked into slices of 2–5 mm. Sections were rinsed in PBS and stained in fresh XGAL solution (5 mM potassium ferricyanide/5 mM potassium ferrocyanide/2 mM MgCl2/0.5mg/ml XGAL in DMF (Gold Scientific)/1×PBS). Tissue was embedded in paraffin (~50 degrees), sectioned at 5 microns (PML, San Diego), and counterstained with Hematoxylin/Eosin. Sections were compared from both periportal and peripheral regions from normal liver (XGAL stain only), control liver (no WY16463, with vector), WY control liver (WY 16463 only, no vector), liver from group I (IP WY 16463 plus vector), liver from group II (gavage WY 16463 plus vector), and spleen from Group I. Numerous blue cells were observed in both treatment groups, both periportally and on the liver periphery. Very rare blue cells were observed in the control liver (without mitogen). No blue cells were seen in the normal liver (no mitogen or vector) or the WY liver (mitogen, no vector). The results indicate that the mitogen, administered either IP or by gavage, promoted liver transduction by beta-galactosidase-expressing vector, while no background staining was induced by mitogen in the absence of vector.

EXAMPLE 23

Figure 27:
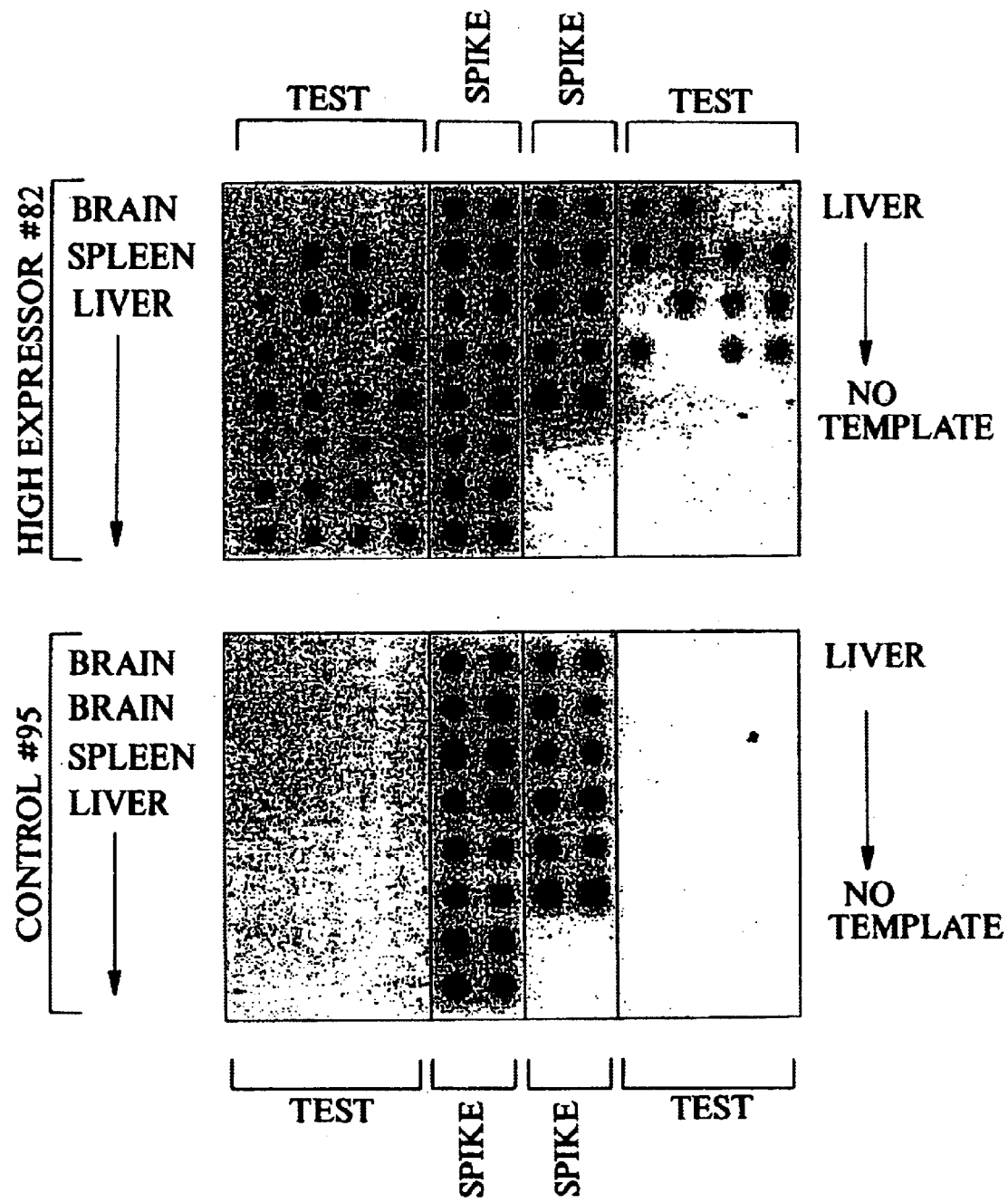
FIG. 27: PCR localization of vector in B-del-1 treated rabbits. Rabbits #82 and 95 shown in FIG. 22, herein were sacrificed on Day 511. DNA was extracted from indicated organs, subjected to 40 cycles of PCR, and dot blotted, and hybridized to 32-P labeled probe as described in text. Several replicate PCR reactions were run. Lanes indicated "spike" had 5 copies of amplicon added to the template.

Biolocalization of Intravenously Administered Retroviral Vector Following Long-Term Expression of Gene of Interest Rabbits which had received intravenous administration retroviral vector resulting in >373 days of expression of human factor VIII (See Example 18, herein) were sacrificed on day 511. Brain, spleen, and liver samples were collected using a fresh set of sterilized instruments for each organ in each animal. DNA was isolated using lysis buffer (8M urea, 2% SDS, 0.35M NaCl, 10 mM Tris, pH 8.0) followed by phenol/chloroform extraction. DNA was quantitated by fluorometry and diluted to 500 ng/25 ul. Integrity of each genomic DNA samples was verified by 0.6% agarose gel electrophoresis. PCR was performed on each sample (0.5 uM primer LTR 492S (CCC TGT GCC TTA TTT GAA CTA ACC) (Seq ID No. 12), 0.55 uM primer LTR 1072AS (CCC ACC ACA ACC ACA TAT CCC TCC) (Seq ID No. 13), 1×PCR Buffer, 2.5 mM MgCl2, 200 uM dNTPs, 2.5 U Taq in a total volume of 50 ul (Perkin-Elmer)). The reactions are incubated 10 min at 94o, then subjected to 32 cycles of 94o×30 sec. 68o×30 sec, 72o×30 sec. The amplicon consisted of a 580 bp region spanning the LTR/Psi region of the vector backbone (see Example 1). Each sample was subjected to four replicate reactions. Two other replicate reactions were spiked with 5 copies of positive control DNA (DA6A3 HBV-IT VCL genomic DNA; see Townsend et al., 1997, *J. Virol.* 71:3365, to control for interference with PCR amplification. Ten microliters of each amplification reaction were dot-blotted onto a nylon membrane (Zeta Probe). The membrane was prehybridized in buffer (6×SSPE, 30% formamide, 5×Denhardt's Solution, 0.5% SDS, 1.5 mg/ml herring sperm DNA) at 42o for 60 min, the hybridized at 42o for 4 hr in the same buffer to a 32P-end labeled probe (LTR-P-CCA GTC CTC CGA TTG ACT G [Seq ID No. 14]) corresponding to a sequence internal to the LTR-Psi amplicon. The blot was washed (at room temperature in 2×SSPE/ 1% SDS, then 3×10 min at 42o in 2×SSPE/1% SDS) and exposed to film. The film was inspected for number of positive blots per total number of reactions. Tissue samples from Rabbit #82, which expressed high levels of human factor VIII protein, and from Rabbit #95, a control animal that had received no vector, are shown in FIG. 27. The spiked reactions from all tissues were positive, indicating that negatives are not due to PCR inhibiting substances from the tested tissues. Liver samples from 10 locations, a spleen sample, and samples from two brains locations were all negative in the control rabbit. The brain sample was negative in the expressing rabbit, while spleen and all 10 liver samples were positive in the expressing rabbit. The results suggest that liver and spleen have been transduced in the vector-treated rabbit, that marked cells are still present after 511 days, and that these are candidate organs for the source of the circulating factor VIII.

Figure 28:
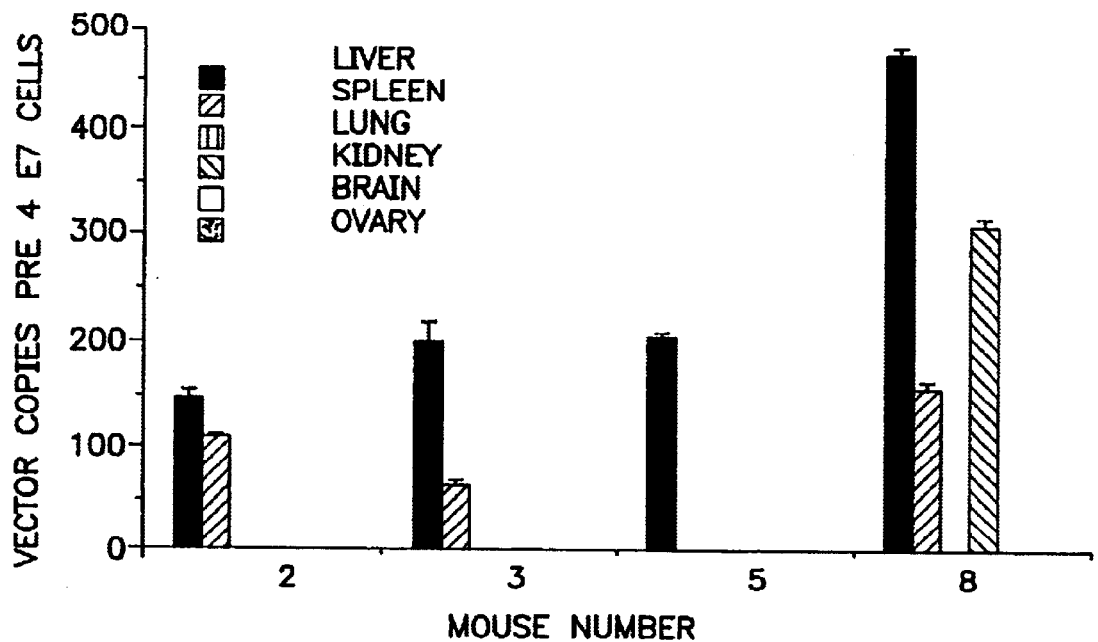
FIG. 28: Quantitative PCR of beta-galactosidase vector in organs of transduced mice. Juvenile mice, transduced as described in the text, were sacrificed on Day 59. DNA was obtained from indicated organs and subjected to quantitative PCR as described.
Figure 29:
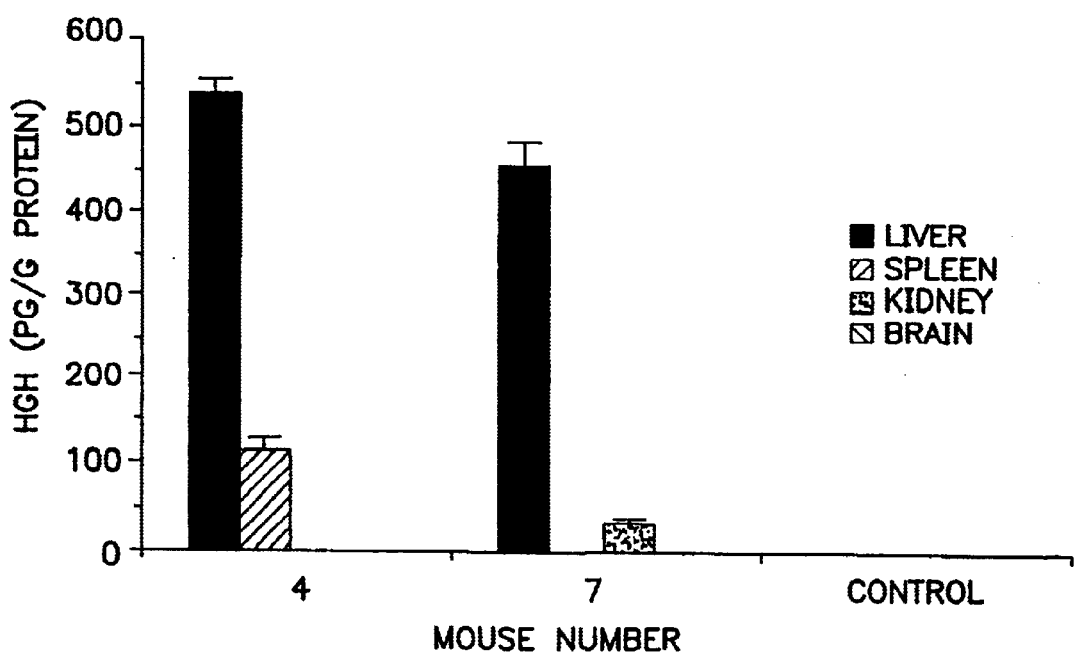
FIG. 29: Human growth hormone antigen in organs of transduced mice. Indicated organs were lysed and analyzed by ELISA as described in the text. Results are shown normalized to the amount of total protein recovered from the organ.

Juvenile mice were treated with DA/beta-gal vector as in Example 20 herein. Expressing mice were sacrificed at Day 59 or 105. Brain, liver, kidney, lung, and spleen were analyzed for vector sequences by quantitative PCR. Quantitative PCR is performed as described above, except that 1 µl of alpha-32P-dCTP is included in the PCR buffer, and a standard curve is prepared from the same positive control DNA in 3-fold dilutions from 1000 copies/sample down to 1.4 copies/sample, maintaining a constant concentration of 500 ng DNA/reaction by adding human PBMC DNA to each dilution. Five µl of each reaction is blotted onto Whatman DE81 Ion Exchange Chromatography paper, dried at 42o×5 min, washed 3× (40 ml 5M NaCl, 21 ml 1M monobasic sodium phosphate, 29 ml 1 M dibasic sodium phosphate, qs to 1 liter), and quantitated relative to the standard curve on the PhosphoImager (Molecular Dynamics). Liver was positive in all four animals tested, spleen in 3/4, and kidney in 1/4. Lung and brain were negative in all four, and ovary was negative in the two animals tested (See FIG. 28). Tissue lysates were also prepared from several animals. One third to ½ of each tissue was placed in homogenization buffer (Dianon PCNA ELISA kit) and stored on ice, until all of the samples were collected. Samples were liquefied in dounce homogenizers. The lysates were transferred to 1.5 ml microfuge tubes, and centrifuged at 14,000 rpm, 4° C., for 15 minutes. The aqueous layer between the lipid and cell debris layers was aspirated by syringe and stored at −80° C. Samples were thawed at 37° C., diluted 1:3 and 1:10, and tested in duplicate for hGH by ELISA (BMB kit). Protein in each sample was determined in a Bradford protein assay, and results are expressed relative to total protein levels. Growth hormone antigen was found in liver in 4/4 animals tested, in spleen in 2/4, and kidney in 1/4. Brain was negative in 2/2 animals tested (See FIG. 29). These data are consistent with the proposal that liver and spleen are the major sites of transduction and synthesis of genes of interest when retroviral vectors are introduced intravenously.

EXAMPLE 24
Long Tern Expression of Human Factor VIII in Normal Dogs Following Intravenous Expression of Vector Recombinant retroviral vector expressing B domain deleted factor VIII was constructed, packaged, and expressed as described in Example 2 herein. Large scale production was carried out in Cell Factories as described for DX/ND7 in Example 14 herein. The retroviral vector was then lactose formulated as described in Example 9 herein. High titer formulated retroviral vector was injected into 8 week old normal juvenile dogs according to the following schedule: 4E8 vector particles were injected into the cephalic vein at 2.5 hr intervals, three times per day for three days (Day 0, 1, and 2). On days 4, 7, 10, 13, 20 and every 7 days subsequently, citrated plasma was obtained by venipuncture of the cephalic vein and analyzed for human factor VIII antigen as in Example 18, except that the diluent was 1:3 citrated dog plasma (Harlan).

Figure 30:
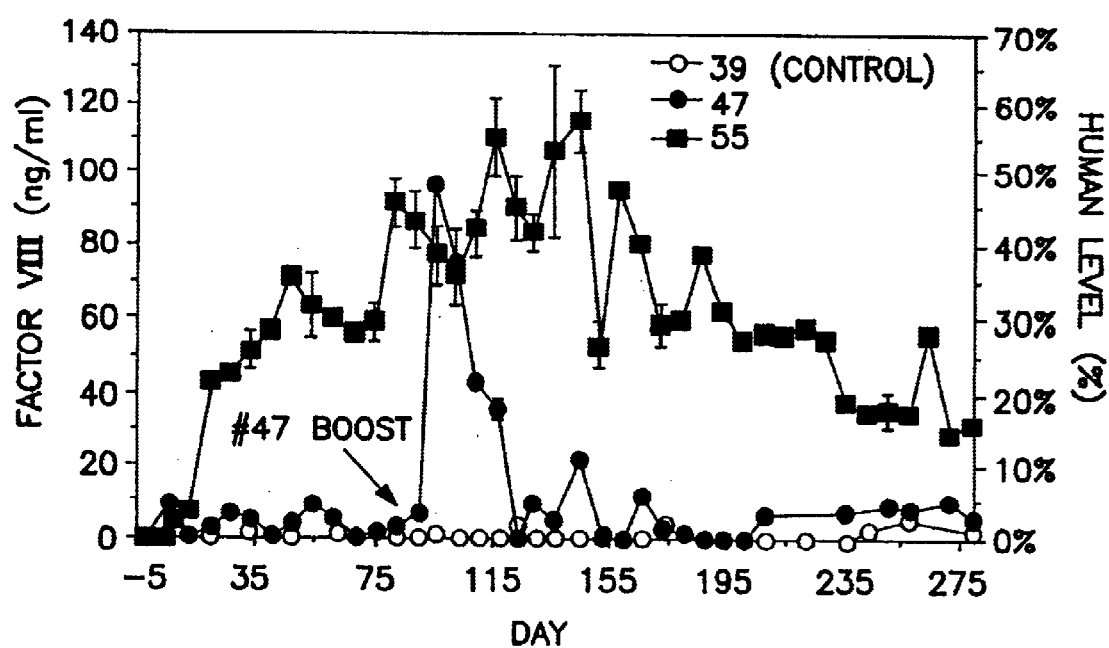
FIG. 30: Expression of human factor VIII antigen in transduced normal dogs. Juvenile dogs (#47 and #55) were injected with a total of 4E9 cfu of factor VIII vector B-del-1 in a total of 9 injections over days 0,1, and 2. Control dog #39 received formulation buffer on the same schedule. Dog #47 was boosted with the same amount of vector on days 90, 91, and 92. At indicated times, cuitrated plasma was obtained and analyzed by ELISA for human factor VIII antigen. Percent human level is calculated based on a level of 200 ng/ml factor VIII in pooled in normal human plasma.

Data from Day 0 (prebleeds) to day 279 from 2 experimental and one control dog are shown in FIG. 30. Levels remained undetectable through Day 7, with no significant differences being seen between the experimental and control groups (p>0.25). On Day 7 and 10, low levels (3–10 ng/ml) of factor VIII were observed in all three dogs. On day 13 and subsequent days until day 90, Control Dog 39 and Experimental Dog 47 ("nonresponder") displayed 0–8 ng/ml human factor VIII antigen in their plasmas. In contrast, Experimental Dog 55 ("responder") displayed levels of 40–110 ng/ml factor VIII. Levels of factor VIII in Dog 55 peaked around Day 160, gradually declining until Day 279, the last date tested. On day 90,91, and 92, the nonresponder dog #47 was boosted with dosage schedule recapitulating that used on day 0,1, and 2. On Day 95, dog 47 displayed 95 ng/ml, comparable to the 77 ng/ml found in the unboosted responder dog 55 on that date. Unlike Dog 55, boosted Dog 47 did not maintain these levels, which declined to barely detectable levels by Day 125.

Figure 31:
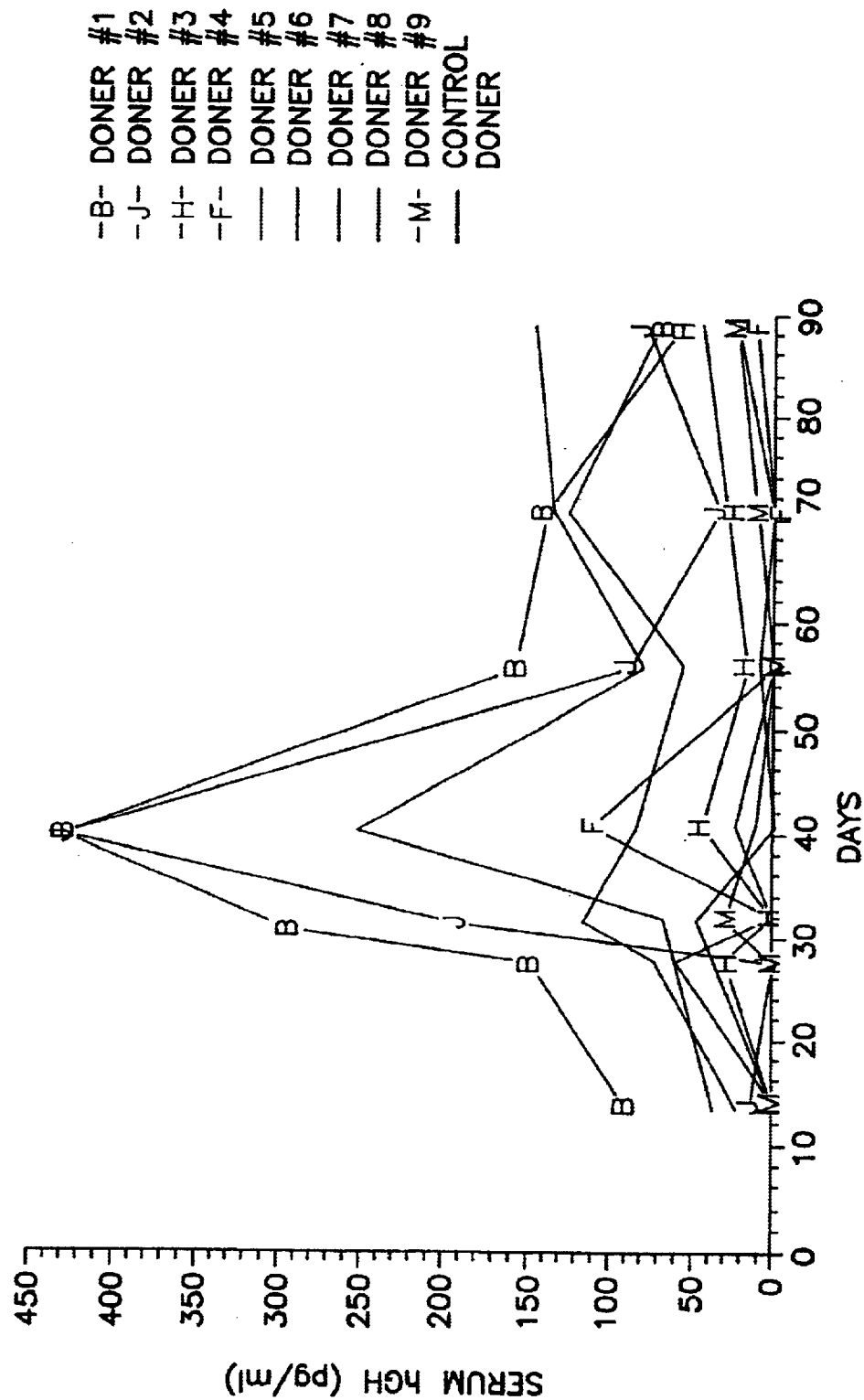
FIG. 31: Transfer of expression of human growth hormone following adoptive transfer of splenocytes from transduced donor mice to lethally irradiated syngeneic recipients. Juvenile mice were transduced with growth hormone retroviral vector as described in the text. On day 59, Donors #1–5 were sacrificed, and splenocytes from each were injected into two lethally irradiated recipients (A and B, numbered according to donor number). Every 14 days subsequent to reconstitution, serum from the recipients was monitored for growth hormone levels.

EXAMPLE 25
Transduction of Splenocytes and Possible Stem Cell Transduction by Intravenous Administration of Retroviral Vector Data in Example 24 herein show transduction of spleen and liver in long-term expressing animals treated with retroviral vector intravenously. To test for expression of hGH by splenocytes, an adoptive transfer experiment was carried out. Fragments of spleens (1/4 to 1/3 spleen) were collected from BALB/c mice which had received 1E7 cfu DA-827 51 days earlier via tail vein injection as described in Example 20 herein. Spleens were processed individually. Single-cell suspensions were prepared in sterile Hank's balanced salt solution (HBSS; Irvinc Scientific) by passing tissue fragments through a 70 mm nylon mesh strainer (Becton Dickenson #2350). After pelleting, cells from each spleen were resuspended in 0.8 ml HBSS; 0.3 ml of this suspension was injected intravenously into lethally irradiated (900 R) recipient BALB/c mice. An estimated 6–7×10$^6$ cells were transferred to each recipient. Serum levels of hGH were monitored every two weeks in recipients as in Example 20, levels of hGH expression in recipients roughly corresponded to the levels that had been present in the original donors (See FIG. 31), suggesting that these levels correlated with transduced cell number. Peak expression was observed 56 days following spleen cell transfer, with a decrease by day 70. The increase of expression with time as the animals reconstituted indicates that stem cells have been transduced.

Figure 32:
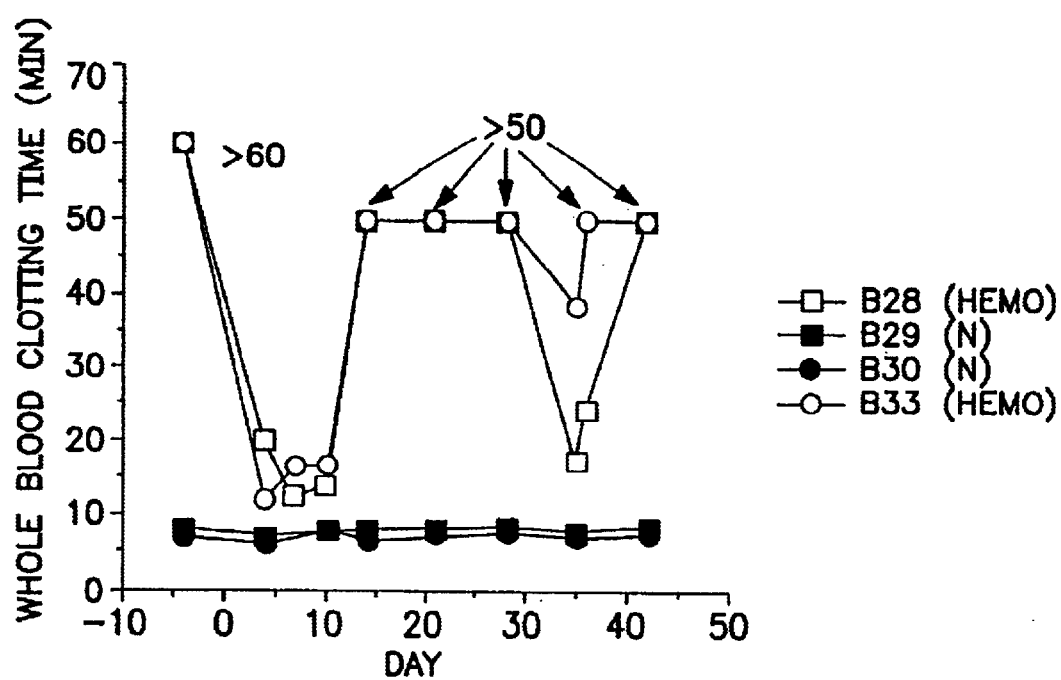
FIG. 32: Whole blood clotting times in hemophiliac dogs treated with factor VIII vector. Two hemophiliac dogs (#28 and #33) were injected with B-del-1 as described in the text. At indicated times, citrated whole blood samples were obtained and clotting times were determined following recalcification. Clotting times of two untreated normal littermates are included for reference.

EXAMPLE 26
Expression of Human Factor VIII in Hemophiliac Dogs Following Intravenous Expression of Vector Two factor VIII-deficient hemophiliac dogs (8 weeks old) were obtained from the closed colony at U. North Carolina, Chapel Hill. Two normal littermates were also obtained and used without further treatment to provide baseline values for assays. The two test dogs were injected with retroviral vector as in Example 24, herein, except that the injection dates were Days 1,2, and 3. Blood samples were obtained on Days 4,7,10, 14, and every 7 days subsequently. Citrated samples were used for measurements of whole blood clotting time (See FIG. 32). On day 4, samples from the hemophiliac dogs were incoagulable (WBCT>60 min), whereas the normal littermates had WBCT of 6–8 minutes.

The WBCT of the normal littermates were maintained throughout the experiment. On day 4–10, the WBCT of the injected hemophiliac dogs dropped to 12–16 minutes. This represents expression of pg levels of factor VIII (Dr. Tim Nichols, UNC-Chapel Hill, personal communication). On day 14–28, the hemophiliac dog WBCT was again incoagulable (>50 min). Starting at day 35, the clotting time was again reduced, reaching 17 minutes for one dog and 16 minutes for the second, indicating a second peak of factor VW clotting activity. This data demonstrates the successful expression of biologically active factor VIII in dogs by intravenous administration of a retroviral vector expressing a B-domain deleted factor VIII protein.

EXAMPLE 27

Figure 33:
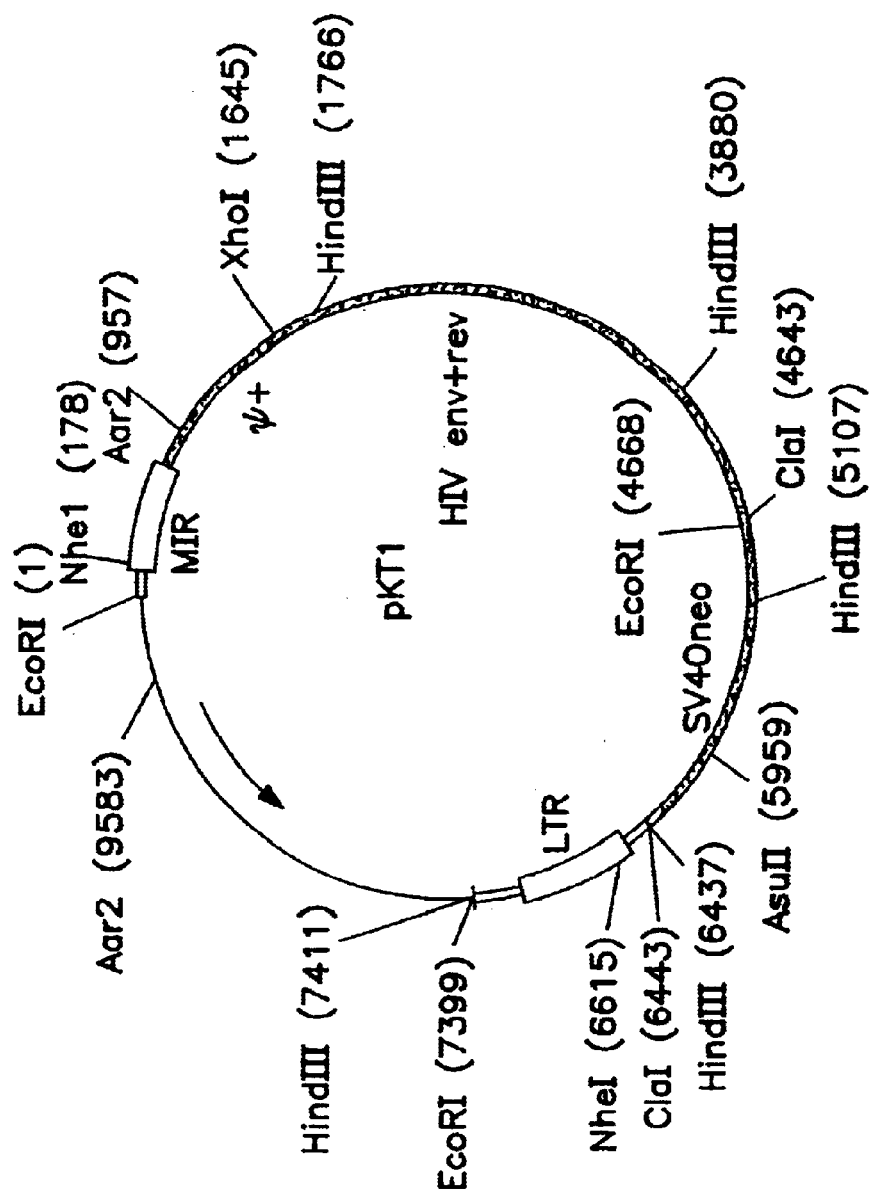
FIG. 33 is a schematic illustration of pKT1.
Figure 36:
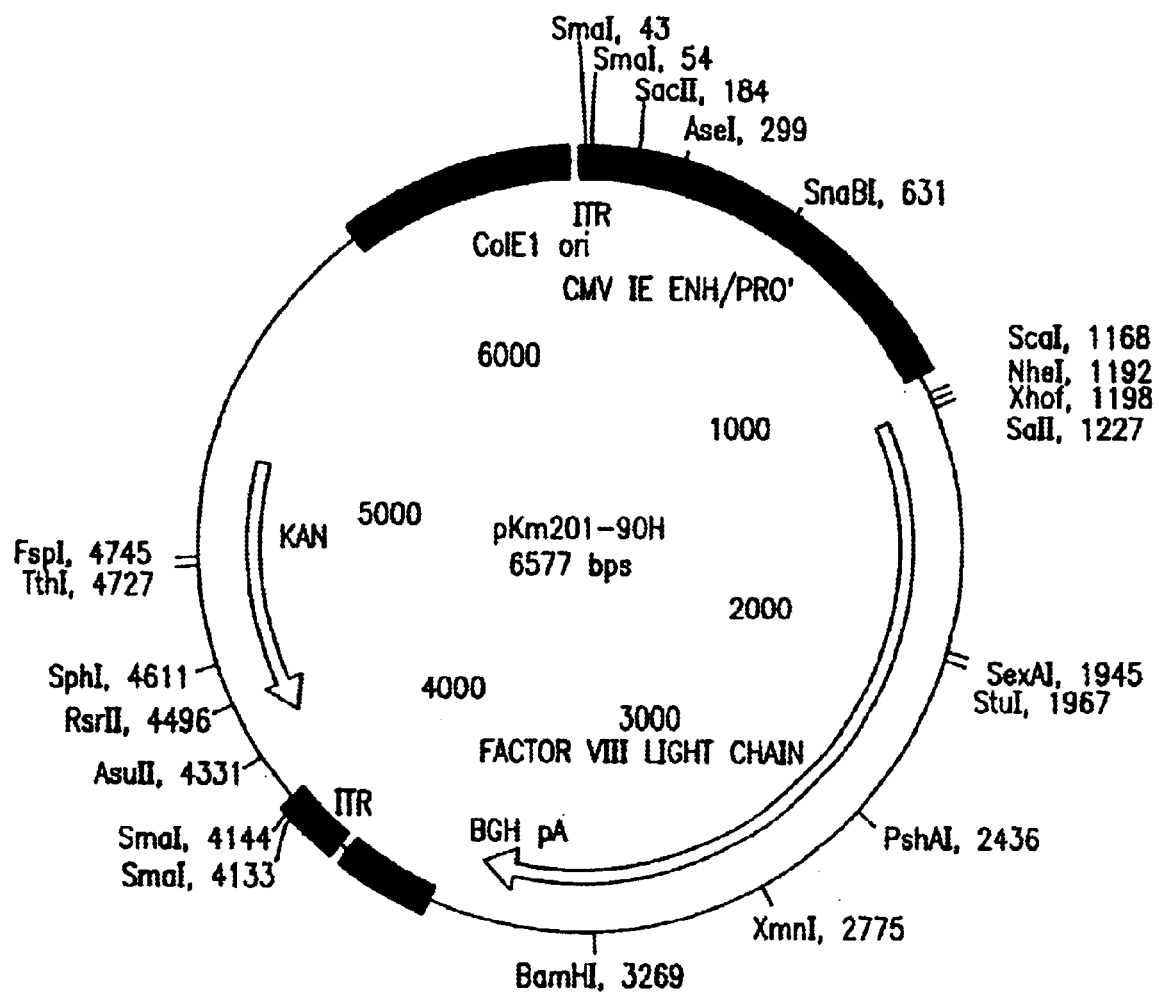
FIG. 36: Schematic representation of pKm201-90-H.

Construction of pBA-5a, pBA-5b, and pBA-5c, PBA-9b and pBA-8bL1 Retroviral Vector Backbones This example describes several modifications of the retroviral vector pKT1 resulting in decreased sequence homology to the retroviral gag/pol and envelope expression constructs. pKT-1 is described in Example 1 herein and is shown schematically in FIG. 33. The construction of the pKT-1 starting material used in the present example is further described in detail in co-owned U.S. Pat. No. 6,013,517, issued Jan. 1, 2000 and U.S. Pat. No. 6,333,195, issued Dec. 25, 2001, both of which are hereby incorporated by reference in their entirety. In addition, two stop codons were introduced in the DNA sequences of the packaging signal sequence in order to increase the safety of these vectors. All modifications are summarized in FIG. 36 and the resulting retroviral backbones are called pBA-5b, pBA-5b and pBA-5c. Further details on the construction of pBA-5a, pBA-5b and pBA-5c are provided in co-owned U.S. Pat. Nos. 6,013,517 and 6,333,195 and are hereby incorporated by reference.

A. Substitution of Nonsense Codons in the Extended Packaging Sequence (Ψ+)

This example describes modification of the extended packaging signal (Ψ+) by PCR on the template KT-1 using primers that introduce two stop codons in the extended packaging signal sequence. In particular, the template pKT-1 contains the modification ATT at the normal ATG start site of gag (position 621–623 of SEQ ID NO: 15). Here the start site was further modified to the stop codon, TAA, and an additional stop codon TGA was added to replace the codon TTA at position 645–647 of SEQ ID NO: 15.

Briefly, two sets of PCR reactions were carried out on pKT1, each introducing one stop codon. The primers for the PCR were designed such that the two PCR products had overlapping regions and a splice-overlap extension PCR (SOE-PCR) was carried out with the two PCR products in order to combine the two introduced stop codons on one strand. The first set of oligonucleotides introducing the change from ATT to TAA were 5'-GGG-AGT-GGT-AAC-AGT-CTG-GCC-TTA-ATT-CTC-AG (SEQ ID NO: 16) and 5'-CGG-TCG-ACC-TCG-AGA-ATT-AAT-TC (SEQ ID NO: 17) and the second set of oligonucleotides introducing the change from TTA to TGA were 5'CTG-GGA-GAC-GTC-CCA-GGG-ACT-TC (SEQ ID NO: 18) and 5'GGC-CAG-ACT-GTT-ACC-ACT-CCC-TGA-AGT-TTG-AC (SEQ ID NO: 19). The flanking primers of the final 708 base pair PCR product introduced the AatII and the XhoI sites, at the 5' and 3', respectively.

Figure 34:
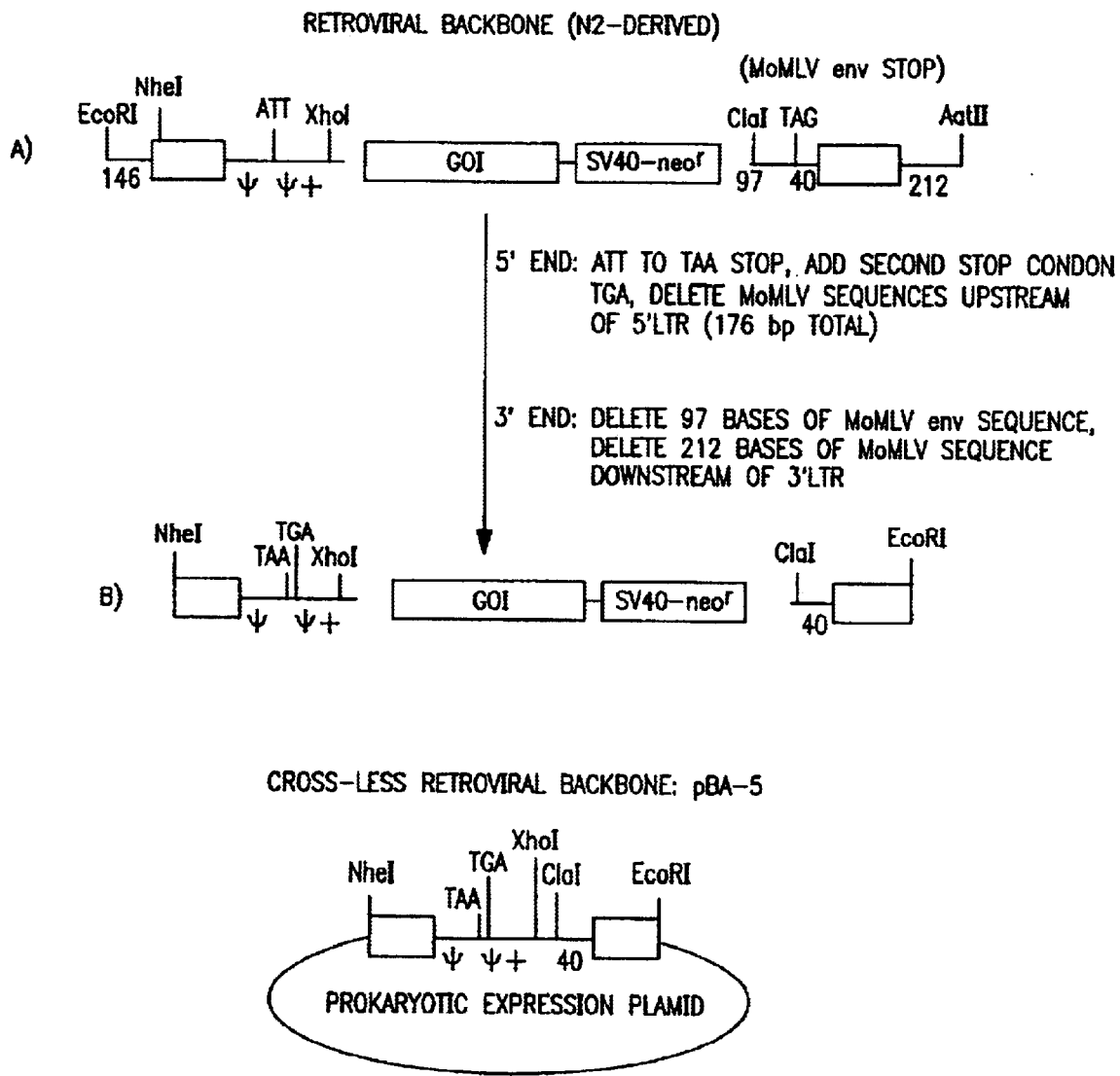
FIG. 34 is a description of all modifications carried out on retroviral vector as shown in A), resulting in the cross-less retroviral vector shown in B). The cross-less retroviral backbone cloned into a prokaryotic vector is called pBA-5.

The ends of the 708 base pair product were blunted and phosphorylated and the product introduced into the SmaI and EcoRV digested vector pBluescript SK– (Stratagene, San Diego, Calif.). The resulting plasmid was designated pBA-2, and is shown diagramatically in FIG. 34.

B. Removal of Retroviral Sequences Upstream and Downstream from the 3' LTR and Upstream and within the 5' LTR Retroviral envelope sequence was removed upstream of the 3' LTR between the ClaI site and the TAG stop codon of the envelope coding sequence. The DNA sequence was modified by PCR such that the TAG stop codon was replaced by a ClaI site and the 97 nucleotides upstream from this new ClaI site to the original ClaI site were deleted, as well as the 212 base pairs of retroviral sequence downstream of the 3' LTR.

Briefly, the following two oligonucleotides were used for the PCR: 5'-CATCGATAAA ATAAAAGATT TTATT-TAGTC (SEQ ID NO: 20) and 5'-CAAATGAAAG ACCCCCGCTG AC (SEQ ID NO: 21) and the template was pKT1. The PCR product was cloned into pPCRII (Invitrogen, San Diego, Calif.) using the TA cloning kit (Invitrogen, San Diego, Calif.) and called pBA-1.

Subsequently, pBA-2 (described in section A above) was digested with XbaI and AatII which deleted a part of the multiple cloning site and into this linearized vector the 780 base pair fragment from NheI to AatII from pKT1 was cloned, resulting in the plasmid pBA-3. This plasmid pBA-3 combined the shortened 5' LTR with the above described packaging region including the two introduced stop codons.

Subsequently, pBA-1 was digested with ClaI and ApaI resulting in a 640 base pair fragment that was cloned into the ClaI and ApaI digested pBA-3 resulting in the plasmid pBA-4. This plasmid combines the above described 5' LTR and the packaging signal with the 3' LTR.

Subsequently, pBA-4 was digested with ApaI and EcoRI, ends blunted and religated in order to remove extraneous 3' polylinker sites, resulting in plasmid pBA-5a.

Subsequently, pBA-5a was cut with NotI (blunted) and EcoRI and introduced into SmaI and EcoRI digested pUC18 (GIBCO/BRL, Gaithersburg, Md.) resulting in pBA-5b. This construct moved the retroviral vector from a pBluescript into an alternate pUC18 vector.

pBA-5c is constructed as identical to pUC-18 derived pBA-5b except for the XhoI/ClaI multicloning site was introduced into pUC-19.

This example further describes several modifications of the retroviral vector pBA-5b which result in a vector with multiple unique restriction enzyme sites for convenient cloning. In order to prepare the pBA-9b vector, the herpes simplex virus thymidine kinase (HSVTK) gene was retrieved by digesting pBH-1 with XhoI and EcoRI resluting in a 1.2 kb fragment. (pBH-1 was prepared as described in WO 91/02805 entitled "Recombinant Retroviruses Delivering Vector Constructs to Target Cells" which is hereby incorporated by reference.) The neomycin gene driven by the SV40 promoter was retrieved by digesting pKT-1 with EcoRI and BstBI resulting in a 1.3 kb fragment. Both fragments were cloned into a XhoI and Cla digested pBA-5b resulting in the retroviral vector pMO-TK.

The TK gene from the retroviral vector pMO-TK was isolated as a XhoI-ClaI fragment and inserted into the XhoI-ClaI digested pBA-5b, resulting in the plasmid pBA-5bTK. In order to deleted the restriction enzyme sites HindIII, SphI, PstI, SalI and HincII upstream of the 5' LTR, pBA-5bTK was digested with HindIII and HincII, overhanging ends removed using T4 polymerase and blunt ends ligated unsing the T4 DNA ligase resulting in plasmid pTJBA-5bTK with 16 bases (TGC ATG CCT GCA GGT C) (SEQ ID NO:84) removed from upstream of the 5'LTR. The plasmid pTJBA-5bTK has a BamHI upstream of the 5'LTR. It is desirable to remove this BamHI site since it is a common site used for cloning. In order to destroy the BamHI site upstream of the 5'LTR, the BamHI-containing TK gene in pTJBA-5bTK was replaced by the IL-2 gene via XhoI-ClaI digest, resulting in plasmid pTJBA-5bIL-2. The plasmid pTJBA-5bIL-2 was digested with BamHI, the ends filled in with the Klenow fragment and the ends religated, resulting in pTJBA-5bIL-2 (BamHI del.).

In order to produce the plasmid pBA-9b, the IL-2 gene from pTJBA-5bIL-2 (BamHI del.) is deleted via XhoI-ClaI digest and replaced with an linker that introduces a multiple cloning site (MCS) and codes for the restriction enzyme sites 5'-XhoI-ApaI-BglII-NotI-NruI-SalI-HindIII-BamHI-ClaI-3'. The sequence of the two primers that is used to produce the linker are as follows: 5'-TCG AGG GGC CCA GAT CTG CGG CCG CTC GCG AGT CGA CAA GCT TGG ATC CAT-3' (Seq ID No. 26) as the primer for the + strand and 5'-CGA TGG ATC CAA GCT TGT CGA CTC GCG AGC GGC CGC AGA TCT GGG CCC C-3' (Seq ID No. 27) as the primer for the − strand.

This example describes several modifications of the retroviral vector pBA-5b which result in a vector coding for the human placental alkaline phosphatase gene (PLAP), driven by the SV40 promoter.

The plasmid pBA-8bL1 was constructed in a three-way ligation using the following three fragments: The NdeI-ClaI fragment from pBA-5b (described above) containing the 3'LTR and the pUC18 backbone, the ClaI-HindIII fragment from pCI-PLAP coding for PLAP and the HindIII-NdeI fragment from pBA-6bL1 containing the 5'LTR and the SV40 promoter. Plasmid pBA-6bL1 is based on pBA-6b (described above) where the HIVenv/rev coding region was deleted via XhoI-ClaI digest and replaced with the L1 linker coding for several restriction enzyme sites including XhoI at the 5'end and ClaI at the 3'end.

EXAMPLE 28
Preparation of pBA-5a, pBA-5b, and pBA-5c Retroviral Vectors Expressing B-Domain Deleted Factor VIII A B-domain deleted factor VIII cDNA fragment thus constructed was obtained by XhoI/NotI digestion, as described below. A retroviral vector (pMBF8) expressing B-domain-deleted factor VIII is constructed from the expression plasmid pSVF8-200 which is prepared as described in Truett, 1985, *DNA* 4:333) and in U.S. Pat. No. 5,045,455 and which was deposited with the ATCC on Jul. 17, 1985, and which has been assigned ATCC number 40190.

A DNA fragment encoding the β-domain deleted Factor VIII molecule was obtained from pSVF8-302, which has a nine base pair deletion in the 5' non-coding region after the poly G tail. Plasmid SVF8-302 was constructed in a similar manner as pSVF8-200 which is described in detail in Truett and in U.S. Pat. No. 5,045,455. Construction of pSVF8-302 is also described in U.S. Pat. No. 5,595,886.

The procedure outlined below describes the construction of retroviral vectors expressing a β-domain deleted Factor VIII protein obtained from pSVF8-302. However, alternatively, the same procedure can be used to construct such retroviral vectors from pSVF8-200.

The full-length cDNA sequence of the factor III is shown in Seq ID No. 44 and the full-length amino acid sequence is shown in Seq ID No. 45. The cDNA sequence of the B-domain deleted SQN deletion is shown in Seq ID No. 46 and the SQN deletion amino acid sequence is shown in Seq. ID No. 47.

Fragment 1, encompassing nt 5500–6248 of pSVF8-200 (see FIG. 8 of Truett), was obtained by VENT-PCR using factor VIII primers encoding a PFIM1 site at the 3' end and the 5' SQN sequence plus a HindIII site at the 5' end. The 5' primer encompasses the region 2446–2460 of the 5' SQN and the region 5144–5167 just downstream of the 3' SQN sequence. Thus, this fragment spans the sequence between the two SQN sites within the B domain (positions 2461 and 5142). The particular primer sequences used were:

1. 5' GAAGCTTCTCCCAGAACCCACCAGTCT-TGAAACGCCATC  (Seq ID No. 22)

2. 5' GTACCAGCTTTTGGTCTCATCAAAG  (Seq ID No. 23).

Fragment 1 was blunt-end cloned into vector SK− that had been cut with SmaI and dephosphorylated, forming pSK-Pfl. Fragment 2, encompassing nt 1190 and 2448 was isolated following HindIII digestion and cloned into the HindIII site of SK-Pfl to form SK-Pfl-Hind. The orientation of the insert was determined using AccI and PstI digests. pSVF8-200 was digested with HpaI and religated to remove two small HpaI fragments 3' to the factor VIII cDNA insert, forming pF8-300-del-Hpa. The remaining HpaI site was converted to a NotI site using NotI phosphorylated linkers, forming F8-300-Hpa/Not. Fragment 3, encompassing nt 5885–7604, was isolated following PflMI and NotI digestion and cloned into SK-Pfl-Hind following PflMI and NotI digestion of the latter to form pF8:213. Fragment 4 (encompassing nt .104–133 to 1204) was obtained following VENT-PCR of PSV7dF8-300 with primers containing 5' XhoI and 3' AccI sites respectively. The 5' primer encompasses nt 104–133 and the 3' primer encompasses nt 1200–1224. pF8:213 was digested sequentially with XhoI followed by AccI and ligated to Fragment 4 which was digested with XhoI and AccI, pF8:4213. The primer sequences for the 5' UT and XhoI primers were:

3. 5' CTCCTCGAGCTAAAGATATTTTAGAG AAGAATTAAC  (Seq ID No. 24)

4. 5' TTCCTCTGGACAGCTGTCTACTTTG  (Seq ID No. 25)

The crossless backbones pBA-9b, pBA-5a, pBA-5b and pBA-5c were modified by linearizing with ClaI, blunt ending and religating in the presence of NotI phosphorylated linkers. The modified cDNA fragment was cloned into the XhoI/NotI linearized vectors. Similarly, the modified cDNA described above is cloned into the backbone pMBA backbone described above which has been digested with XhoI and NotI.

EXAMPLE 29
Construction of Recombinant Adeno-Associated Birus (rAAV) Vectors that Express the Heavy and Light Chains of Human Factor VIII We constructed two rAAV vectors, one expressed the light chain, and the other expressed the heavy chain. Both chains contain the Factor VIII leader sequence and a variable amount of the B domain.

To clone the heavy chain, a region of the Factor VIII gene from 174 bp 5' of the ATG to amino acid 745 was amplified by PCR. This fragment includes the entire heavy chain and first five amino acids of the B domain. The oligos used were: forward, 5'-CACCGTCGTCGACTTATGCT-3' (Seq ID No. 28), and reverse, 5'-GACCGTCGACTCAATTCTGGGAGAAGC TTCTTGG-3' (Seq ID No. 29). The plasmid used as a template in the PCR reaction was pCMVKmHSTB, a B deleted factor VIII expression construct. The amplified fragment was digested with Sal I, and cloned into a CMV expression vector, pCMVKmLINK digested with Sal I and Xho I. This plasmid was called pCMVKm90H. pCMVkM-LINK is an expression vector containing the CMV promoter/intron, a polylinker for cloning genes of interest, and a bovine growth homone polyadenylation signal. To make a rAAV vector expressing the heavy chain, pCMVKm90H was digested with Sal I and Bam HI, the Bam HI site was filled in with T4 DNA polymerase, and this fragment was cloned into the rAAV vector pKm201CMV-CI digested with Sal I and Eco RV. pKm201CMV-CI contains the inverted terminal repeats of AAV, the CMV promoter, the chimeric intron from pCI (Promega, Madison. Wis.), and the bovine growth hormone polyadenylation signal. The final AAV vector was called pKm201-90H.

Figure 35:
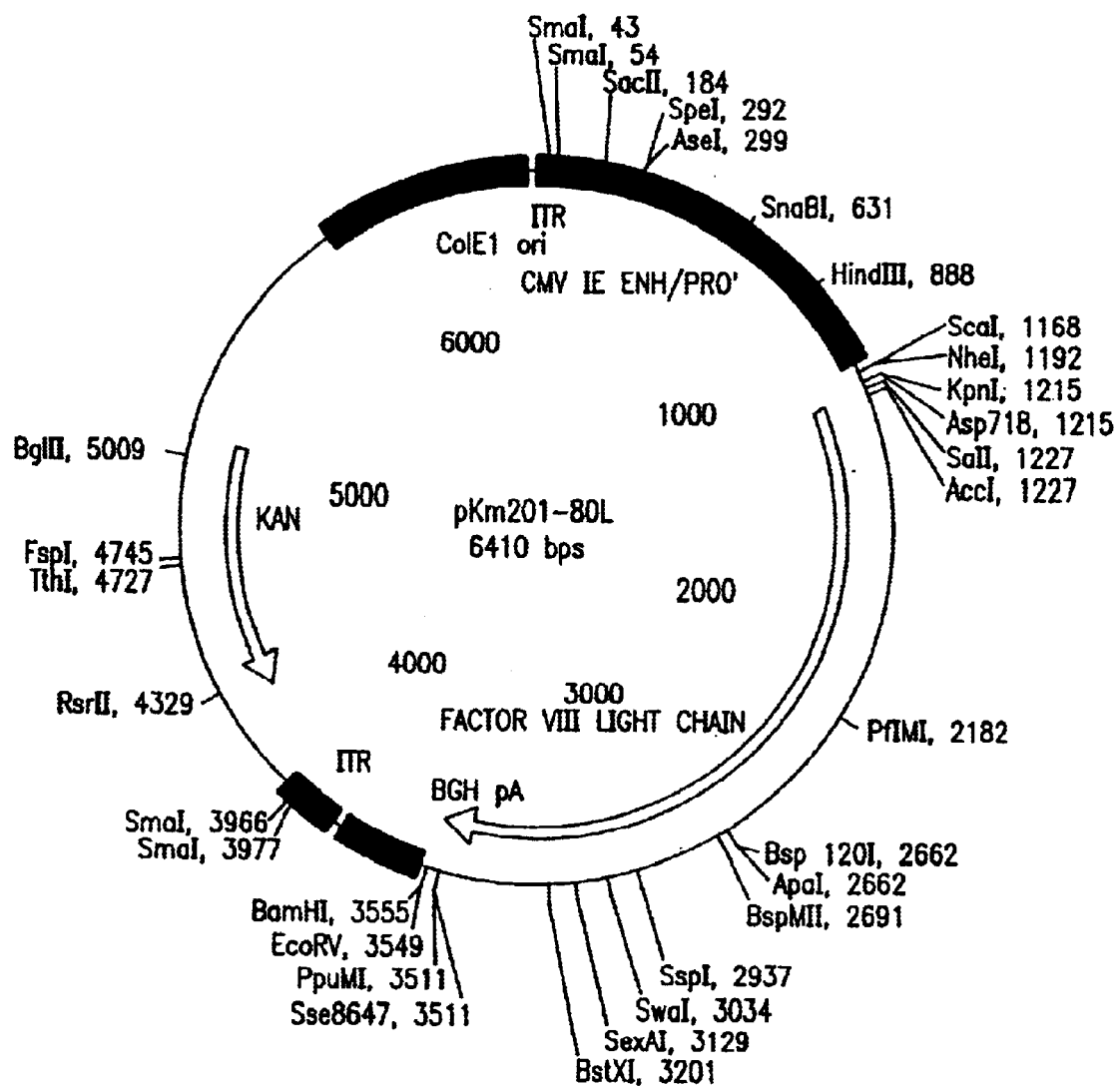
FIG. 35: Schematic representation of pKm201-80L.

To clone the light chain, we first amplified the factor VIII 5' untranslated and leader region using the following primers: forward, 5'-CACCGTCGTCGACTTATGCT-3' (Seq ID No. 30), and reverse, 5'-CAACGCTCGAGAAGCAGAATCGCAAAAGGC-3' (Seq ID No. 31). Again, pCMVKmHSTB was used as a template in the PCR reaction. The amplified region includes sequences from 174 bp upstream of the ATG to amino acid 19 of factor VIII. This fragment was digested with Xho I and Sal I and cloned into pCMVKmLINK digested with Xho I and Sal I. This plasmid was called pCMVKmF8L (for factor VIII leader). To amplify the light chain, the following primers were used: forward, 5'-TCGGCTCGAGGCATCAACGGGAAATAACTCGT-3' (Seq ID No. 32), and reverse, 5'-CCGACTCGAGTCAGTAGAGGTCCTGTGCCTC-3' (Seq ID No. 33). Again, pCMVkMHSTB served as the template for the PCR. The amplified fragment included sequences from amino acid 1645 of factor VIII to the STOP codon after amino acid 2332. This included the last four amino acids of the B domain and the complete light chain. This fragment was digested with Xho I and cloned into the Xho I site of pCMVKmF8L. This resulted in a light chain construct containg the factor VIII leader which was called pCMVKm80L. pCMVKm80L was digested with Sal I and Bam HI to remove the light chain construct, and this fragment was cloned into pKm201CMV-CI digested with Sal I and Bam HI to generate pKm201-80L. See FIGS. 35 and 36 for diagrams pKm201-80L and pKm201-90H, repectively.

EXAMPLE 30
Co-infection of Cells with rAAV Vectors Expressing the Heavy and Light Chains of Factor VIII Results in the Production of Biologically Active Factor VIII The heavy and light chain constructs, pKm201-80L and pKm201-90H, were packaged following standard procedures for the production of rAAV (Zhou et al., 1994, *J. Exp. Med.* 179:1867–1875). rAAV was purified as described (Wang et al., 1995, *Proc. Natl. Acad. Sci. USA* 92:12416–12420) and used to infect 293 cells plated in 6-well plates. Supernatants of infected cells were collected at 48 h after infection and assayed for biologically acitve factor VIII by Coamatic Factor VIII (KabiVitrum, Stockholm) following manufacturer's instructions. Normal human plasma (George King Bio-Medical, Inc., Overland Park, Kans.) was used to generate a standard curve. Cells were infected at a multiplicity of infection (MOI) of 6000 rAAV particles per cell. The experiment was done both with and without the addition of etopiside (0.3.M) to the medium. Etopiside has been shown to increase the transduction efficiency of rAAV vectors (Russell et al., 1995. *Proc. Natl. Acad. Sci. USA* 92:51719–51723). As shown in Table 5 below, co-infection of rAAV-80L and rAAV-90H resulted in the production of biologically active factor VIII. The amount of factor VIII was increased in the presence of etoposide.

TABLE 5

Co-infection of rAAV-SOL and rAAV-90H results in the production of biologically active factor VIII.

| | Factor VIII (ng/ml) | |
|---|---|---|
| Virus | −etoposicle | +etoposide |
| 80L | 0 | 0 |
| 90H | 0 | 0 |
| 80L + 90H | 1.4 | 6.1 |

EXAMPLE 31
Construction of a Retroviral Vector Expressing Human LDL Receptor The human LDL-receptor expression plasmid pLDLR17 was obtained from Bev Davidson, Univ of Iowa. Alternatively, the expression plasmid can be prepared as described in JBC 264, 21682–88(1989)). The 5' fragment was reconstructed using VENT-PCR. The 3' primer contained a XhoI site and the 3' primer encompasses the unique EcoRI site within the LDLR cDNA. The EcoRI digested 5' fragment was subcloned into Bluescript SK− and cut with SmaI and EcoRI. The SmaI site at the 3' end of LDLR cDNA in LDLR17 was modified using Not I linker to yield pLDLR17-S/N. The two fragments (The 5' fragment: XhoI to EcoRI and the 3' fragment: EcoRI to NotI) were ligated to pBA-6b (see Example 27, herein) which was digested with XhoI and NotI. The sequence of the PCR primers used was:

1. 5' GCGACTCGAGCATGGGGCCCTGGGGC  (Seq ID No. 34)

2. 5' GCACTGGAATTCGTCAGGGCG  (Seq ID No. 35)

The resulting vector was named p6b-LDLR.

A high titer DA producer clone for p6b-LDLR was selected under G418. The G418 vector titer in the supernatant was around 2e7 cfu/ml. Expression in target cells in vitro was demonstrated to be comparable to normal levels using either a Western blot or a functional assay.

EXAMPLE 32
Human Alpha 1 Antitrypsin Retroviral Vectors for the Treatment of Antitrypsin Deficiency The human alpha-1 antitrypsin cDNA clone was obtained from ATCC (Clone #256976). The plasmid was digested with EcoRI and blunted using T4 DNA polymerase large fragment (Klenow). The fragment containing the cDNA is cloned into the SrfI linearized pBA-9 vector (see Example 27 herein) to produce the provector pBA9-AAT. An oxidation resistant cDNA clone prepared as described in U.S. Pat. No. 4,732,973 was digested with restriction enzymes and ligated to pBA-5b (described above).

EXAMPLE 33
Construction of the Retroviral Vector Encoding Interferon-α2a, α2b and α2c (a) Preparation of Interferon-alpha Sequences Utilizing PCR Construction of the Retroviral Vector Encoding Interferon-α2a, α2b, α2c, α54, and α76

DNA clones of interferon-α2a, α2b, α2c α54, and α76 are prepared utilizing PCR. The interferon-α2a DNA is obtained from a cDNA library as described by Goeddel et al, 1980, *Nature* 287:411–416. The interferon-α2b DNA is obtained from a cDNA library described by Streuli et al., 1980, *Science* 209:1343–1347, and the interferon-α2c DNA is obtained as described by Saveliev et al., 1986, *Antibiot. Med. Biotekhnol.* 3:592–596. DNA clones of interferon-α54 and α76 are prepared utilizing PCR. Both the interferon-α54 DNA and the interferon-α76 DNA are obtained as described in U.S. Pat. Nos. 4,975,276 and 5,098,703.

A reaction mixture is then prepared according to procedures specified by New England Biolabs (Beverly, Mass.). More specifically, a reaction mixture is prepared containing 1 ug purified plasmid, 10 ul of 10×ThermoPol reaction buffer, 2 ul 2.5 mM of each dATP, dCTP, dGTP and dTTP, 0.5 ul of 2 units/100 ul Vent polymerase, 1–3 ul of 100 mM $MgSO_4$, and 0.5–1.0 ug of the primers specified below (Mattila et al., 1991, *Nucleic Acids Research* 19:4967–4973, Eckert, K. A, and Kunkel, T. A., PCR Methods and Applications 1, 17–24, 1991).

a. Interferon-α2a and α2b

For interferon-α2a and α2b, the coding region is identical except for AAA codon at position 23 for interferon-α2a and AGA codon at position 23 for interferon-α2b. The sense primer for both interferon-α2a and α2b is from the 5' region of the coding sequence, 6 bp upstream from the ATG start codon until 25 bp downstream from the start codon. The 5' end of the primer contains the Xho I restriction site.

5'-3': CGCG CCG CTC GAG TCT ACA ATG GCC TTG ACC TTT GCT TTA CTG G (Seq ID No. 36)

For interferon-α2a and α2b, the second primer corresponds to the anti-sense nucleotide sequence, extending 31 bp into the coding sequence from the 3' end of the interferon gene. The 5' end of the primer contains the Cla I restriction site.

5'-3': GCG CCC ATC GAT TCA TTC CTT ACT TCT TAA ACT TTC TTG CAA G (Seq ID No. 37)

b. Interferon-α2c

For interferon-α2c, the sense primer is from the 5' region of the coding sequence, 7 bp upstream from the ATG start codon until 28 bp downstream from the start codon. The 5' end of the primer contains the Xho I restriction site.

5'-3': CGCG CCG CTC GAG CAT CCA ATG GCC CTG TCC TTT TCT TTA CTT ATG G (Seq ID No. 38)

For interferon-α2c, the second primer corresponds to the anti-sense nucleotide sequence, extending 31 bp into the coding sequence from the 3 'end of the interferon gene. The 5' end of the primer contains the Cla I restriction site.

5'-3': CC ATC GAT TCA ATC CTT CCT CCT TAA TCT TTT TTG CAA G (Seq ID No. 39)

c. Interferon-α54

The sense primer is from the 5' region of the coding sequence, 6 bp upstream from the ATG start codon until 24 bp downstream from the start codon. The 5' end of the primer contains the Xho I restriction site.

5'-3': CGCG CCG CTC GAG TCT ACA ATG GCT TTG CCT TTT GCT TTA CTG (Seq ID No. 53)

The second primer corresponds to the anti-sense nucleotide sequence, extending 31 bp into the coding sequence from the 3' end of the interferon gene. The 5' end of the primer contains the Cla I restriction site.

5'-3': GCG CCC ATC GAT TTA TTC CTT CCT CCT TAA CCT TTC TTG CAA G (Seq ID No. 54)

d. Interferon-α76

For interferon-76, the sense primer is from the 5' region of the coding sequence, 7 bp upstream from the ATG start codon until 28 bp downstream from the start codon. The 5' end of the primer contains the Xho I restriction site.

5'-3': CGCG CCG CTC GAG CAT CCC AAT GGC CCT GTC CTT TTC TTT ACT GAT GG (Seq ID No. 55)

The second primer corresponds to the anti-sense nucleotide sequence, extending 31 bp into the coding sequence from the 3 'end of the interferon gene. The 5' end of the primer contains the Cla I restriction site.

5'-3': CC ATC GAT TCA ATC CTT CCT CCT TAA TCT TTT TTG CAA G (Seq ID No. 56)

The reaction mixture is brought up to 100 μl with DI $H_2O$, and each tube is placed into a thermocycler (Gene Amp PCR System 9600, Perkin-Elmer, Cetus, Calif.). The PCR program regulates the temperature of the reaction vessel first at 94° C. for 10 minutes to hot start reactions. Vent polymerase is added next and the cycle begins with 94° C. for 2 minutes, next at 56° C. for 30–60 seconds, and 72° C. for 30–60 seconds. This cycle is repealed 35 times. the 35th cycle, product ends are sealed by the reactions at 72° C. for 3–5 minutes Reactions are held at 4° C. If necessary, PCR amplification can be optimized using touchdown or stepdown PCR protocol (White, B. A., PCR Cloning Protocols 67, 39–45, 1997).

The PCR product from the reaction yields the interferon-α2a, α2b and α2c gene. Following the PCR reaction, the solution is transferred to a fresh 1.5 ml microfuge tube. Fifty microliters of 3 M sodium acetate is added to this solution followed by 500 μl of chloroform:isoamy alcohol (24:1). The mixture is vortexed and then centrifuged at 14,000 rpm for 5 minutes. The aqueous phase is transferred to a fresh mirofuge tube and 1.0 ml 100% EtOH is added. This solution is incubated at −20° C. for 4.5 hours, and then centrifuged at 10,000 rpm for 20 minutes. The supernatant is decanted, and the pellet rinsed with 500 ul of 70% EtOH. The pellet is dried by centrifugation at 10,000 rpm under vacuum and then resuspended in 10 ul deionized $H_2O$. One microliter of the PCR product is analyzed by electrophoresis in a 1.0% agarose gel.

These PCR products, approximately 570 bp in length, are digested with Xho I and Cla I restriction endonucleases, electrophoresed through a 1.0% agarose gel and the DNA is purified from the gel slice by Geneclean II (Bio 101, Vista, Calif). These Xho I-Cla I PCR products are subcloned into the respective sites of pBluescript KSII+ (Stratagene, La Jolla, Calif.). These constructs are designated KSII+ Xho-Cla IFN-α2a, α2b, α2c, α54 and α76 respectively, and are verified by DNA sequencing.

(b) Insertion of Interferon-alpha Sequences into Retroviral Vectors

1. Retroviral Vector Backbone—pBA6bL1

The pBA6bL1 retroviral vector backbone is described above. Two fragments are purified for the construction of the interferon (α2a, α2b, α2c, α54 and α76 pBA6bL1 retroviral vector. First, pBA6bL1 is digested with Xho I and Cla I and the 6.2 kb fragment containing the retroviral vector backbone is isolated. Second, from KSII+ Xho-Cla IFN-α2a, α2b, α2c, α54 and α76, the 570 Xho I-Cla I bp fragment containing the interferon-α2a, α2b, α2c, α54 and α76 gene is isolated and inserted into the Xho I-Cla I sites of pBA6bl1. The vector constructs are designated pBA6b-IFNα2a, pBA6b-IFNα2b, pBA6b-IFNα2c, pBA6b-IFNα54 and pBA6b-IFNα76, respectively.

2. Retroviral Vector Backbone—pLXSN

The retroviral vector backbone, pLXSN is available by Clontech (Palo, Alto, Calif.). Two fragments are purified for the construction of the LXSN retroviral vector encoding interferon-α2a, α2b, α2c, α54 and α76. First, pLXSN is digested with Xho I and Bam HI and the 5.9 kb fragment containing the retroviral vector backbone is isolated. Second, from KSII+ Xh-Cla IFN-α2a, α2b, α2c, α54 and α76, the 570 bp Xho-Bam HI fragment containing either the interferon-α2a, α2b, α2c, α54 or α76 gene is isolated and inserted into the respective sites of pLXSN. This vector construct is designated pLXSN-IFNα2a, pLXSN-IFNα2b, pLXSN-IFNα2c, pLXSN-IFNα54 and pLXSN-IFNα76.

3. Lentiviral Backbone

An HIV retroviral vector backbone is made, similar to V653RSN as described by Parolin et al. (*J. Virol.* 68:3888–3895, 1994). From KSII+ Xho-Cla IFN-α2a, α2b, α2c, α54 and α76, the 570 bp Xho I-Xba I fragment containing the interferon-α2a, α2b, 602c, α54 and α76 is isolated and inserted into the Xho I-Xba I sites of a CMV expression vector, pCI (Promega, Madison, Wis.) and is designated pCI-IFNα2a, IFNα2b, IFNα2c, IFNα54 and IFNα76, respectively. From pCI-IFNα2a, IFNα2b, IFNα2c, IFNα54 and IFNα76, the Bgl II-Bam HI fragment is isolated and inserted into the Bam HI sites of V653RSN where the SL3NEO sequences have been removed. To determine the orientation of the interferon α insert, vector constructs are sequenced. These vector constructs are designated V653-IFNα2a, V653-IFNα2b, V653-IFNα2c, V653-IFNα54 and V653-IFNα76, respectively.

4. Retroviral Vector Backbone—pBA8bL1

The pBA8bL1 retroviral vector backbone has been described before in Example 27.

a. Interferon-α2a and α2b

In a separate set of PCR reactions, the sense primer for both interferon-α2a and α2b is from the 5' region of the coding sequence, 6 bp upstream from-the ATG start codon until 25 bp downstream from the start codon. The 5' end of the primer contains the Bam HI restriction site.

5'-3': CC GGA TCC TCT ACA ATG GCC TTG ACC TTT GCT TTA CTG GC    (Seq ID No. 40)

For interferon-α2a and α2b, the second primer corresponds to the anti-sense nucleotide sequence, extending 31 bp into the coding sequence from the 3' end of the interferon gene. The 5' end of the primer contains the Not I restriction site.

5'-3': CGCG CCG GCG GCC GC TCA TTC CTT ACT TCT TAA ACT TTC TTG CAA G    (Seq ID No. 41)

b. Interferon-α2c

For interferon-α2c, the sense primer is from the 5' region of the coding sequence, 7 bp upstream from the ATG start codon until 28 bp downstream from the start codon. The 5' end of the primer contains the Bam HI restriction site.

5'-3': CC GGA TCC CAT CCA ATG GCC CTG TCC TTT TCT TTA CTT ATG G    (Seq ID No. 42)

For interferon-α2c, the second primer corresponds to the anti-sense nucleotide sequence, extending 31 bp into the coding sequence from the 3 'end of the interferon gene. The 5' end of the primer contains the Not I restriction site.

5'-3': CGCG CCG GCG GCC GC TCA ATC CTT CCT CCT TAA TCT TTT TTG CAA G    (Seq ID No. 43)

c. Interferon-α54

In a separate set of PCR reactions, the sense primer for both interferon-α54 is from the 5' region of the coding sequence, 6 bp upstream from the ATG start codon until 25 bp downstream from the start codon. The 5' end of the primer contains the Bam HI restriction site.

5'-3':CC GGA TCC TCT ACA ATG GCT TTG CCT TTT GCT TTA CTG    (Seq ID No. 57)

For interferon-α54, the second primer corresponds to the anti-sense nucleotide sequence, extending 31 bp into the coding sequence from the 3' end of the interferon gene. The 5' end of the primer contains the Not I restriction site.

5'-3':CGCG CCG GCG GCC GC TTA TTC CTT CCT CCT TAA CCT TTC TTG CAA G    (Seq ID No. 58)

d. Interferon-α76

For interferon-α76, the sense primer is from the 5' region of the coding sequence, 7 bp upstream from the ATG start codon until 28 bp downstream from the start codon. The 5' end of the primer contains the Bam HI restriction site.

5'-3': CC GGA TCC CAT CCC AAT GGC CCT GTC CTT TTC TTT ACT GAT GG    (Seq ID No. 59)

For interferon-α76, the second primer corresponds to the anti-sense nucleotide sequence, extending 31 bp into the coding sequence from the 3 'end of the interferon gene. The 5' end of the primer contains the Not I restriction site.

5'-3': CGCG CCG GCG GCC GC TCA ATC CTT CCT CCT TAA TCT TTT TTG CAA G    (Seq ID No. 60)

These PCR products, approximately 570 bp in length, are digested with Bam HI and Not I restriction endonucleases, electrophoresed through a 1.0% agarose gel and the DNA is purified from the gel slice by Geneclean II (Bio 101, Vista, Calif.). This Ban HI-Not I PCR product is subcloned into the respective sites of pBluescript KSII+ (Stratagene, La Jolla, Calif). These constructs, designated KSII+ Bam-Not IFN-α2a, α2b, α2c, α54 and α76 are verified by DNA sequencing.

Two fragments are purified for the construction of the interferon α2a, α2b, α2c, α54 and α76 pBA8bL1 retroviral vector. First, pBA8bL1 is digested with Not I and Srf I and the 6.1 kb fragment containing the retroviral vector backbone is isolated. Second, from KSII+ Bam-Not IFN α2a, α2b, α2c, α54 and α76, the 570 bp Sma I-Not I fragments containing the interferon-α2a, α2b, α2c, α54 or α76 are isolated and inserted into the Srf I-Not I sites of pBA8bL1. These vector constructs are designated pBA8b-IFN-α2a, pBA8b-IFN-α2b, pBA8b-α2c, pBA8b-IFN-α54 and pBA8b-IFN α76.

5. Retroviral Vector Backbone—pBA6bL1/TK

The herpes simplex virus (HSV) thymidine kinase (TK) cDNA is excised from pTJBA-5bTK retroviral vector by Xho I/Cla I double digestion as described before in Example 27B and inserted into the Sal I/Cla I sites of pSP72 plasmid (Promega, Madison, Wis.) and designated pSP72-TK. The human interleukin-2 (IL-2) cDNA is excised from KT3-IL-2 (described in PCT Patent Publication Nos. WO 94/21792 and WO 96/21015) and inserted into the Xho I/Cla I sites of pBluescript SK– and designated pBSSK-IL2. The Hind III/Sma I double digest of pSP72-TK excises TK cDNA and this fragment is inserted into the Hind III/Sma I sites of pBSSK-IL2. This construct has the following: Xho I-IL2 cDNA-Cla I-Hind III-TK cDNA-Sma I sequence and is designated pBSSK-IL2/TK.

From KSII+ Xho-Cla IFN-α2a, α2b, α2c, α54 or α76, the 570 Xho I-Cla I bp fragment containing the interferon-α2a, α2b, α2c, α54 or α76 gene is isolated. From pBSSK-IL2/TK, the IL2 fragment is excised by Xho I/Cla I double digestion, and replaced with Xho/Cla I fragments containing the interferon-α2a, α2b, α2c, α54 or α76 genes. The vector constructs are designated pBSSK-IFNα2a/TK, pBSSK-IFNα2b/TK, pBSSK-IFNα2c/TK, pBSSK-IFNα54/TK and pBSSK-IFNα76/TK, respectively. The Xho I/Not I fragments from pBSSK-IFNα2a /TK, pBSSK-IFNα2b/TK, pBSSK-IFNα2c/TK, pBSSK-IFNα54/TK and pBSSK-IFNα76/TK are excised and inserted into the Xho I-Not I sites of pBA6bl1. These di-cistronic retroviral vectors encoding IFN α2a, α2b, α2c α54 and α76 are designated pBA6bL1 IFN α2a/TK, pBA6bL1 IFN α2b/TK, pBA6bL1 IFN α2c/TK, pBA6bL1 IFN α54/TK and pBA6bL1 IFN α76/TK.

6. Retroviral Vector Backbone with a Liver-specific Promoter

The ApoE enhancer-alpha 1-antitrypsin promoter yields high levels of expression from liver cells (Okuyama et al., 1996, *Hum Gene Ther* 7:637–645). The retroviral vector encoding the liver-specific promoter is constructed as follows.

a. ApoE Enhancer Cassette

The apolipoprotein E (Apo E) enhancer sequence has been identified as a 154 bp fragment by Shachter et al., 1993, *J. Lipid Res* 34:1699–1707. The ApoE enhancer cassette was generated by sets of four oligonucleotides that span the entire sequence. For the, first reaction, four oligonucleotides were synthesized that were phosphorylated at the 5' end. The first oligonucleotide is the sense strand and contains Hind III restriction site at the 5' end.

5'-3': AG CTT GCT GTT TGT GTG CTG CCT CTG AAG TCC ACA CTG AAC AAA CTT CAG CCT ACT CAT GTC CCT AAA ATG GGC AAA CAT TGC AAG CAG C(Seq ID No. 61)

The second oligonucleotide is the sense strand, spanning the second half of the Apo E enhancer and contains the Hind III restriction site at the 3' end.

5'-3': AAA CAG CAA ACA CAC AGC CCT CCC TGC CTG CTG ACC TTG GAG CTG GGG CAG AGG TCA GAG ACC TCT CTG A (Seq ID No. 62)

The third oligonucleotide is the antisense strand of the second half of the Apo E enhancer and contains the Hind III site at the 5' end.

5'-3': AG CTT CAG AGA GGT CTC TGA CCT CTG CCC CAG CTC CAA GGT CAG CAG GCA GGG AGG GCT GTG TGT TTG CTG TTT GCT GCT TG (Seq ID No. 63)

The fourth oligonucleotide is the antisense strand of the first half of the Apo E enhancer and contains the Hind III site at the 3' end.

5'-3': CAA TGT TTG CCC ATT TTA GGG ACA TGA GTA GGC TGA AGT TTG TTC AGT GTG GAC TTC AGA GGC AGC ACA CAA ACA GC A (Seq ID No. 64)

This set of four oligonucleotides of approximately 80 bases in length are annealed, and ligated into the dephosphorylated Hind III sites of pBluescript KSII+ (Stratagene, La Jolla, Calif.) following standard molecular cloning protocols. Recombinants are selected and sequenced. Correct monomer Apo E enhancer elements are excised by Hind III, electrophoresed through a polyacrylamide gel and the DNA is purified following procedures described by Asubel et al., *Current Protocols in Molecular Biology,* Greene Publishing and Wiley-Interscience, New York (1987). The monomer enhancer element is ligated into the dephosphorylated Hind III sites of pBluescript KSII+ at an insert:vector ratio of 10:1 in order to generate recombinants containing dimers. Recombinant plasmids were assessed by DNA sequencing to select clones which carried both enhancer fragments in the same orientation with the 5' end closer to the Eco RV site and the 3' end closer to the Cla I site within the multi-cloning site of pBluescript. This construct is designated KSII+ Hind III ApoE(x2).

For the second reaction, another set of four oligonucleotides were synthesized that were phosphorylated at the 5' end. The first oligonucleotide is the sense strand and contains Eco RI restriction site at the 5' end.

5'-3': AAT TC GCT GTT TGT GTG CTG CCT CTG AAG TCC ACA CTG AAC AAA CTT CAG CCT ACT CAT GTC CCT AAA ATG GGC AAA CAT TGC AAG CAG C(Seq ID No. 65)

The second oligonucleotide is the sense strand, spanning the second half of the APO E enhancer and contains the Eco RI restriction site at the 3' end.

5'-3': AAA CAG CAA ACA CAC AGC CCT CCC TGC CTG CTG ACC TTG GAG CTG GGG CAG AGG TCA GAG ACC TCT CTG G (Seq ID No. 66)

The third oligonucleotide is the antisense strand of the second half of the Apo E enhancer and contains the Eco RI site at the 5' end.

5'-3': AA TTC CAG AGA GGT CTC TGA CCT CTG CCC CAG CTC CAA GGT CAG CAG GCA GGG AGG GCT GTG TGT TTG CTG TTT GCT GCT TG (Seq ID No. 67)

The fourth oligonucleotide is the antisense strand of the first half of the Apo E enhancer and contains the Eco RI site at the 3' end.

5'-3': CAA TGT TTG CCC ATT TTA GGG ACA TGA GTA GGC TGA AGT TTG TTC AGT GTG GAC TTC AGA GGC AGC ACA CAA ACA GC G (Seq ID No. 68)

In a second reaction, this set of four oligonucleotides of approximately 80 bases in length are annealed, and ligated into the dephosphorylated Eco RI sites of pBluescript KSII+ (Stratagene, La Jolla, Calif.). Recombinants are selected and sequenced. Correct monomer Apo E enhancer elements are excised by Eco RI, electrophoresed through a polyacrylamide gel and the DNA is purified following standard procedures. The monomer enhancer element is ligated into the dephosphorylated Eco RI sites of pBluescript KSII+ at an insert:vector ratio of 10:1 in order to generate a second set of recombinants containing dimers. Recombinant plasmids were assessed by DNA sequencing to select clones which carried both enhancer fragments in the same orientation with the 5' end closer to the Pst I site and the 3' end closer to the Eco RV site. This construct is designated KSII+ Eco RI ApoE(x2).

The 300 base pair Pst I/Eco RV fragment from KSII+ Eco RI ApoE(x2) is inserted into the Pst I and Eco RV sites within the multi-cloning sites of KSII+ Hind III ApoE(x2). This construct is designated KSII+ ApoE(x4), and contains 4 copies of the 154 base pair Apo E enhancer.

b. Human Alpha 1-antitrypsin Promoter

The human alpha 1-antitrypsin (hAAT) promoter has been identified as a 400 base pair region by Shen et al., 1989, *DNA* 8:101–108. The hAAT promoter DNA is obtained from a genomic library as was done by Long et al., 1984, *Biochem* 23:4828–4837, or can be obtained from ATCC (ATCC No. 61596).

A PCR reaction is conducted in order to isolate the hAAT promoter. The 5' end of the primer contains the Sma I restriction site.

5'-3': CGCG CCG CCC GGG GTA GAT CTT GCT ACC AGT
GG                                            (Seq ID No. 69)

The second primer corresponding to the anti-sense nucleotide sequence contains the Not I restriction site.

5'-3': GCG CCC GCG GCC GC CAC TGT CCC AGG TCA GTG
GTG GTG CC                                    (Seq ID No. 70)

This PCR product, approximately 400 bp in length, is digested with Sma I and Not I and is cloned into the Sma I and Not I sites within the multi-cloning sites of KSII+ ApoE(x4). This construct is confirmed by sequencing and is designated KSII+ ApoE/hAAT.

c. Construction of the Retroviral Vector pBA6 ApoE/hAAT-IFN α2a and pBA6 ApoE/hAAT-IFN α2b 1. Interferon-α2a and α2b The sense primer for both interferon-α2a and α2b is from the 5' region of the coding sequence, 6 bp upstream from the ATG start codon until 25 bp downstream from the start codon. The 5' end of the primer contains the Not I restriction site.

5'-3': CGCG CCG GCGG CCGC TCT ACA ATG GCC TTG ACC
TTT GCT TTA CTG G                             (Seq ID No. 71)

For interferon-α2a and α2b, the second primer corresponds to the anti-sense nucleotide sequence, extending 31 bp into the coding sequence from the 3' end of the interferon gene. The 5' end of the primer contains the Cla I restriction site.

5'-3': GCG CCC ATC GAT TCA TTC CTT ACT TCT TAA ACT
TTC TTG CAA G                                 (Seq ID No. 72)

The product of this PCR reaction is digested with Not I and Cla I and purified. KSII+ ApoE/hAAT is digested with Not I and Cla I and the 1 kb fragment containing the Apo E enhancer and the hAAT promoter is isolated. From pBA6bL1, the 6.1 kb Xho/Cla I retroviral vector backbone is isolated. In a three part ligation (a) the Xho I/Not I fragment containing the Apo E enhancer and the hAAT promoter, (b) the Not I/Cla I fragment encoding the IFN α2a or α2b gene and (c) the Xho I/Cla I fragment encoding the retroviral vector backbone are joined to generate pBA6 ApoE/hAAT-IFN α2a or α2b.

7. Construction of the Marker-less Retroviral Vector pBA9 ApoE/hAAT-IFN α2a and pBA9 ApoE/hAAT-IFN α2b a. Interferon-α2a and α2b The sense primer for both interferon-α2a and α2b is from the 5' region of the coding sequence, 6 bp upstream from the ATG start codon until 25 bp downstream from the start codon. The 5' end of the primer contains the Not I restriction site.

5'-3': CGCG CCG GCGG CCGC TCT ACA ATG GCC TTG ACC
TTT GCT TTA CTG G                             (Seq ID No. 73)

For interferon-α2a and α2b, the second primer corresponds to the anti-sense nucleotide sequence, extending 31 bp into the coding sequence from the 3' end of the interferon gene. The 5' end of the primer contains the Cla I restriction site.

5'-3': GCG CCC ATC GAT TCA TTC CTT ACT TCT TAA ACT
TTC TTG CAA G                                 (Seq ID No. 74)

The product of this PCR reaction is digested with Not I and Cla I and purified. KSII+ ApoE/hAAT is digested with Not I and Cla I and the 1 kb fragment containing the Apo E enhancer and the hAAT promoter is isolated. From pBA9b, the 4.8 kb Xho/Cla I retroviral vector backbone is isolated. In a three part ligation (a) the Xho I/Not I fragment containing the Apo E enhancer and the hAAT promoter, (b) the Not I/Cla I fragment encoding the IFN α2a or α2b gene and (c) the Xho I/Cla I fragment encoding the pBA9b retroviral vector backbone are joined to generate pBA9 ApoE/hAAT-IFN α2a or α2b.

8. Construction of the Retroviral Vector pBA6 TK/ApoE/hAAT-IFN α2a and pBA6 TK/ApoE/hAAT-IFN α2b The thymidine kinase (TK) gene is excised form pTJ5b-TK with Xho/Cla I and inserted into the Xho I/Cla I sites of KSII+ ApoE/hAAT. This construct is designated KSII+ TK/ApoE/hAAT.

PCR products containing either the IFN α2a or IFN α2b genes described in the example above is digested with Not I and Cla I and purified. The Xho/Not fragment containing the TK/ApoE/hAAT sequence is excised from KSII+ TK/ApoE/hAAT. From pBA6bL1, the 6.1 kb Xho/Cla I retroviral vector backbone is isolated.

In a three part ligation (a) the Xho I/Not I fragment containing the TK gene and the Apo E enhancer with the hAAT promoter, (b) the Not I/Cla I fragment encoding the IFN α2a or α2b gene and (c) the Xho I/Cla I fragment encoding the retroviral vector backbone are joined to generate pBA6 TK/ApoE/hAAT-IFN α2a or pBA6 TK/ApoE/hAAT-IFN α2b.

9. Construction of the Marker-less Retroviral Vector pBA9 TK/ApoE/hAAT-IFN α2a and DBA9 TK/ApoE/hAAT-IFN α2b The thymidine kinase (TK) gene is excised from pTJ5b-TK with Xho/Cla I and inserted into the Xho I/Cla I sites of KSII+ ApoE/hAAT. This construct is designated KSII+ TK/ApoE/hAAT.

PCR products containing either the IFN α2a or IFN α2b genes described in the example above is digested with Not I and Cla I and purified. The Xho/Not fragment containing the TK/ApoE/hAAT sequence is excised from KSII+ TK/ApoE/hAAT. From pBA9b, the 4.8 kb Xho/Cla I pBA9 retroviral vector backbone is isolated.

In a three part ligation (a) the Xho I/Not I fragment containing the TK gene and the Apo E enhancer with the hAAT promoter, (b) the Not I/Cla I fragment encoding the IFN α2a or α2b gene and (c) the Xho I/Cla I fragment encoding the pBA9 retroviral vector backbone are joined to generate pBA9 TK/ApoE/hAAT-IFN α2a or pBA9 TK/ApoE/hAAT-IFN α2b.

What is claimed is:

1. A TK-1 retroviral vector which expresses a factor VIII protein.

2. The retroviral vector of claim 1 wherein said factor VIII protein is a B-domain deleted factor VIII protein.

3. The retroviral vector of claim 2 wherein said B-domain deleted factor VIII protein is the factor VIII SQN deletion.

4. The retroviral vector of claim 3 wherein said factor VIII protein comprises the amino acid sequence depicted in Seq. ID No. 47.

5. The retroviral vector of claim 4 wherein said factor VIII protein is encoded by the nucleic acid sequence depicted in Seq. ID No. 46.

6. A retroviral vector which expresses a factor VIII protein, wherein said retroviral vector is selected from the group consisting of pBA-5a, pBA-5b and pBA-5c.

7. The retroviral vector of claim 6 wherein said factor VIII protein is a B-domain deleted factor VIII protein.

8. The retroviral vector of claim 7 wherein said B-domain deleted factor VIII protein is the factor VIII SQN deletion.

9. The retroviral vector of claim 8 wherein said factor VIII protein comprises the amino acid sequence depicted in Seq. ID No. 47. 4

10. The retroviral vector of claim 9 wherein said factor VIII protein is encoded by the nucleic acid sequence depicted in Seq. ID No. 46.

11. A pBA-9b retroviral vector which expresses a factor VIII protein.

12. The retroviral vector of claim 11 wherein said factor VIII protein is a B-domain deleted factor VIII protein.

13. The retroviral vector of claim 12 wherein said B-domain deleted factor VIII protein is the factor VIII SQN deletion.

14. The retroviral vector of claim 13 wherein said factor VIII protein comprises the amino acid sequence depicted in Seq. ID No. 47.

15. The retroviral vector of claim 14 wherein said factor VIII protein is encoded by the nucleic acid sequence depicted in Seq. ID No. 46.

16. A pBA-8b retroviral vector which expresses a factor VIII protein.

17. The retroviral vector of claim 16 wherein said factor VIII protein is a B-domain deleted factor VIII protein.

18. The retroviral vector of claim 17 wherein said B-domain deleted factor VIII protein is the factor VIII SQN deletion.

19. The retroviral vector of claim 18 wherein said factor VIII protein comprises the amino acid sequence depicted in Seq. ID No. 47.

20. The retroviral vector of claim 19 wherein said factor VIII protein is encoded by the nucleic acid sequence depicted in Seq. ID No. 46.

* * * * *